(12) United States Patent
Burton et al.

(10) Patent No.: US 10,190,130 B2
(45) Date of Patent: Jan. 29, 2019

(54) POLYSACCHARIDE SYNTHASES

(71) Applicants: Adelaide Research & Innovation Pty Ltd, Adelaide SA (AU); Grains Research & Development Corporation, Kingston ACT (AU); The University of Melbourne, Parkville VIC (AU)

(72) Inventors: Rachel Anita Burton, Panorama (AU); Geoffrey Bruce Fincher, Hazelwood Park (AU); Antony Bacic, Eaglemont (AU)

(73) Assignees: Adelaide Research & Innovation Pty Ltd, Adelaide (AU); Grains Research & Development Corporation, Kingston (AU); The University of Melbourne, Parkville (AU)

( * ) Notice: Subject to any disclaimer, the term of this patent is extended or adjusted under 35 U.S.C. 154(b) by 0 days.

(21) Appl. No.: 15/621,132

(22) Filed: Jun. 13, 2017

(65) Prior Publication Data

US 2017/0342432 A1   Nov. 30, 2017

Related U.S. Application Data

(60) Continuation of application No. 14/465,679, filed on Aug. 21, 2014, now Pat. No. 9,708,623, which is a division of application No. 11/997,667, filed as application No. PCT/AU2006/001107 on Aug. 3, 2006, now abandoned.

(30) Foreign Application Priority Data

Aug. 3, 2005 (AU) .................................. 2005904155

(51) Int. Cl.
*C12N 15/82* (2006.01)
*C12P 19/04* (2006.01)
*C12N 9/10* (2006.01)

(52) U.S. Cl.
CPC ....... *C12N 15/8246* (2013.01); *C12N 9/1059* (2013.01); *C12N 15/8245* (2013.01); *C12P 19/04* (2013.01)

(58) Field of Classification Search
None
See application file for complete search history.

(56) References Cited

U.S. PATENT DOCUMENTS

2004/0123343 A1   6/2004  La Rosa et al.

OTHER PUBLICATIONS

International Search Report from PCT/AU2006/001107, dated Oct. 30, 2006.
Supplementary Search Report from EP Appl. No. 06774788.1, dated Feb. 17, 2009.
Bacic, Antony et al.; "Cellulose synthase (CESA) and cellulose-synthase-like (CSL) gene families of barley"; 2004, *Abstracts of Papers of the American Chemical Society*, vol. 227, No. 1, pp. U292.
Becker, M., et al., Biosynthesis of (1,3)(1,4)-β-glucan and (1,3)-β-glucan in barley (*Hordeum vulgare* L.), *Planta*, vol. 195, pp. 331-338 (1995).
Buckeridge, M., et al., "Mixed Linkage (1→3),(1→4)-β-D-Glucans of Grasses," *Cereal Chemistry*, vol. 81(1), pp. 115-127 (2004).
Burton, R., et al., "Cellulose Synthase-Like CslF Genes Mediate the Synthesis of Cell Wall (1,3;1,4)-β-D-Glucans," *Science*, vol. 311, pp. 1940-1942 (2006).
Burton, Rachel A. et al.; "The CesA gene family of barley. Quantitative analysis of transcripts reveals two groups of co-expressed genes"; 2004, *Plant Physiology*, vol. 134, No. 1, pp. 224-236.
Burton, Rachel A. et al.; "The genetics and transcriptional profiles of the cellulose synthase-like HvCslf gene family in barley"; 2008, *Plant Physiology*, vol. 146, No. 4, pp. 1821-1833.
Carpita, Nicholas C.; "Structure and bigenesis of the cell walls of grasses"; 1996, *Annual Review of Plant Physiology and Plant Molecular Biology Annual Reviews*, pp. 445-476.
Database EMBL, 2001, "*Oryza sativa* SCLF6 mRNA, partial cds"; EBI Accession No. EMBL:AF435645, 4 pages.
Doblin, M., et al., "Cellulose Biosynthesis in Plants: from Genes to Rosettes," *Plant Cell Physiol.*, vol. 43(12), pp. 1407-1420 (2002).
Gibeaut, DM and Carpita, NC, "Synthesis of (1→3),(1→4)-β-D-glucan in the Golgi apparatus of maize coleoptiles," *Proc. Nat'l Acad. Sci. USA*, vol. 90, pp. 3850-3854 (1993).
Han, F et al.; "Mapping of beta-glucan content and beta-glucanase activity loci in barley grain and malt"; 1995, *Theoretical and Applied Genetics*, vol. 91, No. 6-7, pp. 921-927.
Hazen, S., et al., "Cellulose Synthase-Like Genes of Rice," *Plant Physiology*, vol. 128, pp. 336-340 (2002).
Held et al.; "Towards the identification of the catalytic components of the (1,3),(1,4)-β-glucan synthase complex"; *American Society of Plant Biologists*; Abstract No. 411 (2005) Retrieved from site: abstracts.aspb.org/pb2005/public/p49/7474.html.
Horvathe et al.; "The production of recombinant proteins in transgenic barley grains"; *Proc. Natl. Acad. Sci. USA*; 97(4):1914-1919 (Feb. 2000).
Hunter, Charles, T. et al.; "Analysis of Mu-induced knockout mutations in cell wall blosynthetic genes of maize identified through revers genetics"; 2005, *Plant Biology*, vol. 2005, pp. 177.

(Continued)

*Primary Examiner* — Brent T Page
(74) *Attorney, Agent, or Firm* — Kilpatrick Townsend and Stockton LLP

(57) ABSTRACT

The present invention relates generally to polysaccharide synthases. More particularly, the present invention relates to (1,3;1,4)-β-D-glucan synthases. The present invention provides, among other things, methods for influencing the level of (1,3;1,4)-β-D-glucan produced by a cell and nucleic acid and amino acid sequences which encode (1,3;1,4)-β-D-glucan synthases.

15 Claims, 27 Drawing Sheets

Specification includes a Sequence Listing.

(56) References Cited

OTHER PUBLICATIONS

Mayer, R. et al.; "Polypeptide Composition of Bacterial Cyclic Diguanylic Acid- Dependent Cellulose Synthase and the Occurrence of Immunologically Crossreacting Proteins in Higher Plants"; 1991, *Proceedings of the National Academy of Sciences*, vol. 88, No. 12, pp. 5472-5476.

Medhurst, A. et al.; "Towards determining a role in cell wall synthesis for the cellulose sythase-like D and F genes of barley"; 2005, *Comparative Biochemistry and Physiology Part A Molecular & Integrative Physiology*, vol. 141, No. 3, Suppl. S., pp. S265-S266

Richmond, Todd A. et al.; "Integrative approaches to determining Csl function"; 2001, *Plant Molecular Biology*, vol. 47, No. 1-2, pp. 131-143.

Urbanowicz, B., et al., "Topology of the Maize Mixed Linkage (1→3),(1→4)- β-D-Glucan Synthase at the Golgi Membrane," *Plant Physiology*, vol. 134, pp. 758-768 (2004).

FIG 6A

```
HvCslF1    ........MA PAVAGGGRVR SNEPVAAAAA APAASGKPCV CGFQVCACTG
OsCslF5    ........MA PAVAGGGGRR NNEGVNGNAA APA.....CV CGFPVCACAG
HvCslF2    ........MA SAAGAAG... .SN..ASLAA PLL......A SRE.......
OsCslF3    ........MA SPASVAGGGE DSNGCSSLID PLL......V SRTSSIG...
HvCslF5    ........ML SPRTDAG... .AGAATDLSQ PLL......W NRNGVHAGAL
OsCslF1    ........MS AAAAVTSWT. .......... .......... .......NGC
OsCslF2    MAATAASTMS AAAAVTRRIN AALRVDATSG DVA......A ..GADGQNGR
OsCslF4    ........MS AAAVTRRINA GGLRVEVTNG NGA......A GVYVAAAAAP
HvCslF4    .........M APAVTRRAN. .ALRVEAPDG NAE......S G...RASLAA
HvCslF3    ........MA SPAAVG.GGR .......LAD PLL......A ADVVVVG...
OsCslF9    .......MAL SPAAAGRTGR NNNNDAGLAD PLL......P AGGGGGG...
HvCslF6    ........MG SLAAANGAGH ASNGAGVADQ ALA......L ENGTGNGHKA
OsCslF8    ........MA ANGGGGGAGG CSNGGGGGAV NGA......A ANGGGGGGGG
OsCslF7    ........MP PSAGLATESL PAATCP.... .......... ..........

HvCslF1    SAAVASAASS LDMDIVAMGQ IGAVNDESWV GVELGEDGET DESG...AAV
OsCslF5    AAAVASAASS ADMDIVAAGQ IGAVNDESWV AVDLSDSDDA PAAGDVQGAL
HvCslF2    .......... GGAKKPVG.. ...AKGKHWE AADKDERRAA KESGGE..DG
OsCslF3    .......... GAERKAAGGG GGGAKGKHWA AADKGERRAA KECGGE..DG
HvCslF5    VVMPVVANGH GGGDKLKG.. APKAKDKYWK DVDQPDDMAA APDLDN..GG
OsCslF1    WS........ ..PAATRVND GG..KDDVWV AVDEADVSGA RGSDGG....
OsCslF2    RS........ ..PVAKRVND GGGGKDDVWV AVDEKDVCGA RGGDGA....
OsCslF4    CS........ ..PAAKRVND GGG.KDDVWV AVDEADVSGP SGGDG.....
HvCslF4    DS........ ..PAAKRAID AK...DDVWV AAAEGDASGA SAGNG.....
HvCslF3    .......... .......... ...AKDKYWV PADEREILAS QSSGGGEQDG
OsCslF9    .......... .......... ...GKDKYWV PADEEEEICR GEDGG..RPP
HvCslF6    SDANRATPVQ QANGSSKAAG KVSPKDKYWV AVDEGEMAAA IADGG..EDG
OsCslF8    S......... ..KGATTRRA KVSPMDRYWV PTDEKEMAAA VADGG..EDG
OsCslF7    .......... .......... ...AKKDAYA AAASPESETK LAAGD.....

HvCslF1    DDRPVFRTEK IKGVLLHPYR VLIFVRLIAF TLFVIWRISH KN........
OsCslF5    DDRPVFRTEK IKGVLLHPYR VLIFVRLIAF TLFVIWRIEH KN........
HvCslF2    R.PLLFRTYK VKGTLLHPYR ALIFIRLIAV LLFFVWRIKH NK........
OsCslF3    RRPLLFRSYR VKGSLLHPYR ALIFARLIAV LLFFGWRIRH NN........
HvCslF5    GRPLLFSNLR VQNIILYPGE VLILIRVIAV ILFVGWRIKH NN........
OsCslF1    GRPPLFQTYK VKGSILHPYR FLILARLIAI VAFFAWRIRH KN........
OsCslF2    ARPPLFRTYK VKGSILHPYR FLILLRLIAI VAFFAWRVRH KN........
OsCslF4    VRPTLFRTYK VKGSILHPYR FLILVRLIAI VAFFAWRVRH KN........
HvCslF4    DRPPLFRTMK VKGSILHPYR FMILVRLVAV VAFFAWRLKH KN........
HvCslF3    RAPLLYRTFR VKGFFINLYR LLTLVRVIVV ILFFTWRMRH RD........
OsCslF9    APPLLYRTFK VSGVLLHPYR LLTLVRLIAV VLFLAWRLKH RD........
HvCslF6    RRPLLYRTFK VKGILLHPYR LLSLIRLVAI VLFFVWRVRH PY........
OsCslF8    RRPLLFRTFT VRGILLHPYR LLTLVRLVAI VLFFIWRIRH PY........
OsCslF7    ERAPLVRTTR ISTTTIKLYR LTIFVRIAIF VLFFKWRITY AARAISSTDA

HvCslF1    .....PDAMW LWVTSICGEF WFGFSWLLDQ LPKLNPINRV PDLAVLRQRF
OsCslF5    .....PDAMW LWVTSIAGEF WFGFSWLLDQ LPKLNPINRV PDLAVLRRRF
HvCslF2    .....SDIMW FWTISVVGDV WFGFSWLLNQ LPKFNPIKTI PDMVALRRQY
OsCslF3    .....SDIMW FWTMSVAGDV WFGFSWLLNQ LPKFNPVKTI PDLTALRQYC
HvCslF5    .....SDVMW FWMMSVVADV WFSLSWLSYQ LPKYNPVKRI PDLATLRKQY
OsCslF1    .....RDGAW LWTMSMVGDV WFGFSWVLNQ LPKQSPIKRV PDIAALADRH
OsCslF2    .....RDGVW LWTMSMVGDV WFGFSWVLNQ LPKLSPIKRV PDLAALADRH
OsCslF4    .....RDGAW LWTMSMAGDV WFGFSWALNQ LPKLNPIKRV ADLAALADRQ
HvCslF4    .....HDGMW LWATSMVADV WFGFSWLLNQ LPKLNPIKRV PDLAALADQC
```

FIG 6B

```
HvCslF3         .....SDAMW  LWWISVVGDL  WFGVTWLLNQ  ITKLKPRKCV  PSISVLREQL
OsCslF9         .....SDAMW  LWWISIAGDF  WFGVTWLLNQ  ASKLNPVKRV  PDLSLLRRRF
HvCslF6         .....ADGMW  LWWISMVGDL  WFGVTWLLNQ  VAKLNPVKRV  PNLALLQQQF
OsCslF8         .....ADGMF  FWWISVIGDF  WFGVSWLLNQ  VAKLKPIRRV  PDLNLLQQQF
OsCslF7         GGIGMSKAAT  FWTASIAGEL  WFAFMWVLDQ  LPKTMPVRRA  VDVTALNDDT

HvCslF1         DR.PDGTSTL  PGLDIFVTTA  DPIKEPILST  ANSVLSILAA  DYPVDRNTCY
OsCslF5         DH.ADGTSSL  PGLDIFVTTA  DPIKEPILST  ANSILSILAA  DYPVDRNTCY
HvCslF2         DL.SDGTSTL  PGIDVFVTTA  DPIDEPILYT  MNCVLSILAS  DYPVDRCACY
OsCslF3         DL.ADGSYRL  PGIDVFVTTA  DPIDEPVLYT  MNCVLSILAA  DYPVDRSACY
HvCslF5         DT.PGRSSQL  PSIDVIVTTA  SATDEPILYT  MNCVLSILAA  DYHIGRCNCY
OsCslF1         ......SGDL  PGVDVFVTTV  DPVDEPILYT  VNTILSILAA  DYPVDRYACY
OsCslF2         ......SGDL  PGVDVFVTTV  DPVDEPILYT  VNTILSILAA  DYPVDRYACY
OsCslF4         QHGTSGGGEL  PGVDVFVTTV  DPVDEPILYT  VNSILSILAA  DYPVDRYACY
HvCslF4         G..SSGDANL  PGIDIFVTTV  DPVDEPILYT  VNTILSILAT  DYPVDKYACY
HvCslF3         DQ.PDGGSDL  PLLDVFINTV  DPVDEPMLYT  MNSILSILAT  DYPVQKYATY
OsCslF9         D...DGG..L  PGIDVFINTV  DPVDEPMLYT  MNSILSILAT  DYPADRHAAY
HvCslF6         DL.PDGNSNL  PCLDVFINTV  DPINEPMIYT  MNSIISILAA  DYPVDKHACY
OsCslF8         DL.PDGNSNL  PGLDVFINTV  DPINEPMIYT  MNAILSILAA  DYPVDKHACY
OsCslF7         ........LL  PAMDVFVTTA  DPDKEPPLAT  ANTVLSILAA  GYPAGKVTCY

HvCslF1         VSDDSGMLLT  YEALAESSKF  ATLWVPFCRK  HGIEPRGPES  YFE.......
OsCslF5         LSDDSGMLLT  YEAMAEAAKF  ATLWVPFCRK  HAIEPRGPES  YFE.......
HvCslF2         LPDDSGALIQ  YEALVETAKF  ATLWVPFCRK  HCIEPRAPES  YFE.......
OsCslF3         LSDDSGALIL  YEALVETAKF  ATLWVPFCRK  HCIEPRSPES  YFE.......
HvCslF5         LSDDSGSLVL  YEALVETAKF  AALWVPFCRK  HQIEPRAPES  YFE.......
OsCslF1         LSDDGGTLVH  YEAMVEVAKF  AELWVPFCRK  HCVEPRSPEN  YFA.......
OsCslF2         LSDDGGTLVH  YEAMVEVAKF  AELWVPFCRK  HCVEPRSPEN  YFA.......
OsCslF4         LSDDGGTLVH  YEAMVEVAKF  AELWVPFCRK  HCVEPRSPEN  YFA.......
HvCslF4         LSDDGGTLVH  YEAMIEVANF  AVMWVPFCRK  HCVEPRSPEN  YFG.......
HvCslF3         FSDDGGSLVH  YEGLLLTAEF  AASWVPFCRK  HCVEPRAPES  YFW.......
OsCslF9         LSDDGASLAH  YEGLIETARF  AALWVPFCRK  HRVEPRAPES  YFA.......
HvCslF6         LSDDGGSIIH  YDGLLETAKF  AALWVPFCRK  HSIEPRAPES  YFS.......
OsCslF8         LSDDGGSIIH  YDGLLETAKF  AALWVPFCRK  HSIEPRAPES  YFA.......
OsCslF7         VSDDAGAEVT  RGAVVEAARF  AALWVPFCRK  HGVEPRNPEA  YFNGGEGGGG

HvCslF1         ......LKSH  PYMG.RAQDE  FVNDRRRVRK  EYDEFKARIN  SLEHDIKQRN
OsCslF5         ......LKSH  PYMG.RAQEE  FVNDRRRVRK  EYDDFKARIN  GLEHDIKQRS
HvCslF2         ......IEAP  LYTG.TAPEE  FKNDYSSVHK  EYDEFKERLD  SLSDAISKRS
OsCslF3         ......LEAP  SYTG.SAPEE  FKNDSRIVHL  EYDEFKVRLE  ALPETIRKRS
HvCslF5         ......LKGP  LYGG.TPHKE  FFQDYKHVRT  QYEEFKKNLD  MLPNTIHQRS
OsCslF1         ......MKTQ  AYKG.GVPGE  LMSDHRRVRR  EYEEFKVRID  SLSSTIRQRS
OsCslF2         ......MKTQ  AYKG.GVPGE  LMSDHRRVRR  EYEEFKVRID  SLSSTIRQRS
OsCslF4         ......MKTQ  AYRG.GVAGE  LMSDRRRVRR  EYEEFKVRID  SLFSTIRKRS
HvCslF4         ......MKTQ  PYVG.SMAGE  FMREHRRVRR  EYDEFKVRID  SLSTTIRQRS
HvCslF3         ......AKMR  GEYAGSAAKE  FLDDHRRMRA  AYEEFKARLD  GLSAVIEQRS
OsCslF9         ......AKAA  PYAGPALPEE  FFGDRRLVRR  EYEEFKARLD  ALFTDIPQRS
HvCslF6         ......LNTR  PYTG.NAPQD  FVNDRHMCR   EYDEFKERLD  ALFTLIPKRS
OsCslF8         ......VKSR  PYAG.SAPED  FLSDHRYMRR  EYDEFKVRLD  ALFTVIPKRS
OsCslF7         GGKARVVARG  SYKG.RAWPE  LVRDRRRVRR  EYEEMRLRID  ALQAADARR.

HvCslF1         DGYNAAIAHS  QGVPRPTWMA  DG.TQWEGTW  VDASENHRRG  DHAGIVLVLL
```

FIG 6C

```
OsCslF5    DSYNAAAGVK DGEPRATWMA DG.SQWEGTW IEQSENHRKG DHAGIVLVLL
HvCslF2    DAYNSMKTEE GD.AKATWMA NG.TQWPGSW IDTTEIHRKG HHAGIVKVVL
OsCslF3    DVYNSMKTDQ GA.PNATWMA NG.TQWPGTW IEPIENHRKG HHAGIVKVVL

HvCslF5    GTYSKTGTED ED.AKVTWMA DG.TQWPGTW LDPAEKHRAG HHAGIVKIVQ
OsCslF1    DVYN....AK HAGENATWMA DG.THWPGTW FEPADNHQRG KHAGIVQVLL
OsCslF2    DVYN....AK HAGENATWMA DG.THWPGTW FEPADNHQRG KHAGIVQVLL
OsCslF4    DAYNRAKDGK DDGENATWMA DG.THWPGTW FEPAENHRKG QHAGIVQVLL
HvCslF4    DAYNSS..NK GDGVRATWMA DG.TQWPGTW IEQVENHRRG QHAGIVQVIL
HvCslF3    EACNRAANEK EGCGNATWMA DGSTQWQGTW IKPAKGHRKG HHPAILQVML
OsCslF9    EASVGNANTK G..AKATLMA DG.TPWPGTW TEPAENHKKG QHAGIVKVML
HvCslF6    DVYNHAAGKE G..AKATWMA DG.TQWPGTW IDPAENHKKG QHAGIVKVLL
OsCslF8    DAYNQAHAEE G..VKATWMA DG.TEWPGTW IDPSENHKKG NHAGIVQVML
OsCslF7    .......... ....RRCGAA DD........ .......... .HAGVVQVLI

HvCslF1    NHPSHRRQTG PPASADNPLD LSGVDVRLPM LVYVSREKRP GHDHQKKAGA
OsCslF5    NHPSHARQLG PPASADNPLD FSGVDVRLPM LVYVAREKRP GCNHQKKAGA
HvCslF2    DHSIRGHNLG SQEST.HNLS FANTDERLPM LVYISRGKNP SYDHNKKAGA
OsCslF3    DHPIRGHNLS LKDSTGNNLN FNATDVRIPM LVYVSRGKNP NYDHNKKAGA
HvCslF5    SHPEHVVQPG VQESLDNPLS FDDVDVRLPM LVYVAREKSP GIEHNKKAGA
OsCslF1    NHPSCKPRLG LAASAENPVD FSGVDVRLPM LVYISREKRP GYNHQKKAGA
OsCslF2    NHPSCKPRLG LAASAENPVD FSGVDVRLPM LVYISREKRP GYNHQKKAGA
OsCslF4    NHPTSKPRFG VAASVDNPLD FSGVDVRLPM LVYISREKRP GYNHQKKAGA
HvCslF4    SHPSCKPQLG SPASTDNPLD FSNVDTRLPM LVYMSREKRP GYNHQKKAGA
HvCslF3    DQPSKDPELG MAASSDHPLD FSAVDVRLPM LVYIAREKRP GYDHQKKAGA
OsCslF9    SHPGEEPQLG MPASSGHPLD FSAVDVRLPI LVYIAREKRP GYDHQKKAGA
HvCslF6    KHPSYEPELG LGASTNSPLD FSAVDVRLPM LVYISREKSP SCDHQKKAGA
OsCslF8    NHPSNQPQLG LPASTDSPVD FSNVDVRLPM LVYIAREKRP GYDHQKKAGA
OsCslF7    DSAGSAPQLG .VADGSKLID LASVDVRLPA LVYVCREKRR GRAHHRKAGA

HvCslF1    MNALTRASAL LSNSPFILNL DCDHYINNSQ ALRAGICFMV GRDS......
OsCslF5    MNALTRASAV LSNSPFILNL DCDHYINNSQ ALRAGICFML GRDS......
HvCslF2    LNAQLRASAL LSNAQFIINF DCDHYINNSQ ALRAAMCFML DQRQ.....G
OsCslF3    LNAQLRASAL LSNAQFIINF DCDHYINNSQ AFRAAICFML DQRE.....G
HvCslF5    LNAELRISAL LSNAPFFINF DCDHYINNSE ALRAAVCFML DPRE.....G
OsCslF1    MNVMLRVSAL LSNAPFVINF DGDHYVNNSQ AFRAPMCFML DGRGR...GG
OsCslF2    MNVMLRVSAL LSNAPFVINF DGDHYVNNSQ AFRAPMCFML DGRGR...GG
OsCslF4    MNALLRVSAL LSNAPFIINF DCDHYVNNSQ AFRAPMCFML DRRG....GG
HvCslF4    MNVMLRVSAL LSNAPFVVNF DCDHYINNTQ ALRAPMCFML DPRD.....G
HvCslF3    MNVQLRVSAL LSNAPFIINF DGDHYINNSQ AFRAAMCFML DPRD.....G
OsCslF9    MNAQLRVSAL LSNAPFIFNF DGDHYINNSQ AFRAALCFML DCRH.....G
HvCslF6    MNVQLRVSAL LTNAPFIINF DGDHYVNNSK AFRAGICFML DRRE.....G
OsCslF8    MNVQLRVSAL LTNAPFIINF DGDHYVNNSK AFRAGICFML DRRE.....G
OsCslF7    MNALLRASAV LSNAPFILNL DCDHYVNNSQ ALRAGICFMI ERRGGGAEDA

HvCslF1    DTVAFVQFPQ RFEGVDPTDL YANHNRIFFD GTLRALDGMQ GPIYVGTGCL
OsCslF5    DTVAFVQFPQ RFEGVDPTDL YANHNRIFFD GTLRALDGLQ GPIYVGTGCL
HvCslF2    DNTAFVQFPQ RFDNVDPSDR YGNHNRVFFD GTMLALNGLQ GPSYLGTGCM
OsCslF3    DNTAFVQFPQ RFDNVDPKDR YGNHNRVFFD GTMLALNGLQ GPSYLGTGCM
HvCslF5    DNTGFVQFPQ RFDNVDPTDR YGNHNRVFFD GAMYGLNGQQ GPTYLGTGCM
OsCslF1    ENTAFVQFPQ RFDDVDPTDR YANHNRVFFD GTMLSLNGLQ GPSYLGTGTM
OsCslF2    ENTAFVQFPQ RFDDVDPTDR YANHNRVFFD GTMLSLNGLQ GPSYLGTGTM
OsCslF4    DDVAFVQFPQ RFDDVDPTDR YANHNRVFFD GTTLSLNGLQ GPSYLGTGTM
HvCslF4    QNTAFVQFPQ RFDDVDPTDR YANHNRVFFD GTMLSLNGLQ GPSYLGTGTM
HvCslF3    ADTAFVQFPQ RFDDVDPTDR YCNHNRMFFD ATLLGLNGIQ GPSFVGTGCM
OsCslF9    DDTAFVQFPQ RFDDVDPTDR YCNHNRVFFD ATLLGLNGVQ GPSYVGTGCM
```

FIG 6D

```
HvCslF6      DNTAFVQFPQ RFDDVDPTDR YCNHNRVFFD ATLLGSNGIQ GPSYVGTGCM
OsCslF8      DNTAFVQFPQ RFDDVDPTDR YCNHNRVFFD ATLLGLNGIQ GPSYVGTGCM
OsCslF7      GDVAFVQFPQ RFDGVDPGDR YANHNRVFFD CTELGLDGLQ GPIYVGTGCL

HvCslF1      FRRITVYGFD PPRINVGGPC FPRLAGLFAK TKYEKPGLEM TTAKAKAAPV
OsCslF5      FRRITLYGFE PPRINVGGPC FPRLGGMFAK NRYQKPGFEM TKPGAKPVAP
HvCslF2      FRRIALYGID PPDWRHDN.. ...IIVDDKK .......... ..........
OsCslF3      FRRLALYGID PPHWRQDN.. ...ITPEASK .......... ..........
HvCslF5      FRPLALYGID PPCWRAED.. ...IIVDSNR .......... ..........
OsCslF1      FRRVALYGVE PPRWGAAAS. QIKAMDIANK .......... ..........
OsCslF2      FRRVALYGVE PPRWGAAAS. QIKAMDIANK .......... ..........
OsCslF4      FRRAALYGLE PPRWGAAGS. QIKAMDNANK .......... ..........
HvCslF4      FRRVTLYGME PPRYRAEN.. .IKLVGKTYE .......... ..........
HvCslF3      FRRVALYSAD PPRWRSDDAK EAKASHRPNM .......... ..........
OsCslF9      FRRVALYGAD PPRWRPEDD. DAKALGCPGR .......... ..........
HvCslF6      FRRVALYGVD PPRWRPDDV. ..KIVDSSSK .......... ..........
OsCslF8      FRRVALYGVD PPRWRPDDG. ..NIVDSSKK .......... ..........
OsCslF7      FRRVALYGVD PPRWRSPGG. ...GVAADPAK .......... ..........

HvCslF1      P.....AKGK HGFLPLPKKT YGKSDAFVDT IPRASHPSPY AAAAEG.IVA
OsCslF5      PPAATVAKGK HGFLPMPKKA YGKSDAFADT IPRASHPSPY AAEAA..VAA
HvCslF2      .......... .......... FGSSIPFLDS VSKAINQER. STIPP...PI
OsCslF3      .......... .......... FGNSILLLES VLEALNQDR. FATPS...PV
HvCslF5      .......... .......... FGNSLPFLNS VLAAIKQEEG VTLPP...PL
OsCslF1      .......... .......... FGSSTSFVGT MLDGANQERS .ITPL..AVL
OsCslF2      .......... .......... FGSSTSFVGT MLDGANQERS .ITPL..AVL
OsCslF4      .......... .......... FGASSTLVSS MLDGANQERS .ITPP..VAI
HvCslF4      .......... .......... FGSSTSFINS MPDGAIQERS .ITP...VLV
HvCslF3      .......... .......... FGKSTSFINS MPAAANQERS VPSPA.....
OsCslF9      .......... .......... YGNSMPFINT IPAAASQERS IASPAAASLD
HvCslF6      .......... .......... FGSSESFISS ILPAADQERS IMSPP...AL
OsCslF8      .......... .......... FGNLDSFISS IPIAANQERS IISPP...AL
OsCslF7      .......... .......... FGESAPFLAS VRAEQSHSRD
             ..........

HvCslF1      DEATIVEAVN VTAAAFEKKT GWGKEIGWVY DTVTEDVVTG YRMHIKGWRS
OsCslF5      DEAAIAEAVM VTAAAYEKKT GWGSDIGWVY GTVTEDVVTG YRMHIKGWRS
HvCslF2      SETLVAEMER VVSASHDKAT GWGKGVGYIY DIATEDIVTG FRIHGQGWRS
OsCslF3      NDIFVNELEM VVSASFDKET DWGKGVGYIY DIATEDIVTG FRIHGQGWRS
HvCslF5      DDSFLEEMTK VVSCSYDDST DWGRGIGYIY NMATEDIVTG FRIHGQGWCS
OsCslF1      DESVAGDLAA LTACAYEDGT SWGRDVGWVY NIATEDVVTG FRMHRQGWRS
OsCslF2      DESVAGDLAA LTACAYEDGT SWGRDVGWVY NIATEDVVTG FRMHRQGWRS
OsCslF4      DGSVARDLAA VTACGYDLGT SWGRDAGWVY DIATEDVATG FRMHQQGWRS
HvCslF4      DEALSNDLAT LMTCAYEDGT SWGRDVGWVY NIATEDVVTG FRMHRQGWRS
HvCslF3      .TVGEAELAD AMTCAYEDGT EWGNDVGWVY NIATEDVVTG FRLHRTGWRS
OsCslF9      ETAAMAEVEE VMTCAYEDGT EWGDGVGWVY DIATEDVVTG FRLHRKGWRS
HvCslF6      EESVMADLAH VMTCAYEDGT EWGREVGWVY NIATEDVVTG FRLHRNGWRS
OsCslF8      EESILQELSD AMACAYEDGT DWGKDVGWVY NIATEDVVTG FRLHRTGWRS
OsCslF7      DGDAIAEASA LVSCAYEDGT AWGRDVGWVY GTVTEDVATG FCMHRRGWRS

HvCslF1      RYCSIYPHAF IGTAPINLTE RLFQVLRWST GSLEIFFSKN NPLFGS..TY
OsCslF5      RYCSIYPHAF IGTAPINLTE RLFQVLRWST GSLEIFFSRN NPLFGS..TF
HvCslF2      MYCTMERDAF CGIAPINLTE RLHQIVRWSG GSLEMFFSLN NPLIGG..RR
OsCslF3      MYCTMEHDAF CGTAPINLTE RLHQIVRWSG GSLEMFFSHN NPLIGG..RR
HvCslF5      MYVTMEREAF RGTAPINLTE RLRQIVRWSG GSLEMFFSHI SPLFAG..RR
```

FIG 6E

```
OsCslF1    VYASVEPAAF RGTAPINLTE RLYQILRWSG GSLEMFFSHS NALLAG..RR
OsCslF2    VYASVEPAAF RGTAPINLTE RLYQILRWSG GSLEMFFSHS NALLAG..RR
OsCslF4    VYTSMEPAAF RGTAPINLTE RLYQILRWSG GSLEMFFSHS NALLAG..RR
HvCslF4    MYCSMEPAAF RGTAPINLTE RLYQVLRWSG GSLEMFFSHS NALMAG..RR
HvCslF3    TYCAMEPDAF RGTAPINLTE RLYQILRWSG GSLEMFFSRF CPLLAG..RR

OsCslF9    MYCAMEPDAF RGTAPINLTE RLYQILRWSG GSLEMFFSRN CPLLAG..CR
HvCslF6    MYCRMEPDAF AGTAPINLTE RLYQILRWSG GSLEMFFSHN CPLLAG..RR
OsCslF8    MYCRMEPDAF RGTAPINLTE RLYQILRWSG GSLEMFFSHN CPLLAG..RR
OsCslF7    AYYAAAPDAF RGTAPINLAD RLHQVLRWAA GSLEIFFSRN NALLAGGRRR

HvCslF1    LHPLQRVAYI NITTYPFTAI FLIFYTTVPA LSF.VTGHFI VQRPTTMFYV
OsCslF5    LHPLQRVAYI NITTYPFTAL FLIFYTTVPA LSF.VTGHFI VQRPTTMFYV
HvCslF2    IHALQRVSYL NMTVYPVTSL FILLYALSPV MWL.IPDEVY IQRPFTKYVV
OsCslF3    LQPLQRVSYL NMTIYPVTSL FILLYAISPV MWL.IPDEVY IQRPFTRYVV
HvCslF5    LSLVQRLSYI NFTIYPLTSL FILMYAFCPV MWL.LPTEIL IQRPYTRYIV
OsCslF1    LHPLQRVAYL NMSTYPIVTV FIFFYNLFPV MWL.ISEQYY IQRPFGEYLL
OsCslF2    LHPLQRVAYL NMSTYPIVTV FIFFYNLFPV MWL.ISEQYY IQRPFGEYLL
OsCslF4    LHPLQRIAYL NMSTYPIVTV FIFFYNLFPV MWL.ISEQYY IQQPFGEYLL
HvCslF4    IHPLQRVAYL NMSTYPIVTV FILAYNLFPV MWL.FSEQFY IQRPFGTYIM
HvCslF3    LHPMQRVAYI NMTTYPVSTF FILMYYFYPV MWL.FQGEFY IQRPFQTFAL
OsCslF9    LRPMQRVAYA NMTAYPVSAL FMVVYDLLPV IWLSHHGEFH IQKPFSTYVA
HvCslF6    LHPMQRIAYA NMTAYPVSSV FLVFYLLFPV IWI.FRGQFY IQKPFPTYVL
OsCslF8    LNFMQRIAYI NMTGYPVTSV FLLFYLLFPV IWI.FRGIFY IQKPFPTYVL
OsCslF7    LHPLQRAAYL NTTVYPFTSL FLMAYCLFPA IPLIAGGGGW NAAPTPTYVA

HvCslF1    YLGIVLSTLL VIAVLEVKWA GVTVFEWFRN GQFWMTASCS AYLAAVCQVL
OsCslF5    YLAIVLGTLL ILAVLEVKWA GVTVFEWFRN GQFWMTASCS AYLAAVLQVV
HvCslF2    FLLVIILMIH IIGWLEIKWA GVTWLDYWRN EQFFMIGSTS AYPAAVLHMV
OsCslF3    YLLVIILMIH MIGWLEIKWA GITWLDYWRN EQFFMIGSTS AYPTAVLHMV
HvCslF5    YLIIVVAMIH VIGMFEIMWA GITWLDWWRN EQFFMIGSVT AYPTAVLHMV
OsCslF1    YLVAVIAMIH VIGMFEVKWA GITLLDWCRN EQFYMIGSTG VYPTAVLYMA
OsCslF2    YLVAVIAMIH VIGMFEVKWA GITLLDWCRN EQFYMIGSTG VYPTAVLYMA
OsCslF4    YLVAIIAMIH VIGMFEVKWS GITVLDWCRN EQFYMIGSTG VYPTAVLYMA
HvCslF4    YLVGVIAMIH VIGMFEVKWA GITLLDWCRN EQFYMIGATG VYPTAVLYMA
HvCslF3    FVVVVIATVE LIGMVEIRWA GLTLLDWVRN EQFYIIGTTG VYPMAMLHIL
OsCslF9    YLVAVIAMIE VIGLVEIKWA EQFYMIGATG VYLAAVLHIV
HvCslF6    YLVIVIALTE LIGMVEIKWA GLTLLDWIRN EQFYIIGATA VYPTAVFHIV
OsCslF8    YLVIVIFMSE MIGMVEIKWA GLTLLDWIRN EQFYIIGATA VYPLAVLHIV
OsCslF7    FLAALMVTLA AVAVLETRWS GIALGEWWRN EQFWMVSATS AYLAAVAQVA

HvCslF1    TK.VIFRRDI SFKLTSKLPS GDE.....KK DPYADLYVVR WTPLMITPII
OsCslF5    TK.VVFRRDI SFKLTSKLPA GDE.....KK DPYADLYVVR WTWLMITPII
HvCslF2    VN.LLTKKGI HFRVTSKQTT AD......TN DKFADLYDMR WVPMLIPTTV
OsCslF3    VN.LLTKKGI HFRVTSKQTT AD......TN DKFADLYEMR WVPMLIPTMV
HvCslF5    VN.ILTKKGI HFRVTTKQPV AD......TD DKYAEMYEVH WVPMMVPAVV
OsCslF1    LK.LVTGKGI YFRLTSKQTA AS......SG DKFADLYTVR WVPLLIPTIV
OsCslF2    LK.LVTGKGI YFRLTSKQTT AS......SG DKFADLYTVR WVPLLIPTIV
OsCslF4    LK.LFTGKGI HFRLTSKQTT AS......SG DKFADLYTVR WVPLLIPTIV
HvCslF4    LK.LVTGKGI YFRLTSKQTD AC......SN DKFADLYTVR WVPLLFPTVA
HvCslF3    LR.SLGIKGV SFKLTAKKLT GG......AR ERLAELYDVQ WVPLLVPTVV
OsCslF9    LKRLLGLKGV RFKLTAKQLA GG......AR ERFAELYDVH WSPLLAPTVV
HvCslF6    LK.LFGLKGV SFKLTAKQVA SS......TS DKFAELYAVQ WAPMLIPTMV
OsCslF8    LK.CFGLKGV SFKLTAKQVA SS......TS EKFAELYDVQ WAPLLFPTIV
OsCslF7    LK.VATGKEI SFKLTSKHLA SSATPVAGKD RQYAELYAVR WTALMAPTAA
```

FIG 6F

```
HvCslF1      IIFVNIIGSA VAFAKVLDGE .....WTHWL KVAGGVFFNF WVLFHLYPFA
OsCslF5      IILVNIIGSA VAFAKVLDGE .....WTHWL KVAGGVFFNF WVLFHLYPFA
HvCslF2      VLIANVGAIG VAMGKTIVYM G.AWTIAQKT HAALGLLFNV WIMVLLYPFA
OsCslF3      VLVANIGAIG VAIGKTAVYM G.VWTIAQKR HAAMGLLFNM WVMFLLYPFA
HvCslF5      VLFSNILAIG VAIGKSVLYM G.TWSVAQKR HGALGLLFNL WIMVLLYPFA

OsCslF1      IMVVNVAAVG VAVGKAAAWG ...PLTEPGW LAVLGMVFNV WILVLLYPFA
OsCslF2      IIVVNVAAVG VAVGKAAAWG ...PLTEPGW LAVLGMVFNV WILVLLYPFA
OsCslF4      VLAVNVGAVG VAVGKAAAWG ...LLTEQGR FAVLGMVFNV WILALLYPFA
HvCslF4      VLIVNVAAVG AAIGKAAAWG ...FFTDQAR HVLLGMVFNV WILVLLYPFA
HvCslF3      VMAVNVAAIG AAAGKAIVGR ...WSAAQVA GAASGLVFNV WMLLLLYPFA
OsCslF9      VMAVNVTAIG AAAGKAVVGG ...WTPAQVA GASAGLVFNV WVLVLLYPFA
HvCslF6      VIAVNVCAIG ASIGKAVVGG ...WSLMQMA DAGLGLVFNA WILVLIYPFA
OsCslF8      VIAVNICAIG AAIGKALFGG ...WSLMQMG DASLGLVFNV WILLLIYPFA
OsCslF7      ALAVNVASMA AAGGGGRWWW WDAPSAAAAA AAALPVAFNV WVVVHLYPFA

HvCslF1      KGILGKHGKT P.VVVLVWWA FTFVITAVLY INIPHMHTSG ..GKHTTVHG
OsCslF5      KGILGKHGKT P.VVVLVWWA FTFVITAVLY INIPHIHGPG RHGAASPSHG
HvCslF2      LAIMGRWAKR P.VILVVLLP VAFTIVCLVY VSVHILLLS. ..........
OsCslF3      LAIMGRWAKR S.IILVVLLP IIFVIVALVY VATHILLAN. ..........
HvCslF5      LAIIGRWAKR T.GILFILLP IAFLATALMY IGIHTFLLH. ..........
OsCslF1      LGVMGQWGKR P.AVLFVAMA MAVAAVAAMY VAFGAPYQAE LS.GVAASLG
OsCslF2      LGVMGQWGKR P.AVLFVAMA MAVAAVAAMY VAFGAPYQAE LS.GGAASLG
OsCslF4      LGIMGQRGKR P.AVLFVATV MAVAAVAIMY AAFGAPYQAG LS.GVAASLG
HvCslF4      LGIMGKWGKR P.IILFVMLI MAIGAVGLVY VAFHDPYPTD FS.EVAASLG
HvCslF3      LGIMGHWSKR P.YILFLVLV TAVAATAS.. ..VYVALAG. ....SLLYLH
OsCslF9      LGIMGRWSKR P.CALFALLV AACAAVAAGF VAVHAVLAAG SAAPSWLGWS
HvCslF6      LGMIGRWSKR P.YILFILFV IAFILIALVD IAIQAMRSG. ...IVRFHFK
OsCslF8      LGIMGRWSKR P.YILFVLIV ISFVIIALAD IAIQAMRSG. ...SVRLHFR
OsCslF7      LGLMGRRSKA VRPILFLFAV VAYLAVRFLC LLLQFHTA.. ..........

HvCslF1      HHGKKLVDTG ..LYGWLH
OsCslF5      HHSAHGTKKY DFTYAWP.
HvCslF2      .....FLPF. ........
OsCslF3      .....IIPF. ........
HvCslF5      .....FFPSM LV......
OsCslF1      KVAAASLTGP SG......
OsCslF2      K.AAASLTGP SG......
OsCslF4      K..AASLTGP SG......
HvCslF4      E...ASLTGP SG......
HvCslF3      SGIKLV.... ........
OsCslF9      RGATAILPSS WRLKRGF.
HvCslF6      SSGGATFPTS WGL.....
OsCslF8      RSGGANFPTS WGF.....
OsCslF7      .......... ........
```

| | OsCslF1 | | OsCslF2 | | OsCslF3 | | OsCslF4 | | OsCslF5 | | OsCslF7 | | OsCslF8 | | OsCslF9 | |
|---|---|---|---|---|---|---|---|---|---|---|---|---|---|---|---|---|
| OsCslF1 | 100% | | | | | | | | | | | | | | | |
| OsCslF2 | 97 | | 100% | | | | | | | | | | | | | |
| | 96 | 96 | | | | | | | | | | | | | | |
| OsCslF3 | 61 | | 62 | | 100% | | | | | | | | | | | |
| | 59 | 74 | 58 | 73 | | | | | | | | | | | | |
| OsCslF4 | 88 | | 90 | | 62 | | 100% | | | | | | | | DNA Iden. | |
| | 86 | 90 | 85 | 89 | 61 | 74 | | | | | | | | | Pr Id | Pr Sim |
| OsCslF5 | 62 | | 64 | | 55 | | 65 | | 100% | | | | | | | |
| | 51 | 64 | 51 | 63 | 47 | 61 | 50 | 61 | | | | | | | | |
| OsCslF7 | 63 | | 63 | | 54 | | 63 | | 57 | | 100% | | | | | |
| | 47 | 60 | 47 | 60 | 42 | 56 | 46 | 59 | 45 | 55 | | | | | | |
| OsCslF8 | 74 | | 73 | | 61 | | 74 | | 64 | | 64 | | 100% | | | |
| | 61 | 74 | 61 | 75 | 57 | 71 | 60 | 71 | 48 | 61 | 47 | 57 | | | | |
| OsCslF9 | 64 | | 65 | | 66 | | 65 | | 57 | | 55 | | 68 | | 100% | |
| | 61 | 76 | 61 | 76 | 58 | 74 | 60 | 74 | 48 | 62 | 45 | 59 | 66 | 77 | | |
| HvCslF1 | 62 | | 64 | | 55 | | 64 | | 84 | | 58 | | 58 | | 59 | |
| | 50 | 64 | 49 | 63 | 49 | 64 | 48 | 61 | 85 | 90 | 45 | 56 | 49 | 66 | 50 | 65 |
| HvCslF2 | 63 | | 62 | | 79 | | 63 | | 55 | | 55 | | 66 | | 59 | |
| | 58 | 74 | 57 | 73 | 80 | 87 | 58 | 71 | 48 | 64 | 42 | 57 | 57 | 75 | 58 | 72 |
| HvCslF3 | 71 | | 70 | | 61 | | 71 | | 62 | | 63 | | 67 | | 73 | |
| | 60 | 74 | 60 | 75 | 54 | 70 | 60 | 74 | 46 | 62 | 45 | 58 | 69 | 82 | 70 | 79 |
| HvCslF4 | 79 | | 79 | | 64 | | 79 | | 62 | | 61 | | 66 | | 67 | |
| | 78 | 86 | 77 | 85 | 60 | 75 | 75 | 83 | 49 | 63 | 46 | 59 | 62 | 79 | 62 | 75 |
| HvCslF5 | 59 | | 60 | | 69 | | 61 | | 54 | | 54 | | 63 | | 55 | |
| | 54 | 70 | 53 | 70 | 63 | 75 | 53 | 68 | 44 | 60 | 40 | 54 | 54 | 72 | 54 | 70 |
| HvCslF6 | 65 | | 67 | | 65 | | 67 | | 58 | | 56 | | 82 | | 64 | |
| | 62 | 78 | 60 | 75 | 57 | 74 | 61 | 77 | 47 | 64 | 44 | 59 | 81 | 88 | 68 | 78 |

| | HvCslF1 | | HvCslF2 | | HvCslF3 | | HvCslF4 | | HvCslF5 | | HvCslF6 | |
|---|---|---|---|---|---|---|---|---|---|---|---|---|
| HvCslF1 | 100% | | | | | | | | | | | |
| HvCslF2 | 55 | | 100% | | | | | | | | | |
| | 48 | 64 | | | | | | | | | | |
| HvCslF3 | 61 | | 63 | | 100% | | | | | | | |
| | 45 | 63 | 56 | 71 | | | | | | | | |
| HvCslF4 | 61 | | 65 | | 69 | | 100% | | | | | |
| | 49 | 64 | 60 | 74 | 61 | 76 | | | | | | |
| HvCslF5 | 54 | | 69 | | 60 | | 62 | | 100% | | | |
| | 44 | 60 | 64 | 78 | 52 | 69 | 55 | 72 | | | | |
| HvCslF6 | 58 | | 65 | | 67 | | 67 | | 63 | | 100% | |
| | 47 | 66 | 58 | 76 | 68 | 81 | 61 | 79 | 54 | 71 | | |

FIG 8

POLYSACCHARIDE SYNTHASES

CROSS-REFERENCE TO RELATED APPLICATIONS

This application is a continuation of U.S. application Ser. No. 14/465,679, filed Aug. 21, 2014, which is a Divisional of U.S. application Ser. No. 11/997,667, filed Jul. 22, 2008, now abandoned, as the US National Stage (371) of International Application No. PCT/AU2006/001107, filed Aug. 3, 2006, which claims priority to Australia Application No. 2005904155, filed Aug. 3, 2005; each of which is hereby incorporated by reference in its entirety.

REFERENCE TO SUBMISSION OF A SEQUENCE LISTING

The Sequence Listing written in file SEQTXT_91762-917467.txt, created on Jun. 9, 2017, 186,111 bytes, machine format IBM-PC, MS-Windows operating system, is hereby incorporated by reference in its entirety for all purposes.

FIELD OF THE INVENTION

The present invention relates generally to polysaccharide synthases. More particularly, the present invention relates to (1,3;1,4)-β-D-glucan synthases.

BACKGROUND OF THE INVENTION

The various tissues of cereal grains have diverse functions during grain development, dormancy and after germination.

For example, the pericarp and seed coat tissues are concerned with the protection of the seed during development and during dormancy. However, by grain maturity, these outer grain tissues have died and the tissue residues consist almost entirely of cell wall residues. The nuclear tissue between the seed coat and the aleurone surface is involved in transfer of nutrients to the developing grain, however, at maturity, this tissue has also collapsed to leave cell wall remnants. The thin walled cells of the starchy endosperm of mature grain are dead, but are packed with starch and storage protein. In contrast, the thick-walled, nucleated, aleurone cells are alive at grain maturity, and are packed with protein bodies and lipid droplets. At the interface of the starchy endosperm lies the scutellum, which functions in delivering nutrients to the developing endosperm and, during germination, transfers digestion products of the endosperm reserves to the developing embryo.

The different structure and function of each tissue type in the grain are determined, at least in part, by the cell wall composition of each of these cell types.

Non-cellulosic polysaccharides are key components in the cell walls of cereal grain tissues and include, for example, (1,3;1,4)-β-D-glucans, heteroxylans (mainly arabinoxylans), glucomannans, xyloglucans, pectic polysaccharides and callose. These non-cellulosic polysaccharides usually constitute less than 10% of the overall weight of the grain, but nevertheless are key determinants of grain quality.

Although the precise physical relationships between individual non-cellulosic polysaccharides and other wall components have not been described, it is generally considered that in the wall, microfibrils of cellulose are embedded in a matrix phase of non-cellulosic polysaccharides and protein. Wall integrity is maintained predominantly through extensive non-covalent interactions, especially hydrogen bonding, between the matrix phase and microfibrillar constituents. In the walls of some grain tissues covalent associations between heteroxylans, lignin and proteins are present. The extent of covalent associations between components also varies with the wall type and genotype.

Non-cellulosic polysaccharides, especially heteroxylans and (1,3;1,4)-β-D-glucans, constitute a relatively high proportion of the walls of the aleurone and starchy endosperm, and probably also of the scutellum. In these tissues, cellulose contents are correspondingly lower. The generally low cellulose content of these walls, together with the fact that they contain no lignin, are thought to be related to a limited requirement for structural rigidity of walls in central regions of the grain, and to a requirement to rapidly depolymerize wall components following germination of the grain.

In contrast, in the cell walls of the pericarp-seed coat, which provides a protective coat for the embryo and endosperm and which is not mobilized during germination, cellulose and lignin contents are much higher and the concentrations of non-cellulosic polysaccharides are correspondingly lower.

(1,3;1,4)-β-D-glucans, also referred to as mixed-linkage or cereal β-glucans, are non-cellulosic polysaccharides which naturally occur in plants of the monocotyledon family Poaceae, to which the cereals and grasses belong, and in related families of the order Poales.

These non-cellulosic polysaccharides are important constituents of the walls of the starchy endosperm and aleurone cells of most cereal grains, where they can account for up to 70%-90% by weight of the walls.

Barley, oat and rye grains are rich sources of (1,3;1,4)-β-D-glucan, whereas wheat, rice and maize have lower concentrations of this polysaccharide. The (1,3;1,4)-β-D-glucans are also relatively minor components of walls in vegetative tissues of cereals and grasses. Although present as a relatively minor component in vegetative tissues (1,3;1,4)-β-D-glucan) is still important in terms of, for example, the digestibility of vegetative tissue by animals and in the use of crop residues for bioethanol production.

(1,3;1,4)-β-D-glucans are important in large-scale food processing activities that include brewing and stockfeed manufacture. Moreover, the non-starchy polysaccharides of cereals, such as (1,3;1,4)-β-D-glucans, have attracted renewed interest in recent years because of their potentially beneficial effects in human nutrition.

However, despite this interest, major gaps remain in our knowledge of the genes and enzymes that control non-cellulosic polysaccharide biosynthesis, including (1,3;1,4)-β-D-glucan biosynthesis, in cereal grain.

(1,3;1,4)-β-D-glucan concentrations in grain are thought to be influenced by both genotype and environment. For example, the concentration of (1,3;1,4)-β-D-glucan in cereal grains depends on the genotype, the position of the grain on the spike and environmental factors such as planting location, climatic conditions during development and soil nitrogen.

However, the genes that contribute to (1,3;1,4)-β-D-glucan content in grain have not yet been identified.

The identification of genes encoding (1,3;1,4)-β-D-glucan synthases through traditional biochemical approaches has been seriously hampered by an inability to purify the enzymes to homogeneity. (1,3;1,4)-β-D-glucan synthases are membrane-bound and, therefore, are difficult to solubilise in an active form. In addition, (1,3;1,4)-β-D-glucan synthases rapidly lose activity following disruption of cells, and are likely to be present at very low abundance in the cell. Despite numerous attempts, purification of (1,3;1,4)-β-D- glucan synthases to homogeneity has not been achieved and, as a result, there are no reports of amino acid sequences obtained from the enzymes themselves. The inability to obtain even partial amino acid sequences from the purified (1,3;1,4)-β-D-glucan synthase enzyme has also prevented the identification and isolation of genes encoding (1,3;1,4)-β-D-glucan synthases.

However, identification of the genes encoding (1,3;1,4)-β-D-glucan synthases would be desirable, as this would facilitate modulation of the level of (1,3;1,4)-β-D-glucan produced by a cell, and therefore, allow the qualities of grain or vegetative tissue to be altered. Therefore, in order to enable the modulation of the level of (1,3;1,4)-β-D-glucan in a cell and associated changes in grain or vegetative tissue quality, there is a clear need to identify genes that encode (1,3;1,4)-β-D-glucan synthases.

Reference to any prior art in this specification is not, and should not be taken as, an acknowledgment or any form of suggestion that this prior art forms part of the common general knowledge in any country.

SUMMARY OF THE INVENTION

The present invention is predicated, in part, on the identification of genes which encode the biosynthetic enzyme for (1,3;1,4)-β-D-glucans, referred to herein as "(1,3;1,4)-β-D-glucan synthases".

In accordance with the present invention, it has been revealed that (1,3;1,4)-β-D-glucan synthases are encoded by members of the CslF gene family.

As a result of the identification of the nucleotide sequences, and corresponding amino acid sequences that encode (1,3;1,4)-β-D-glucan synthases, the present invention provides, inter alia, methods and compositions for influencing the level and/or activity of (1,3;1,4)-β-D-glucan synthase in a cell and thereby the level of (1,3;1,4)-β-D-glucan produced by the cell.

Therefore, in a first aspect, the present invention provides a method for influencing the level of (1,3;1,4)-β-D-glucan produced by a cell, the method comprising modulating the level and/or activity of a (1,3;1,4)-β-D-glucan synthase in the cell.

In one particularly preferred embodiment, the cell is a plant cell, more preferably a monocot plant cell and most preferably a cereal crop plant cell.

In a second aspect, the present invention provides a method for modulating the level and/or activity of a (1,3;1,4)-β-D-glucan synthase in a cell, the method comprising modulating the expression of a (1,3;1,4)-β-D-glucan synthase encoding nucleic acid in the cell.

In a third aspect, the present invention provides a method for modulating the level and/or activity of a (1,3;1,4)-β-D-glucan synthase in a cell, the method comprising modulating the expression of a CslF gene or functional homolog thereof in the cell.

In a fourth aspect, the present invention provides a method for producing (1,3;1,4)-β-D-glucan, the method comprising expressing a (1,3;1,4)-β-D-glucan synthase encoding nucleic acid in a cell.

In a fifth aspect, the present invention also provides (1,3;1,4)-β-D-glucan produced according to the method of the fourth aspect of the invention.

In a sixth aspect, the present invention provides a cell comprising any one or more of:
(i) a modulated level of (1,3;1,4)-β-D-glucan relative to a wild type cell of the same taxon;
(ii) a modulated level and/or activity of (1,3;1,4)-β-D-glucan synthase relative to a wild type cell of the same taxon;
(iii) modulated expression of a (1,3;1,4)-β-D-glucan synthase encoding nucleic acid relative to a wild type cell of the same taxon.

Furthermore, in a seventh aspect, the present invention provides a multicellular structure comprising one or more cells according to the sixth aspect of the invention.

As mentioned above, in one preferred embodiment of the invention, the cell is a plant cell and as such, the present invention includes a whole plant, plant tissue, plant organ, plant part, plant reproductive material or cultured plant tissue, comprising one or more plant cells according to the sixth aspect of the invention. In a more preferred embodiment, the present invention provides a cereal plant comprising one or more cells according to the sixth aspect of the invention. In a particularly preferred embodiment, the present invention provides cereal grain comprising one or more cells according to the sixth aspect of the invention.

Therefore, in an eighth aspect, the present invention provides a cereal grain comprising an altered level of (1,3;1,4)-β-D-glucan, wherein the grain comprises one or more cells comprising an altered level and/or activity of (1,3;1,4)-β-D-glucan synthase and/or altered expression of a (1,3;1,4)-β-D-glucan synthase encoding nucleic acid molecule.

In a ninth aspect, the present invention also provides flour comprising:
(i) flour produced by the milling of the grain of the eighth aspect of the invention; and
(ii) optionally, flour produced by the milling of one or more other grains.

As set out above, the present invention is predicated, in part, on the identification and isolation of nucleotide and amino acid sequences that encode (1,3;1,4)-β-D-glucan synthases.

Therefore, in a tenth aspect, the present invention provides an isolated nucleic acid molecule that encodes a (1,3;1,4)-β-D-glucan synthase.

In an eleventh aspect, the present invention also provides an isolated nucleic acid molecule comprising one or more of:
(i) the nucleotide sequence set forth in any of SEQ ID NO: 1, SEQ ID NO: 3, SEQ ID NO: 5, SEQ ID NO: 7, SEQ ID NO: 9 and SEQ ID NO: 11;
(ii) a nucleotide sequence which is at least 50% identical to the nucleotide sequence set forth in any of SEQ ID NO: 1, SEQ ID NO: 3, SEQ ID NO: 5, SEQ ID NO: 7, SEQ ID NO: 9 and SEQ ID NO: 11;
(iii) a nucleotide sequence which hybridises to a nucleic acid molecule comprising the nucleotide sequence set forth in any of SEQ ID NO: 1, SEQ ID NO: 3, SEQ ID NO: 5, SEQ ID NO: 7, SEQ ID NO: 9 and SEQ ID NO: 11 under low stringency, more preferably medium stringency and most preferably high stringency conditions;
(iv) a nucleotide sequence which encodes the amino acid sequence set forth in any of SEQ ID NO: 2, SEQ ID NO: 4, SEQ ID NO: 6, SEQ ID NO: 8, SEQ ID NO: 10 and SEQ ID NO: 12.
(v) a nucleotide sequence which is the complement of any one of (i) to (iv);
(vi) a nucleotide sequence which is the reverse complement of any one of (i) to (iv);
(vii) a fragment of any one of (i) to (vi).

In a twelfth aspect, the present invention provides a genetic construct or vector comprising an isolated nucleic acid molecule of the eleventh aspect of the invention.

In a thirteenth aspect, the present invention extends to a cell comprising the isolated nucleic acid molecule of the tenth or eleventh aspects of the invention or genetic construct of the twelfth aspect of the invention.

In a fourteenth aspect, the present invention provides a multicellular structure which comprises one or more of the cells of the thirteenth aspect of the invention.

As set out above, the present invention also provides amino acid sequences for (1,3;1,4)-β-D-glucan synthases.

Accordingly, in a fifteenth aspect, the present invention provides an isolated polypeptide comprising an amino acid sequence encoding a (1,3;1,4)-β-D-glucan synthase protein.

In a sixteenth aspect, the present invention provides an isolated polypeptide comprising one or more of:

(i) the amino acid sequence set forth in any of SEQ ID NO: 2, SEQ ID NO: 4, SEQ ID NO: 6, SEQ ID NO: 8, SEQ ID NO: 10 and SEQ ID NO: 12;

(ii) an amino acid sequence comprising at least 50% identity to the amino acid sequence set forth in any of SEQ ID NO: 2, SEQ ID NO: 4, SEQ ID NO: 6, SEQ ID NO: 8, SEQ ID NO: 10 and SEQ ID NO: 12;

(iii) an amino acid sequence encoded by the nucleotide sequence set forth in any of SEQ ID NO: 1, SEQ ID NO: 3, SEQ ID NO: 5, SEQ ID NO: 7, SEQ ID NO: 9 and SEQ ID NO: 11; and/or (iv) a fragment of any one of (i), (ii) or (iii).

In a preferred embodiment, the isolated polypeptide of the present invention comprises an amino acid sequence defining a "(1,3;1,4)-β-D-glucan synthase" as hereinbefore defined.

As set out above, the sixteenth aspect of the invention also provides fragments of isolated polypeptides including (1,3;1,4)-β-D-glucan synthase epitopes.

The isolated polypeptides and (1,3;1,4)-β-D-glucan synthase epitope-bearing polypeptides of the sixteenth aspect of the invention are useful, for example, in the generation of antibodies that bind to the isolated (1,3;1,4)-β-D-glucan synthase proteins Accordingly, in a seventeenth aspect, the present invention provides an antibody or an epitope binding fragment thereof, raised against an isolated (1,3;1,4)-β-D-glucan synthase protein as hereinbefore defined or an epitope thereof.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). The SEQ ID NOs: correspond numerically to the sequence identifiers <400 >1 (SEQ ID NO: 1), <400 >2 (SEQ ID NO: 2), etc. A summary of the sequence identifiers is provided in Table 1. A sequence listing is provided at the end of the specification.

TABLE 1

Summary of Sequence Identifiers

| Sequence Identifier | Sequence |
| --- | --- |
| SEQ ID NO: 1 | HvCsIF1 coding region nucleotide sequence |
| SEQ ID NO: 2 | HvCsIF1 amino acid sequence |

TABLE 1-continued

Summary of Sequence Identifiers

| Sequence Identifier | Sequence |
| --- | --- |
| SEQ ID NO: 3 | HvCsIF2 coding region nucleotide sequence |
| SEQ ID NO: 4 | HvCsIF2 amino acid sequence |
| SEQ ID NO: 5 | HvCsIF3 coding region nucleotide sequence |
| SEQ ID NO: 6 | HvCsIF3 amino acid sequence |
| SEQ ID NO: 7 | HvCsIF4 coding region nucleotide sequence |
| SEQ ID NO: 8 | HvCsIF4 amino acid sequence |
| SEQ ID NO: 9 | HvCsIF5 coding region nucleotide sequence |
| SEQ ID NO: 10 | HvCsIF5 amino acid sequence |
| SEQ ID NO: 11 | HvCsIF6 coding region nucleotide sequence |
| SEQ ID NO: 12 | HvCsIF6 amino acid sequence |
| SEQ ID NO: 13 | HvCsIF1 genomic nucleotide sequence |
| SEQ ID NO: 14 | HvCsIF2 genomic nucleotide sequence |
| SEQ ID NO: 15 | HvCsIF3 genomic nucleotide sequence |
| SEQ ID NO: 16 | HvCsIF4 genomic nucleotide sequence |
| SEQ ID NO: 17 | HvCsIF5 genomic nucleotide sequence |
| SEQ ID NO: 18 | HvCsIF6 genomic nucleotide sequence |
| SEQ ID NO: 19 | OsCsIF1 nucleotide sequence |
| SEQ ID NO: 20 | OsCsIF1 amino acid sequence |
| SEQ ID NO: 21 | OsCsIF2 nucleotide sequence |
| SEQ ID NO: 22 | OsCsIF2 amino acid sequence |
| SEQ ID NO: 23 | OsCsIF3 nucleotide sequence |
| SEQ ID NO: 24 | OsCsIF3 amino acid sequence |
| SEQ ID NO: 25 | OsCsIF4 nucleotide sequence |
| SEQ ID NO: 26 | OsCsIF4 amino acid sequence |
| SEQ ID NO: 27 | OsCsIF5 nucleotide sequence |
| SEQ ID NO: 28 | OsCsIF5 amino acid sequence |
| SEQ ID NO: 29 | OsCsIF7 nucleotide sequence |
| SEQ ID NO: 30 | OsCsIF7 amino acid sequence |
| SEQ ID NO: 31 | OsCsIF8 nucleotide sequence |
| SEQ ID NO: 32 | OsCsIF8 amino acid sequence |
| SEQ ID NO: 33 | OsCsIF9 nucleotide sequence |
| SEQ ID NO: 34 | OsCsIF9 amino acid sequence |
| SEQ ID NO: 35 | OsF2BII5 oligonucleotide primer |
| SEQ ID NO: 36 | OsF2ML3 oligonucleotide primer |
| SEQ ID NO: 37 | OsF3BII5 oligonucleotide primer |
| SEQ ID NO: 38 | OsF3ML3 oligonucleotide primer |
| SEQ ID NO: 39 | OsF4H5 oligonucleotide primer |
| SEQ ID NO: 40 | OsF4S3 oligonucleotide primer |
| SEQ ID NO: 41 | OsF8H5 oligonucleotide primer |
| SEQ ID NO: 42 | OsF8S3 oligonucleotide primer |
| SEQ ID NO: 43 | GAPDH At oligonucleotide primer (forward) |
| SEQ ID NO: 44 | GAPDH At oligonucleotide primer (reverse) |
| SEQ ID NO: 45 | Tubulin At oligonucleotide primer (forward) |
| SEQ ID NO: 46 | Tubulin At oligonucleotide primer (reverse) |
| SEQ ID NO: 47 | Actin At oligonucleotide primer (forward) |
| SEQ ID NO: 48 | Actin At oligonucleotide primer (reverse) |
| SEQ ID NO: 49 | Cyclophilin At oligonucleotide primer (forward) |
| SEQ ID NO: 50 | Cyclophilin At oligonucleotide primer (reverse) |
| SEQ ID NO: 51 | OsCsIF2 oligonucleotide primer (forward) |
| SEQ ID NO: 52 | OsCsIF2 oligonucleotide primer (reverse) |
| SEQ ID NO: 53 | OsCsIF3 oligonucleotide primer (forward) |
| SEQ ID NO: 54 | OsCsIF3 oligonucleotide primer (reverse) |
| SEQ ID NO: 55 | OsCsIF4 oligonucleotide primer (forward) |
| SEQ ID NO: 56 | OsCsIF4 oligonucleotide primer (reverse) |
| SEQ ID NO: 57 | OsCsIF8 oligonucleotide primer (forward) |
| SEQ ID NO: 58 | OsCsIF8 oligonucleotide primer (reverse) |
| SEQ ID NO: 59 | HvFD5END oligonucleotide primer |
| SEQ ID NO: 60 | HvFDRQ oligonucleotide primer |
| SEQ ID NO: 61 | HvFC5N oligonucleotide primer |
| SEQ ID NO: 62 | HvFC3N oligonucleotide primer |
| SEQ ID NO: 63 | HvFH5 oligonucleotide primer |
| SEQ ID NO: 64 | HyFF3N oligonucleotide primer |
| SEQ ID NO: 65 | Hyg oligonucleotide primer (forward) |
| SEQ ID NO: 66 | Hyg oligonucleotide primer (reverse) |
| SEQ ID NO: 67 | HvCsIF1 oligonucleotide primer (forward) |
| SEQ ID NO: 68 | HvCsIF1 oligonucleotide primer (reverse) |
| SEQ ID NO: 69 | HvCsIF4 oligonucleotide primer (forward) |
| SEQ ID NO: 70 | HvCsIF4 oligonucleotide primer (reverse) |
| SEQ ID NO: 71 | HvCsIF6 oligonucleotide primer (forward) |
| SEQ ID NO: 72 | HvCsIF6 oligonucleotide primer (reverse) |

BRIEF DESCRIPTION OF THE FIGURES

FIGS. 6A to 6F show a ClustalW multiple sequence alignment of CslF amino acid sequences derived from Barley (*Hordeum vulgare*) and Rice (*Oryza sativa*).

FIG. 7A shows the detection of (1,3;1,4)-β-D-glucan in transformed *Arabidopsis* lines A28 and A29. In FIG. 7B, walls from the epidermal layers of leaves from transgenic *Arabidopsis* line A18 are shown to accumulate (1,3;1,4)-β-D-glucan over a period of about fourteen days. Finally, FIG. 7C shows a representative section of WT *Arabidopsis* leaf epidermal cell wall where minimal or no background labelling is commonly observed.

FIG. 8 shows the nucleotide sequence identity, protein sequence identity and protein sequence similarity between CslF sequences derived from Rice (*Oryza sativa*) and Barley (*Hordeum vulgare*)

FIG. 18A) G98-10 and FIG. 18B) G98-24, both showing increased fluorescence in the epidermal cells and the sclerenchyma fibre cells on the leaf tip, when compared with control sections; FIG. 18C) G103-5 showing increased fluorescence in all cell types when compared with the control sections; FIG. 18D) G99-12 showing increased fluorescence in stomata and vascular tissue when compared with the control sections.

FIG. 19A shows a representative epidermal cell wall of the transgenic control G89-1, showing labeling of endogenous levels of (1,3;1,4)-β-D-glucan. FIG. 19B shows a representative epidermal cell wall of the transgenic G98-10 showing significantly heavier labeling of (1,3;1,4)-β-D-glucan in the walls of these plants.

FIG. 20A is a representative sclerenchyma fibre cell wall from the transgenic control G89-1 showing labeling of endogenous levels of (1,3;1,4)-β-D-glucan. FIG. 20B shows a representative sclerenchyma fibre cell wall from the transgenic G98-10 showing heavier labeling of the (1,3;1,4)-β-D-glucan. FIG. 20C shows a representative sclerenchyma fibre cell wall from the transgenic G103-5 showing heavier labeling of the (1,3;1,4)-β-D-glucan.

DESCRIPTION OF PREFERRED EMBODIMENTS

Figure 1:
FIG. 1 shows a region on chromosome 7 of rice which is syntenous to a region of barley chromosome 2H, where a cluster of six cellulose synthase-like (Csl) genes was detected within an interval of 119 Kb, corresponding to the 21.59-21.72 Mb region of the chromosome.

It is to be understood that following description is for the purpose of describing particular embodiments only and is not intended to be limiting with respect to the above description.

The present invention is predicated, in part, on the identification of genes which encode the biosynthetic enzyme for (1,3;1,4)-β-D-glucans, referred to herein as "(1,3;1,4)-β-D-glucan synthases".

"(1,3;1,4)-β-D-glucans" should be understood to include linear, unbranched polysaccharides in which β-D-glucopyranosyl monomers are polymerized through both (1→4)- and (1→3)-linkages.

The ratio of (1→4)- to (1→3)-linkages, in naturally occurring (1,3;1,4)-β-D-glucans, is generally in the range 2.2-2.6:1, although the ratio may also be outside of this range. For example, in the (1,3;1,4)-β-D-glucan from sorghum endosperm the ratio is 1.15:1. The two types of linkages are not arranged in regular, repeating sequences. Single (1→3)-linkages are separated by two or more (1→4)-linkages. Regions of two or three adjacent (1→4)-linkages predominate, but again there is no regularity in the arrangement of these units.

The linkage sequence does not depend on preceding linkages further away than two glucose units and follows a second order Markov chain distribution. Moreover, up to 10% of the chain may consist of longer stretches of 5 to 20 adjacent (1→4)-linkages. Thus, cereal (1,3;1,4)-β-D-glucans may be considered as (1→3)-β-linked copolymers of cellotriosyl (G4G4G$_{Red}$), cellotetraosyl (G4G4G4G$_{Red}$) units and longer (1→4)-β-D-oligoglucosyl units.

The ratio of tri- to tetra-saccharide units in endogenous (1,3;1,4)-β-D-glucans varies between cereal species. For example, in wheat the ratio is 3.0-4.5:1, in barley 2.9-3.4:1, in rye 2.7:1 and in oats 1.8-2.3:1. Furthermore, the observed ratios may also vary according to the temperature and conditions of (1,3;1,4)-β-D-glucan extraction.

The average molecular masses reported for cereal (1,3;1,4)-β-D-glucans range from 48,000 (DP ~300) to 3,000,000 (DP ~1850), depending on the cereal species, cell wall type, extraction procedure and the method used for molecular mass determination. They are invariably polydisperse with respect to molecular mass and this is illustrated by a weight average to number average molecular mass ratio ($M_w/M_n$) of 1.18 for barley (1,3;1,4)-β-D-glucan. Certain barley (1,3;1,4)-β-D-glucans are also covalently-associated with small amounts of protein and have estimated molecular masses of up to 40,000,000.

The extractability of (1,3;1,4)-β-D-glucans from walls of cereal grains is a function of their degree of self-association and their association with other wall polysaccharides and proteins. In particular, extractability depends on the molecular mass and linkage distribution in the (1,3;1,4)-β-D-glucan chains. Extensive association with other polymers and very high molecular masses render the (1,3;1,4)-β-D-glucans more difficult to extract from grain.

For example, a portion of the (1,3;1,4)-β-D-glucan from barley, oat and rye flours may be extracted by water at pH 7.0 and 40° C. Further fractions can be solubilized at higher temperatures. The proportion of total (1,3;1,4)-β-D-glucan that is water-soluble at 40° C. varies within and between species. For example, waxy (high amylose) barleys have a higher proportion of water-soluble (1,3;1,4)-3-D-glucan than normal barleys. (1,3;1,4)-β-D-glucans extracted from barley at 40° C. have a slightly lower tri-/tetrasaccharide ratio (1.7:1) than those extracted at 65° C. (2.0:1). Complete extraction of cereal (1,3;1,4)-β-D-glucans from grain requires the use of alkaline extractants such as 4 M NaOH or aqueous Ba(OH)$_2$, containing NaBH$_4$ to prevent alkali-induced degradation from the reducing terminus. Alkali-extracted barley (1,3;1,4)-β-D-glucan fractions have higher molecular masses, higher ratios of (1→4): (1→3) linkages, more contiguously linked (1→4)-linked segments and higher tri-: tetra-saccharide ratios than their water-extractable counterparts. Other extractants, such as dimethylsulphoxide, hot perchloric acid, trichloroacetic acid, N-methylmorpholino-N-oxide and dimethylacetamide-LiCl, may also be used to solubilize (1,3;1,4)-β-D-glucans, but these extractants may cause some depolymerisation or degradation of the polymer. Once extracted with hot water or alkali, the (1,3;1,4)-β-D-glucans are often soluble at neutral pH and room temperature. However, upon cooling, (1,3;1,4)-β-D-glucans can aggregate and precipitate.

As mentioned above, the present invention is predicated, in part, on the identification of the biosynthetic enzyme, and encoding gene, that catalyses the synthesis of (1,3;1,4)-β-D-glucan. As used herein, this enzyme is referred to herein as "(1,3;1,4)-β-D-glucan synthase".

The present invention arises, in part, from an analysis of expressed sequence tag libraries and other sequence databases including cellulose synthase (CesA) genes. More particularly, it was noted in these analyses that the CesA genes were in fact members of a much larger super-family of genes, which included both the CesA genes and the cellulose synthase-like (Csl) gene family.

However, despite significant research effort, the particular functions of individual Csl genes are largely unknown. The Csl genes have been sub-divided into eight groups, designated CslA-CslH. However, the only Csl gene for which a specific biochemical function has been defined are CslA genes from guar and *Arabidopsis*, which encodes (1→4)-β-D-mannan synthases.

Given the similarities in structures of cellulose and (1,3;1,4)-β-D-glucan, the present inventors postulated that genes encoding (1,3;1,4)-β-D-glucan synthases might be members of the Csl gene family.

However, the Csl gene families in most vascular plants are very large and have been divided into several groups, designated CslA to CslH. In *Arabidopsis thaliana* there are 29 known Csl genes and in rice about 37. Overall, the *Arabidopsis* genome is believed to contain more than 700 genes involved in cell wall metabolism. However, in general, the specific functions of these genes are poorly understood. For example, the specific functions of only two of more than 170 genes involved in pectin biosynthesis have been defined. Furthermore, in contrast to the CesA genes, it has proved difficult to define the functions of the Csl genes. In fact, of the multiple Csl genes in higher plants, only the CslA group has been assigned a function.

The present invention used a genetic approach to identify the nucleotide sequences, and corresponding amino acid sequences, that encode (1,3;1,4)-β-D-glucan synthase. In accordance with the present invention, it has been revealed that (1,3;1,4)-β-D-glucan synthases are encoded by members of the CslF gene family.

As a result of the identification of the nucleotide sequences, and corresponding amino acid sequences that encode (1,3;1,4)-β-D-glucan synthases, the present invention provides, inter alia, methods and compositions for influencing the level and/or activity of (1,3;1,4)-β-D-glucan synthase in a cell and thereby the level of (1,3;1,4)-β-D-glucan produced by the cell.

Therefore, in a first aspect, the present invention provides a method for influencing the level of (1,3;1,4)-β-D-glucan produced by a cell, the method comprising modulating the level and/or activity of a (1,3;1,4)-β-D-glucan synthase in the cell.

The "cell" may be any suitable eukaryotic or prokaryotic cell. As such, a "cell" as referred to herein may be a eukaryotic cell including a fungal cell such as a yeast cell or mycelial fungus cell; an animal cell such as a mammalian cell or an insect cell; or a plant cell. Alternatively, the cell may also be a prokaryotic cell such as a bacterial cell including an *E. coli* cell, or an archaea cell.

Preferably, the cell is a plant cell, more preferably a vascular plant cell, including a monocotyledonous or dicotyledonous angiosperm plant cell or a gymnosperm plant cell. In an even more preferred embodiment, the plant is a monocotyledonous plant cell.

In one particularly preferred embodiment, the monocotyledonous plant cell is a cereal crop plant cell.

As used herein, the term "cereal crop plant" includes members of the Poales (grass family) that produce edible grain for human or animal food. Examples of Poales cereal crop plants which in no way limit the present invention include wheat, rice, maize, millets, sorghum, rye, triticale, oats, barley, teff, wild rice, spelt and the like. However, the term cereal crop plant should also be understood to include a number of non-Poales species that also produce edible grain and are known as the pseudocereals, such as amaranth, buckwheat and quinoa.

Although cereal crop plants are particularly preferred monocotyledonous plants, the other monocotyledonous plants are also preferred, such as other non-cereal plants of the Poales, specifically including pasture grasses such as *Lolium* spp.

As set out above, the present invention is predicated, in part, on modulating the level and/or activity of (1,3;1,4)-β-D-glucan synthase in a cell.

"(1,3;1,4)-β-D-glucan synthase" should be regarded as any protein which catalyses the synthesis of (1,3;1,4)-β-D-glucan and, optionally, catalyses the polymerisation of glucopyranosyl monomers.

Preferably, the (1,3;1,4)-β-D-glucan synthase comprises the amino acid sequence set forth in any of SEQ ID NO: 2, SEQ ID NO: 4, SEQ ID NO: 6, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34, or an amino acid sequence which is at least 40% identical thereto.

More preferably, the (1,3;1,4)-β-D-glucan synthase comprises at least 50% amino acid sequence identity, yet more preferably at least 60% amino acid sequence identity, even more preferably at least 70% amino acid sequence identity, and even more preferably at least 80% amino acid sequence identity and most preferably at least 90% amino acid sequence identity to any SEQ ID NO: 2, SEQ ID NO: 4, SEQ ID NO: 6, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34. In a particularly preferred embodiment, the (1,3;1,4)-β-D-glucan synthase comprises the amino acid sequence set forth in any of SEQ ID NO: 2, SEQ ID NO: 4, SEQ ID NO: 6, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34.

When comparing amino acid sequences, the compared sequences should be compared over a comparison window of at least 100 amino acid residues, more preferably at least 200 amino acid residues, yet more preferably at least 400 amino acid residues, even more preferably at least 800 amino acid residues and most preferably over the full length of any of SEQ ID NO: 2, SEQ ID NO: 4, SEQ ID NO: 6, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (Nucl. Acids Res. 25: 3389-3402, 1997). A detailed discussion of sequence analysis can be found in Unit 19. 3 of Ausubel et al. ("Current Protocols in Molecular Biology" John Wiley & Sons Inc, 1994-1998, Chapter 15, 1998).

In a more preferred embodiment, the (1,3;1,4)-β-D-glucan synthase is encoded by a CslF gene or a functional homolog thereof (as defined later).

As referred to herein, the modulation of the "level" of the (1,3;1,4)-β-D-glucan synthase should be understood to include modulation of the level of (1,3;1,4)-β-D-glucan synthase transcripts and/or polypeptides in the cell. Modulation of the "activity" of the (1,3;1,4)-β-D-glucan synthase should be understood to include modulation of the total activity, specific activity, half-life and/or stability of the (1,3;1,4)-β-D-glucan synthase in the cell.

By "modulating" with regard to the level and/or activity of the (1,3;1,4)-β-D-glucan synthase is intended decreasing or increasing the level and/or activity of (1,3;1,4)-β-D-glucan synthase in the cell. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the level or activity of (1,3;1,4)-β-D-glucan synthase in the cell. By "increasing" is intended, for example, a 1%, 5%, 10%, 20%, 30%, 40%, 50%, 60%, 70%, 80%, 90%, 100%, 2-fold, 5-fold, 10-fold, 20 fold, 50-fold, 100-fold increase in the level of activity of (1,3;1,4)-β-D-glucan synthase in the cell. "Modulating" also includes introducing a (1,3;1,4)-β-D-glucan synthase into a cell which does not normally express the introduced enzyme, or the substantially complete inhibition of (1,3;1,4)-β-D-glucan synthase activity in a cell that normally has such activity.

In one preferred embodiment, the level of (1,3;1,4)-β-D-glucan produced by a cell is increased by increasing the level and/or activity of (1,3;1,4)-β-D-glucan synthase in the cell. In another preferred embodiment, the level of (1,3;1,4)-β-D-glucan produced by a cell is decreased by decreasing the level and/or activity of (1,3;1,4)-β-D-glucan synthase in the cell.

The methods of the present invention contemplates any means known in the art by which the level and/or activity of (1,3;1,4)-β-D-glucan synthase in a cell may be modulated. This includes methods such as the application of agents which modulate (1,3;1,4)-β-D-glucan synthase activity in a cell, such as the application of a (1,3;1,4)-β-D-glucan synthase agonist or antagonist; the application of agents which mimic (1,3;1,4)-β-D-glucan synthase activity in a cell; modulating the expression of a nucleic acid which encodes (1,3;1,4)-β-D-glucan synthase in the cell; or effecting the expression of an altered or mutated (1,3;1,4)-β-D-glucan synthase encoding nucleic acid in a cell such that a (1,3;1,4)-β-D-glucan synthase with increased or decreased specific activity, half-life and/or stability is expressed by the cell.

In a preferred embodiment, the level and/or activity of the (1,3;1,4)-β-D-glucan synthase is modulated by modulating the expression of a (1,3;1,4)-β-D-glucan synthase encoding nucleic acid in the cell.

Therefore, in a second aspect, the present invention provides a method for modulating the level and/or activity of a (1,3;1,4)-β-D-glucan synthase in a cell, the method comprising modulating the expression of a (1,3;1,4)-β-D-glucan synthase encoding nucleic acid in the cell.

As described herein, it has been identified that (1,3;1,4)-β-D-glucan synthase is encoded by members of the CslF gene family. Therefore, in a preferred embodiment, the (1,3;1,4)-β-D-glucan synthase encoding nucleic acid is a CslF gene or a functional homolog thereof.

Accordingly, in a third aspect, the present invention provides a method for modulating the level and/or activity of a (1,3;1,4)-β-D-glucan synthase in a cell, the method comprising modulating the expression of a CslF gene or functional homolog thereof in the cell.

As used herein, the term "CslF gene or functional homolog thereof" should be understood to include to a nucleic acid molecule which:
(i) encodes a (1,3;1,4)-β-D-glucan synthase as defined herein; and
(ii) preferably, comprises at least 50% nucleotide sequence identity to the nucleotide sequence set forth in any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33; and/or (iii) preferably, hybridises to a nucleic acid molecule comprising the nucleotide sequence set forth in any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33 under stringent conditions.

More preferably, the CslF gene functional homolog thereof comprises a nucleotide sequence which is at least 54% identical to any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, more preferably the CslF gene or functional homolog thereof comprises a nucleotide sequence which is at least 70% identical to any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33 and most preferably the CslF gene or functional homolog thereof comprises a nucleotide sequence which is at least 85% identical to any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

In a particularly preferred embodiment, the CslF gene or functional homolog thereof comprises the nucleotide sequence set forth in any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

When comparing nucleic acid sequences to any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33 to calculate a percentage identity, the compared nucleotide sequences should be compared over a comparison window of at least 300 nucleotide residues, more preferably at least 600 nucleotide residues, yet more preferably at least 1200 nucleotide residues, even more preferably at least 2400 nucleotide residues and most preferably over the full length of SEQ ID NO: 1. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19. 3 of Ausubel et al. ("Current Protocols in Molecular Biology" John Wiley & Sons Inc, 1994-1998, Chapter 15, 1998).

As set out above, the CslF gene or functional homolog thereof may also comprise a nucleic acid, which hybridises to a nucleic acid molecule comprising the nucleotide sequence set forth in any of SEQ ID NO: 1, SEQ ID NO: 3, SEQ ID NO: 5, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33, under stringent conditions. As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilizing agents such as formamide. Stringent hybridisation conditions may be low stringency conditions, more preferably medium stringency conditions and most preferably high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity of hybridisation is typically the function of post-hybridization washes, the critical factors being the ionic strength and temperature of the final wash solution. For DNA-DNA hybrids, the $T_m$ can be approximated from the equation of Meinkoth and Wahl (*Anal. Biochem.* 138: 267-284, 1984), i.e. $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilize a hybridization and/or wash at, for example, 1, 2, 3, or 4° C. lower than the thermal melting point ($T_m$); medium stringency conditions can utilize a hybridization and/or wash at, for example, 6, 7, 8, 9, or 10° C. lower than the thermal melting point ($T_m$); low stringency conditions can utilize a hybridization and/or wash at, for example, 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (*Laboratory Techniques in Biochemistry and Molecular Biology-Hybridization with Nucleic Acid Probes*, Pt I, Chapter 2, Elsevier, New York, 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, $2^{nd}$ ed., Cold Spring Harbor Laboratory Press, Plainview, N.Y., 1989).

The CslF gene or functional homolog thereof may also comprise a genomic nucleotide sequence from an organism which may include one or more non-protein-coding regions or one or more intronic regions. Exemplary genomic nucleotide sequences which comprise a CslF gene including the *Hordeum vulgare* genomic nucleotide sequences set forth in any of SEQ ID NO: 13, SEQ ID NO: 14, SEQ ID NO: 15, SEQ ID NO: 16, SEQ ID NO: 17 and SEQ ID NO: 18.

As mentioned above, the present invention provides methods for modulating the expression of a (1,3;1,4)-β-D-glucan synthase encoding nucleic acid in a cell. The present invention contemplates any method by which the expression of a (1,3;1,4)-β-D-glucan synthase encoding nucleic acid molecule in a cell may be modulated.

Preferably, the term "modulating" with regard to the expression of the (1,3;1,4)-β-D-glucan synthase encoding nucleic acid is intended decreasing or increasing the transcription and/or translation of a (1,3;1,4)-β-D-glucan synthase encoding nucleic acid. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the transcription and/or translation of a (1,3;1,4)-β-D-glucan synthase encoding nucleic acid. By "increasing" is intended, for example a 1%, 5%, 10%, 20%, 30%, 40%, 50%, 60%, 70%, 80%, 90%, 100%, 2-fold, 5-fold, 10-fold, 20-fold, 50-fold, 100-fold or greater increase in the transcription and/or translation of a (1,3;1,4)-β-D-glucan synthase encoding nucleic acid. Modulating also comprises introducing expression of a (1,3;1,4)-β-D-glucan synthase encoding nucleic acid not normally found in a particular cell; or the substantially complete inhibition (e.g. knockout) of expression of a (1,3;1,4)-β-D-glucan synthase encoding nucleic acid in a cell that normally has such activity.

Methods for modulating the expression of a particular nucleic acid molecule in a cell are known in the art and the present invention contemplates any such method. Exemplary methods for modulating the expression of a (1,3;1,4)-β-D-glucan synthase encoding nucleic acid include: genetic modification of the cell to upregulate or downregulate endogenous (1,3;1,4)-β-D-glucan synthase expression; genetic modification by transformation with a (1,3;1,4)-β-D-glucan synthase encoding nucleic acid; administration of a nucleic acid molecule to the cell which modulates expression of an endogenous (1,3;1,4)-β-D-glucan synthase encoding nucleic acid in the cell; and the like.

In one preferred embodiment, the expression of a (1,3;1,4)-β-D-glucan synthase encoding nucleic acid is modulated by genetic modification of the cell. The term "genetically modified", as used herein, should be understood to include any genetic modification that effects an alteration in the expression of a (1,3;1,4)-β-D-glucan synthase encoding nucleic acid in the genetically modified cell relative to a non-genetically modified form of the cell. Exemplary types of genetic modification contemplated herein include: random mutagenesis such as transposon, chemical, UV and phage mutagenesis together with selection of mutants which overexpress or underexpress an endogenous (1,3;1,4)-β-D-glucan synthase encoding nucleic acid; trasient or stable introduction of one or more nucleic acid molecules into a cell which direct the expression and/or overexpression of (1,3;1,4)-β-D-glucan synthase encoding nucleic acid in the cell; inhibition of an endogenous (1,3;1,4)-β-D-glucan synthase by site-directed mutagenesis of an endogenous (1,3;1,4)-β-D-glucan synthase encoding nucleic acid; introduction of one or more nucleic acid molecules which inhibit the expression of an endogenous (1,3;1,4)-β-D-glucan synthase encoding nucleic acid in the cell, e.g. a cosuppression construct or an RNAi construct; and the like.

In one particularly preferred embodiment, the genetic modification comprises the introduction of a nucleic acid into a cell of interest.

The nucleic acid may be introduced using any method known in the art which is suitable for the cell type being used, for example, those described in Sambrook and Russell (*Molecular Cloning—A Laboratory Manual*, $3^{rd}$ Ed., Cold Spring Harbor Laboratory Press, 2000).

In preferred embodiments of the invention, wherein the cell is a plant cell, suitable methods for introduction of a nucleic acid molecule may include: *Agrobacterium*-mediated transformation, microprojectile bombardment based transformation methods and direct DNA uptake based methods. Roa-Rodriguez et al. (*Agrobacterium-mediated transformation of plants,* $3^{rd}$ Ed. CAMBIA Intellectual Property Resource, Canberra, Australia, 2003) review a wide array of suitable *Agrobacterium*-mediated plant transformation methods for a wide range of plant species. Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology Vol.* 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art.

The introduced nucleic acid may be single stranded or double stranded. The nucleic acid may be transcribed into mRNA and translated into (1,3;1,4)-β-D-glucan synthase or another protein; may encode for a non-translated RNA such as an RNAi construct, cosuppression construct, antisense RNA, tRNA, miRNA, siRNA, ntRNA and the like; or may act directly in the cell. The introduced nucleic acid may be an unmodified DNA or RNA or a modified DNA or RNA which may include modifications to the nucleotide bases, sugar or phosphate backbones but which retain functional equivalency to a nucleic acid. The introduced nucleic acid may optionally be replicated in the cell; integrated into a chromosome or any extrachromosomal elements of the cell; and/or transcribed by the cell. Also, the introduced nucleic acid may be either homologous or heterologous with respect to the host cell. That is, the introduced nucleic acid may be derived from a cell of the same species as the genetically modified cell (i.e. homologous) or the introduced nucleic may be derived from a different species (i.e. heterologous). The transgene may also be a synthetic transgene.

In one particularly preferred embodiment, the present invention contemplates increasing the level of (1,3;1,4)-β-D-glucan produced by a cell, by introducing a (1,3;1,4)-β-D-glucan synthase encoding nucleic acid into the cell. More preferably, the (1,3;1,4)-β-D-glucan synthase encoding nucleic acid comprises a CslF gene or functional homolog thereof.

By identifying the nucleotide sequences which encode (1,3;1,4)-β-D-glucan synthases, in further embodiments the present invention also provides methods for down-regulating expression of a (1,3;1,4)-β-D-glucan synthase encoding nucleic acid in a cell.

For example, the identification of (1,3;1,4)-β-D-glucan synthase encoding nucleic acid sequences, in accordance with the present invention, facilitates methods such as knockout or knockdown of an endogenous (1,3;1,4)-β-D-glucan synthase encoding nucleic acid in a cell using methods such as:

(i) insertional mutagenesis of a (1,3;1,4)-β-D-glucan synthase encoding nucleic acid in a cell including knockout or knockdown of a (1,3;1,4)-β-D-glucan synthase encoding nucleic acid in a cell by homologous recombination with a knockout construct (for an example of targeted gene disruption in plants see Terada et al., *Nat. Biotechnol.* 20: 1030-1034, 2002);

(ii) post-transcriptional gene silencing (PTGS) or RNAi of a (1,3;1,4)-β-D-glucan synthase encoding nucleic acid in a cell (for review of PTGS and RNAi see Sharp, *Genes Dev.* 15(5): 485-490, 2001; and Hannon, *Nature* 418: 244-51, 2002);

(iii) transformation of a cell with an antisense construct directed against a (1,3;1,4)-β-D-glucan synthase encoding nucleic acid (for examples of antisense suppression in plants see van der Krol et al., *Nature* 333: 866-869; van der Krol et al., *BioTechniques* 6: 958-967; and van der Krol et al., *Gen. Genet.* 220: 204-212);

(iv) transformation of a cell with a co-suppression construct directed against a (1,3;1,4)-β-D-glucan synthase encoding nucleic acid (for an example of co-suppression in plants see van der Krol et al., *Plant Cell* 2(4): 291-299);

(v) transformation of a cell with a construct encoding a double stranded RNA directed against a (1,3;1,4)-β-D-glucan synthase encoding nucleic acid (for an example of dsRNA mediated gene silencing see Waterhouse et al., *Proc. Natl. Acad. Sci. USA* 95: 13959-13964, 1998); and (vi) transformation of a cell with a construct encoding an siRNA or hairpin RNA directed against a (1,3;1,4)-β-D-glucan synthase encoding nucleic acid (for an example of siRNA or hairpin RNA mediated gene silencing in plants see Lu et al., *Nucl. Acids Res.* 32(21): e171; doi:10.1093/nar/gnh170, 2004).

The present invention also facilitates the downregulation of a (1,3;1,4)-β-D-glucan synthase encoding nucleic acid in a cell via the use of synthetic oligonucleotides such as siRNAs or microRNAs directed against a (1,3;1,4)-β-D-glucan synthase encoding nucleic acid which are administered to a cell (for examples of synthetic siRNA mediated silencing see Caplen et al., *Proc. Natl. Acad. Sci. USA* 98: 9742-9747, 2001; Elbashir et al., *Genes Dev.* 15: 188-200, 2001; Elbashir et al., *Nature* 411: 494-498, 2001; Elbashir et al., *EMBO J.* 20: 6877-6888, 2001; and Elbashir et al., *Methods* 26: 199-213, 2002).

In addition to the examples above, the introduced nucleic acid may also comprise a nucleotide sequence which is not directly related to a (1,3;1,4)-β-D-glucan synthase sequence but, nonetheless, may directly or indirectly modulate the expression of (1,3;1,4)-β-D-glucan synthase encoding nucleic acid in a cell. Examples include nucleic acid molecules that encode transcription factors or other proteins which promote or suppress the expression of an endogenous (1,3;1,4)-β-D-glucan synthase encoding nucleic acid molecule in a cell; and other non-translated RNAs which directly or indirectly promote or suppress endogenous (1,3;1,4)-β-D-glucan synthase expression and the like.

In order to effect expression of an introduced nucleic acid in a genetically modified cell, where appropriate, the introduced nucleic acid may be operably connected to one or more control sequences. The term "control sequences" should be understood to include all components known in the art, which are necessary or advantageous for the transcription, translation and or post-translational modification of the operably connected nucleic acid or the transcript or protein encoded thereby. Each control sequence may be native or foreign to the operably connected nucleic acid. The control sequences may include, but are not limited to, a leader, polyadenylation sequence, propeptide sequence, promoter, enhancer or upstream activating sequence, signal peptide sequence, and transcription terminator. Typically, a control sequence at least includes a promoter.

The term "promoter" as used herein, describes any nucleic acid which confers, activates or enhances expression of a nucleic acid molecule in a cell. Promoters are generally positioned 5' (upstream) to the genes that they control. In the construction of heterologous promoter/structural gene combinations, it is generally preferred to position the promoter at a distance from the gene transcription start site that is approximately the same as the distance between that promoter and the gene it controls in its natural setting, i.e. the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e. the genes from which it is derived. Again, as is known in the art, some variation in this distance can also occur.

A promoter may regulate the expression of an operably connected nucleotide sequence constitutively, or differentially with respect to the cell, tissue, organ or developmental stage at which expression occurs, in response to external stimuli such as physiological stresses, pathogens, or metal ions, amongst others, or in response to one or more transcriptional activators. As such, the promoter used in accordance with the methods of the present invention may include a constitutive promoter, an inducible promoter, a tissue-specific promoter or an activatable promoter.

The present invention contemplates the use of any promoter which is active in a cell of interest. As such, a wide array of promoters which are active in any of bacteria, fungi, animal cells or plant cells would be readily ascertained by one of ordinary skill in the art. However, in particularly preferred embodiments of the invention, plant cells are used. Therefore, plant-active constitutive, inducible, tissue-specific or activatable promoters are particularly preferred.

Plant constitutive promoters typically direct expression in nearly all tissues of a plant and are largely independent of environmental and developmental factors. Examples of constitutive promoters that may be used in accordance with the present invention include plant viral derived promoters such as the Cauliflower Mosaic Virus 35S and 19S (CaMV 35S and CaMV 19S) promoters; bacterial plant pathogen derived promoters such as opine promoters derived from *Agrobacterium* spp., e.g. the *Agrobacterium*-derived nopaline synthase (nos) promoter; and plant-derived promoters such as the rubisco small subunit gene (rbcS) promoter, the plant ubiquitin promoter (Pubi) and the rice actin promoter (Pact).

"Inducible" promoters include, but are not limited to, chemically inducible promoters and physically inducible promoters. Chemically inducible promoters include promoters which have activity that is regulated by chemical compounds such as alcohols, antibiotics, steroids, metal ions or other compounds.

Examples of chemically inducible promoters include: alcohol regulated promoters (e.g. see European Patent 637 339); tetracycline regulated promoters (e.g. see U.S. Pat. Nos. 5,851,796 and 5,464,758); steroid responsive promoters such as glucocorticoid receptor promoters (e.g. see U.S.

Pat. No. 5,512,483), estrogen receptor promoters (e.g. see European Patent Application 1 232 273), ecdysone receptor promoters (e.g. see U.S. Pat. No. 6,379,945) and the like; metal-responsive promoters such as metallothionein promoters (e.g. see U.S. Pat. Nos. 4,940,661, 4,579,821 and 4,601,978); and pathogenesis related promoters such as chitinase or lysozyme promoters (e.g. see U.S. Pat. No. 5,654,414) or PR protein promoters (e.g. see U.S. Pat. Nos. 5,689,044, 5,789,214, Australian Patent 708850, U.S. Pat. No. 6,429,362).

The inducible promoter may also be a physically regulated promoter which is regulated by non-chemical environmental factors such as temperature (both heat and cold), light and the like. Examples of physically regulated promoters include heat shock promoters (e.g. see U.S. Pat. No. 5,447,858, Australian Patent 732872, Canadian Patent Application 1324097); cold inducible promoters (e.g. see U.S. Pat. Nos. 6,479,260, 6,084,08, 6,184,443 and 5,847,102); light inducible promoters (e.g. see U.S. Pat. No. 5,750,385 and Canadian Patent 132 1563); light repressible promoters (e.g. see New Zealand Patent 508103 and U.S. Pat. No. 5,639,952).

"Tissue specific promoters" include promoters which are preferentially or specifically expressed in one or more specific cells, tissues or organs in an organism and/or one or more developmental stages of the organism. It should be understood that a tissue specific promoter may be either constitutive or inducible.

Examples of plant tissue specific promoters include: root specific promoters such as those described in U.S. Patent Application 2001047525; fruit specific promoters including ovary specific and receptacle tissue specific promoters such as those described in European Patent 316 441, U.S. Pat. No. 5,753,475 and European Patent Application 973 922; and seed specific promoters such as those described in Australian Patent 612326 and European Patent application 0 781 849 and Australian Patent 746032.

In one preferred embodiment, the tissue specific promoter is a seed and/or grain specific promoter. Exemplary seed or grain specific promoters include puroindoline-b gene promoters (for example see Digeon et al., *Plant Mol.* 39: 1101-1112, 1999); Pbf gene promoters (for example see Mena et al., *Plant J.* 16: 53-62, 1998); $GS_{1-2}$ gene promoters (for example see Muhitch et al., *Plant Sci.* 163: 865-872, 2002); glutelin Gt1 gene promoters (for example see Okita et al., *J. Biol. Chem.* 264: 12573-12581, 1989; Zheng et al., *Plant J.* 4: 357-366, 1993; Sindhu et al., *Plant Sci.* 130: 189-196, 1997; Nandi et al., *Plant Sci.* 163: 713-722, 2002); Hor2-4 gene promoters (for example see Knudsen and Müller, *Planta* 195: 330-336, 1991; Patel et al., *Mol. Breeding* 6: 113-123, 2000; Wong et al., *Proc. Natl. Acad. Sci. USA* 99: 16325-16330, 2002); lipoxygenase 1 gene promoters (for example see Rouster et al., *Plant J.* 15: 435-440, 1998); Chi26 gene promoters (for example see Leah et al., *Plant J.* 6: 579-589, 1994); Glu-D1-1 gene promoters (for example see Lamacchia et al., *J. Exp. Bot.* 52: 243-250, 2001; Zhang et al., *Theor. Appl. Genet.* 106: 1139-1146, 2003); Hor3-1 gene promoters (for example see Sörensen et al., *Mol. Gen. Genet.* 250: 750-760, 1996; Horvath et al., *Proc. Natl. Acad. Sci. USA* 97: 1914-1919, 2000) and Waxy (Wx) gene promoters (for example see Yao et al., *Acta Phytophysiol. Sin.* 22: 431-436, 1996; Terada et al., *Plant Cell Physiol.* 41: 881-888, 2000; Liu et al., *Transgenic Res.* 12: 71-82, 2003). In a particularly preferred embodiment, the seed specific promoter is an endosperm specific promoter.

The promoter may also be a promoter that is activatable by one or more transcriptional activators, referred to herein as an "activatable promoter". For example, the activatable promoter may comprise a minimal promoter operably connected to an Upstream Activating Sequence (UAS), which comprises, inter alia, a DNA binding site for one or more transcriptional activators.

As referred to herein the term "minimal promoter" should be understood to include any promoter that incorporates at least an RNA polymerase binding site and, preferably a TATA box and transcription initiation site and/or one or more CAAT boxes. More preferably, when the cell is a plant cell, the minimal promoter may be derived from the Cauliflower Mosaic Virus 35S (CaMV 35S) promoter. Preferably, the CaMV 35S derived minimal promoter may comprise a sequence that corresponds to positions −90 to +1 (the transcription initiation site) of the CaMV 35S promoter (also referred to as a −90 CaMV 35S minimal promoter), −60 to +1 of the CaMV 35S promoter (also referred to as a −60 CaMV 35S minimal promoter) or −45 to +1 of the CaMV 35S promoter (also referred to as a −45 CaMV 35S minimal promoter).

As set out above, the activatable promoter may comprise a minimal promoter fused to an Upstream Activating Sequence (UAS). The UAS may be any sequence that can bind a transcriptional activator to activate the minimal promoter. Exemplary transcriptional activators include, for example: yeast derived transcription activators such as Gal4, Pdr1, Gcn4 and Ace1; the viral derived transcription activator, VP16; Hap1 (Hach et al., *J Biol Chem* 278: 248-254, 2000); Gaf1 (Hoe et al., *Gene* 215(2): 319-328, 1998); E2F (Albani et al., *J Biol Chem* 275: 19258-19267, 2000); HAND2 (Dai and Cserjesi, *J Biol Chem* 277: 12604-12612, 2002); NRF-1 and EWG (Herzig et al., *J Cell Sci* 113: 4263-4273, 2000); P/CAF (Itoh et al., *Nucl Acids Res* 28: 4291-4298, 2000); MafA (Kataoka et al., *J Biol Chem* 277: 49903-49910, 2002); human activating transcription factor 4 (Liang and Hai, *J Biol Chem* 272: 24088-24095, 1997); Bcl10 (Liu et al., *Biochem Biophys Res Comm* 320(1): 1-6, 2004); CREB-H (Omori et al., *Nucl Acids Res* 29: 2154-2162, 2001); ARR1 and ARR2 (Sakai et al., *Plant J* 24(6): 703-711, 2000); Fos (Szuts and Bienz, *Proc Natl Acad Sci USA* 97: 5351-5356, 2000); HSF4 (Tanabe et al., *J Biol Chem* 274: 27845-27856, 1999); MAML1 (Wu et al., *Nat Genet* 26: 484-489, 2000).

In one preferred embodiment, the UAS comprises a nucleotide sequence that is able to bind to at least the DNA-binding domain of the GAL4 transcriptional activator. UAS sequences, which can bind transcriptional activators that comprise at least the GAL4 DNA binding domain, are referred to herein as $UAS_G$. In a particularly preferred embodiment, the $UAS_G$ comprises the sequence 5'-CGGAGTACTGTCCTCCGAG-3' (SEQ ID NO:73) or a functional homolog thereof.

As referred to herein, a "functional homolog" of the $UAS_G$ sequence should be understood to refer to any nucleotide sequence which can bind at least the GAL4 DNA binding domain and which preferably comprises a nucleotide sequence having at least 50% identity, more preferably at least 65% identity, even more preferably at least 80% identity and most preferably at least 90% identity with the $UAS_G$ nucleotide sequence.

The UAS sequence in the activatable promoter may comprise a plurality of tandem repeats of a DNA binding domain target sequence. For example, in its native state, $UAS_G$ comprises four tandem repeats of the DNA binding domain target sequence. As such, the term "plurality" as used herein with regard to the number of tandem repeats of a DNA binding domain target sequence should be understood to include at least 2 tandem repeats, more preferably at least 3 tandem repeats and even more preferably at least 4 tandem repeats.

As mentioned above, the control sequences may also include a terminator. The term "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

As would be appreciated by one of skill in the art, the method of the present invention for modulating the level of (1,3;1,4)-β-D-glucan in a cell, by modulating the level and/or activity of (1,3;1,4)-β-D-glucan synthase in the cell, has several industrial applications.

For example, (1,3;1,4)-β-D-glucans are known to form viscous solutions. The viscosity-generating properties of soluble cereal (1,3;1,4)-β-D-glucans are critical determinants in many aspects of cereal processing. For example, incompletely degraded (1,3;1,4)-β-D-glucans from malted barley and cereal adjuncts can contribute to wort and beer viscosity and are associated with problems in wort separation and beer filtration (e.g. see Bamforth, Brew. Dig. 69 (5): 12-16, 1994) Therefore, for example, in one embodiment, the present invention may be applied to reduce the level of (1,3;1,4)-β-D-glucan in barley grain, by reducing the level and/or activity of (1,3;1,4)-β-D-glucan synthase in one or more cells of the barley grain, to increase its suitability for beer production.

Soluble cereal (1,3;1,4)-β-D-glucans are also considered to have antinutritive effects in monogastric animals such as pigs and poultry. The "antinutritive" effects have been attributed to the increased viscosity of gut contents, which slows both the diffusion of digestive enzymes and the absorption of degradative products of enzyme action. This, in turn, leads to slower growth rates. Moreover, in dietary formulations for poultry, high (1,3;1,4)-β-D-glucan concentrations are associated with 'sticky' faeces, which are indicative of the poor digestibility of the (1,3;1,4)-β-D-glucans and which may present major handling and hygiene problems for producers. Therefore, in another embodiment, the present invention may be applied to reducing the level of (1,3;1,4)-β-D-glucan in one or more cells of a plant used for animal feed, to improve the suitability of the plant as animal feed.

However, cereal (1,3;1,4)-β-D-glucans are important components of dietary fibre in human and animal diets. As used herein, the term "dietary fibre" should be understood to include the edible parts of plants or analogous carbohydrates that are resistant to digestion and absorption in the human small intestine with complete or partial fermentation in the large intestine. "Dietary fibre" includes polysaccharides (specifically including (1,3;1,4)-β-D-glucans), oligosaccharides, lignin and associated plant substances. In at least human diets, dietary fibres promote beneficial physiological effects including general bowel health, laxation, blood cholesterol attenuation, and/or blood glucose attenuation.

Humans and monogastric animals produce no enzymes that degrade (1,3;1,4)-β-D-glucans, although there are indications that some depolymerization occurs in the stomach and small intestine, presumably due to the activity of commensal microorganisms. By comparison the soluble (1,3;1,4)-β-D-glucans and other non-starchy polysaccharides are readily fermented by colonic micro-organisms and make a small contribution to digestible energy. In contrast to their antinutritive effects in monogastric animals, oat and barley (1,3;1,4)-β-D-glucans at high concentrations in human foods have beneficial effects, especially for non-insulin-dependent diabetics, by flattening glucose and insulin responses that follow a meal. High concentrations of (1,3;1,4)-β-D-glucans (20% w/v) in food have also been implicated in the reduction of serum cholesterol concentrations, by lowering the uptake of dietary cholesterol or resorption of bile acids from the intestine.

Therefore, in another embodiment, the present invention may be applied to increasing the dietary fibre content of an edible plant or edible plant part, by increasing the level of (1,3;1,4)-β-D-glucan in the plant, or part thereof. In a particularly preferred embodiment, the edible plant or edible part of a plant is a cereal crop plant or part thereof.

(1,3;1,4)-β-D-glucans, in common with a number of other polysaccharides, in particular (1→3)-β-D-glucans, are also thought to modify immunological responses in humans by a process that is mediated through binding to receptors on cells of the reticuloendothelial system (leucocytes and macrophages). In addition, they may have the capacity to activate the proteins of the human complement pathway, a system that is invoked as a first line of defense before circulating antibodies are produced.

The method of the first aspect of the present invention also facilitates the production of (1,3;1,4)-β-D-glucan in a recombinant expression system. For example, a (1,3;1,4)-β-D-glucan may be recombinantly produced by introducing a (1,3;1,4)-β-D-glucan synthase encoding nucleotide sequence as described herein, under the control of a promoter, into a cell, wherein the cell subsequently expresses the (1,3;1,4)-β-D-glucan synthase and produces (1,3;1,4)-β-D-glucan.

A vast array of recombinant expression systems that may be used to express a (1,3;1,4)-β-D-glucan synthase encoding nucleic acid are known in the art. Exemplary recombinant expression systems include: bacterial expression systems such as E. coli expression systems (reviewed in Baneyx, Curr. Opin. Biotechnol. 10: 411-421, 1999; e.g. see also Gene expression in recombinant microorganisms, Smith (Ed.), Marcel Dekker, Inc. New York, 1994; and Protein Expression Technologies: Current Status and Future Trends, Baneyx (Ed.), Chapters 2 and 3, Horizon Bioscience, Norwich, U K, 2004), Bacillus spp. expression systems (e.g. see Protein Expression Technologies: Current Status and Future Trends, supra, chapter 4) and Streptomyces spp. expression systems (e.g. see Practical Streptomyces Genetics, Kieser et al., (Eds.), Chapter 17, John Innes Foundation, Norwich, U K, 2000); fungal expression systems including yeast expression systems such as Saccharomyces spp., Schizosaccharomyces pombe, Hansenula polymorpha and Pichia spp. expression systems and filamentous fungi expression systems (e.g. see Protein Expression Technologies: Current Status and Future Trends, supra, chapters 5, 6 and 7; Buckholz and Gleeson, Bio/Technology 9(11): 1067-1072, 1991; Cregg et al., Mol. Biotechnol. 16(1): 23-52, 2000; Cereghino and Cregg, FEMS Microbiology Reviews 24: 45-66, 2000; Cregg et al., Bio/Technology 11: 905-910, 1993); mammalian cell expression systems including Chinese Hamster Ovary (CHO) cell based expression systems (e.g. see *Protein Expression Technologies: Current Status and Future Trends*, supra, chapter 9); insect cell cultures including baculovirus expression systems (e.g. see *Protein Expression Technologies: Current Status and Future Trends*, supra, chapter 8; Kost and Condreay, *Curr. Opin. Biotechnol.* 10: 428-433, 1999; *Baculovirus Expression Vectors: A Laboratory Manual* WH Freeman & Co., New York, 1992; and *The Baculovirus Expression System: A Laboratory Manual*, Chapman & Hall, London, 1992); Plant cell expression systems such as tobacco, soybean, rice and tomato cell expression systems (e.g. see review of Hellwig et al., *Nat Biotechnol* 22: 1415-1422, 2004); and the like.

Therefore, in a fourth aspect, the present invention provides a method for producing (1,3;1,4)-β-D-glucan, the method comprising expressing a (1,3;1,4)-β-D-glucan synthase encoding nucleic acid in a cell.

In one preferred embodiment, the cell is a cell from a recombinant expression system as hereinbefore defined.

In another preferred embodiment, the (1,3;1,4)-β-D-glucan synthase encoding nucleic acid is a CslF gene or functional homolog thereof.

In a fifth aspect, the present invention also provides (1,3;1,4)-β-D-glucan produced according to the method of the fourth aspect of the invention.

In a sixth aspect, the present invention also provides a cell comprising any one or more of:
  (i) a modulated level of (1,3;1,4)-β-D-glucan relative to a wild type cell of the same taxon;
  (ii) a modulated level and/or activity of (1,3;1,4)-β-D-glucan synthase relative to a wild type cell of the same taxon;
  (iii) modulated expression of a (1,3;1,4)-β-D-glucan synthase encoding nucleic acid relative to a wild type cell of the same taxon.

In one preferred embodiment, the cell of the sixth aspect of the invention is produced according to the methods of the first, second or third aspects of the present invention as described herein. In another preferred embodiment, the cell is a plant cell, more preferably a monocot plant cell and most preferably a cereal crop plant cell.

Furthermore, in a seventh aspect, the present invention provides a multicellular structure comprising one or more cells according to the sixth aspect of the invention.

As referred to herein, a "multicellular structure" includes any aggregation of one or more cells. As such, a multicellular structure specifically encompasses tissues, organs, whole organisms and parts thereof. Furthermore, a multicellular structure should also be understood to encompass multicellular aggregations of cultured cells such as colonies, plant calli, suspension cultures and the like.

As mentioned above, in one preferred embodiment of the invention, the cell is a plant cell and as such, the present invention includes a whole plant, plant tissue, plant organ, plant part, plant reproductive material or cultured plant tissue, comprising one or more plant cells according to the sixth aspect of the invention.

In a more preferred embodiment, the present invention provides a cereal plant comprising one or more cells according to the sixth aspect of the invention.

In a particularly preferred embodiment, the present invention provides cereal grain comprising one or more cells according to the sixth aspect of the invention.

Therefore, in an eighth aspect, the present invention provides a cereal grain comprising an altered level of (1,3;1,4)-β-D-glucan, wherein the grain comprises one or more cells comprising an altered level and/or activity of (1,3;1,4)-β-D-glucan synthase and/or altered expression of a (1,3;1,4)-β-D-glucan synthase encoding nucleic acid molecule.

In one embodiment, the grain of the eighth aspect of the invention may have an increased level of (1,3;1,4)-β-D-glucan compared to wild type grain from the same species. In an alternate embodiment, the grain may have a decreased level of (1,3;1,4)-β-D-glucan compared to wild type grain from the same species.

In a ninth aspect, the present invention also provides flour comprising:
  (i) flour produced by the milling of the grain of the eighth aspect of the invention; and
  (ii) optionally, flour produced by the milling of one or more other grains.

As such, the flour produced by the milling of the grain of the eighth aspect of the invention may comprise, for example approximately 10%, 20%, 30%, 40%, 50%, 60%, 70%, 80%, 90% or 100% by weight of the flour of the ninth aspect of the invention.

As referred to herein "milling" contemplates any method known in the art for milling grain, such as those described by Brennan et al. (*Manual of Flour and Husk Milling*, Brennan et al. (Eds.), AgriMedia, ISBN: 3-86037-277-7).

Preferably the flour produced by the milling of the grain of the eighth aspect of the invention used in the flour of the ninth aspect of the invention comprises an increased level of (1,3;1,4)-β-D-glucan compared to wild type flour.

The "flour produced by the milling of one or more other grains" may be flour produced by milling grain derived from any cereal plant, as hereinbefore defined. This component of the flour of the eighth aspect of the invention may, for example, comprise 0%, 10%, 20%, 30%, 40%, 50%, 60%, 70%, 80% or 90% by weight.

In a preferred embodiment, the flour produced by the milling of one or more other grains is a wheat flour and, therefore, the flour of the ninth aspect of the invention may be suitable for producing bread, cakes, biscuits and the like.

As set out above, the present invention is predicated, in part, on the identification and isolation of nucleotide and amino acid sequences that encode (1,3;1,4)-β-D-glucan synthases.

Therefore, in a tenth aspect, the present invention provides an isolated nucleic acid molecule that encodes a (1,3;1,4)-β-D-glucan synthase.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (e.g. polymerase chain reaction and the like).

The isolated nucleic acid molecules of the present invention may be composed of any polyribonucleotide or polydeoxribonucleotide, which may be unmodified RNA or DNA or modified RNA or DNA. For example, the isolated nucleic acid molecules of the invention can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the isolated nucleic acid molecules can be composed of triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In an eleventh aspect, the present invention also provides an isolated nucleic acid molecule comprising one or more of:
  (i) the nucleotide sequence set forth in any of SEQ ID NO: 1, SEQ ID NO: 3, SEQ ID NO: 5, SEQ ID NO: 7, SEQ ID NO: 9 and SEQ ID NO: 11;
  (ii) a nucleotide sequence which is at least 50% identical to the nucleotide sequence set forth in any of SEQ ID NO: 1, SEQ ID NO: 3, SEQ ID NO: 5, SEQ ID NO: 7, SEQ ID NO: 9 and SEQ ID NO: 11;
  (iii) a nucleotide sequence which hybridises to a nucleic acid molecule comprising the nucleotide sequence set forth in any of SEQ ID NO: 1, SEQ ID NO: 3, SEQ ID NO: 5, SEQ ID NO: 7, SEQ ID NO: 9 and SEQ ID NO: 11 under low stringency, more preferably medium stringency and most preferably high stringency conditions;
  (iv) a nucleotide sequence which encodes the amino acid sequence set forth in any of SEQ ID NO: 2, SEQ ID NO: 4, SEQ ID NO: 6, SEQ ID NO: 8, SEQ ID NO: 10 and SEQ ID NO: 12.
  (v) a nucleotide sequence which is the complement of any one of (i) to (iv);
  (vi) a nucleotide sequence which is the reverse complement of any one of (i) to (iv);
  (vii) a fragment of any one of (i) to (vi).

As referred to in this eleventh aspect of the invention, the term "at least 50% identical" should be understood to also include nucleotide sequence percentage identities greater than 50%. For example, the term "at least 50% identical" preferably encompasses at least 60% identity, at least 70% identity, at least 80% identity, at least 90% identity and at least 95% identity.

In a preferred embodiment, the isolated nucleic acid molecule or fragment thereof comprises a nucleotide sequence encoding a (1,3;1,4)-β-D-glucan synthase, as herein before defined. In a more preferred embodiment, the isolated nucleic acid molecule comprises a nucleotide sequence defining a CslF gene, or functional homolog thereof, as hereinbefore defined.

As set out above, the eleventh aspect of the invention provides fragments of a nucleotide sequence. "Fragments" of a nucleotide sequence should be at least 15 nucleotides (nt), and more preferably at least 20 nt, still more preferably at least 30 nt, and even more preferably, at least 40, 50, 100, 150, 200, 250, 300, 325, 350, 375, 400, 450, 500, 550, or 600 nt in length. These fragments have numerous uses that include, but are not limited to, diagnostic probes and primers. Of course, larger fragments, such as those of 601-3000 nt in length are also useful according to the present invention as are fragments corresponding to most, if not all, of the nucleotide sequences SEQ ID NO: 1. By a fragment at least 20 nt in length, for example, is intended fragments which include 20 or more contiguous bases from, for example, the nucleotide sequence of SEQ ID NO: 1.

Preferably, the polynucleotide fragments of the invention encode a polypeptide, having (1,3;1,4)-β-D-glucan synthase functional activity as defined herein.

Polypeptides or proteins encoded by these polynucleotides are also encompassed by the invention.

In a twelfth aspect, the present invention provides a genetic construct or vector comprising an isolated nucleic acid molecule of the eleventh aspect of the invention.

In addition to the nucleic acid of the eleventh aspect of the invention, the vector or construct of the twelfth aspect of the invention preferably further comprises one or more of: an origin of replication for one or more hosts; a selectable marker gene which is active in one or more hosts; or one or more control sequences which enable transcription of the isolated nucleic acid molecule in a cell.

As used herein, the term "selectable marker gene" includes any gene that confers a phenotype on a cell, in which it is expressed, to facilitate the identification and/or selection of cells which are transfected or transformed with a genetic construct of the invention.

"Selectable marker genes" include any nucleotide sequences which, when expressed by a cell, confer a phenotype on the cell that facilitates the identification and/or selection of these transformed cells. A range of nucleotide sequences encoding suitable selectable markers are known in the art.

Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (e.g. nptI and nptII) and hygromycin phosphotransferase genes (e.g. hpt); herbicide resistance genes including glufosinate, phosphinothricin or bialaphos resistance genes such as phosphinothricin acetyl transferase encoding genes (e.g. bar), glyphosate resistance genes including 3-enoyl pyruvyl shikimate 5-phosphate synthase encoding genes (e.g. aroA), bromyxnil resistance genes including bromyxnil nitrilase encoding genes, sulfonamide resistance genes including dihydropterate synthase encoding genes (e.g. sul) and sulfonylurea resistance genes including acetolactate synthase encoding genes; enzyme-encoding reporter genes such as GUS and chloramphenicolacetyltransferase (CAT) encoding genes; fluorescent reporter genes such as the green fluorescent protein-encoding gene; and luminescence-based reporter genes such as the luciferase gene, amongst others.

Furthermore, it should be noted that the selectable marker gene may be a distinct open reading frame in the construct or may be expressed as a fusion protein with the (1,3;1,4)-β-D-glucan synthase protein.

The twelfth aspect of the invention extends to all genetic constructs essentially as described herein, which include further nucleotide sequences intended for the maintenance and/or replication of the genetic construct in prokaryotes or eukaryotes and/or the integration of the genetic construct or a part thereof into the genome of a eukaryotic or prokaryotic cell.

In one preferred embodiment, the construct of the twelfth aspect of the invention is adapted to be at least partially transferred into a plant cell via *Agrobacterium*-mediated transformation. Accordingly, in a particularly preferred embodiment, the construct according to the twelfth aspect of the invention comprises left and/or right T-DNA border sequences.

Suitable T-DNA border sequences would be readily ascertained by one of skill in the art. However, the term "T-DNA border sequences" should be understood to encompass any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA*, 82(15): 5112-5116, 1985) and the review of Gelvin (Microbiology and Molecular Biology Reviews, 67(1): 16-37, 2003).

Although in one preferred embodiment, the construct of the twelfth aspect of the invention is adapted to be transferred into a plant via *Agrobacterium*-mediated transformation, the present invention also contemplates any suitable modifications to the genetic construct which facilitate bacterial mediated insertion into a plant cell via bacteria other than *Agrobacterium* sp., as described in Broothaerts et al. (*Nature* 433: 629-633, 2005).

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell. Exemplary methods for cloning nucleic acid molecules are described in Sambrook et al. (2000, supra)

In a thirteenth aspect, the present invention provides a cell comprising the isolated nucleic acid molecule of the tenth or eleventh aspects of the invention or genetic construct of the twelfth aspect of the invention.

The isolated nucleic acid molecule of the tenth or eleventh aspects of the invention or genetic construct of the twelfth aspect of the invention may be introduced into a cell via any means known in the art.

The isolated nucleic acid molecule or construct referred to above may be maintained in the cell as a DNA molecule, as part of an episome (e.g. a plasmid, cosmid, artificial chromosome or the like) or it may be integrated into the genomic DNA of the cell.

As used herein, the term "genomic DNA" should be understood in it's broadest context to include any and all DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like.

Preferably, the isolated nucleic acid molecule is operably connected to, inter alia, a promoter such that the cell may express the isolated nucleic acid molecule.

The cell of the thirteenth aspect of the invention may be any prokaryotic or eukaryotic cell. As such, the cell may be a prokaryotic cell such as a bacterial cell including an *E. coli* cell or an *Agrobacterium* spp. cell, or an archaea cell. The cell may also be a eukaryotic cell including a fungal cell such as a yeast cell or mycelial fungus cell; an animal cell such as a mammalian cell or an insect cell; or a plant cell. In a preferred embodiment, the cell is a plant cell. In a more preferred embodiment, the plant cell is a monocot plant cell. In a most preferred embodiment, the plant cell is a cereal plant cell.

In a fourteenth aspect, the present invention provides a multicellular structure, as hereinbefore defined, comprising one or more of the cells of the thirteenth aspect of the invention.

As mentioned above, in one preferred embodiment, the cell is a plant cell and as such, the present invention should be understood to specifically include a whole plant, plant tissue, plant organ, plant part, plant reproductive material, or cultured plant tissue, comprising one or more cells of the thirteenth aspect of the invention.

In a more preferred embodiment, the present invention provides a cereal plant or part thereof, comprising one or more cells of the thirteenth aspect of the invention.

In a particularly preferred embodiment, the fourteenth aspect of the invention provides cereal grain comprising one or more cells of the thirteenth aspect of the invention.

As set out above, the present invention also provides amino acid sequences for (1,3;1,4)-β-D-glucan synthases.

Accordingly, in a fifteenth aspect, the present invention provides an isolated polypeptide comprising an amino acid sequence encoding a (1,3;1,4)-β-D-glucan synthase protein. Accordingly, the present invention provides an isolated (1,3;1,4)-β-D-glucan synthase protein.

As used herein, the term "polypeptide" should be understood to include any length polymer of amino acids. As such the term "polypeptide" should be understood to encompass peptides, polypeptides and proteins.

In a sixteenth aspect, the present invention provides an isolated polypeptide comprising one or more of:
(i) the amino acid sequence set forth in any of SEQ ID NO: 2, SEQ ID NO: 4, SEQ ID NO: 6, SEQ ID NO: 8, SEQ ID NO: 10 and SEQ ID NO: 12;
(ii) an amino acid sequence comprising at least 50% identity to the amino acid sequence set forth in any of SEQ ID NO: 2, SEQ ID NO: 4, SEQ ID NO: 6, SEQ ID NO: 8, SEQ ID NO: 10 and SEQ ID NO: 12;
(iii) an amino acid sequence encoded by the nucleotide sequence set forth in any of SEQ ID NO: 1, SEQ ID NO: 3, SEQ ID NO: 5, SEQ ID NO: 7, SEQ ID NO: 9 and SEQ ID NO: 11; and/or
(iv) a fragment of any one of (i), (ii) or (iii).

As referred to in this sixteenth aspect of the invention, the term "at least 50% identical" should be understood to also include percentage amino acid sequence identities greater than 50%. For example, the term "at least 50% identical" preferably encompasses at least 60% identity, at least 70% identity, at least 80% identity, at least 90% identity and at least 95% identity.

In a preferred embodiment, the isolated polypeptide of the present invention comprises an amino acid sequence defining a "(1,3;1,4)-β-D-glucan synthase" as hereinbefore defined.

The isolated polypeptides of the sixteenth aspect may be composed of amino acids joined to each other by peptide bonds or modified peptide bonds, i.e., peptide isosteres, and may contain amino acids other than the 20 gene-encoded amino acids. The isolated polypeptides of the present invention may be modified by either natural processes, such as post-translational processing, or by chemical modification techniques which are well known in the art. Such modifications are well described in basic texts and in more detailed monographs, as well as in the literature.

Modifications can occur anywhere in the isolated polypeptide, including the peptide backbone, the amino acid side-chains and/or the termini. It will be appreciated that the same type of modification may be present in the same or varying degrees at several sites in a given isolated polypeptide. Also, an isolated polypeptide of the present invention may contain many types of modifications.

The proteins may be branched, for example, as a result of ubiquitination, and/or they may be cyclic, with or without branching. Cyclic, branched, and branched cyclic polypeptides may result from post-translation natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties* $2^{nd}$ Ed., Creighton (ed.), W. H. Freeman and Company, New York, 1993); *Posttranslational Covalent Modification Of Proteins*, Johnson (Ed.), Academic Press, New York, 1983; Seifter et al., *Meth Enzymol* 182: 626-646, 1990); Rattan et al., *Ann NY Acad Sci* 663: 48-62, 1992.).

As set out above, the sixteenth aspect of the invention also provides fragments of isolated polypeptides. Polypeptide fragments may be "free-standing," or comprised within a larger polypeptide of which the fragment forms a part or region, most preferably as a single continuous region.

The protein fragments can be at least 3, 4, 5, 6, 8, 9, 10, 11, 12, 13, 15, 20, 25, 30, 35, 40, 45, 50, 60, 70, 80, 90, 100, 110, 120, 130, 140, or 150 amino acids in length. In one preferred embodiment, the fragment comprises an amino acid sequence which is a part of the sequence set forth in SEQ ID NO: 2.

In one preferred embodiment, the fragment comprises (1,3;1,4)-β-D-glucan synthase functional activity. However, even if the fragment does not retain one or more biological functions of the (1,3;1,4)-β-D-glucan synthase protein, other functional activities may still be retained. For example, the fragments may lack (1,3;1,4)-β-D-glucan synthase functional activity but retain the ability to induce and/or bind to antibodies which recognize the complete or mature forms of an isolated (1,3;1,4)-β-D-glucan synthase protein. A peptide, polypeptide or protein fragment which has the ability to induce and/or bind to antibodies which recognize the complete or mature forms of the isolated (1,3;1,4)-β-D-glucan synthase protein is referred to herein as a "(1,3;1,4)-β-D-glucan synthase epitope".

A (1,3;1,4)-β-D-glucan synthase epitope may comprise as few as three or four amino acid residues, preferably at least 5 amino acids and more preferably at least 10 amino acid residues. Whether a particular epitope of an isolated (1,3;1,4)-β-D-glucan synthase protein retains such immunologic activities can readily be determined by methods known in the art. As such, one preferred (1,3;1,4)-β-D-glucan synthase protein fragment is a polypeptide comprising one or more (1,3;1,4)-β-D-glucan synthase epitopes.

A polypeptide comprising one or more (1,3;1,4)-β-D-glucan synthase epitopes may be produced by any conventional means for making polypeptides including synthetic and recombinant methods known in the art. In one embodiment, (1,3;1,4)-β-D-glucan synthase epitope-bearing polypeptides may be synthesized using known methods of chemical synthesis. For instance, Houghten has described a simple method for the synthesis of large numbers of peptides (Houghten, *Proc. Natl. Acad. Sci. USA* 82: 5131-5135, 1985).

The isolated polypeptides and (1,3;1,4)-β-D-glucan synthase epitope-bearing polypeptides of the sixteenth aspect of the invention are useful, for example, in the generation of antibodies that bind to the isolated (1,3;1,4)-β-D-glucan synthase proteins of the invention.

Such antibodies are useful, inter alia, in the detection and localization of (1,3;1,4)-β-D-glucan synthase proteins and in affinity purification of (1,3;1,4)-β-D-glucan synthase proteins. The antibodies may also routinely be used in a variety of qualitative or quantitative immunoassays using methods known in the art. For example see Harlow et al., *Antibodies: A Laboratory Manual*, (Cold Spring Harbor Laboratory Press $2^{nd}$ Ed., 1988).

Accordingly, in a seventeenth aspect, the present invention provides an antibody or an epitope binding fragment thereof, raised against an isolated (1,3;1,4)-β-D-glucan synthase protein as hereinbefore defined or an epitope thereof.

The antibodies of the present invention include, but are not limited to, polyclonal, monoclonal, multispecific, chimeric antibodies, single chain antibodies, Fab fragments, F(ab') fragments, fragments produced by a Fab expression library and epitope-binding fragments of any of the above.

The term "antibody", as used herein, refers to immunoglobulin molecules and immunologically active portions of immunoglobulin molecules, i.e., molecules that contain an antigen-binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the present invention may be monospecific, bispecific, trispecific, or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. For example, see PCT publications WO 93/17715; WO 92/08802; WO 91/00360; WO 92/05793; Tutt et al., *J. Immunol.* 147: 60-69, 1991; U.S. Pat. Nos. 4,474,893; 4,714,681; 4,925,648; 5,573,920; 5,601,819; and Kostelny et al. *J. Immunol.* 148: 1547-1553, 1992).

In one embodiment, the antibodies of the present invention may act as agonists or antagonists of (1,3;1,4)-β-D-glucan synthase. In further embodiments, the antibodies of the present invention may be used, for example, to purify, detect, and target the polypeptides of the present invention, including both in vitro and in vivo diagnostic and therapeutic methods. For example, the antibodies have use in immunoassays for qualitatively and quantitatively measuring levels of (1,3;1,4)-β-D-glucan synthase in biological samples. See, e.g., Harlow et al., *Antibodies: A Laboratory Manual* (Cold Spring Harbor Laboratory Press, 2nd ed. 1988).

The term "antibody", as used herein, should be understood to encompass derivatives that are modified, e.g. by the covalent attachment of any type of molecule to the antibody such that covalent attachment does not prevent the antibody from binding to (1,3;1,4)-β-D-glucan synthase or an epitope thereof. For example, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc.

Furthermore, any of numerous chemical modifications may also be made using known techniques. These include specific chemical cleavage, acetylation, formylation, metabolic synthesis of tunicamycin, etc. Additionally, the derivative may contain one or more non-classical amino acids.

Antibodies may be generated using methods known in the art, such as in vivo immunization, in vitro immunization, and phage display methods. For example, see Bittle et al. (*J. Gen. Virol.* 66: 2347-2354, 1985).

If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For example, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

Animals such as rabbits, rats and mice are immunized with either free or carrier-coupled peptides, for instance, by intraperitoneal and/or intradermal injection of emulsions containing about 100 micrograms of peptide or carrier protein and Freund's adjuvant. Several booster injections may be needed, for example, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

For example, polyclonal antibodies to a (1,3;1,4)-β-D-glucan synthase protein or a polypeptide comprising one or more (1,3;1,4)-β-D-glucan synthase epitopes can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, for example, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

As another example, monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed., 1988) and Hammerling et al., in: *Monoclonal Antibodies and T-Cell Hybridomas* (Elsevier, N Y, 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. For example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Antibody fragments which recognize one or more (1,3; 1,4)-β-D-glucan synthase epitopes may also be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phages used in these methods are typically filamentous phage including fd and M13 binding domains expressed from phage with Fab, Fv or disulfide stabilized Fv antibody domains recombinantly fused to either the phage gene III or gene VIII protein.

Examples of phage display methods that can be used to make the antibodies of the present invention include those disclosed by Brinkman et al. (*J. Immunol. Methods* 182: 41-50, 1995), Ames et al. (*J. Immunol. Methods* 184: 177-186, 1995), Kettleborough et al. (*Eur. J. Immunol.* 24: 952-958, 1994), Persic et al. (*Gene* 187: 9-18, 1997), Burton et al. (*Advances in Immunology* 57: 191-280, 1994); PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571, 698; 5,427,908; 5,516,637; 5,780,225; 5,658,727; 5,733,743 and 5,969,108.

After phage selection, the antibody coding regions from the phage can be isolated and used to generate whole antibodies or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al. (*BioTechniques* 12(6): 864-869, 1992); and Sawai et al. (*AJRI* 34:26-34, 1995); and Better et al. (*Science* 240: 1041-1043, 1988).

Examples of techniques which can be used to produce single-chain Fvs and antibodies include those described in U.S. Pat. Nos. 4,946,778 and 5,258,498; Huston et al. (*Methods in Enzymology* 203: 46-88, 1991); Shu et al. (*Proc.*

Natl. Acad. Sci. USA 90: 7995-7999, 1993); and Skerra et al. (Science 240: 1038-1040, 1988).

The present invention is further described by the following non-limiting examples.

EXAMPLE 1

Identification of Candidate Genes Through Natural Variation of (1,3;1,4)-β-D-glucan Content in Barley Grain Comparative mapping studies have revealed that there is a high level of conservation of gene order along chromosomes of species of the Poaceae, although macro-colinearity at this level does not always predict gene presence or order at the micro level. Nevertheless, co-linearity at the megabase level is essential for the use of model species for positional cloning of genes, for development of molecular markers and for identifying candidate genes that affect a trait of interest in one species through reference to the syntenous region of a model species. Therefore, this approach was adopted to identify candidate genes for (1,3;1,4)-β-D-glucan synthases in cereals.

Quantitative trait loci (QTL) mapping and comparative genomics has been used to identify genes involved in cell wall biosynthesis in maize (Zea mays). Because of the central role played by (1,3;1,4)-β-D-glucans in malting and brewing quality, QTL analyses of grain (1,3;1,4)-β-D-glucan content are available. As shown in FIG. 1, the QTL that has the largest effect on grain (1,3;1,4)-β-D-glucan content was located on barley chromosome 2H, between the Adh8 and ABG019 markers.

Using the sequences of the two DNA markers that flank the barley QTL on chromosome 2H, a syntenic region was located on chromosome 7 of rice, where a cluster of six cellulose synthase-like (Csl) genes was detected within an interval of 119 Kb, corresponding to the 21.59-21.72 Mb region of the chromosome (FIG. 1).

Each of these genes was classified in the CslF group of rice and they were designated OsCslF1 (SEQ ID NO: 19), OsCslF2 (SEQ ID NO: 21), OsCslF3 (SEQ ID NO: 23), OsCslF4 (SEQ ID NO: 25), OsCslF8 (SEQ ID NO: 31) and OsCslF9 (SEQ ID NO: 33). Other known genes in this interval of rice chromosome 7 include truncated OsCslF genes that might represent pseudogenes.

The OsCslF5 (SEQ ID NO: 27) and OsCslF7 (SEQ ID NO: 29) genes are located elsewhere on the rice genome (data not shown).

On this basis, the comparative genomics approach enabled the identification of the CslF group of genes as potential candidate genes for (1,3;1,4)-β-D-glucan synthases in cereals. It is noteworthy that the CslF group of Csl genes is only found in monocotyledons, which is consistent with the exclusive occurrence of (1,3;1,4)-β-D-glucans in cell walls of the Poales.

Materials and Methods
(i) Plant Tissues

Tissues were collected from mature rice plants (Oryzae sativa cv Nippon Bare) grown at 28° C. day and 22° C. night temperatures under high humidity, a photointensity of 300 umol/m/s and an 11/13 hour day/night regime. Material was also collected from five day-old seedlings germinated at 28° C. in the dark on damp filter paper in Petri dishes.

(ii) Synteny Analysis

DNA sequences for the markers under the QTLs for barley (1,3;1,4)-β-D-glucan were obtained from the Grain-Genes database on the world wide web at wheat.pw.usda. gov. Additional markers from within the corresponding chromosomal locations on the Barley-Consensus2 (Qi et al., Genome 39: 379-394, 1996) and Barley-Consensus2003 (Karakousis et al., Australian Journal of Agricultural Research 54: 1173-1185, 2003) maps were also included in the investigation. The syntenic chromosomal location(s) for the markers on the rice genome were determined by BLASTN analyses at the GRAMENE website at gramene.org. Syntenic regions were examined for gene annotations of enzymes encoding for synthesis of cell wall polysaccharides. A thorough analysis of the region on rice chromosome 7 that corresponded to the QTL peak for (1,3;1,4)-β-D-glucan on barley chromosome 2H was carried out and six co-located CslF genes were identified for further analyses.

EXAMPLE 2

Transformation of Arabidopsis thaliana with Rice CslF Genes

The possible role of the rice OsCslF genes in (1,3;1,4)-β-D-glucan synthesis was tested by gain-of-function in transgenic Arabidopsis plants. Arabidopsis walls contain no (1,3;1,4)-β-D-glucan and the Arabidopsis genome does not contain any known CslF genes. Therefore, the deposition of (1,3;1,4)-β-D-glucan into walls of transgenic Arabidopsis plants carrying rice OsCslF genes would indicate that the introduced gene(s) encoded (1,3;1,4)-β-D-glucan synthases. This approach assumed and depended upon the availability in Arabidopsis of any precursors, intermediates, cofactors or ancillary enzymes needed for (1,3;1,4)-β-D-glucan synthesis.

Figure 2:
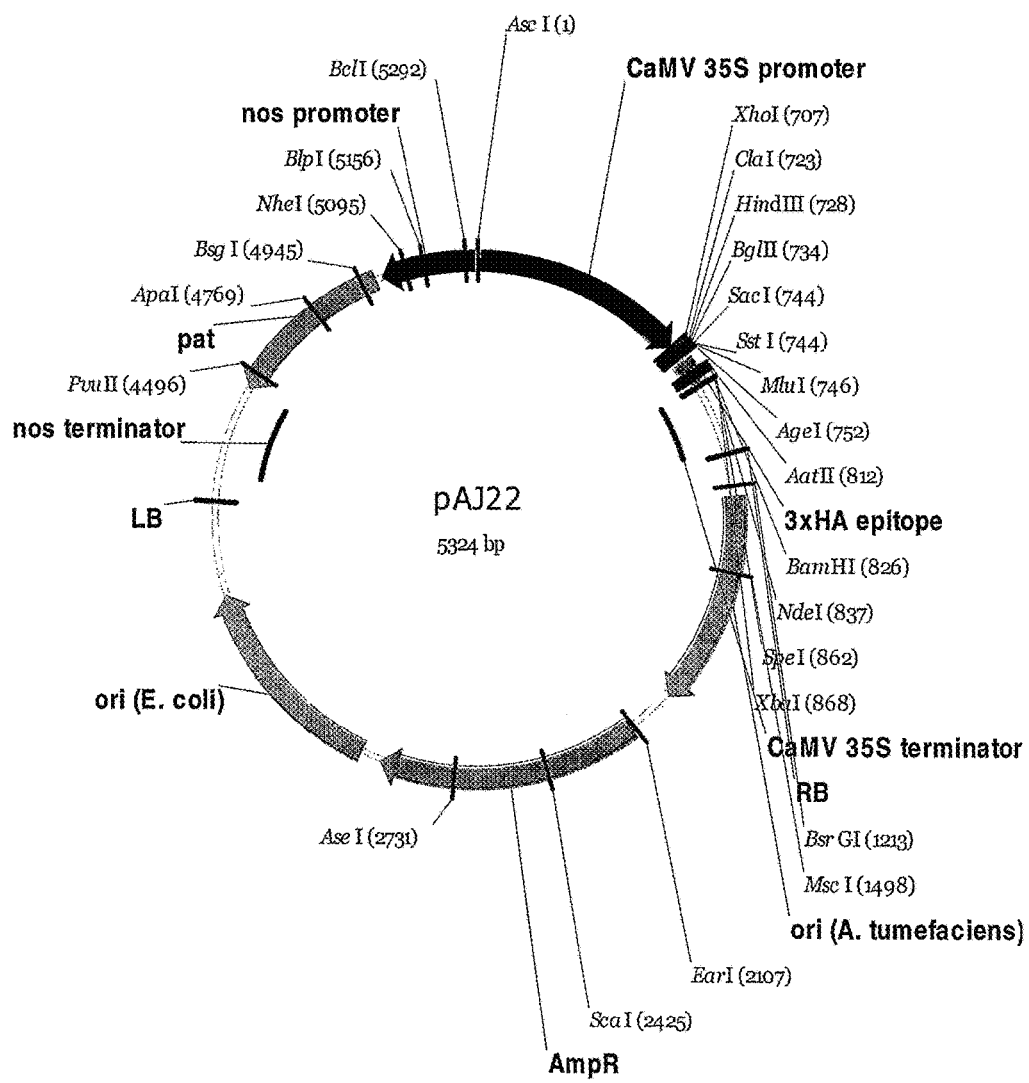
FIG. 2 shows a vector map of the pAJ22 vector used to express CslF genes in *Arabidopsis*.

Accordingly, the rice CslF1,2,3,4,8 genes were successfully amplified from cDNA by PCR and cloned into the pAJ22 binary vector, behind the 35S promoter, as shown in FIG. 2.

The plasmid vectors were subsequently inserted into Agrobacterium tumefaciens, which was used to transform Arabidopsis by standard floral dip procedures (Clough and Bent, Plant J. 16: 735, 1998). In case multiple OsCslF genes might be required for (1,3;1,4)-β-D-glucan synthesis, transformation was performed not only with single gene constructs, but also with various combinations of the OsCslF genes.

Following selection with the herbicide BASTA, DNA and RNA were isolated from selected transgenic plants to check for the presence of the transgene(s) and to monitor transcription of the transgenes by real-time, quantitative PCR (Q-FOR; as described by Burton et al. (2004, supra).

Figure 3:
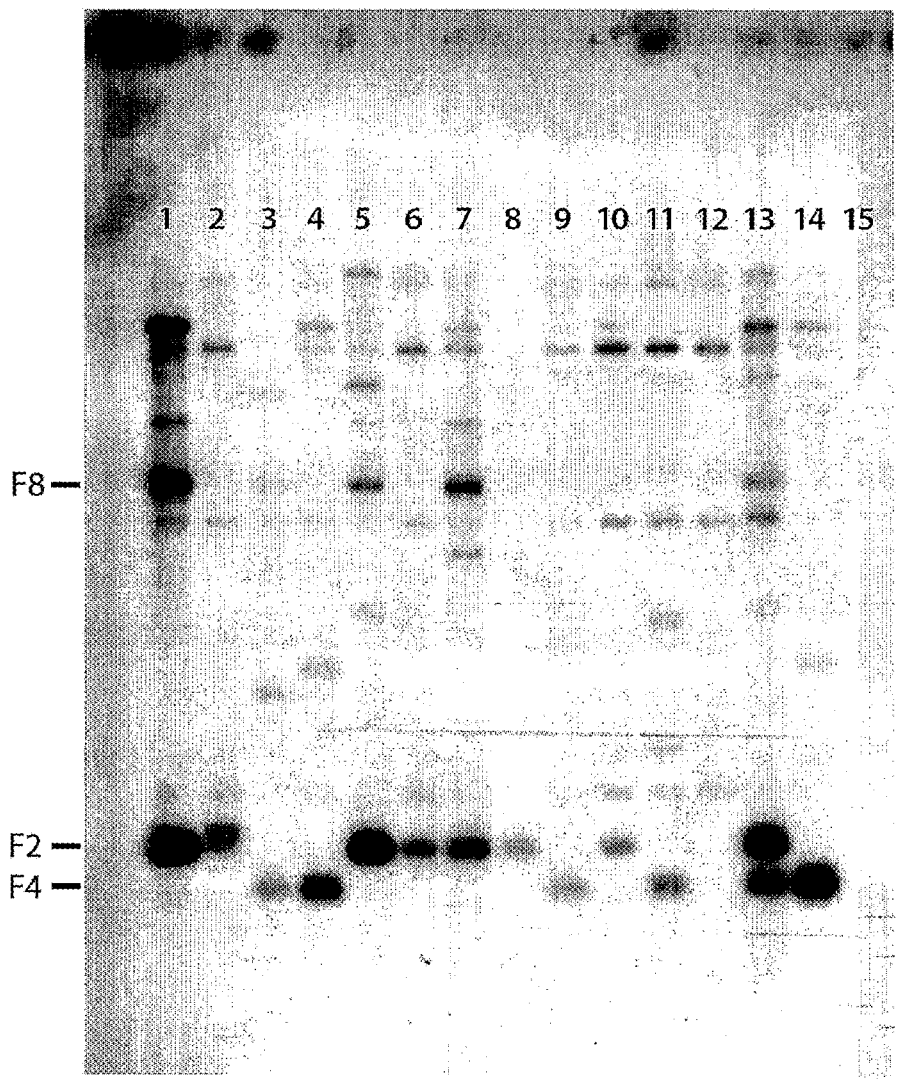
FIG. 3 is a Southern Blot showing XbaI and ScaI digested DNA derived from transformed *Arabidopsis* plants, which has been probed with fragments from OsCslF2, OsCslF4 and OsCslF8. The hybridizing fragments for these are marked on the figure as F2, F4 and F8. Track Numbers 1 to 14 are plant lines A2, A3, A7, A12, A16, A18, A21, A23, A28, A29, A31, A33, A41 and A42, respectively, while track 15 shows DNA derived from a wild-type Columbia plant.
Figure 4:
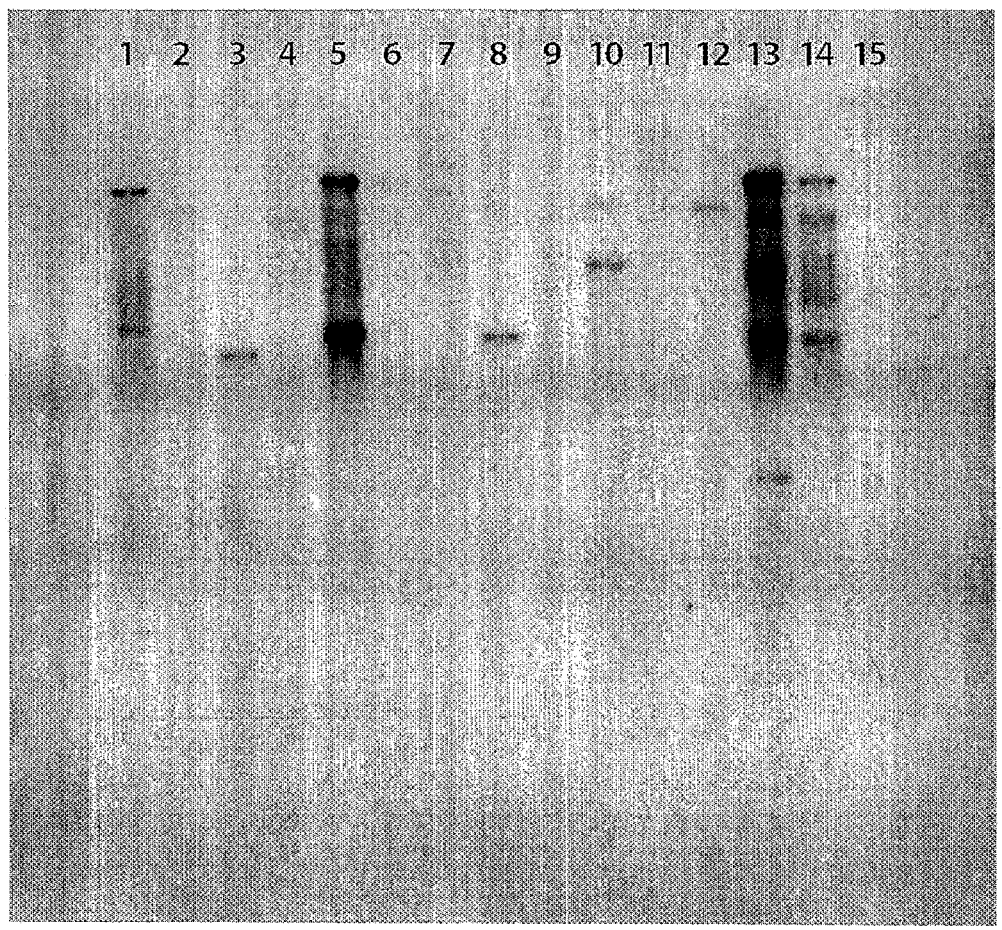
FIG. 4 is a Southern Blot showing XbaI digested DNA derived from transformed *Arabidopsis* plants, which has been probed with a fragment of the BAR gene. Track Numbers 1 to 14 are plant lines A2, A3, A7, A12, A16, A18, A21, A23, A28, A29, A31, A33, A41 and A42, respectively, while track 15 shows DNA derived from a wild-type Columbia plant.

Southern hybridization analyses confirmed the presence of the transgenes (FIG. 3). As shown in FIG. 4, at least some lines were found to contain single copies of the various OsCslF genes. Where the Arabidopsis was transformed with multiple OsCslF genes, all of those genes could be detected (FIG. 3).

Figure 5:
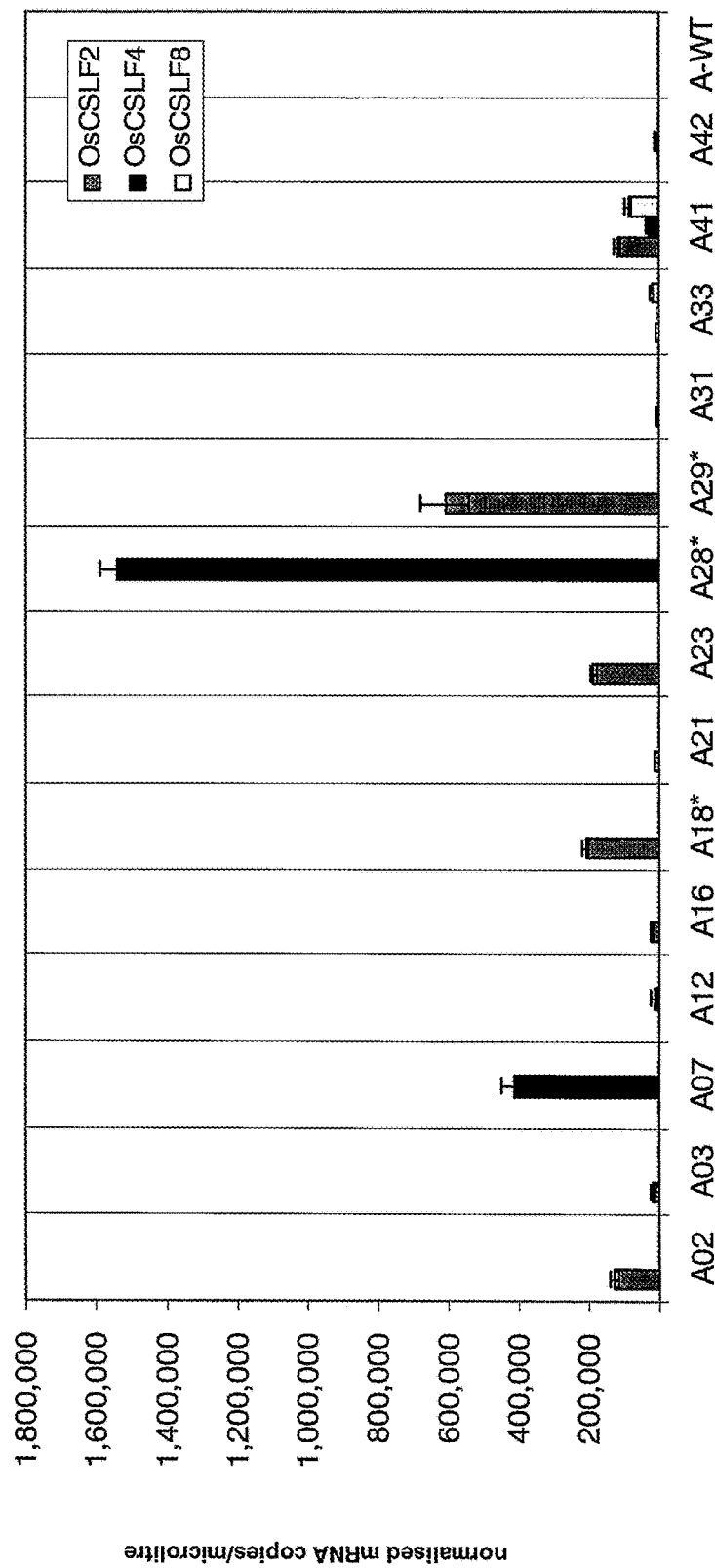
FIG. 5 shows normalized mRNA levels, as determined by Q-PCR, in the leaves of 14-day old transgenic *Arabidopsis* plant which express one or more of OsCslF2, OsCslF4 or OsCslF8.

Transcription of the OsCslF genes in 14-day old leaves of the transgenic lines was also confirmed. Normalized mRNA levels are shown for selected transgenic plants in FIG. 5, where large differences in transcriptional activity of the transgenes are evident between plant lines and where similarly large differences are observed between individual OsCslF genes in lines carrying more than one transgene. For example, in lines transformed with the OsCslF2, OsCslF4 and OsCslF8 genes, OsCslF4 transcripts were usually the highest in abundance. The results showed that the 35S promoter was clearly driving high level transcription in many lines.

Materials and Methods (i) Plants

Arabidopsis plants were grown in Arabidopsis soil mix at 23° C. in a growth chamber under either long 12/12 hr day/night or short 8/16 hr day/night conditions. Seed collected from transgenic plants was dried, cleaned, vernalised for 2 days at 4° C. and sown onto solid MS media containing 25 mg/l Bialophos for selection. Survivors were transplanted into soil at the five leaf stage and grown in growth rooms under the conditions described above.

(ii) Binary Vector Construction

The binary vector pAJ22 (FIG. 2) was kindly supplied by Dr. Andrew Jacobs (University of Adelaide) and is based on the pAMPAT-MCS backbone (accession no. AY436765). It contains a double 35S promoter with a pNOS terminator region, separated by a modified multiple cloning site that incorporates a triple HA epitope, which was not used in this instance. Full-length PCR products corresponding to the rice OsCslF cDNAs amplified as described above were cloned into the TEASY vector (Promega). Clones carrying an insert of the correct size were digested with the appropriate restriction enzymes (Table 2) and an enzyme to cut the TEASY backbone into two segments. The reactions were separated by agarose gel electrophoresis, the CslF fragments were excised and purified using the QIAquick (QIAGEN) gel extraction kit according to the manufacturer's instructions. The binary vector pAJ22 was digested with the corresponding pair of restriction enzymes and the CslF fragment was ligated into the pAJ22 vector. Plasmid DNA was extracted from positive clones using the QIAquick miniprep kit and inserts were sequenced using BigDye 3.1 chemistry (ABI) on an Applied Biosystems ABI3700 capillary sequencer. Plasmid DNA preparations containing verified inserts were transformed into Agrobacterium tumefaciens cv GV3101 via electroporation using the method of Mersereau et al. (Gene 90: 149, 1990) and positive colonies were selected on media containing 25 mg/l rifampicin, 48 mg/l carbenicillin and 50 mg/l kanamycin.

(iii) Arabidopsis Transformation

Arabidopsis transformants were generated by the floral dip method of Clough and Bent (Plant J. 16: 735, 1998).

(iv) DNA Extraction and Southern Hybridisation Analyses

Genomic DNA was extracted from young leaves and flower buds using the Qiagen miniprep plant kit. Approximately 5 μg genomic DNA per plant was digested with the relevant restriction enzymes and separated on a 1% agarose TAE gel. DNA was transferred to Highbond+ membranes. Membranes were pre-hybridised and hybridised and probe fragments were labelled using the Rediprime labelling kit (Amersham, High Wycome, UK) following the manufacturer's instructions.

(v) RNA Extraction, cDNA Synthesis and RT-PCR

All RNA extractions and cDNA syntheses were carried out as described in Burton et al. (Plant Physiol. 134: 224-236, 2004). Samples of cDNA from appropriate tissues were used as templates to amplify full-length CslF sequences, using Elongase Taq polymerase (Invitrogen) by PCR. Primer pairs, as listed in Table 2, were used in the PCR, following a standard recipe suggested by the manufacturer. Dimethylsulphoxide (DMSO, 5% v/v; Sigma, St Louis, Mo., USA) was added and PCR was performed for 40 cycles as follows; 94° C. for 30 sec, 50° C. to 58° C. (depending on the $T_m$ of individual primers) for 30 sec and 68° C. for 3 min. The primers contained restriction sites at each end, as indicated in Table 2, to facilitate cloning of the amplified fragment into the binary vector.

TABLE 2

Oligonucleotides used for amplification of rice CslF cDNAs.

| cDNA | Oligo | Oligonucleotide sequence | R.E. Site | Sequence Identifier |
|---|---|---|---|---|
| OsCslF2 | OsF2BII5 | AGTCAGATCTGTTCCG TGCATGGCGGCCACCG | BglII | SEQ ID NO: 35 |
| OsCslF2 | OsF2ML3 | CAGTACGCGTCGCGAT CGAACTGTCCCTACCC | MluI | SEQ ID NO: 36 |
| OsCslF3 | OsF3BII5 | AGTCAGATCTATAGAG TGCTCGTCATGGC | BglII | SEQ ID NO: 37 |
| OsCslF3 | OsF3ML3 | CAGTACGCGTTTTATC TATGCACCTAGAATGG | MluI | SEQ ID NO: 38 |
| OsCslF4 | OsF4H5 | AGTCAAGCTTGCTACG GCCTCCACGATGTCCG | HindIII | SEQ ID NO: 39 |
| OsCslF4 | OsF4S3 | CAGTACTAGTCATGTC GTCCCTACCCAGATGG | SpeI | SEQ ID NO: 40 |
| OsCslF8 | OsF8H5 | AGTCAAGCTTGCGACG ATCGATGGCGCTTTCG | HindIII | SEQ ID NO: 41 |
| OsCslF8 | OsF8S3 | CAGTACTACTTGCATC AATCAGAAACCCCGC | SpeI | SEQ ID NO: 42 |

(vi) Quantitative Real Time PCR (Q-PCR) Analysis

The primer pairs for control genes and specific CslF genes were used as indicated in Table 3. Stock solutions of PCR products for the preparation of dilution series were prepared by PCR from a cDNA derived from either a composite of rice or Arabidopsis tissue cDNAs, and was subsequently purified and quantified by HPLC, as described by Burton et al. (2004, supra). A dilution series covering seven orders of magnitude was prepared from the $10^9$ copies/μl stock solution as follows; one microliter of the stock solution was added to 99 μl of water, and six 1:10 serial dilutions were prepared to produce a total of seven solutions covering $10^7$ copies/μl to $10^1$ copies/μl. Three replicates of each of the seven standard solutions were included with every Q-PCR experiment, together with a minimum of three no-template controls. For all genes, a 1:20 dilution of the cDNA was sufficient to produce expression data with an acceptable standard deviation. Three replicate PCRs for each of the cDNAs were included in every run. All Q-PCR reaction mixes were prepared on a CAS-1200 robot (Corbett Robotics, Brisbane, Australia).

Two micrometers of the diluted cDNA solution were used in a reaction containing 5 μl QuantiTect SYBR Green PCR reagent, 1 μl each of the forward and reverse primers at 4 μM, 0.3 μl 10× SYBR Green in water (10,000× in DMSO, BioWhittaker Molecular Applications, Rockland, USA, 0.5 μl in 500 μl of water, prepared daily) and 0.7 μl water. The total volume of each Q-PCR reaction mixture was 10 μl. Reactions were performed in a RG 3000 Rotor-Gene Real Time Thermal Cycler (Corbett Research, Sydney, Australia) as follows; 15 min at 95° followed by 45 cycles of 20 sec at 95°, 30 sec at 55°, 30 sec at 72° and 15 sec at the optimal acquisition temperature (AT) described in Table 3. A melt curve was obtained from the product at the end of the amplification by heating from 70° to 99°. After the experiment, the optimal cycle threshold (CT) was determined from the dilution series and the raw expression data was derived. The mean expression level and standard deviation for each set of three replicates for each cDNA was calculated.

The raw expression data for the exogenous CslF genes was scaled using the approach of Vandesompele et al. (*Genome Biol.* 3: 1-11, 2002). The normalisation factor derived from the best three of four *Arabidopsis* control genes was generated using the Genorm software (Vandesompele et al., supra, 2002). The raw expression data for the exogenous CslF genes in each cDNA was scaled by dividing the raw expression value by the normalisation factor for the particular cDNA.

Figure 7A:
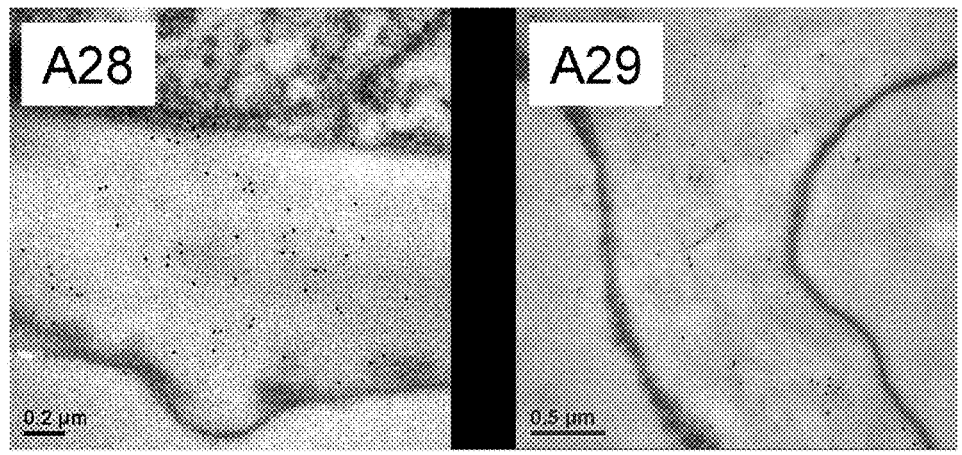
FIGS. 7A to 7C show transmission electron micrographs illustrating the detection of (1,3;1,4)-β-D-glucan in cell walls of several transgenic *Arabidopsis* plants with specific monoclonal antibodies.
Figure 7B:
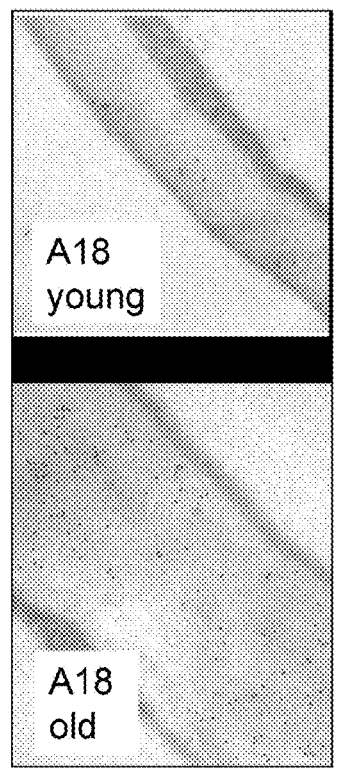
Figure 7C:
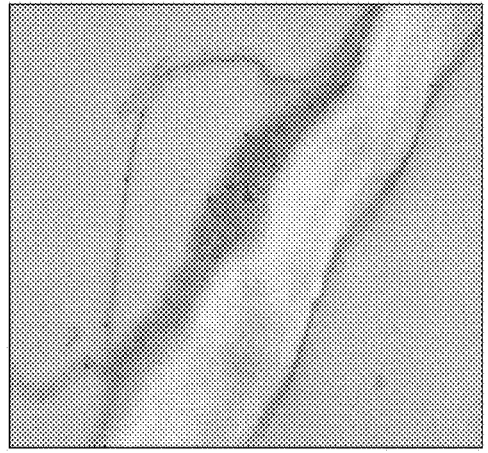

*Arabidopsis* lines A28, A29 and A18, as shown in FIGS. 7A to 7C. In FIG. 7B, walls from the epidermal layers of leaves from transgenic *Arabidopsis* line A18 are shown to accumulate (1,3;1,4)-β-D-glucan over a period of about fourteen days. The polysaccharide was not detected in other tissues of this line. Finally, FIG. 17C shows a representative control panel of a section of WT *Arabidopsis* leaf epidermal cell wall where minimal or no background labelling is commonly observed.

TABLE 3

Primers used for Q-PCR analysis.

| Gene | Forward Primer | Reverse Primer | amplicon (bp) | A T (° C.) |
|---|---|---|---|---|
| GAPDH At | TGGTTGATCTCGTTG TGCAGGTCTC (SEQ ID NO: 43) | GTCAGCCAAGTCAAC AACTCTCTG (SEQ ID NO: 44) | 262 | 77 |
| Tubulin At | ATGTGGGTGAGGGTA TGGAA (SEQ ID NO: 45) | CCGACAACCTTCTTA GTxCTCCTCT (SEQ ID NO: 46) | 143 | 78 |
| Actin At | GAGTTCTTCACGCGA TACCTCCA (SEQ ID NO: 47) | GACCACCTTTATTAA CCCCATTTACCA (SEQ ID NO: 48) | 180 | 76 |
| Cyclophilin At | TGGCGAACGCTGGTC CTAATACA (SEQ ID NO: 49) | CAAAAACTCCTCTGC CCCAATCAA (SEQ ID NO: 50) | 223 | 79 |
| OsCSLF2 | GTGCGCATACGAGGA TGGGACG (SEQ ID NO: 51) | AGAACATCTCCAGCG AGCCGCC (SEQ ID NO: 52) | 220 | 83 |
| OsCSLF3 | CCGATTGGGGCAAGG GTGTTGG (SEQ ID NO: 53) | GACACGCTGGAGAGG TTGGAGC (SEQ ID NO: 54) | 256 | 79 |
| OsCSLF4 | CTCCGTGTACACCTC CATGGAG (SEQ ID NO: 55) | CTCGGAGATGAGCCA CATCACC (SEQ ID NO: 56) | 255 | 82 |
| OsCSLF8 | TACGACATCGCGACG GAGGACG (SEQ ID NO: 57) | GTCATGTTGGCGTAC GCGACGC (SEQ ID NO: 58) | 244 | 83 |

EXAMPLE 3

Immunological Characterization of Transgenic *Arabidopsis* Lines

Transgenic *Arabidopsis* lines in which OsCslF transcript levels were highest were chosen for further analysis, in particular with respect to the deposition of (1,3;1,4)-β-D-glucan in cell walls. In the first instance, immunocytochemical methods involving monoclonal antibodies specific for (1,3;1,4)-β-D-glucans and electron microscopy were used to screen transgenic lines for the presence of the polysaccharide in the *Arabidopsis* lines. The antibody used does not bind with cellooligosaccharides or the (1→3)-β-D-glucan, callose. Inhibition studies showed that it binds relatively weakly to (1,3;1,4)-β-D-oligoglucosides.

Pieces of 14- and 28-day old leaves were sectioned for monoclonal antibody probing, and the antibody was routinely checked by pre-incubating tissue sections with commercially available barley (1,3;1,4)-β-D-glucan. Pre-incubation with the polysaccharide blocks the binding of gold-labelled secondary antibody. (1,3;1,4)-β-D-glucan was detected in cell walls of several transgenic *Arabidopsis* plants with the specific monoclonal antibodies, such as Materials and Methods (i) Preparation of Transformed *Arabidopsis* Leaves for Electron Microscopy

*Arabidopsis* leaves were fixed in 4% (v/v) glutaraldehyde (EM Grade) in phosphate-buffered saline (PBS), pH 7.2, and stored at 4° C. Samples were washed three times in PBS and post-fixed in a 2% osmium tetroxide solution in PBS for 1 h at room temperature. After three rinses in MilliQ water the samples were dehydrated in a graded ethanol series and slowly infiltrated with LR White resin over several days. Individual leaves were placed in gelatin capsules, which were filled with fresh resin and polymerized overnight at 65° C.

(ii) Immunolocation for Transmission Electron Microscopy

Sections (80 nm) of *Arabidopsis* leaves were prepared on a Leica Ultracut R microtome using a diamond knife and collected on 100 and 200 mesh, Formvar coated gold grids. The ultrathin sections were blocked for 30 min in 1% bovine serum albumin in PBS before incubation in murine monoclonal antibodies raised against barley (1,3;1,4)-β-D-glucan (diluted 1:500; Biosupplies Australia, Parkville, VIC 3052, Australia) for 1 hr at room temperature and overnight at 4° C. The grids were washed twice in PBS and three times in blocking buffer before a 1 h incubation in 18 nm Colloidal Gold-AffiniPure Goat-Anti Mouse IgG+IgM (H+L) (Jackson ImmunoResearch Laboratories, Inc., PA, USA). All grids were washed twice in PBS and several times in MilliQ water before staining in 2% aqueous uranyl acetate followed by triple lead citrate stain. The sections were viewed on a Philips BioTwin Transmission Electron Microscope and images captured on a Gatan Multiscan CCD Camera.

In some experiments the primary antibody was omitted to control for non-specific secondary antibody binding. Other control experiments involved pre-absorbing the primary antibodies to their respective polysaccharides to ensure the specificity of the antibody. Solutions (1 mg/ml) of (1,3;1,4)-β-D-glucan from barley (Biosupplies Australia) were mixed in equal volumes with their respective diluted primary antibodies. No labelling was observed in any of these negative control experiments.

Supplementary data relating to this experiment can be found in Burton et al., Science 311: 1940-1942, 2006.

EXAMPLE 4

Identification of CslF Sequences from Barley

Where available, partial EST barley sequences were assembled into complete CslF sequences, using the rice CslF sequences as a guide.

Where no barley EST sequences were available, putative wheat CslF EST sequences were identified, which were potentially highly homologous to the equivalent barley sequences. Primers were then designed on the basis of the wheat EST sequences and were then used on barley cDNA populations to amplify the equivalent barley sequence. 3' and 5' RACE approaches were then used to extend the barley sequences.

In a few cases additional parts of closely related barley genes for which there were no wheat ESTs were amplified, and these were also extended using RACE. In total, 6 different barley CslF sequences were identified, which were designated HvCslF1, HvCslF2, HvCslF3, HvCslF4, HvCslF5 and HvCslF6.

EXAMPLE 5

Alignment of CslF DNA and Amino Acid Sequences from Rice and Barley

An alignment of the DNA and amino acid sequences for the CslF sequences in both rice and barley was performed, the results of which are shown in FIG. 8.

The protein sequences were aligned and compared using the default parameters for the bl2seq pairwise alignment program at NCBI found on the world wide web at ncbi.nlm.nih.gov/blast/b12seq/wblast2.cgi. For the DNA alignments, the EMBOSS pairwise alignment algorithms found on the world wide web at ebi.ac.uk/emboss/align/ with the water(local) method was used.

Figure 9:
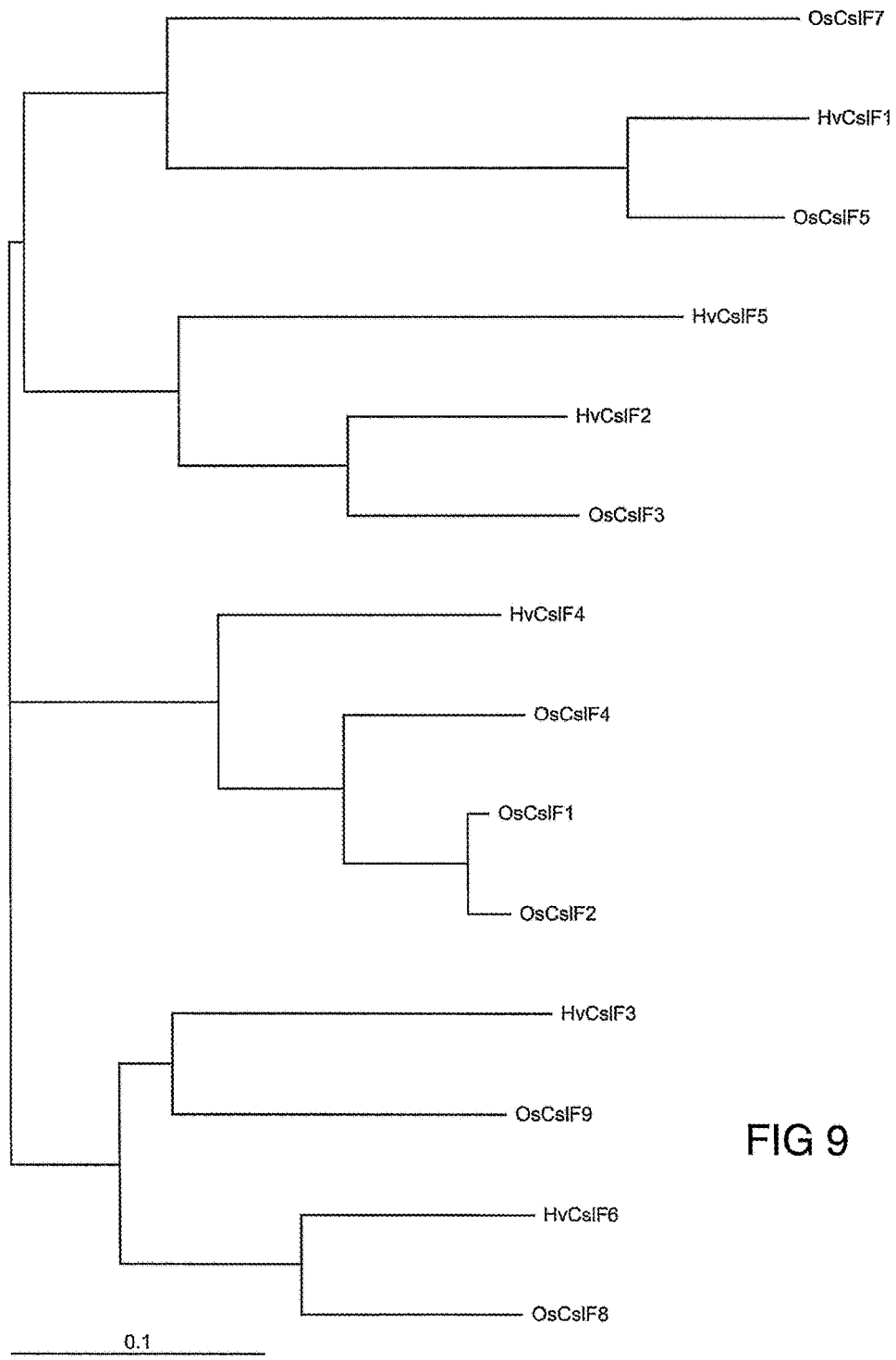
FIG. 9 is a phylogenetic tree showing the relationship of complete and partial CslF amino acid sequences derived from Barley (*Hordeum vulgare*) and Rice (*Oryza sativa*).

Multiple sequence alignments and phylogenetic tree generation was performed using the ClustalX program as described by Thompson et al. (*Nucl Acids Res* 25: 4876-4882, 1997). The resultant phylogenetic tree is shown in FIG. 9.

EXAMPLE 6

Mapping of the Barley CslF Genes

The QTL that has the largest effect on grain (1,3;1,4)-β-D-glucan content is located on barley chromosome 2H, between the Adh8 and ABG019 markers, markers, as mapped in the Steptoe×Morex doubled haploid (DH) population by Han et al. (*Theor. Appl. Genet.* 91: 921, 1995).

Specific gene fragments of the six barley CslF cDNAs generated by PCR were radiolabelled and used as probes on DNA from a set of wheat barley addition lines (Islam and the Clipper×Sahara barley DH populations to establish firstly their chromosomal location and then to fine map the genes.

Figure 10:
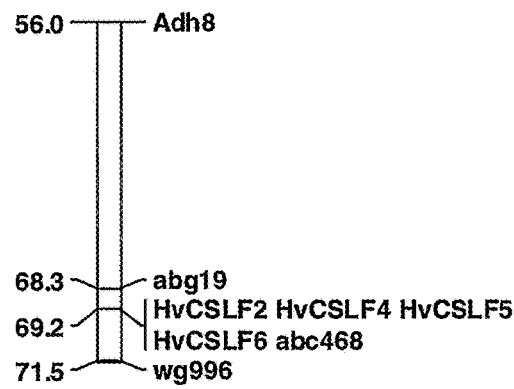
FIG. 10 shows the location of HvCslF2, 4, 5 and 6 genes on chromosome 2H of the Steptoe×Morex (S×M 2H) Bin map. Key markers (as FIG. 1) are shown on the right-hand side and distances from the top of the chromosome in centimorgans are indicated on the left-hand side.

Use of the wheat-barley addition lines showed that HvCslF2, 4, 5 and 6 are found on chromosome 2H, HvCslF1 is found on 7H and HvCslF3 is found on 1 HS. Identification of polymorphisms between the Clipper and Sahara barley cultivars (parent lines) for HvCsl2, 4, 5 and 6 and the subsequent screening of the DH mapping population created from these parents allowed the accurate map location of these genes to be defined (FIG. 10). These four barley CslF genes are therefore found to be coincident with the major QTL for grain (1,3;1,4)-β-D-glucan content on barley chromosome 2H. This implies that one or more of these genes is likely to directly influence barley grain (1,3;1,4)-β-D-glucan content.

Materials and Methods

Filters of digested genomic DNA of the wheat barley addition lines (Islam et al., *Heredity* 46: 161-174 1981) were used to map the genes to the chromosome level. The barley DH mapping population Clipper×Sahara was used to fine map the HvCslF genes (Karakousis et al., *Aust. J. Ag. Res.* 54: 1137-1140, 2003). Professor Peter Langridge (Australian Centre for Plant Functional Genomics, University of Adelaide) kindly supplied both sets of filters of digested genomic DNA for Southern Hybridization analyses using standard methods. Loci were positioned using the Map Manager QTX software (Manly et al., *Mammalian Genome* 12: 930-932, 2001).

EXAMPLE 7

Overexpression of the Barley CslF Genes in Transgenic Barley Plants

Figure 11:
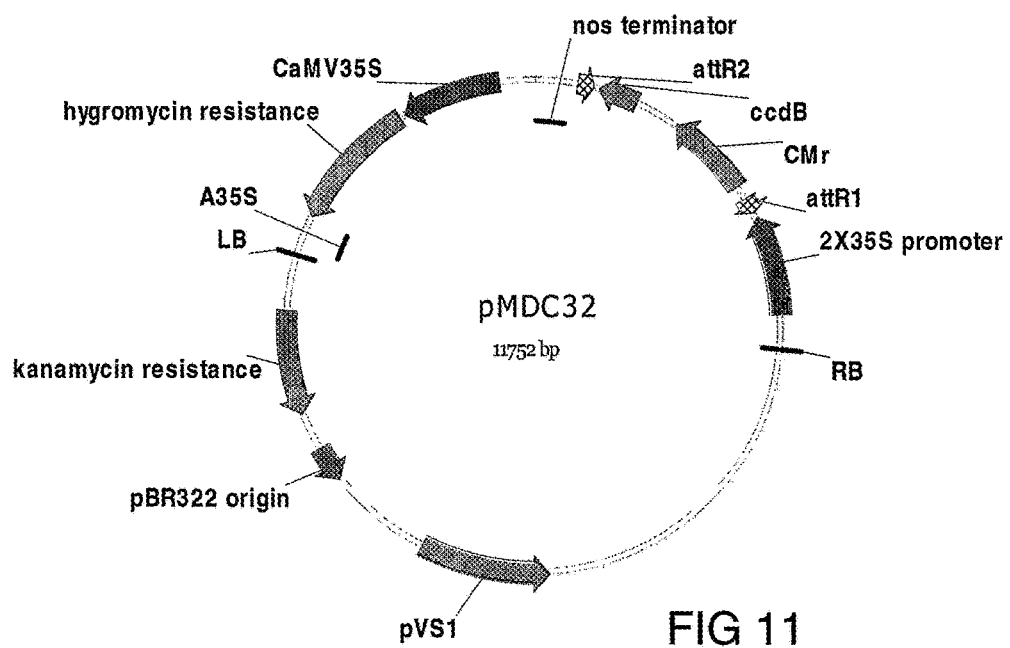
FIG. 11 shows a map of the pMDC32 vector

The role of individual members of the barley CslF gene family in (1,3;1,4)-β-D-glucan synthesis was tested by inserting the genes under the control of the strong constitutive promoter, CaMV 35S, into the genome of Golden Promise barley plants. The complete cDNAs for the barley genes CslF1, CslF4 and CslF6 were amplified by PCR using the primers shown in Table 4 and a high fidelity polymerase and sequenced to ensure that they contained no PCR-induced errors. The PCR fragments were cloned into the binary vector pMDC32, shown in FIG. 11.

The plasmid vectors were subsequently inserted into *Agrobacterium tumefaciens*, which was used to transform the barley cultivar Golden Promise by standard transformation procedures (Tingay et al. *Plant J.* 11: 1369-1376, 1997; Matthews et al. *Mol. Breeding* 7: 195-202, 2001)

Figure 12:
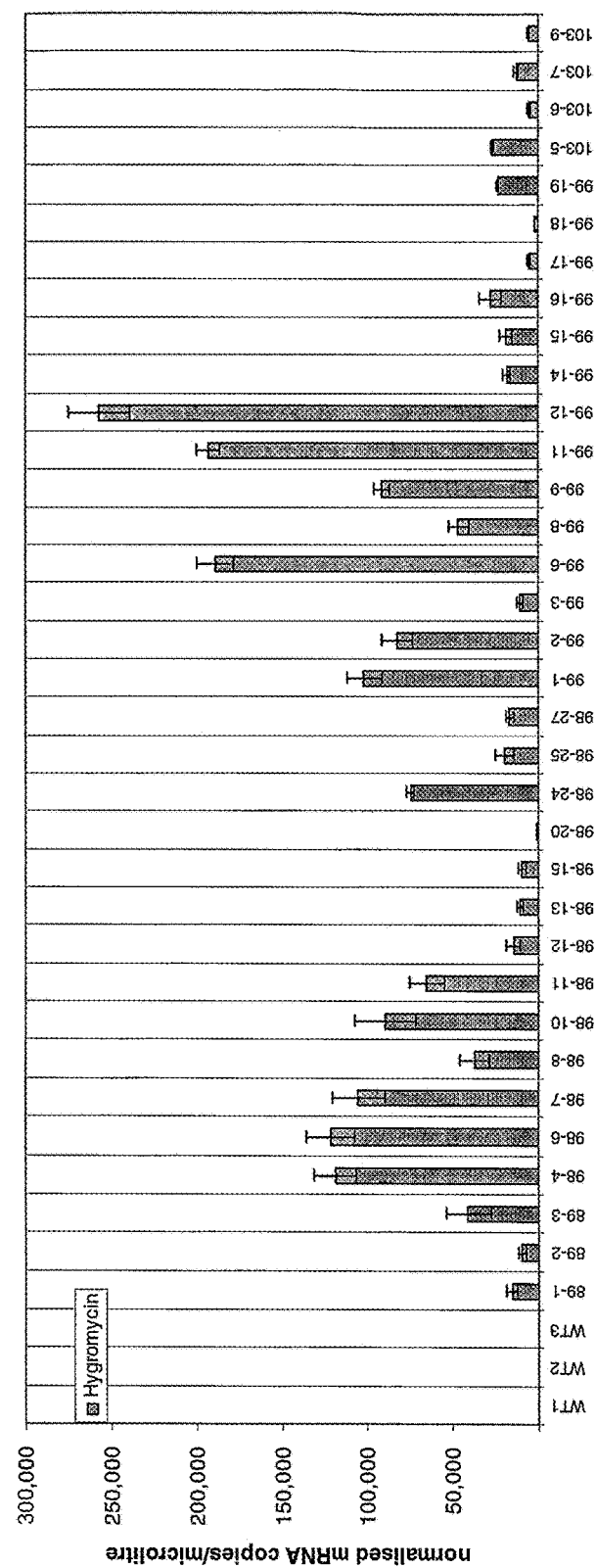
FIG. 12 shows the results of the QPCR analysis of hygromycin transcript levels in control and transgenic barley plants

Following selection with hygromycin, total RNA was extracted from the leaves of transgenic plantlets to monitor transcription of the endogenous and the integrated transgenes by Q-PCR (Burton et al. *Plant Phys.* 134: 224-236, 2004). The QPCR results for transcription of the selectable marker gene, hygromycin, using the primers shown in Table 5, are shown in FIG. 12. There is no PCR product for hygromycin in the cDNA of the wild type, non-transformed control plants (lines WT1-3) whilst all plants transgenic for the hygromycin transgene, including the transformed controls (G89 lines) which contain a gene unrelated to the CslF family, show positive levels of hygromycin QPCR product (FIG. 2)

Figure 13:
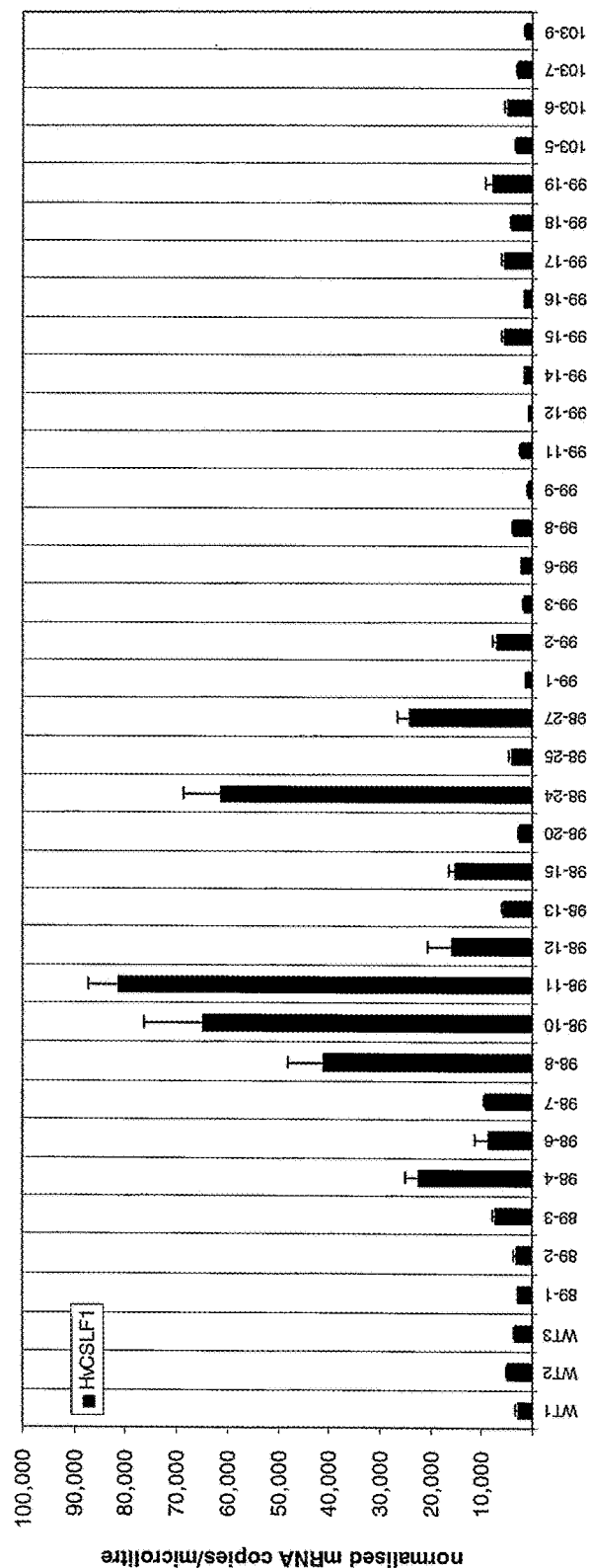
FIG. 13 shows the results of the QPCR analysis of HvCslF1 transcript levels in control and transgenic barley plants.
Figure 14:
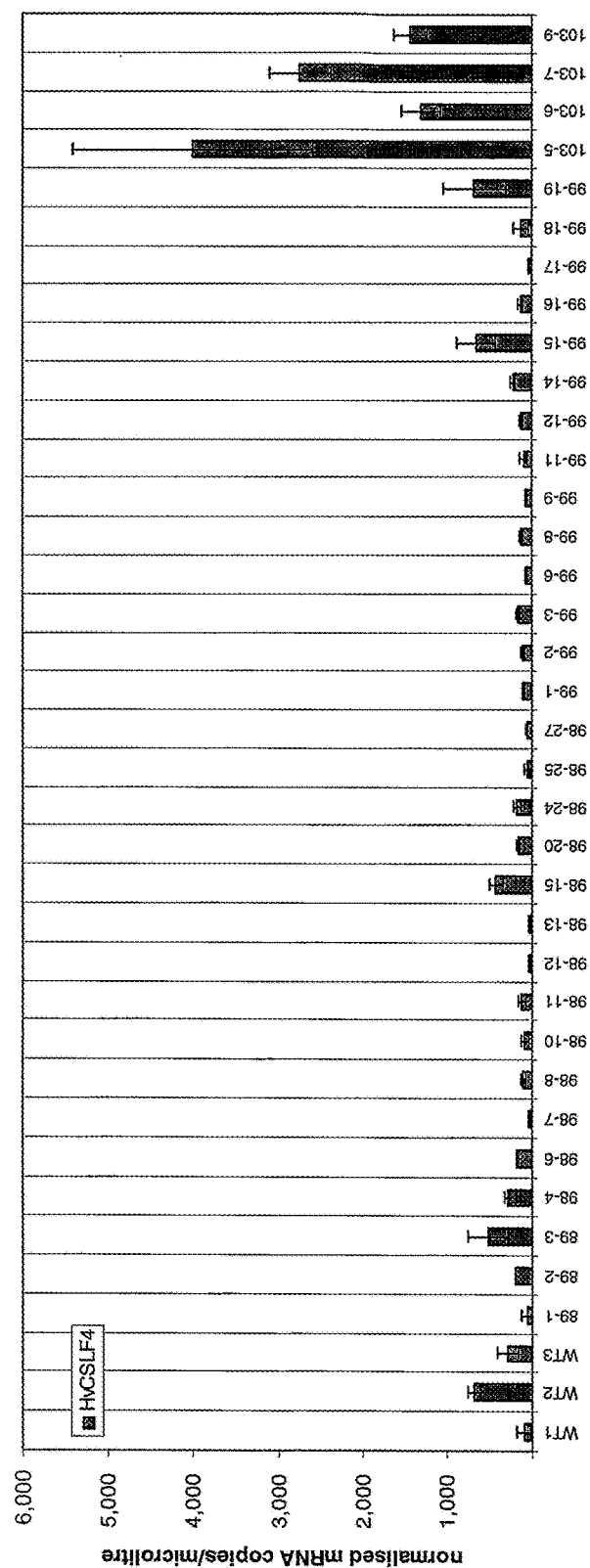
FIG. 14 shows the results of the QPCR analysis of HvCslF4 transcript levels in control and transgenic barley plants
Figure 15:
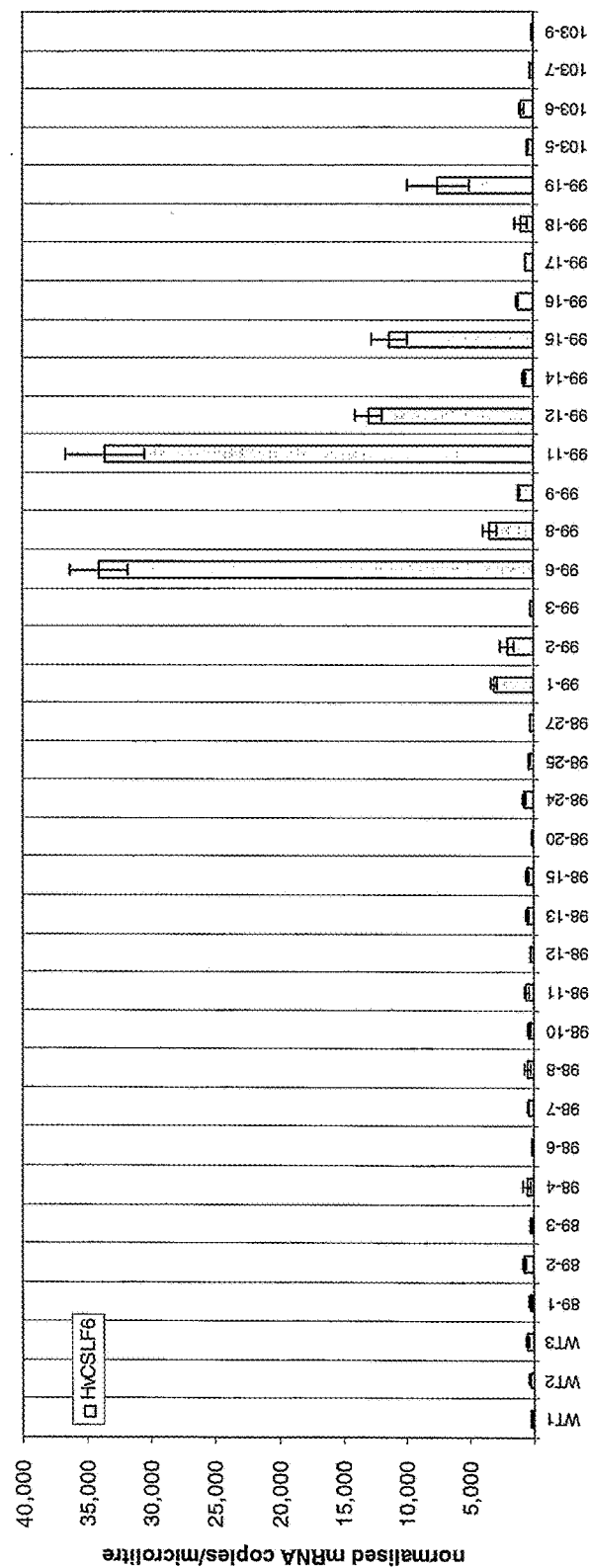
FIG. 15 shows the results of the QPCR analysis of HvCslF6 transcript levels in control and transgenic barley plants

Transcription of the three HvCslF genes was also examined in these plants using the primers given in Table 5. Normalized mRNA levels are shown for HvCslF1, HvCslF4 and HvCslF6 across the whole transgenic population and the control plants. Plants transformed with 35S:HvCslF1 are designated G98 and overexpression of the HvCslF1 gene in these lines is evident at significant levels above that of the endogenous gene in the WTC, G89, G99 and G103 groups (FIG. 13). Particularly high levels of transcripts are seen in plants 98-10, 98-11 and 98-24 (FIG. 13). Plants transformed with 35S:HvCslF4 are designated G103 and overexpression of the HvCslF4 gene in these lines is evident at significant levels above that of the endogenous gene in the WTC, G89, G98 and G99 groups (FIG. 14). The highest level of transcript is seen in plant 103-5 (FIG. 14). Finally, plants transformed with 35S:HvCslF6 are designated G99 and overexpression of the HvCslF6 gene in these lines is evident at significant levels above that of the endogenous gene in the WTC, G89, G98 and G103 groups (FIG. 15), with the highest number of transcripts seen in lines 99-6 and 99-11 (FIG. 15).

Materials and Methods.

(i) Binary Vector Construction

The binary vector pMDC32 was obtained from Dr Mark Curtis, University of Zurich, found on the world wide web at unizh.ch/botinst/Devo_Website/Curtis vector/index_2.html and is a Gateway-enabled (Invitrogen) binary vector carrying the hygromycin resistance gene and the CaMV 35S promoter suitable for use in barley transformation experiments where gene over-expression is desired (Curtis and Gossniklaus, *Plant Phys* 133: 462-469, 2003) Full-length PCR products corresponding to the barley HvCslF cDNAs amplified with the primers given in Table 4 were sequenced using BigDye 3.1 chemistry (ABI) on an Applied Biosystems ABI3700 capillary sequencer. Correct cDNAs were recombined into the Gateway entry vector pDENTR-Topo (Invitrogen). The orientation of the cDNA was verified by restriction enzyme digestion and then the entry clone was used in an LR recombination reaction (Invitrogen) with pMDC32 as the destination vector. Successful insertion into pMDC32 was confirmed by restriction enzyme digestion and plasmid DNA preparations containing verified inserts were transformed into *Agrobacterium tumefaciens* cv AGL0 via electroporation using the method of Mersereau at al. (*Gene* 90: 149, 1990) and positive colonies were selected on media containing 25 mg/l rifampicin, and 25 mg/l kanamycin.

(ii) Barley Transformation

*Agrobacterium tumefaciens*-mediated transformation experiments were performed using the procedure developed by Tingay et al. (1997, supra) and modified by Matthews et al. (2001, supra). The developing spikes were harvested from donor plants (cv. Golden Promise) grown in the glasshouse when the immature embryos were approximately 1-2 mm in diameter. The immature embryos were aseptically excised from the surface-sterilised grain, and the scutella were isolated by removing the embryonic axis. Twenty five freshly isolated scutella were cultured cut side-up in the centre of a 90 mm×10 mm Petri dish that contained callus induction medium, based on the recipe of Wan and Lemaux (*Plant Phys.* 104: 37-48, 1994). This medium was composed of MS macro-nutrients (Murashige and Skoog, *Physiologia Plant.* 15: 473-497, 1962), FHG micro-nutrients supplemented with 30 g/L maltose, 1 mg/L thiamine-HCl, 0.25 g/L myo-inositol, 1 g/L casein hydrolysate, 0.69 g/L L-proline, 10 µM $CuSO_4$, 2.5 mg/L Dicamba (3,6-dichloro-o-anisic acid), and was solidified with 3.5 g/L Phytagel™ (Sigma Chemicals, St. Louis, Mo., USA). *Agrobacterium* suspension (50 µl) was aliquotted onto the scutella, and the Petri dish was held at a 45° angle to drain away excess bacterial suspension. The explants were turned over and dragged across the surface of the medium to the edge of the Petri dish. The scutella were transferred to a fresh plate of callus induction medium and cultured cut side-up for three days in the dark at 22-24° C. Following co-cultivation, the scutella were removed to fresh callus induction medium containing 95 µM hygromycin B (Becton Dickinson Biosciences, Palo Alto, Calif., USA) and cultured in the dark. The entire callus of an individual scutellum was transferred to fresh selection medium every fortnight for a further six weeks. At the end of the callus selection period, the callus derived from each treated scutellum was transferred to shoot regeneration medium. This medium was based on the FHG recipe of Wan and Lemaux (1994, supra). It contained FHG macro- and micro-nutrients, 1 mg/L thiamine-HCl, 1 mg/L benzylaminopurine, 0.25 g/L myo-inositol, 0.73 g/L L-glutamine, 62 g/L maltose, 10 µM $CuSO_4$, 38 µM hygromycin B, and was solidified with 3.5 g/L Phytagel™. The cultures were exposed to light (16 h day/8 h night photo-period) for three to four weeks at 22-24° C. The regenerated shoots were excised from the callus and transferred to culture boxes (Magenta Corporation, Chicago, Ill., USA) that contained hormone-free callus induction medium, supplemented with 95 µM hygromycin B to induce root formation. The tissue culture-derived plants that grew vigorously were established in soil and grown to maturity (Singh et al. Plant Cell, Tissue and Organ Culture 49:121-127 1997). All the media contained 150 mg/L Timentin® (SmithKline Beecham, Pty. Ltd., Melbourne, Australia) to inhibit the growth of *Agrobacterium tumefaciens* following co-cultivation.

(iii) RNA Extraction and cDNA Synthesis.

Total RNA was extracted from the leaves of plantlets growing in Magenta boxes, as described above, using TRIZOL, and cDNA was synthesised using the reverse transcriptase Superscript III (Invitrogen) as described in Burton et al. (*Plant Phys* 134: 224-236, 2004).

(iv) Quantitative Real Time PCR (Q-PCR) Analysis

The primer pairs for control genes (Burton et al., 2004, supra) and specific CslF genes were used as indicated in Table 5. Stock solutions of PCR products for the preparation of dilution series were prepared by PCR from a cDNA derived from either a composite of barley tissue cDNAs, and was subsequently purified and quantified by HPLC, as described by Burton et al. (2004, supra). A dilution series covering seven orders of magnitude was prepared from the $10^9$ copies/µl stock solution as follows; one microliter of the stock solution was added to 99 µl of water, and six 1:10 serial dilutions were prepared to produce a total of seven solutions covering $10^7$ copies/µl to $10^1$ copies/µl. Three replicates of each of the seven standard solutions were included with every Q-PCR experiment, together with a minimum of three no-template controls. For all genes, a 1:20 dilution of the cDNA was sufficient to produce expression data with an acceptable standard deviation. Three replicate PCRs for each of the cDNAs were included in every run. All Q-PCR reaction mixes were prepared on a CAS-1200 robot (Corbett Robotics, Brisbane, Australia).

Two microliters of the diluted cDNA solution were used in a reaction containing 5 µl QuantiTect SYBR Green PCR reagent, 1 µl each of the forward and reverse primers at 4 µM, 0.3 µl 10×SYBR Green in water (10,000× in DMSO, BioWhittaker Molecular Applications, Rockland, USA, 0.5 µl in 500 µl of water, prepared daily) and 0.7 µl water. The total volume of each Q-PCR reaction mixture was 10 µl. Reactions were performed in a RG 3000 Rotor-Gene Real Time Thermal Cycler (Corbett Research, Sydney, Australia) as follows; 15 min at 95° followed by 45 cycles of 20 sec at 95°, 30 sec at 55°, 30 sec at 72° and 15 sec at the optimal acquisition temperature (AT) described in Table 5. A melt curve was obtained from the product at the end of the amplification by heating from 70° to 99°. After the experiment, the optimal cycle threshold (CT) was determined from the dilution series and the raw expression data was derived. The mean expression level and standard deviation for each set of three replicates for each cDNA was calculated.

The raw expression data for the HvCslF genes was scaled using the approach of Vandesompele et al. (*Genome Biol.* 3: 1-11, 2002). The normalisation factor derived from the best three of four barley control genes (Burton et al., 2004, supra) was generated using the Genorm software. (Vandesompele et al., 2002, supra). The raw expression data for the exogenous CslF genes in each cDNA was scaled by dividing the raw expression value by the normalisation factor for the particular cDNA.

TABLE 4

Primers used for amplification of barley CslF cDNAs

| Hv CslF1 | HvFD5END | GGAGAGCGCGTG CATTGAGGACG | SEQ ID NO: 59 |
|---|---|---|---|
| Hv CslF1 | HvFDRQ | TGTCCGGGCAAA GTCATCAA | SEQ ID NO: 60 |
| Hv CslF4 | HvFC5N | GCACGGTAGGCA CTTACACTATGG | SEQ ID NO: 61 |
| Hv CslF4 | HvFC3N | TTGCAGTGACTC TGGCTGTACTTG | SEQ ID NO: 62 |
| Hv CslF6 | HvFH5 | GTAGCTGGCTAC TGTGCATAGC | SEQ ID NO: 63 |
| Hv CSLF6 | HvFF3N | GAACTTACAAAC CCCAGCTTGTGG | SEQ ID NO: 64 |
| Hv CslF1 | HvFD5END | GGAGAGCGCGTG CATTGAGGACG | SEQ ID NO: 59 |

TABLE 5

Primers used for Q-PCR analysis.

| Gene | Forward Primer | Reverse Primer | amplicon (bp) | A T (° C.) |
|---|---|---|---|---|
| Hyg | GTCGATCGACAGATC CGGTC (SEQ ID NO: 65) | GGGAGTTTAGCGAGA GCCTG (SEQ ID NO: 66) | 291 | 82 |
| Hv CslF1 | TGGGCATTCACCTTC GTCAT (SEQ ID NO: 67) | TGTCCGGGCAAACTC ATCAA (SEQ ID NO: 68) | 157 | 81 |
| Hv CslF4 | CCGTCGGGCTCGTGT ATGTC (SEQ ID NO: 69) | TTGCAGTGACTCTGG CTGTACTTG (SEQ ID NO: 70) | 144 | 79 |
| Hv CslF6 | GGGATTGTTCGGTTC CACTTT (SEQ ID NO: 71) | GCTGTTGCTTTGCCA CATCTC (SEQ ID NO: 72) | 250 | 77 |

EXAMPLE 8

Immunological Detection of (1,3;1,4)-β-D-glucans in Transgenic Barley Lines at the Light Microscope Level Transgenic barley lines as described in Example 7, in which the HvCslF1, HvCslF4 or HvCslF6 transcript levels driven by the 35S promoter were highest, were chosen for further analysis, with respect to the deposition of (1,3;1,4)-beta-D-glucan in the cell walls. Leaf sections were screened for the presence of the polysaccharide in the barley lines using an immunocytochemical method in which a monoclonal antibody specific for (1,3;1,4)-β-D-glucan (as described in Example 3) is detected by a fluorophore-conjugated secondary antibody and observed by light microscopy. Due to expression of endogenous CslF genes (1,3;1,4)-β-D-glucans are normally deposited in the cell walls of vegetative tissues such as leaf, and their occurrence and distribution in the emergent tissues of the barley seedling has been documented at the TEM level by Trethewey and Harris (*New Phytologist* 154: 347-358, 2002). Here we contrast the distribution pattern of endogenous (1,3;1,4)-β-D-glucans in control leaf sections with patterns displayed by transgenic leaf samples over-expressing barley CslF genes.

Figure 16:
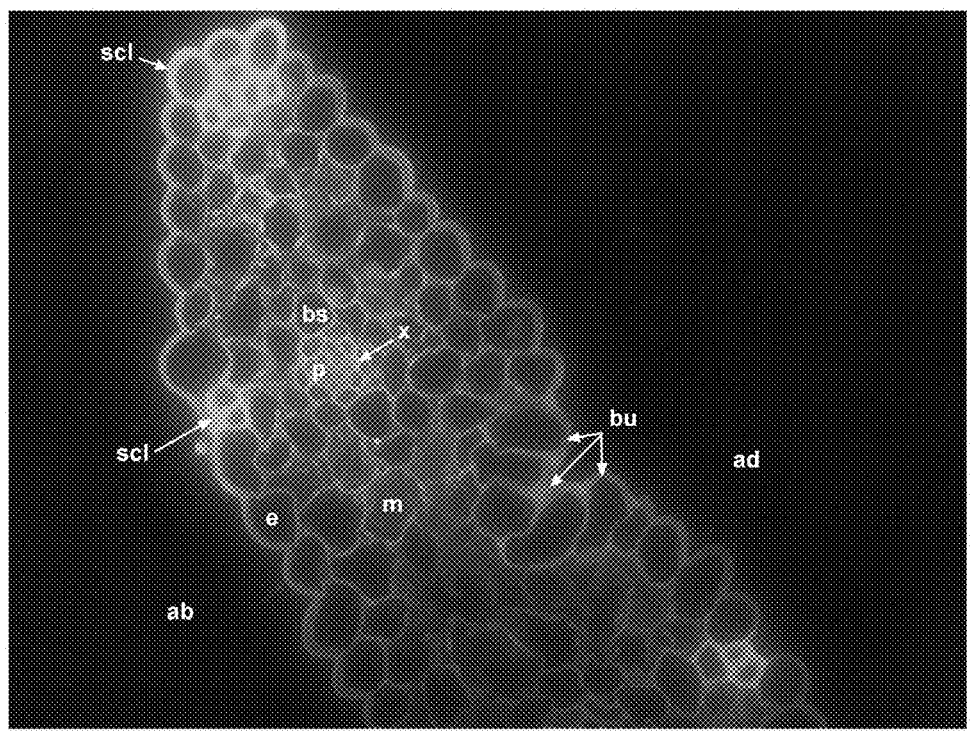
FIG. 16 shows leaf autofluorescence under UV to demonstrate cell morphology. ab=abaxial surface, ad=adaxial surface, bs=bundle sheath cell, bul=bulliform cell, e=epidermal cell, m=mesophyll cell, p=phloem, scl=sclerenchyma fibre, st=stomate, x=xylem.

Leaf pieces representative of the plant groups described in example 7 were harvested, fixed and embedded in paraffin. Slide-mounted sections were treated with the specific monoclonal antibody which binds to (1,3;1,4)-beta-D-glucan (primary antibody) and, after washing, fluorophore-conjugated Alexa 488 (secondary antibody) was added. Sections were rinsed with buffer, mountant was added, and images were captured using a microscope with appropriate fluorescence filters. All images were taken at a standard exposure time of seven seconds. Overall morphology and the position of the various cell types were identified using the UV filter, which causes all cell wall material to fluoresce non-specifically (FIG. 16). Specific antibody signal was viewed using the 13 filter (FIG. 17 and FIGS. 18A-18E).

Figure 17:
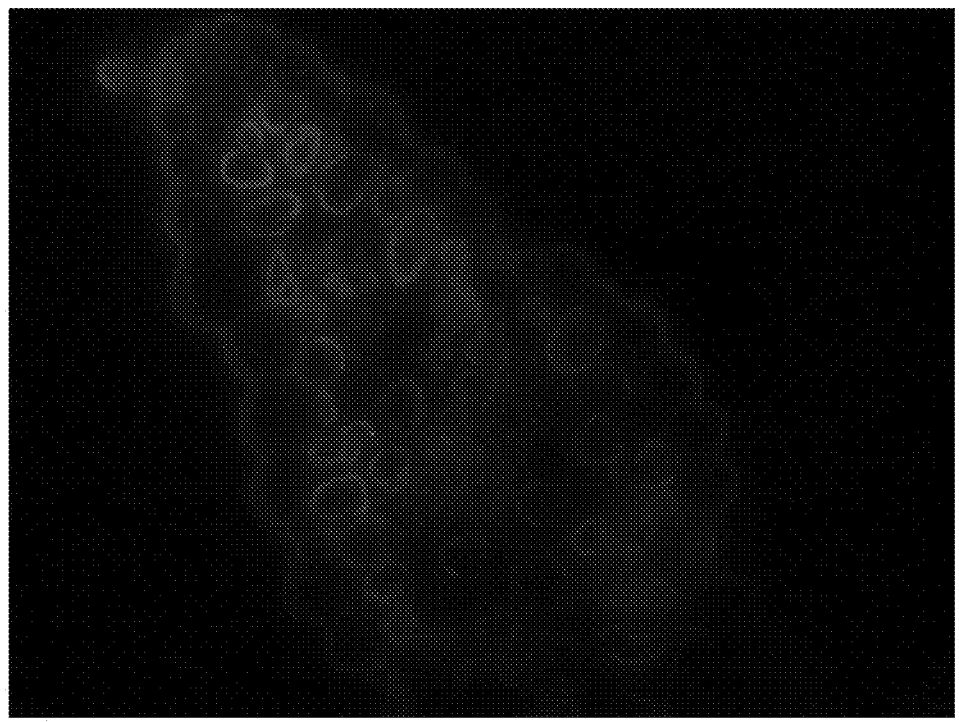
FIG. 17 shows G98-10 with both primary and secondary antibodies omitted from the labeling procedure, photographed at 7 seconds exposure under the 13 filter.
Figure 18A:
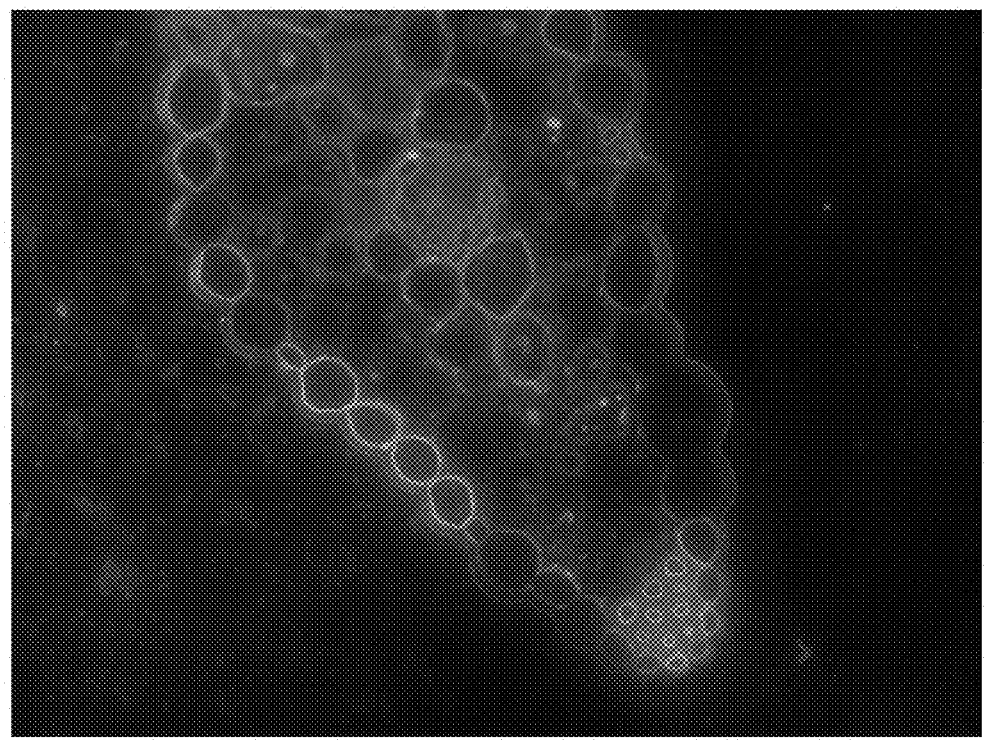
FIGS. 18A to 18D show transgenic plants compared with control plants (FIGS. 18E and 18F) all photographed at 7 seconds exposure under the 13 filter.
Figure 18B:
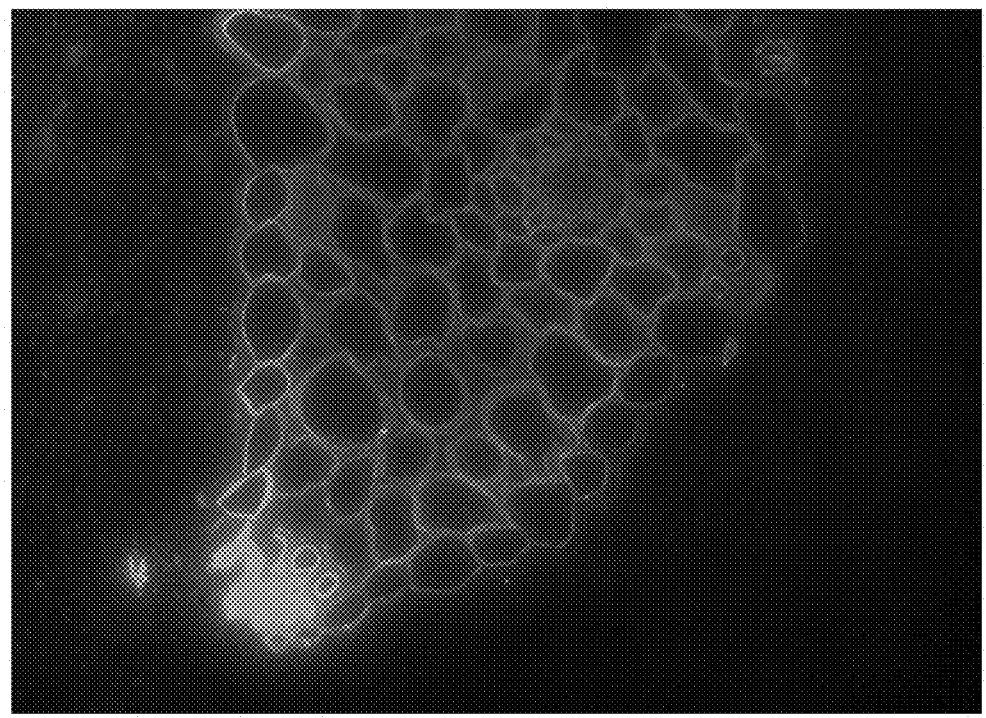
Figure 18C:
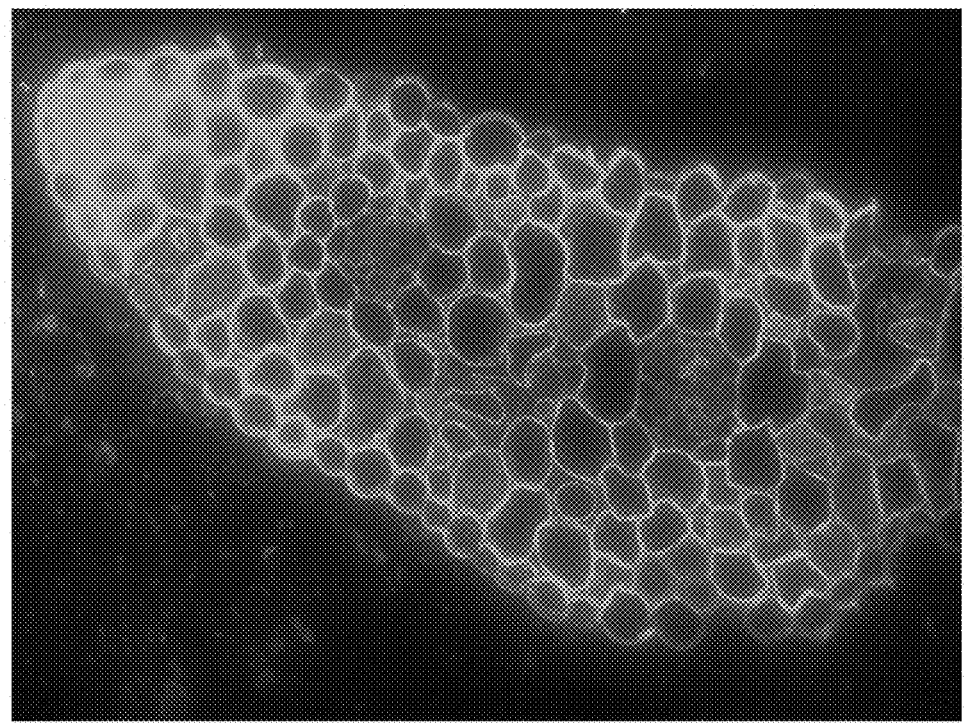
Figure 18D:
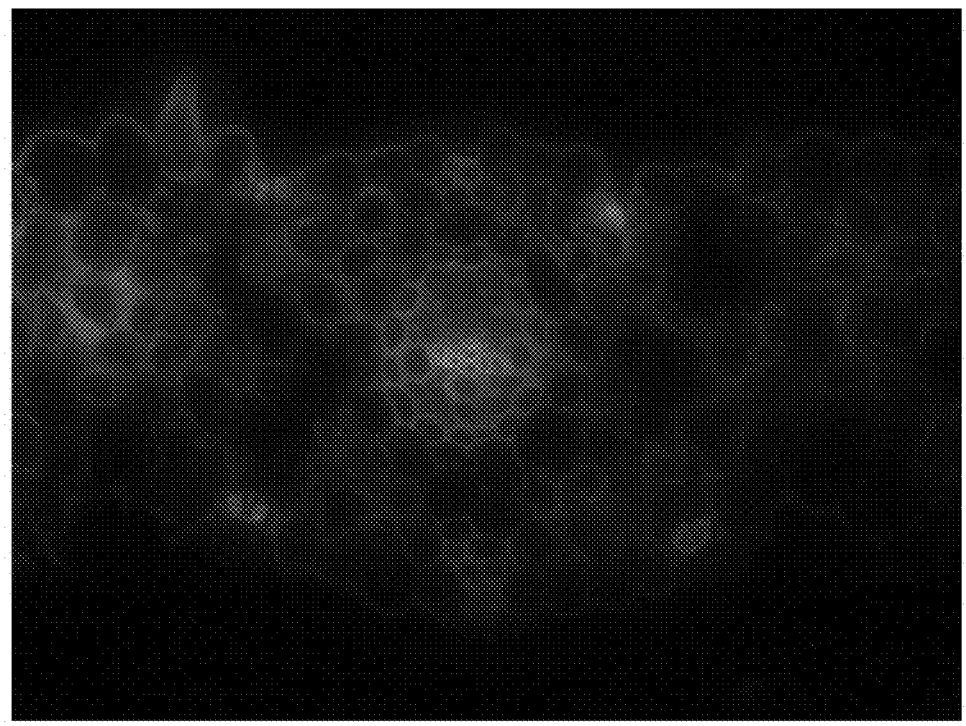
Figure 18E:
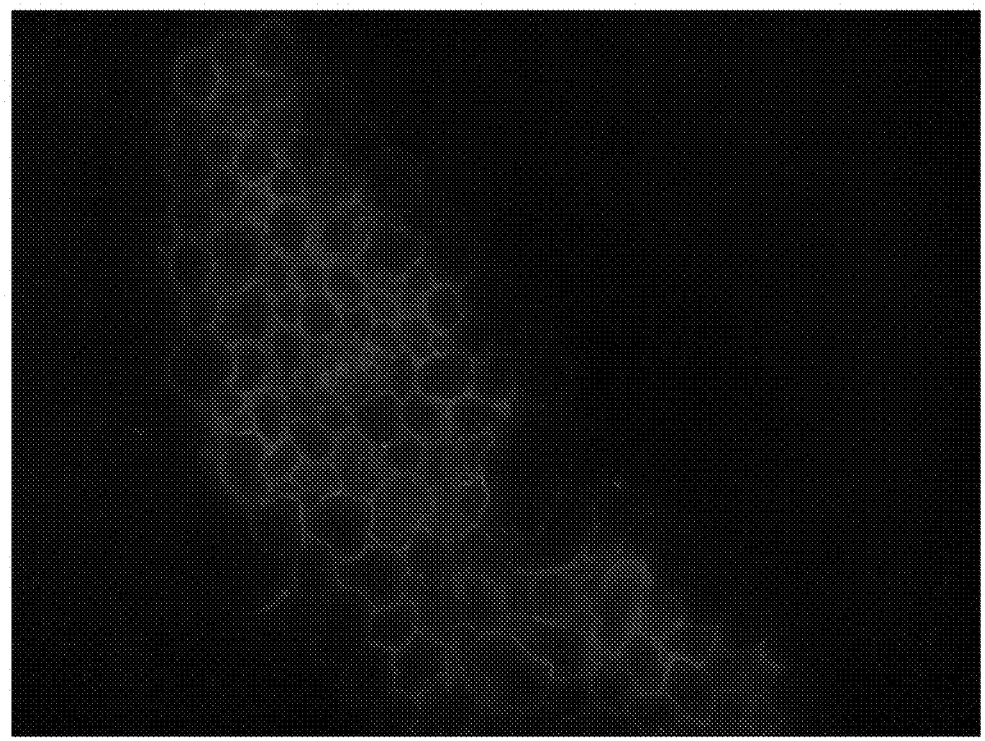
FIG. 18E) WT control showing fluorescence signal from endogenous (1,3;1,4)-β-D-glucans, FIG. 18F) transgene control G89-1 showing fluorescence from endogenous (1,3;1,4)-β-D-glucans.
Figure 18F:
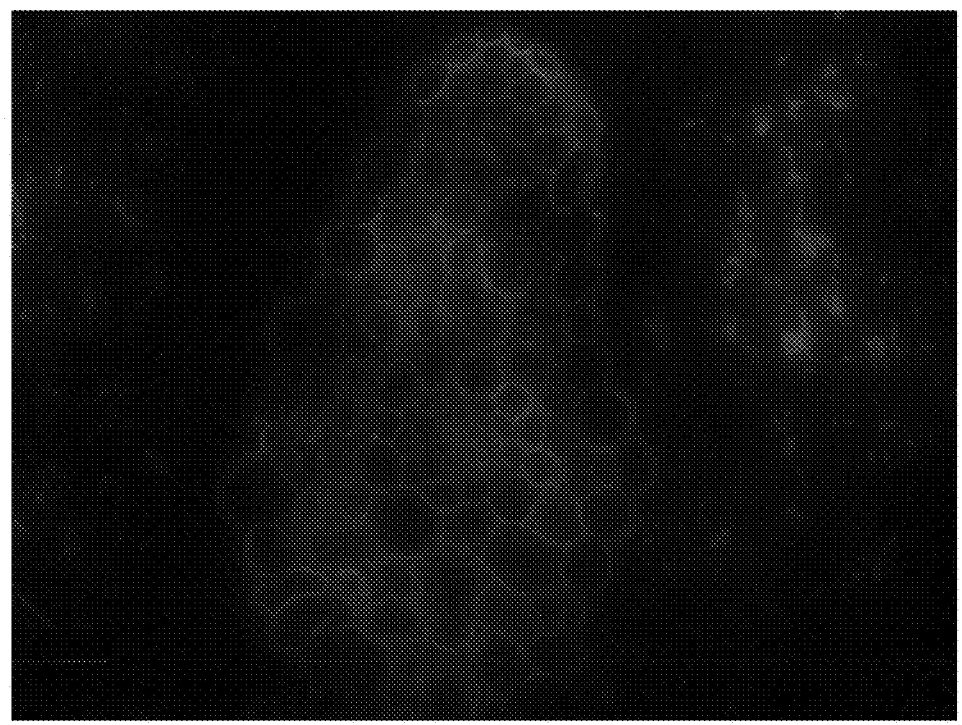

All control sections taken from any sample treated without either primary, secondary or both antibodies showed very low levels of fluorescence at 400× magnification (FIG. 17). Labeling with both primary and secondary antibodies appears as a green signal when using the 13 filter (FIGS. 18A-18E). As expected with both antibodies, a level of endogenous (1,3;1,4)-β-D-glucans was evident on tissue sections taken from wild type (WT, FIG. 18E) and transgenic control (G89, FIG. 18F), where signal was mainly concentrated in the mesophyll cells and vascular bundles in the mid regions of the sections. Under UV it was evident that all cells in all sections were present and intact. In contrast, antibody-labeled sections taken from the transgenic G98 and G103 plants, such as G98-10 (FIG. 18A), G98-24 (FIG. 18B) and G103-5 (FIG. 18C), display an increased intensity of signal, where the walls of the epidermal cells and sclerenchyma fibre cells are much more heavily labelled. The sclerenchyma cells have thickened secondary cell walls and Trethewey and Harris (2002, supra) detected only sparse labelling at the TEM level in these cells from wild type seedlings. The labelling pattern displayed by G99 plants, such as G99-12 (FIG. 18D), varies from that shown by the wild type and transgenic controls and from the G98 and G103 plants. In this case fluorescence is seen only in the stomatal cells and parts of the vascular bundle.

These results indicate that over-expression of individual barley CslF genes may lead to elevated protein levels of the glucan synthase enzymes, which in turn leads to increased deposition of (1,3;1,4)-beta-D-glucans in the cell walls of these transgenic plants.

Materials and Methods (i) Preparation of Transformed Barley Leaves for Light Microscopy Barley leaf pieces were fixed in 0.25% (v/v) glutaraldehyde, 4% (v/v) paraformaldehyde (EM Grade), and 4% sucrose in phosphate-buffered saline (PBS), pH 7.2, and stored at 4° C. overnight. Samples were washed three times in PBS, dehydrated in a graded ethanol series and slowly infiltrated with paraffin over several days. Blocks were trimmed and sectioned at 6 µm.

(ii) Immunolabeling for Light Microscopy With a Fluorophore-Conjugated Antibody

Sections were dewaxed in xylene and rehydrated progressively through 100%, 90% and 70% ethanol solutions. After two rinses with 1× phosphate buffered saline (PBS) the sections were incubated with 0.05M glycine for 20 mins to inactivate residual aldehyde groups. Sections were blocked in incubation buffer (1% bovine serum albumin (BSA) in 1×PBS) for 2×10 mins to prevent non-specific binding. Slides were drained and the specific primary antibody, BG1 (BioSupplies, Melbourne, Australia) was added at a dilution of 1:50 and left to incubate for one hour in a humidity chamber. Unbound primary antibody was removed by rinsing with incubation buffer for 3×10 mins and the secondary antibody, Alexa Fluor® 488 goat anti-mouse IgG (Molecular Probes, Eugene, USA), was added. Slides were wrapped in aluminium foil to exclude light and incubated for 2 hours at room temperature. Unbound secondary antibody was removed by rinsing 3×10 mins with incubation buffer before a few drops of mountant (90% glycerol: 10% water) were applied and sections cover-slipped. Controls were included which omitted either the primary antibody, the secondary antibody or both antibodies. Images were captured on a Leica AS LMD microscope under filter D (UV, excitation 355-425 nm) or filter I3 (blue, excitation 450-490 nm) using a DFC480 CCD camera. All images shown were taken at 400× magnification with a 7 second exposure time to standardise fluorescence intensity.

EXAMPLE 9

Immunological Detection of (1,3;1,4)-β-D-Glucans in Transgenic Barley Using Transmission Electron Microscopy Transgenic barley lines, as described in Examples 7 and 8, in which the HvCslF1, 4 or 6 transcript levels driven by the 35S promoter were highest, were chosen for further analysis, with respect to the deposition of (1,3;1,4)-β-D-glucan in the cell walls. An immunocytochemical method using the monoclonal antibody specific for (1,3;1,4)-β-D-glucan, as described in Example 3, and electron microscopy, was employed to screen leaf sections for the presence of the polysaccharide in the barley lines. Due to expression of the endogenous CslF genes (1,3;1,4)-β-D-glucans are normally deposited in the cell walls of vegetative tissues, such as leaf, and their occurrence and distribution in the emergent tissues of the barley seedling has been documented at the TEM level by Trethewey and Harris (*New Phytologist* 154: 347-358, 2002). In Example 7 we contrasted the distribution of endogenous (1,3;1,4)-β-D-glucans at the light microscope level in control material with that displayed by leaf sections of plantlets over-expressing barley CslF genes. A repeat analysis of a sub-set of the same lines using the specific monoclonal antibody and TEM, which allows a much closer examination of individual cell walls, is described here.

Leaf pieces representative of the plant groups described in Example 7 were harvested, fixed and embedded in LR white resin. Mounted sections were treated with the specific monoclonal antibody which binds to (1,3;1,4)-β-D-glucan and colloidal gold and examined on the transmission electron microscope.

Figure 19A:
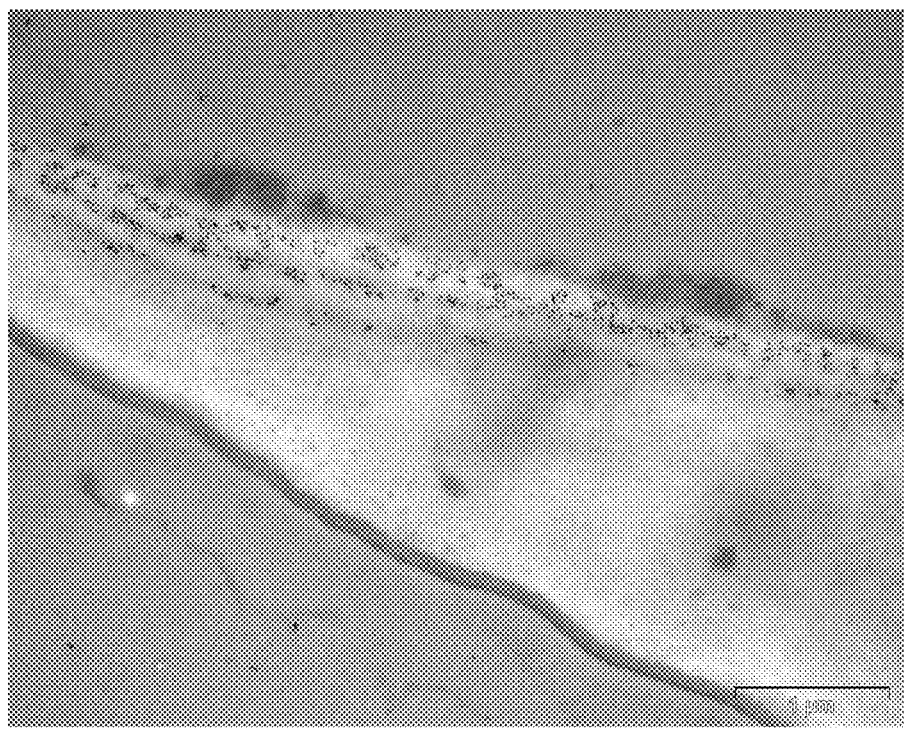
FIGS. 19A and 19B show transmission electron micrographs.
Figure 19B:
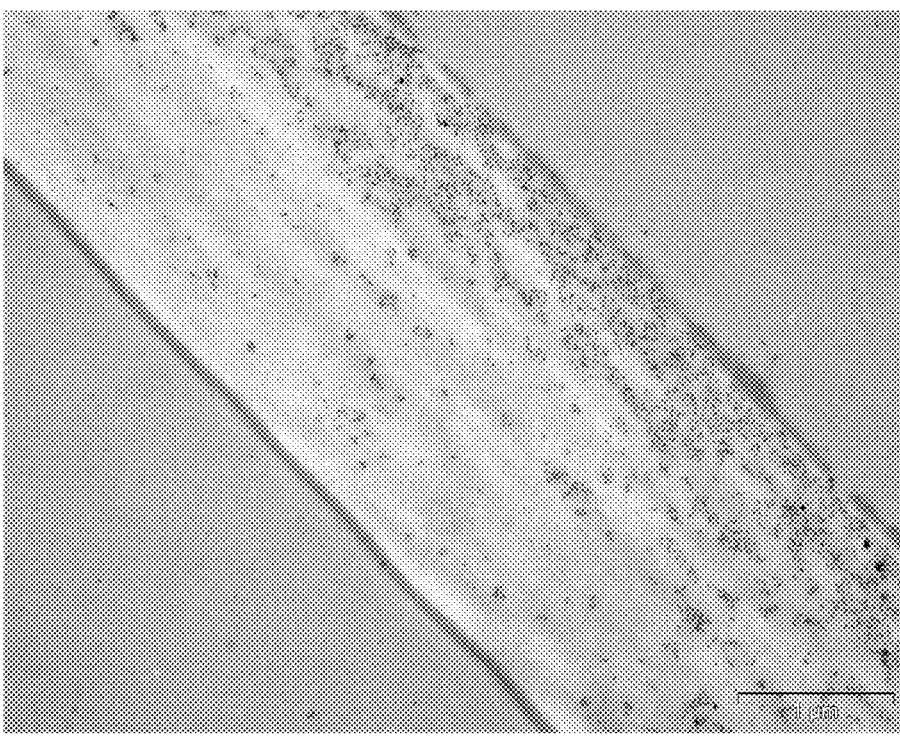
Figure 19C:
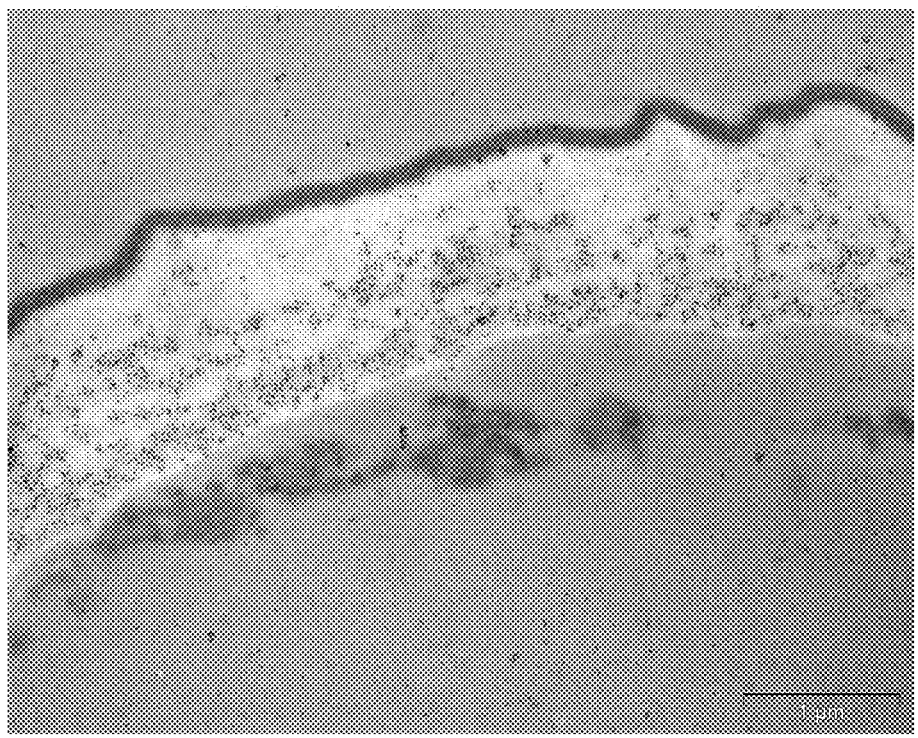
FIG. 19C shows a representative epidermal cell wall of transgenic G103-5 showing significantly heavier labeling of (1,3;1,4)-β-D-glucan in the walls of these plants.
Figure 20A:
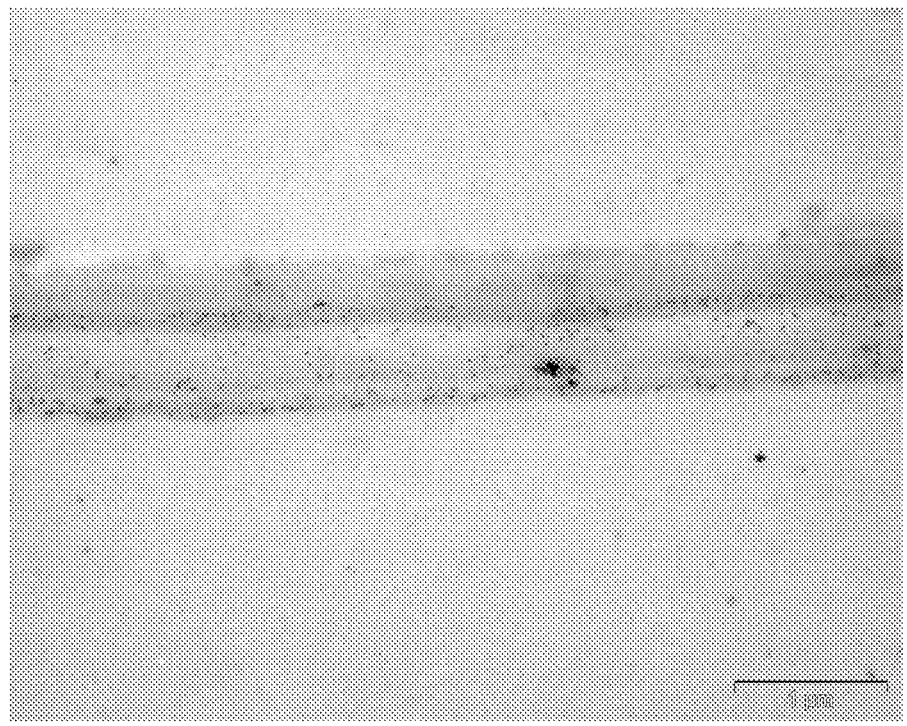
FIGS. 20A to 20C show transmission electron micrographs.
Figure 20B:
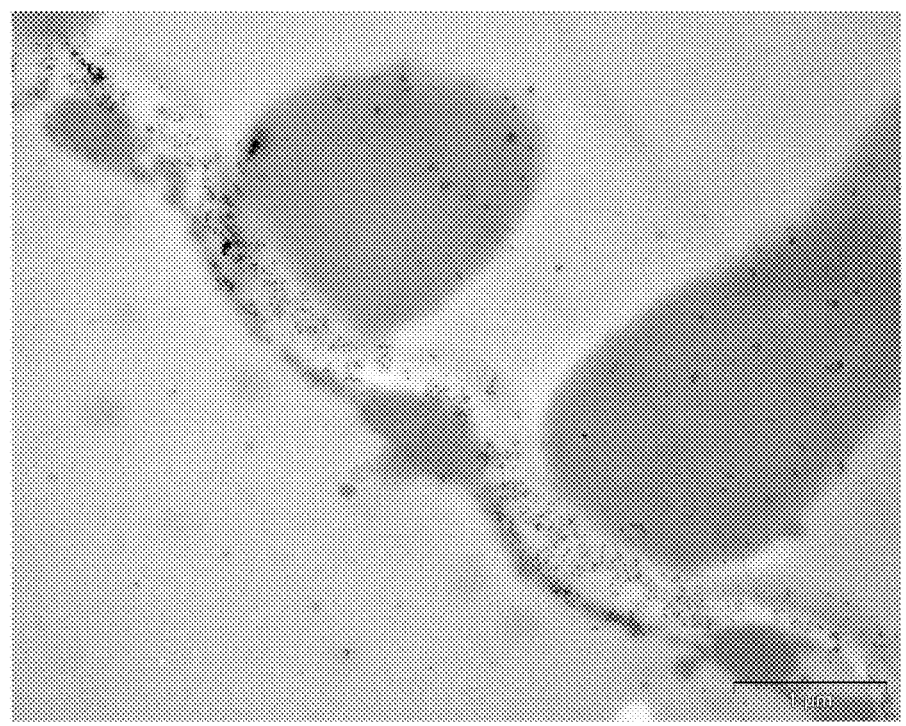
Figure 20C:
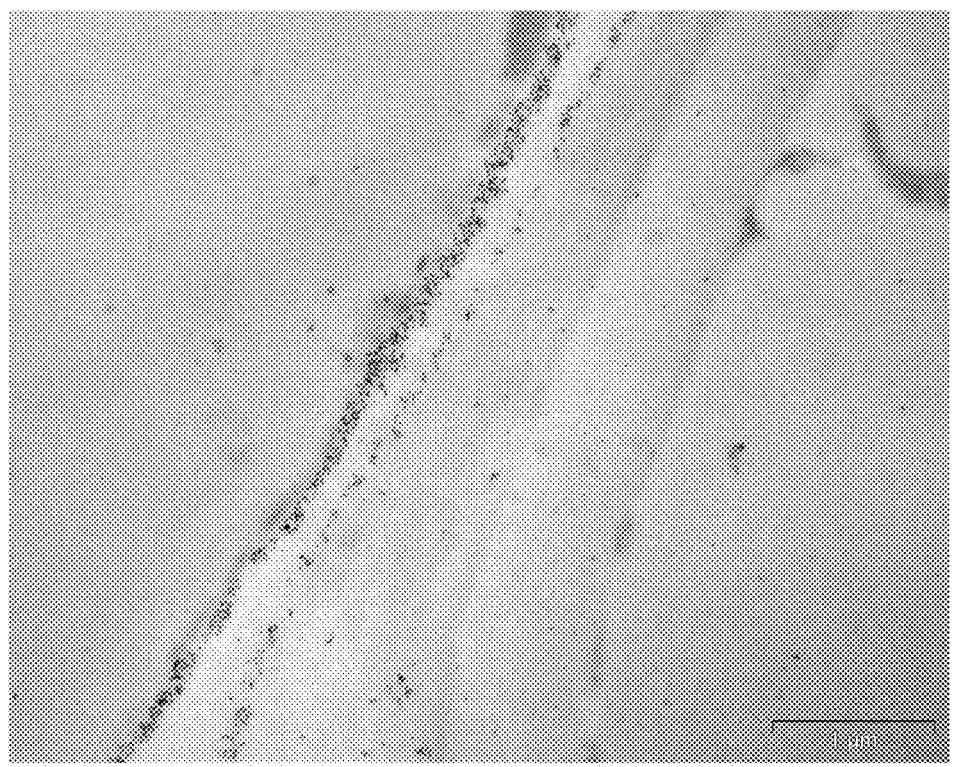

The presence of endogenous (1,3;1,4)-β-D-glucans was clearly evident, as expected, on sections taken from wild type (WT) and transgenic control (G89) leaves. In contrast, sections taken from the transgenic G98 and G103 plants, such as G98-10 and G103-5, display much heavier labeling. A labeled epidermal cell wall of the control G89 is shown in FIG. 19A. Equivalent epidermal cell walls of the transgenics G98-10 and G103-5 are shown in FIG. 19B (G98-10) and 19C (G103-5), where the increased amount of labeling is clearly evident. FIG. 20A shows the wall of a sclerenchyma fibre cell in the G89 control which is lightly labeled. Such cells have thickened secondary cell walls and Trethewey and Harris (2002, supra) also detected sparse labeling at the TEM level in these fibres from wild type seedlings. In comparison the fibre cell walls from the transgenic G98-10 and G103-5 plants, shown in FIGS. 20B and 20C respectively, are more heavily labeled. These results indicate that over-expression of individual CslF genes has the potential to increase deposition of (1,3;1,4)-β-D-glucans in the cell walls of transgenic plants. This has been demonstrated using both a fluorophore for glucan detection at the light microscope level (Example 7) and, as demonstrated here, by employing immunogold labeling at the TEM level.

Materials and Methods (i) Preparation of Transformed Barley Leaves for Electron Microscopy Pieces of barley plantlet leaves were fixed in 0.25% glutaraldehyde, 4% (v/v) paraformaldehyde (EM Grade) and 4% sucrose in phosphate-buffered saline (PBS), pH 7.2, and stored at 4° C. overnight. After three rinses in MilliQ water the samples were dehydrated in a graded ethanol series and slowly infiltrated with LR White resin over several days. Individual leaf pieces were placed in gelatin capsules, which were filled with fresh resin and polymerized overnight at 65° C.

(ii) Immunolocation for Transmission Electron Microscopy

Sections (80 nm) of barley leaves were prepared on a Leica Ultracut R microtome using a diamond knife and collected on 100 and 200 mesh, Formvar coated gold grids. The ultrathin sections were blocked for 30 min in 1% bovine serum albumin in PBS before incubation in murine monoclonal antibodies raised against barley (1,3;1,4)-β-D-glucan (diluted 1:500; Biosupplies Australia, Parkville, VIC 3052, Australia) for 1 hr at room temperature and overnight at 4° C. The grids were washed twice in PBS and three times in blocking buffer before a 1 h incubation in 18 nm Colloidal Gold-AffiniPure Goat-Anti Mouse IgG+IgM (H+L) (Jackson ImmunoResearch Laboratories, Inc., PA, USA). All grids were washed twice in PBS and several times in MilliQ water before viewing on a Philips BioTwin Transmission Electron Microscope and images captured on a Gatan Multiscan CCD Camera.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a transgene" includes a single transgene as well as two or more transgenes; "a plant cell" includes a single cell as well as two or more cells; and so forth.

The claims defining the invention are as follows:

1. A method for decreasing the level of (1,3;1,4)-β-D-glucan produced by a plant or fungal cell, the method comprising decreasing the level and/or activity of a CslF-encoded (1,3;1,4)-β-D-glucan synthase in the cell, wherein the level and/or activity of the CslF-encoded (1,3;1,4)-β-D-glucan synthase is decreased by decreasing the expression of a CslF nucleic acid in the cell, and wherein decreasing the expression of a CslF nucleic acid in the cell results in a decrease of the level of (1,3;1,4)-β-D-glucan produced by the cell compared to a wild-type cell of the same taxon, and wherein the CslF nucleic acid comprises:
   (i) a nucleotide sequence set forth in SEQ ID NO: 1;
   (ii) a nucleotide sequence encoding the amino acid sequence set forth in SEQ ID NO: 2; or
   (iii) a nucleotide sequence encoding an amino acid sequence which is at least 90% identical to the amino acid sequence set forth in SEQ ID NO: 2.

2. The method of claim 1 wherein the cell is a plant cell.

3. The method of claim 2 wherein the cell is a monocot plant cell.

4. The method of claim 3 wherein the cell is a cereal crop plant cell.

5. A plant or fungal cell comprising any one or more of:
   a decreased level and/or activity of a CslF-encoded (1,3;1,4)-β-D-glucan synthase relative to a wild type cell of the same taxon; and/or
   decreased expression of a CslF nucleic acid relative to a wild type cell of the same taxon,
   wherein the cell comprises a decreased level of (1,3;1,4)-β-D-glucan relative to a wild-type cell of the same taxon,
   wherein the CslF nucleic acid comprises:
   (i) a nucleotide sequence set forth in SEQ ID NO: 1;
   (ii) a nucleotide sequence encoding the amino acid sequence set forth in SEQ ID NO: 2; or
   (iii) a nucleotide sequence encoding an amino acid sequence which is at least 90% identical to the amino acid sequence set forth in SEQ ID NO: 2,
   wherein the plant or fungal cell contains a genetic modification that results in the decreased level, activity, or expression.

6. The cell of claim 5 wherein the cell is produced according to the method of claim 1.

7. The cell of claim 5 wherein the cell is a plant cell.

8. The cell of claim 7 wherein the cell is a monocot plant cell.

9. The cell of claim 8 wherein the cell is a cereal crop plant cell.

10. A multicellular structure comprising one or more cells according to claim 5.

11. The multicellular structure of claim 10 wherein the multicellular structure is selected from the list consisting of a whole plant, a plant tissue, a plant organ, a plant part, plant reproductive material or cultured plant tissue.

12. The multicellular structure of claim 10 wherein the multicellular structure comprises a cereal crop plant or a tissue, organ or part thereof.

13. The multicellular structure of claim 12 wherein the multicellular structure comprises a cereal grain.

14. The multicellular structure of claim 10 wherein the multicellular structure comprises a cell having decreased dietary fibre content relative to a wild type cell of the same taxon.

15. The multicellular structure of claim 14 wherein the multicellular structure comprises a cell having a decreased level of $(1,3;1,4)$-$\beta$-D-glucan relative to a wild type cell of the same taxon and a decreased dietary fibre content relative to a wild type cell of the same taxon.

* * * * *

SEQUENCE LISTING

<160> NUMBER OF SEQ ID NOS: 73

<210> SEQ ID NO 1
<211> LENGTH: 2841
<212> TYPE: DNA
<213> ORGANISM: Hordeum vulgare

<400> SEQUENCE: 1

```
atggcgccag cggtggccgg aggggccgc gtgcggagca atgagccggt tgctgctgct      60
gccgccgcgc cggcggccag cggcaagccc tgcgtgtgcg gcttccaggt ttgcgcctgc     120
acggggtcgg ccgcggtggc ctccgccgcc tcgtcgctgg acatggacat cgtggccatg     180
gggcagatcg gcgccgtcaa cgacgagagc tgggtggcg tggagctcgg cgaagatggc      240
gagaccgacg aaagcggtgc cgccgttgac gaccgccccg tattccgcac cgagaagatc     300
aagggtgtcc tcctccaccc ctaccgggtg ctgattttcg ttcgtctgat cgccttcacg     360
ctgttcgtga tctggcgtat ctcccacaag aacccagacg cgatgtggct gtgggtgaca     420
tccatctgcg gcgagttctg gttcggtttc tcgtggctgc tagatcagct gcccaagctg     480
aaccccatca accgcgtgcc ggacctggcg gtgctgcggc agcgcttcga ccgccccgac     540
ggcacctcca cgctcccggg gctggacatc ttcgtcacca cggccgaccc catcaaggag     600
cccatcctct ccaccgccaa ctcggtgctc tccatcctgg ccgccgacta ccccgtggac     660
cgcaacacat gctacgtctc cgacgacagt ggcatgctgc tcacctacga ggccctggca     720
gagtcctcca agttcgccac gctctgggtg cccttctgcc gcaagcacgg gatcgagccc     780
aggggtccgg agagctactt cgagctcaag tcacaccctt acatggggag agcccaggac     840
gagttcgtca cgaccgccg ccgcgttcgc aaggagtacg acgagttcaa ggccaggatc     900
aacagcctgg agcatgacat caagcagcgc aacgacgggt acaacgccgc cattgcccac     960
agccaaggcg tgccccggcc cacctggatg gcggacggca cccagtggga gggcacatgg    1020
gtcgacgcct ccgagaacca ccgcagggggc gaccacgccg gcatcgtact ggtgctgctg    1080
aaccacccga gccaccgccg gcagacgggc ccgccggcga gcgctgacaa cccactggac    1140
ttgagcggcg tggatgtgcg tctccccatg ctggtgtacg tgtcccgtga gaagcgcccc    1200
gggcacgacc accagaagaa ggccggtgcc atgaacgcgc ttacccgcgc ctcggcgctg    1260
ctctccaact cccccttcat cctcaacctc gactgcgatc attacatcaa caactcccag    1320
gcccttcgcg ccggcatctg cttcatggtg ggacgggaca gcgacacggt tgccttcgtc    1380
cagttcccgc agcgcttcga gggcgtcgac cccaccgacc tctacgccaa ccacaaccgc    1440
atcttcttcg acggcacccc tcgtgccctg gacggcatgc agggcccccat ctacgtcggc    1500 actgggtgtc tcttccgccg catcaccgtc tacggcttcg acccgccgag gatcaacgtc    1560
```

```
ggcggtccct gcttccccag gctcgccggg ctcttcgcca agaccaagta cgagaagccc    1620
gggctcgaga tgaccacggc caaggccaag gccgcgcccg tgcccgccaa gggtaagcac    1680
ggcttcttgc cactgcccaa gaagacgtac ggcaagtcgg acgccttcgt ggacaccatc    1740
ccgcgcgcgt cgcacccgtc gccctacgcc gcggcggctg aggggatcgt ggccgacgag    1800
gcgaccatcg tcgaggcggt gaacgtgacg gccgccgcgt tcgagaagaa gaccggctgg    1860
ggcaaagaga tcggctgggt gtacgacacc gtcacggagg acgtggtcac cggctaccgg    1920
atgcatatca aggggtggcg gtcacgctac tgctccatct acccacacgc cttcatcggc    1980
accgccccca tcaacctcac ggagaggctc ttccaggtgc tccgctggtc cacgggatcc    2040
ctcgagatct tcttctccaa gaacaacccg ctcttcggca gcacatacct ccacccgctg    2100
cagcgcgtcg cctacatcaa catcaccact taccccttca ccgccatctt cctcatcttc    2160
tacaccaccg tgccggcgct atccttcgtc accggccact tcatcgtgca gcgcccgacc    2220
accatgttct acgtctacct gggcatcgtg ctatccacgc tgctcgtcat cgccgtgctg    2280
gaggtcaagt gggccggggt cacagtcttc gagtggttca ggaacggcca gttctggatg    2340
acagcaagtt gctccgccta cctcgccgcc gtctgccagg tgctgaccaa ggtgatattc    2400
cggcgggaca tctccttcaa gctcacatcc aagctaccct cggagacga gaagaaggac    2460 ccctacgccg acctctacgt ggtgcgctgg acgccgctca tgattacacc catcatcatc    2520
atcttcgtca acatcatcgg atccgccgtg ccttcgcca aggttctcga cggcgagtgg    2580
acgcactggc tcaaggtcgc cggcggcgtc ttcttcaact tctgggtgct cttccacctc    2640
tacccctccg ccaagggcat cctggggaag cacggaaaga cgccagtcgt ggtgctcgtc    2700
tggtgggcat tcaccttcgt catcaccgcc gtgctctaca tcaacatccc ccacatgcat    2760
acctcgggag gcaagcacac aacggtgcat ggtcaccatg gcaagaagtt ggtcgacaca    2820
gggctctatg gctggctcca t                                             2841
```

<210> SEQ ID NO 2
<211> LENGTH: 947
<212> TYPE: PRT
<213> ORGANISM: Hordeum vulgare

<400> SEQUENCE: 2

```
Met Ala Pro Ala Val Ala Gly Gly Arg Val Arg Ser Asn Glu Pro
1               5                   10                  15

Val Ala Ala Ala Ala Ala Pro Ala Ala Ser Gly Lys Pro Cys Val
                20                  25                  30

Cys Gly Phe Gln Val Cys Ala Cys Thr Gly Ser Ala Ala Val Ala Ser
                35                  40                  45

Ala Ala Ser Ser Leu Asp Met Asp Ile Val Ala Met Gly Gln Ile Gly
50                  55                  60

Ala Val Asn Asp Glu Ser Trp Val Gly Val Glu Leu Gly Glu Asp Gly
65                  70                  75                  80

Glu Thr Asp Glu Ser Gly Ala Ala Val Asp Asp Arg Pro Val Phe Arg
                85                  90                  95

Thr Glu Lys Ile Lys Gly Val Leu Leu His Pro Tyr Arg Val Leu Ile
                100                 105                 110

Phe Val Arg Leu Ile Ala Phe Thr Leu Phe Val Ile Trp Arg Ile Ser
                115                 120                 125

His Lys Asn Pro Asp Ala Met Trp Leu Trp Val Thr Ser Ile Cys Gly
            130                 135                 140
```

-continued

```
Glu Phe Trp Phe Gly Phe Ser Trp Leu Leu Asp Gln Leu Pro Lys Leu
145                 150                 155                 160

Asn Pro Ile Asn Arg Val Pro Asp Leu Ala Val Leu Arg Gln Arg Phe
            165                 170                 175

Asp Arg Pro Asp Gly Thr Ser Thr Leu Pro Gly Leu Asp Ile Phe Val
                180                 185                 190

Thr Thr Ala Asp Pro Ile Lys Glu Pro Ile Leu Ser Thr Ala Asn Ser
        195                 200                 205

Val Leu Ser Ile Leu Ala Ala Asp Tyr Pro Val Asp Arg Asn Thr Cys
        210                 215                 220

Tyr Val Ser Asp Asp Ser Gly Met Leu Leu Thr Tyr Glu Ala Leu Ala
225                 230                 235                 240

Glu Ser Ser Lys Phe Ala Thr Leu Trp Val Pro Phe Cys Arg Lys His
                245                 250                 255

Gly Ile Glu Pro Arg Gly Pro Glu Ser Tyr Phe Glu Leu Lys Ser His
                260                 265                 270

Pro Tyr Met Gly Arg Ala Gln Asp Glu Phe Val Asn Asp Arg Arg Arg
        275                 280                 285

Val Arg Lys Glu Tyr Asp Glu Phe Lys Ala Arg Ile Asn Ser Leu Glu
        290                 295                 300

His Asp Ile Lys Gln Arg Asn Asp Gly Tyr Asn Ala Ala Ile Ala His
305                 310                 315                 320

Ser Gln Gly Val Pro Arg Pro Thr Trp Met Ala Asp Gly Thr Gln Trp
                325                 330                 335

Glu Gly Thr Trp Val Asp Ala Ser Glu Asn His Arg Arg Gly Asp His
                340                 345                 350

Ala Gly Ile Val Leu Val Leu Asn His Pro Ser His Arg Arg Gln
        355                 360                 365

Thr Gly Pro Pro Ala Ser Ala Asp Asn Pro Leu Asp Leu Ser Gly Val
        370                 375                 380

Asp Val Arg Leu Pro Met Leu Val Tyr Val Ser Arg Glu Lys Arg Pro
385                 390                 395                 400

Gly His Asp His Gln Lys Lys Ala Gly Ala Met Asn Ala Leu Thr Arg
                405                 410                 415

Ala Ser Ala Leu Leu Ser Asn Ser Pro Phe Ile Leu Asn Leu Asp Cys
                420                 425                 430

Asp His Tyr Ile Asn Asn Ser Gln Ala Leu Arg Ala Gly Ile Cys Phe
        435                 440                 445

Met Val Gly Arg Asp Ser Asp Thr Val Ala Phe Val Gln Phe Pro Gln
450                 455                 460

Arg Phe Glu Gly Val Asp Pro Thr Asp Leu Tyr Ala Asn His Asn Arg
465                 470                 475                 480

Ile Phe Phe Asp Gly Thr Leu Arg Ala Leu Asp Gly Met Gln Gly Pro
                485                 490                 495

Ile Tyr Val Gly Thr Gly Cys Leu Phe Arg Arg Ile Thr Val Tyr Gly
        500                 505                 510

Phe Asp Pro Pro Arg Ile Asn Val Gly Gly Pro Cys Phe Pro Arg Leu
        515                 520                 525

Ala Gly Leu Phe Ala Lys Thr Lys Tyr Glu Lys Pro Gly Leu Glu Met
        530                 535                 540

Thr Thr Ala Lys Ala Lys Ala Ala Pro Val Pro Ala Lys Gly Lys His
545                 550                 555                 560

Gly Phe Leu Pro Leu Pro Lys Lys Thr Tyr Gly Lys Ser Asp Ala Phe
```

565					570					575
Val Asp Thr Ile Pro Arg Ala Ser His Pro Ser Pro Tyr Ala Ala Ala
				580					585					590

Ala Glu Gly Ile Val Ala Asp Glu Ala Thr Ile Val Glu Ala Val Asn
			595					600					605

Val Thr Ala Ala Ala Phe Glu Lys Lys Thr Gly Trp Gly Lys Glu Ile
		610					615					620

Gly Trp Val Tyr Asp Thr Val Thr Glu Asp Val Val Thr Gly Tyr Arg
625					630					635					640

Met His Ile Lys Gly Trp Arg Ser Arg Tyr Cys Ser Ile Tyr Pro His
				645					650					655

Ala Phe Ile Gly Thr Ala Pro Ile Asn Leu Thr Glu Arg Leu Phe Gln
			660					665					670

Val Leu Arg Trp Ser Thr Gly Ser Leu Glu Ile Phe Phe Ser Lys Asn
		675					680					685

Asn Pro Leu Phe Gly Ser Thr Tyr Leu His Pro Leu Gln Arg Val Ala
	690					695					700

Tyr Ile Asn Ile Thr Thr Tyr Pro Phe Thr Ala Ile Phe Leu Ile Phe
705					710					715					720

Tyr Thr Thr Val Pro Ala Leu Ser Phe Val Thr Gly His Phe Ile Val
				725					730					735

Gln Arg Pro Thr Thr Met Phe Tyr Val Tyr Leu Gly Ile Val Leu Ser
			740					745					750

Thr Leu Leu Val Ile Ala Val Leu Glu Val Lys Trp Ala Gly Val Thr
		755					760					765

Val Phe Glu Trp Phe Arg Asn Gly Gln Phe Trp Met Thr Ala Ser Cys
	770					775					780

Ser Ala Tyr Leu Ala Ala Val Cys Gln Val Leu Thr Lys Val Ile Phe
785					790					795					800

Arg Arg Asp Ile Ser Phe Lys Leu Thr Ser Lys Leu Pro Ser Gly Asp
				805					810					815

Glu Lys Lys Asp Pro Tyr Ala Asp Leu Tyr Val Val Arg Trp Thr Pro
			820					825					830

Leu Met Ile Thr Pro Ile Ile Ile Phe Val Asn Ile Ile Gly Ser
		835					840					845

Ala Val Ala Phe Ala Lys Val Leu Asp Gly Glu Trp Thr His Trp Leu
	850					855					860

Lys Val Ala Gly Gly Val Phe Phe Asn Phe Trp Val Leu Phe His Leu
865					870					875					880

Tyr Pro Phe Ala Lys Gly Ile Leu Gly Lys His Gly Lys Thr Pro Val
				885					890					895

Val Val Leu Val Trp Trp Ala Phe Thr Phe Val Ile Thr Ala Val Leu
			900					905					910

Tyr Ile Asn Ile Pro His Met His Thr Ser Gly Gly Lys His Thr Thr
		915					920					925

Val His Gly His His Gly Lys Lys Leu Val Asp Thr Gly Leu Tyr Gly
	930					935					940

Trp Leu His
945

<210> SEQ ID NO 3
<211> LENGTH: 2553
<212> TYPE: DNA
<213> ORGANISM: Hordeum vulgare

<400> SEQUENCE: 3

```
atggcgtcgg cggccggtgc tgctgggtca aatgccagcc tcgccgcccc gctgctggcg    60
agccgcgagg gaggagccaa gaagccggtc ggtgccaagg gcaagcactg ggaggccgcc   120
gacaaggacg agcggcgggc cgccaaggag agcggcggcg aggacggcag gccgctgctg   180
ttccggacgt acaaggtcaa aggcacccte ctgcacccat acagggcgct aatcttcatt   240
cgcttaattg cggtccttct attcttcgta tggcgcatca agcacaacaa atccgacatc   300
atgtggtttt ggacaatatc agtcgtcggg gacgtatggt tcgggttctc gtggctgctc   360
aaccaactcc caaagttcaa ccctatcaaa accatacctg atatggtcgc ccttaggcga   420
caatacgatc tttcagatgg gacatctaca ctcccgggca tagatgtctt tgtcaccacc   480
gctgacccaa tcgatgagcc gatactatac accatgaatt gtgtcctttc tatccttgct   540
tctgactatc ctgtcgatag gtgtgcctgc tatctcccag atgatagtgg agcattgatt   600
caatacgagg cctagttgac gaccgcaaag tttgctactt tgtgggtccc attttgtcgg   660
aagcattgca ttgagccaag agcccagaa agctactttg aaatagaggc accgttgtac   720
actggaactg caccgagga gttcaagaat gattatagta gtgtacataa agagtatgat   780
gagttcaaag agcgcttgga ctcactatcc gatgctattt ccaagcgttc tgatgcttac   840
aacagcatga agactgagga aggagatgca aaggccacgt ggatggcaaa tgggacacaa   900
tggccaggat catggattga cacaacggaa atccatagaa aggacatca tgccggaatt   960
gttaaggttg tgttggacca ttcgatccgt gggcataatc ttggttcaca agaaagcacc  1020
cacaacctca gtttcgccaa caccgatgag cgcctcccga tgcttgtgta tatctctcgt  1080
ggaaagaacc caagctatga ccacaacaag aaagctggtg ccttgaatgc gcaattgcgt  1140
gcctctgcac tactctccaa cgcacaattc atcatcaact ttgactgcga ccactacatc  1200
aacaactctc aagccctacg tgcagctatg tgcttcatgc ttgatcaaag gcaaggtgat  1260
aacactgcct ttgttcaatt ccctcaacgc ttcgacaatg ttgatccatc agaccgatat  1320
ggaaaccaca accgtgtctt ctttgacggc acaatgctcg ccctcaatgg cctccaaggg  1380
ccatcttacc ttggcactgg ttgcatgttc cgccgcatag cactttatgg cattgaccca  1440
cctgactgga gacatgacaa catcatagtt gatgataaaa agtttggtag ctccataccc  1500
ttcctagatt ccgtatcaaa agccataaac caagaaaggt ctaccatacc tccacccatt  1560
agtgaaacat tggtggctga gatggaaagg gttgtgtcgg cttcacacga taaagccact  1620
ggttggggca agggtgttgg gtacatatat gacatagcca cagaggatat cgtgactggt  1680
ttccgcatcc atgggcaagg ttggcgttcc atgtattgta caatggagcg tgacgccttc  1740
tgtggcattg caccaatcaa cctaaccgag cgcctccacc aaattgtgcg ctggtccggt  1800
ggatctttag agatgttctt ctcactaaat aacccactca taggtggtcg ccggatccac  1860
gcccttcagc gtgtctccta cctcaacatg acagtctacc cagtcacatc actctttatc  1920
ctactctatg ctctcagccc agtgatgtgg cttatccctg atgaagtata catccagagg  1980
ccattcacca aatatgtcgt gttccttctc gtgatcattc tgatgatcca tataattggg  2040
tggctcgaga taaaatgggc gggggtcaca tggttggatt actggaggaa tgaacagttc  2100
tttatgatcg ggtcgacgag tgcatacca gcagccgtgc tgcacatggt ggtgaatctc  2160
cttacaaaga agggtataca cttcagagtt acttcgaagc aaacaacggc agacaccaat  2220
gacaagtttg ctgacttgta tgacatgcga tgggtgccaa tgttaatccc tacaacagtg  2280
```

-continued

```
gtgctgattg ccaatgttgg tgcaatcggt gtagccatgg gtaaaacgat agtatacatg      2340
ggagcatgga caattgcaca gaagacacat gccgcattgg gtctgctctt caacgtgtgg      2400
atcatggtcc tgctctatcc gtttgcattg gcgatcatgg gacggtgggc aaagaggcca      2460
gtcatcctgg tggtcttgtt gccggttgcc tttacaatag tttgccttgt atatgtttct      2520
gttcatatat tacttcttag ttttcttcca ttt                                   2553
```

<210> SEQ ID NO 4
<211> LENGTH: 851
<212> TYPE: PRT
<213> ORGANISM: Hordeum vulgare

<400> SEQUENCE: 4

```
Met Ala Ser Ala Ala Gly Ala Ala Gly Ser Asn Ala Ser Leu Ala Ala
1               5                   10                  15

Pro Leu Leu Ala Ser Arg Glu Gly Gly Ala Lys Lys Pro Val Gly Ala
            20                  25                  30

Lys Gly Lys His Trp Glu Ala Ala Asp Lys Asp Glu Arg Arg Ala Ala
        35                  40                  45

Lys Glu Ser Gly Gly Glu Asp Gly Arg Pro Leu Leu Phe Arg Thr Tyr
    50                  55                  60

Lys Val Lys Gly Thr Leu Leu His Pro Tyr Arg Ala Leu Ile Phe Ile
65                  70                  75                  80

Arg Leu Ile Ala Val Leu Leu Phe Phe Val Trp Arg Ile Lys His Asn
                85                  90                  95

Lys Ser Asp Ile Met Trp Phe Trp Thr Ile Ser Val Val Gly Asp Val
            100                 105                 110

Trp Phe Gly Phe Ser Trp Leu Leu Asn Gln Leu Pro Lys Phe Asn Pro
        115                 120                 125

Ile Lys Thr Ile Pro Asp Met Val Ala Leu Arg Arg Gln Tyr Asp Leu
    130                 135                 140

Ser Asp Gly Thr Ser Thr Leu Pro Gly Ile Asp Val Phe Val Thr Thr
145                 150                 155                 160

Ala Asp Pro Ile Asp Glu Pro Ile Leu Tyr Thr Met Asn Cys Val Leu
                165                 170                 175

Ser Ile Leu Ala Ser Asp Tyr Pro Val Asp Arg Cys Ala Cys Tyr Leu
            180                 185                 190

Pro Asp Asp Ser Gly Ala Leu Ile Gln Tyr Glu Ala Leu Val Glu Thr
        195                 200                 205

Ala Lys Phe Ala Thr Leu Trp Val Pro Phe Cys Arg Lys His Cys Ile
    210                 215                 220

Glu Pro Arg Ala Pro Glu Ser Tyr Phe Glu Ile Glu Ala Pro Leu Tyr
225                 230                 235                 240

Thr Gly Thr Ala Pro Glu Glu Phe Lys Asn Asp Tyr Ser Ser Val His
                245                 250                 255

Lys Glu Tyr Asp Glu Phe Lys Glu Arg Leu Asp Ser Leu Ser Asp Ala
            260                 265                 270

Ile Ser Lys Arg Ser Asp Ala Tyr Asn Ser Met Lys Thr Glu Glu Gly
        275                 280                 285

Asp Ala Lys Ala Thr Trp Met Ala Asn Gly Thr Gln Trp Pro Gly Ser
    290                 295                 300

Trp Ile Asp Thr Thr Glu Ile His Arg Lys Gly His His Ala Gly Ile
305                 310                 315                 320

Val Lys Val Val Leu Asp His Ser Ile Arg Gly His Asn Leu Gly Ser
```

```
                    325                 330                 335
Gln Glu Ser Thr His Asn Leu Ser Phe Ala Asn Thr Asp Glu Arg Leu
            340                 345                 350
Pro Met Leu Val Tyr Ile Ser Arg Gly Lys Asn Pro Ser Tyr Asp His
            355                 360                 365
Asn Lys Lys Ala Gly Ala Leu Asn Ala Gln Leu Arg Ala Ser Ala Leu
            370                 375                 380
Leu Ser Asn Ala Gln Phe Ile Ile Asn Phe Asp Cys Asp His Tyr Ile
385                 390                 395                 400
Asn Asn Ser Gln Ala Leu Arg Ala Ala Met Cys Phe Met Leu Asp Gln
                405                 410                 415
Arg Gln Gly Asp Asn Thr Ala Phe Val Gln Phe Pro Gln Arg Phe Asp
            420                 425                 430
Asn Val Asp Pro Ser Asp Arg Tyr Gly Asn His Asn Arg Val Phe Phe
            435                 440                 445
Asp Gly Thr Met Leu Ala Leu Asn Gly Leu Gln Gly Pro Ser Tyr Leu
450                 455                 460
Gly Thr Gly Cys Met Phe Arg Arg Ile Ala Leu Tyr Gly Ile Asp Pro
465                 470                 475                 480
Pro Asp Trp Arg His Asp Asn Ile Ile Val Asp Lys Lys Phe Gly
            485                 490                 495
Ser Ser Ile Pro Phe Leu Asp Ser Val Ser Lys Ala Ile Asn Gln Glu
            500                 505                 510
Arg Ser Thr Ile Pro Pro Ile Ser Glu Thr Leu Val Ala Glu Met
            515                 520                 525
Glu Arg Val Val Ser Ala Ser His Asp Lys Ala Thr Gly Trp Gly Lys
            530                 535                 540
Gly Val Gly Tyr Ile Tyr Asp Ile Ala Thr Glu Asp Ile Val Thr Gly
545                 550                 555                 560
Phe Arg Ile His Gly Gln Gly Trp Arg Ser Met Tyr Cys Thr Met Glu
                565                 570                 575
Arg Asp Ala Phe Cys Gly Ile Ala Pro Ile Asn Leu Thr Glu Arg Leu
            580                 585                 590
His Gln Ile Val Arg Trp Ser Gly Gly Ser Leu Glu Met Phe Phe Ser
            595                 600                 605
Leu Asn Asn Pro Leu Ile Gly Gly Arg Arg Ile His Ala Leu Gln Arg
            610                 615                 620
Val Ser Tyr Leu Asn Met Thr Val Tyr Pro Val Thr Ser Leu Phe Ile
625                 630                 635                 640
Leu Leu Tyr Ala Leu Ser Pro Val Met Trp Leu Ile Pro Asp Glu Val
                645                 650                 655
Tyr Ile Gln Arg Pro Phe Thr Lys Tyr Val Val Phe Leu Leu Val Ile
            660                 665                 670
Ile Leu Met Ile His Ile Gly Trp Leu Glu Ile Lys Trp Ala Gly
            675                 680                 685
Val Thr Trp Leu Asp Tyr Trp Arg Asn Glu Gln Phe Phe Met Ile Gly
            690                 695                 700
Ser Thr Ser Ala Tyr Pro Ala Ala Val Leu His Met Val Val Asn Leu
705                 710                 715                 720
Leu Thr Lys Lys Gly Ile His Phe Arg Val Thr Ser Lys Gln Thr Thr
                725                 730                 735
Ala Asp Thr Asn Asp Lys Phe Ala Asp Leu Tyr Asp Met Arg Trp Val
            740                 745                 750
```

```
Pro Met Leu Ile Pro Thr Thr Val Leu Ile Ala Asn Val Gly Ala
    755                 760                 765

Ile Gly Val Ala Met Gly Lys Thr Ile Val Tyr Met Gly Ala Trp Thr
770                 775                 780

Ile Ala Gln Lys Thr His Ala Ala Leu Gly Leu Leu Phe Asn Val Trp
785                 790                 795                 800

Ile Met Val Leu Leu Tyr Pro Phe Ala Leu Ala Ile Met Gly Arg Trp
                805                 810                 815

Ala Lys Arg Pro Val Ile Leu Val Val Leu Leu Pro Val Ala Phe Thr
                820                 825                 830

Ile Val Cys Leu Val Tyr Val Ser Val His Ile Leu Leu Leu Ser Phe
                835                 840                 845

Leu Pro Phe
    850

<210> SEQ ID NO 5
<211> LENGTH: 2571
<212> TYPE: DNA
<213> ORGANISM: Hordeum vulgare

<400> SEQUENCE: 5
```

| | | | | | |
|---|---|---|---|---|---|
| atggcttctc | cggcggccgt | cggcggggt | cgtctagccg | acccactgct | ggccgccgac | 60 |
| gtcgtcgtcg | tcggcgccaa | agacaagtac | tgggtgcccg | ccgacgagag | agagatcctg | 120 |
| gcgtcgcaga | gcagcggcgg | cggtgaacag | gacggccggg | caccgctgct | ataccgcacg | 180 |
| ttcagggtca | agggcttctt | catcaacctt | tacaggttat | tgactctggt | cagagttatc | 240 |
| gtggttattc | tattcttcac | gtggcgcatg | aggcaccggg | actcggacgc | gatgtggctg | 300 |
| tggtggatct | cggtcgtggg | cgacctctgg | ttcggagtca | cctggctgct | caaccagatc | 360 |
| accaagctca | agcccaggaa | atgcgtcccc | agcatctccg | tcctgagaga | gcagctcgac | 420 |
| cagcccgacg | gcggctccga | cctgcccctt | ctcgacgtgt | tcatcaacac | cgtcgacccg | 480 |
| gtggacgagc | cgatgctcta | caccatgaac | tccatcctct | ccatcctggc | caccgactac | 540 |
| cccgtccaga | agtacgccac | ctatttctcc | gatgacggcg | gtcgctggt | gcactacgag | 600 |
| gggctgctgc | tgacggcgga | gttcgccgcg | tcgtgggtcc | cgttctgccg | gaagcattgc | 660 |
| gtcgagcctc | gcgccccgga | gagctacttc | tgggccaaga | tgcgcgggga | gtacgccggc | 720 |
| agcgcggcca | aggagttcct | tgacgaccat | cggaggatgc | gcgcggcgta | tgaggagttc | 780 |
| aaggcgaggc | tggacgggct | ttctgccgtc | atcgagcagc | ggtccgaggc | gtgcaaccgc | 840 |
| gctgcaaacg | agaaagaagg | gtgtgggaac | gcgacttgga | tggccgatgg | gtcgacgcaa | 900 |
| tgcaggggga | cgtggatcaa | gccggccaag | ggccaccgga | aaggacacca | tcctgcaatt | 960 |
| cttcaggtta | tgctggatca | acctagcaag | gatcctgagc | tgggaatggc | ggcgagctcc | 1020 |
| gaccaccctc | tggatttcag | cgccgtggac | gtgcgcctcc | cgatgctggt | ctacattgcc | 1080 |
| cgggagaagc | ggcctgggta | tgaccaccag | aagaaggcgg | cgccatgaa | cgtgcagctg | 1140 |
| cgcgtgtccg | cgctgctctc | caacgcgccc | ttcatcatca | acttcgacgg | cgaccactac | 1200 |
| atcaacaact | cgcaggcctt | ccgcgccgcc | atgtgcttca | tgctcgaccc | cgcgacggc | 1260 |
| gccgacaccg | ccttcgtcca | gttcccgcag | cgcttcgacg | acgtcgaccc | caccgaccgc | 1320 |
| tactgcaacc | acaaccgcat | gttcttcgac | gccacccctcc | tcggcctcaa | cggcatccag | 1380 |
| ggcccctcct | tcgtcggcac | cggatgcatg | ttccgccgcg | tcgctctcta | cagcgccgac | 1440 |
| cctccacggt | ggcggtccga | cgacgccaag | gaggccaagg | cctcgcacag | gcccaacatg | 1500 |

```
tttggcaagt ctacgtcctt catcaactca atgccggcgg ccgccaacca agaacggtcc   1560
gtcccgtcac cggcgacagt cggcgaggcg gagctcgcag acgcgatgac ttgcgcgtac   1620
gaggacggca ccgagtgggg caacgacgtt gggtgggtgt acaacatcgc gacggaggac   1680
gtggtgaccg gcttccggct gcaccggacg gggtggcgct ccacgtactg cgccatggag   1740
cccgacgcgt tccgcggcac ggcgcccatc aacctcaccg agcgcctgta ccagatcctg   1800
cgttggtcgg ggggatccct cgagatgttc ttctcccgct tctgcccgct cctggccggc   1860
cgccgcctcc accccatgca gcgcgtcgcc tacatcaaca tgaccaccta cccggtctcc   1920
accttcttca tcctcatgta ttacttctac ccggtcatgt ggctcttcca gggggagttc   1980
tacatccaga ggccgttcca cgttcgcg ctcttcgtcg tcgtcgtcat cgccacggtg      2040
gagctcatcg gcatggtgga gatcaggtgg gcaggcctca cgctgctcga ctgggtccgc   2100
aacgagcagt tctacatcat cggcaccacc ggcgtgtacc cgatggccat gctgcacatc   2160
ctcctcaggt ccctcggcat aaaggggtg tccttcaagc tgacggccaa gaagctcacg      2220
gggggcgcca gggagaggct cgcggagctg tacgacgtgc agtgggtgcc gttgctggtg   2280
cccaccgtgg tggtcatggc cgtgaacgtg ccgccatcg gcgcggcggc gggcaaggcg      2340
atcgttgggc ggtggtcggc agcgcaggtc gcggggcgg cgagcgggct tgttttcaac       2400
gtgtggatgc tgctgctgct ctacccgttc gcgctcggga taatgggca ctggagcaag       2460
aggccctaca tcctgttcct tgtgctggtg accgcggtcg ctgccaccgc gtccgtgtac   2520
gtcgcactcg cggggtcctt gctgtacttg cattcgggga taaaactagt t            2571

<210> SEQ ID NO 6
<211> LENGTH: 857
<212> TYPE: PRT
<213> ORGANISM: Hordeum vulgare

<400> SEQUENCE: 6

Met Ala Ser Pro Ala Ala Val Gly Gly Gly Arg Leu Ala Asp Pro Leu
1               5                  10                  15

Leu Ala Ala Asp Val Val Val Gly Ala Lys Asp Lys Tyr Trp Val
            20                  25                  30

Pro Ala Asp Glu Arg Glu Ile Leu Ala Ser Gln Ser Gly Gly Gly
        35                  40                  45

Glu Gln Asp Gly Arg Ala Pro Leu Leu Tyr Arg Thr Phe Arg Val Lys
    50                  55                  60

Gly Phe Phe Ile Asn Leu Tyr Arg Leu Thr Leu Val Arg Val Ile
65                  70                  75                  80

Val Val Ile Leu Phe Phe Thr Trp Arg Met Arg His Arg Asp Ser Asp
                85                  90                  95

Ala Met Trp Leu Trp Trp Ile Ser Val Val Gly Asp Leu Trp Phe Gly
            100                 105                 110

Val Thr Trp Leu Leu Asn Gln Ile Thr Lys Leu Lys Pro Arg Lys Cys
        115                 120                 125

Val Pro Ser Ile Ser Val Leu Arg Glu Gln Leu Asp Gln Pro Asp Gly
    130                 135                 140

Gly Ser Asp Leu Pro Leu Leu Asp Val Phe Ile Asn Thr Val Asp Pro
145                 150                 155                 160

Val Asp Glu Pro Met Leu Tyr Thr Met Asn Ser Ile Leu Ser Ile Leu
                165                 170                 175

Ala Thr Asp Tyr Pro Val Gln Lys Tyr Ala Thr Tyr Phe Ser Asp Asp
```

```
            180             185             190
Gly Gly Ser Leu Val His Tyr Glu Gly Leu Leu Thr Ala Glu Phe
            195             200             205

Ala Ala Ser Trp Val Pro Phe Cys Arg Lys His Cys Val Glu Pro Arg
210             215             220

Ala Pro Glu Ser Tyr Phe Trp Ala Lys Met Arg Gly Glu Tyr Ala Gly
225             230             235             240

Ser Ala Ala Lys Glu Phe Leu Asp Asp His Arg Arg Met Arg Ala Ala
            245             250             255

Tyr Glu Glu Phe Lys Ala Arg Leu Asp Gly Leu Ser Ala Val Ile Glu
            260             265             270

Gln Arg Ser Glu Ala Cys Asn Arg Ala Ala Asn Glu Lys Glu Gly Cys
            275             280             285

Gly Asn Ala Thr Trp Met Ala Asp Gly Ser Thr Gln Trp Gln Gly Thr
            290             295             300

Trp Ile Lys Pro Ala Lys Gly His Arg Lys Gly His His Pro Ala Ile
305             310             315             320

Leu Gln Val Met Leu Asp Gln Pro Ser Lys Asp Pro Glu Leu Gly Met
            325             330             335

Ala Ala Ser Ser Asp His Pro Leu Asp Phe Ser Ala Val Asp Val Arg
            340             345             350

Leu Pro Met Leu Val Tyr Ile Ala Arg Glu Lys Arg Pro Gly Tyr Asp
            355             360             365

His Gln Lys Lys Ala Gly Ala Met Asn Val Gln Leu Arg Val Ser Ala
            370             375             380

Leu Leu Ser Asn Ala Pro Phe Ile Ile Asn Phe Asp Gly Asp His Tyr
385             390             395             400

Ile Asn Asn Ser Gln Ala Phe Arg Ala Ala Met Cys Phe Met Leu Asp
            405             410             415

Pro Arg Asp Gly Ala Asp Thr Ala Phe Val Gln Phe Pro Gln Arg Phe
            420             425             430

Asp Asp Val Asp Pro Thr Asp Arg Tyr Cys Asn His Asn Arg Met Phe
            435             440             445

Phe Asp Ala Thr Leu Leu Gly Leu Asn Gly Ile Gln Gly Pro Ser Phe
450             455             460

Val Gly Thr Gly Cys Met Phe Arg Arg Val Ala Leu Tyr Ser Ala Asp
465             470             475             480

Pro Pro Arg Trp Arg Ser Asp Asp Ala Lys Glu Ala Lys Ala Ser His
            485             490             495

Arg Pro Asn Met Phe Gly Lys Ser Thr Ser Phe Ile Asn Ser Met Pro
            500             505             510

Ala Ala Ala Asn Gln Glu Arg Ser Val Pro Ser Pro Ala Thr Val Gly
            515             520             525

Glu Ala Glu Leu Ala Asp Ala Met Thr Cys Ala Tyr Glu Asp Gly Thr
            530             535             540

Glu Trp Gly Asn Asp Val Gly Trp Val Tyr Asn Ile Ala Thr Glu Asp
545             550             555             560

Val Val Thr Gly Phe Arg Leu His Arg Thr Gly Trp Arg Ser Thr Tyr
            565             570             575

Cys Ala Met Glu Pro Asp Ala Phe Arg Gly Thr Ala Pro Ile Asn Leu
            580             585             590

Thr Glu Arg Leu Tyr Gln Ile Leu Arg Trp Ser Gly Gly Ser Leu Glu
            595             600             605
```

```
Met Phe Phe Ser Arg Phe Cys Pro Leu Leu Ala Gly Arg Arg Leu His
610                 615                 620

Pro Met Gln Arg Val Ala Tyr Ile Asn Met Thr Thr Tyr Pro Val Ser
625                 630                 635                 640

Thr Phe Phe Ile Leu Met Tyr Tyr Phe Tyr Pro Val Met Trp Leu Phe
                645                 650                 655

Gln Gly Glu Phe Tyr Ile Gln Arg Pro Phe Gln Thr Phe Ala Leu Phe
                660                 665                 670

Val Val Val Val Ile Ala Thr Val Glu Leu Ile Gly Met Val Glu Ile
            675                 680                 685

Arg Trp Ala Gly Leu Thr Leu Leu Asp Trp Val Arg Asn Glu Gln Phe
690                 695                 700

Tyr Ile Ile Gly Thr Thr Gly Val Tyr Pro Met Ala Met Leu His Ile
705                 710                 715                 720

Leu Leu Arg Ser Leu Gly Ile Lys Gly Val Ser Phe Lys Leu Thr Ala
                725                 730                 735

Lys Lys Leu Thr Gly Gly Ala Arg Glu Arg Leu Ala Glu Leu Tyr Asp
                740                 745                 750

Val Gln Trp Val Pro Leu Leu Val Pro Thr Val Val Met Ala Val
            755                 760                 765

Asn Val Ala Ala Ile Gly Ala Ala Ala Gly Lys Ala Ile Val Gly Arg
770                 775                 780

Trp Ser Ala Ala Gln Val Ala Gly Ala Ala Ser Gly Leu Val Phe Asn
785                 790                 795                 800

Val Trp Met Leu Leu Leu Tyr Pro Phe Ala Leu Gly Ile Met Gly
                805                 810                 815

His Trp Ser Lys Arg Pro Tyr Ile Leu Phe Leu Val Leu Val Thr Ala
                820                 825                 830

Val Ala Ala Thr Ala Ser Val Tyr Val Ala Leu Ala Gly Ser Leu Leu
            835                 840                 845

Tyr Leu His Ser Gly Ile Lys Leu Val
    850                 855

<210> SEQ ID NO 7
<211> LENGTH: 2616
<212> TYPE: DNA
<213> ORGANISM: Hordeum vulgare

<400> SEQUENCE: 7
atggccccgg cagtcactcg ccgagccaac gctctccgcg tcgaggcccc ggacggcaat    60
gccgagagcg ggcgcgccag cctagcagca gactcccccg cggccaagcg ggccatcgat   120
gccaaggacg atgtgtgggt ggccgcggct gagggagacg cgtctggagc cagcgccggc   180
aacggcgacc ggccgccgct gttccggacc atgaaggtca aggaagcat cctccatcct   240 tacaggttca tgatcctcgt gcgcttggtc gccgtcgtcg cgttcttcgc gtggcgcctg   300
aagcacaaga accacgacgg catgtggctc tgggccacgt ccatggtcgc cgacgtctgg   360
ttcggcttct catggctcct caaccagctg cccaagctca accccatcaa gcgcgtcccc   420
gacctggccg ccctcgccga ccagtgcggc tcctccggcg acgccaacct gccaggcatc   480
gacatctttg tcaccaccgt ggaccccgtg acgaacccca tcttgtacac cgtgaacacc   540
atactctcca tcctcgccac cgactaccct gtcgataagt acgcctgcta cctctcagac   600
gacggcggca cgttggtgca ctacgaggcc atgatcgaag tggccaattt cgcggtgatg   660
```

```
tgggtccctt tttgccggaa gcactgtgtc gagccaaggt cccccgagaa ctactttggg      720
atgaaaacgc agccgtacgt cgggagtatg gctggagaat tcatgaggga catagggcgt      780
gtgcgcagag agtatgatga gttcaaggtg aggatagact ccctgtccac caccatccgc      840
caaagatctg atgcgtacaa ctcgagcaac aaaggagatg gtgtgcgtgc aacctggatg      900
gctgatggga cacaatggcc tggtacgtgg attgagcagg ttgagaacca ccggagagga      960
caacatgctg gaattgttca ggtcatacta agccatccta gttgcaaacc gcaactgggg     1020
tctccggcga gcactgacaa tccacttgac ttcagcaacg ttgacacgag gctgcccatg     1080
ctcgtctaca tgtcccggga gaagcgcccc ggttataacc accaaaagaa ggcaggcgcc     1140
atgaacgtga tgctccgtgt ctcggcgttg ctctccaacg cgccattcgt cgtcaatttt     1200
gactgcgacc actacatcaa caacacgcaa gctctccgcg cccctatgtg cttcatgctc     1260
gaccctcgcg acggtcagaa cacggccttc gtccagtttc cgcagcgctt cgacgacgtc     1320
gacccgacgg accgctacgc caaccacaac cgtgtcttct cgacggtac  catgctctcc     1380
ctcaacggcc ttcaagggcc ttcctacctc ggcactggca ccatgttccg tcgtgtcacg     1440
ctctatggca tggagccacc acgttacaga gcggagaaca tcaagcttgt aggtaagacc     1500
tatgagttcg gtagctcgac gtctttcatc aattccatgc cggacggcgc aatccaagag     1560
cggtctatca cgccggtgtt ggtcgacgag gcactcagca atgacctggc taccctgatg     1620
acgtgtgctt acgaggacgg gacctcatgg gggagagacg ttgggtgggt gtacaacatc     1680
gcgacggagg acgtggtgac cggattccgc atgcaccggc agggtggcg  ctccatgtat     1740
tgctccatgg agccggccgc cttccgcgga acagcgccga tcaacctcac cgagcgcctt     1800
taccaggtgc tccggtggtc gggcggctct ctcgagatgt tcttctccca cagcaacgct     1860
ctcatggccg gccgcgtat  ccaccctctg cagcgtgtcg cgtacctcaa catgtcgacc     1920
tacccgatcg tcacggtgtt catcctggcc tacaacctct ccccgtcat  gtggctcttc     1980
tccgagcagt tctacatcca gaggccgttc ggcacgtaca tcatgtacct cgtcggcgtc     2040
atagcgatga ttcacgtgat cggcatgttc gaggtgaaat gggcggggat cacgctgctc     2100
gactggtgcc gcaacgagca gttctacatg atcggggcga cgggcgtgta cccgacggcg     2160
gtgctttaca tggcgctcaa gcttgtcacg gggaagggga tatacttcag gctcacatcc     2220
aagcagacgg acgcttgctc caacgacaag ttcgccgacc tgtacacggt gcggtgggtg     2280
ccgctgctgt tcccgacggt cgcagtgctc atcgtgaacg tcgcggctgt cggggcagcg     2340
ataggcaagg cagcagcgtg gggcttcttc acggaccagg cgcggcacgt gctgctcggg     2400
atggtgttca acgtgtggat cctcgtgctc ctctacccgt ttgcgctcgg gatcatgggg     2460
aaatggggga agagacccat catcctgttc gtcatgttga tcatggccat ggcgccgtc      2520
gggctcgtgt atgtcgcctt ccatgatccc tacccaactg atttttcaga agttgcagct     2580
tctcttggtg aagcatcgct gaccgggcca tctggg                                2616
```

<210> SEQ ID NO 8
<211> LENGTH: 872
<212> TYPE: PRT
<213> ORGANISM: Hordeum vulgare

<400> SEQUENCE: 8

Met Ala Pro Ala Val Thr Arg Arg Ala Asn Ala Leu Arg Val Glu Ala
1               5                   10                  15

Pro Asp Gly Asn Ala Glu Ser Gly Arg Ala Ser Leu Ala Ala Asp Ser
            20                  25                  30

```
Pro Ala Ala Lys Arg Ala Ile Asp Ala Lys Asp Val Trp Val Ala
         35                  40                  45
Ala Ala Glu Gly Asp Ala Ser Gly Ala Ser Ala Gly Asn Gly Asp Arg
 50                  55                  60
Pro Pro Leu Phe Arg Thr Met Lys Val Lys Gly Ser Ile Leu His Pro
 65                  70                  75                  80
Tyr Arg Phe Met Ile Leu Val Arg Leu Val Ala Val Ala Phe Phe
                 85                  90                  95
Ala Trp Arg Leu Lys His Lys Asn His Asp Gly Met Trp Leu Trp Ala
             100                 105                 110
Thr Ser Met Val Ala Asp Val Trp Phe Gly Phe Ser Trp Leu Leu Asn
             115                 120                 125
Gln Leu Pro Lys Leu Asn Pro Ile Lys Arg Val Pro Asp Leu Ala Ala
 130                 135                 140
Leu Ala Asp Gln Cys Gly Ser Ser Gly Asp Ala Asn Leu Pro Gly Ile
145                 150                 155                 160
Asp Ile Phe Val Thr Thr Val Asp Pro Val Asp Glu Pro Ile Leu Tyr
                 165                 170                 175
Thr Val Asn Thr Ile Leu Ser Ile Leu Ala Thr Asp Tyr Pro Val Asp
             180                 185                 190
Lys Tyr Ala Cys Tyr Leu Ser Asp Asp Gly Gly Thr Leu Val His Tyr
             195                 200                 205
Glu Ala Met Ile Glu Val Ala Asn Phe Ala Val Met Trp Val Pro Phe
210                 215                 220
Cys Arg Lys His Cys Val Glu Pro Arg Ser Pro Glu Asn Tyr Phe Gly
225                 230                 235                 240
Met Lys Thr Gln Pro Tyr Val Gly Ser Met Ala Gly Glu Phe Met Arg
                 245                 250                 255
Glu His Arg Arg Val Arg Arg Glu Tyr Asp Glu Phe Lys Val Arg Ile
             260                 265                 270
Asp Ser Leu Ser Thr Thr Ile Arg Gln Arg Ser Asp Ala Tyr Asn Ser
             275                 280                 285
Ser Asn Lys Gly Asp Gly Val Arg Ala Thr Trp Met Ala Asp Gly Thr
 290                 295                 300
Gln Trp Pro Gly Thr Trp Ile Glu Gln Val Glu Asn His Arg Arg Gly
305                 310                 315                 320
Gln His Ala Gly Ile Val Gln Val Ile Leu Ser His Pro Ser Cys Lys
                 325                 330                 335
Pro Gln Leu Gly Ser Pro Ala Ser Thr Asp Asn Pro Leu Asp Phe Ser
             340                 345                 350
Asn Val Asp Thr Arg Leu Pro Met Leu Val Tyr Met Ser Arg Glu Lys
             355                 360                 365
Arg Pro Gly Tyr Asn His Gln Lys Lys Ala Gly Ala Met Asn Val Met
 370                 375                 380
Leu Arg Val Ser Ala Leu Leu Ser Asn Ala Pro Phe Val Val Asn Phe
385                 390                 395                 400
Asp Cys Asp His Tyr Ile Asn Asn Thr Gln Ala Leu Arg Ala Pro Met
                 405                 410                 415
Cys Phe Met Leu Asp Pro Arg Asp Gly Gln Asn Thr Ala Phe Val Gln
             420                 425                 430
Phe Pro Gln Arg Phe Asp Asp Val Asp Pro Thr Asp Arg Tyr Ala Asn
             435                 440                 445
```

His Asn Arg Val Phe Phe Asp Gly Thr Met Leu Ser Leu Asn Gly Leu
450                     455                 460

Gln Gly Pro Ser Tyr Leu Gly Thr Gly Thr Met Phe Arg Arg Val Thr
465                 470                 475                 480

Leu Tyr Gly Met Glu Pro Pro Arg Tyr Arg Ala Glu Asn Ile Lys Leu
            485                 490                 495

Val Gly Lys Thr Tyr Glu Phe Gly Ser Ser Thr Ser Phe Ile Asn Ser
                500                 505                 510

Met Pro Asp Gly Ala Ile Gln Glu Arg Ser Ile Thr Pro Val Leu Val
            515                 520                 525

Asp Glu Ala Leu Ser Asn Asp Leu Ala Thr Leu Met Thr Cys Ala Tyr
530                 535                 540

Glu Asp Gly Thr Ser Trp Gly Arg Asp Val Gly Trp Val Tyr Asn Ile
545                 550                 555                 560

Ala Thr Glu Asp Val Val Thr Gly Phe Arg Met His Arg Gln Gly Trp
                565                 570                 575

Arg Ser Met Tyr Cys Ser Met Glu Pro Ala Ala Phe Arg Gly Thr Ala
            580                 585                 590

Pro Ile Asn Leu Thr Glu Arg Leu Tyr Gln Val Leu Arg Trp Ser Gly
            595                 600                 605

Gly Ser Leu Glu Met Phe Phe Ser His Ser Asn Ala Leu Met Ala Gly
610                 615                 620

Arg Arg Ile His Pro Leu Gln Arg Val Ala Tyr Leu Asn Met Ser Thr
625                 630                 635                 640

Tyr Pro Ile Val Thr Val Phe Ile Leu Ala Tyr Asn Leu Phe Pro Val
                645                 650                 655

Met Trp Leu Phe Ser Glu Gln Phe Tyr Ile Gln Arg Pro Phe Gly Thr
            660                 665                 670

Tyr Ile Met Tyr Leu Val Gly Val Ile Ala Met Ile His Val Ile Gly
            675                 680                 685

Met Phe Glu Val Lys Trp Ala Gly Ile Thr Leu Leu Asp Trp Cys Arg
690                 695                 700

Asn Glu Gln Phe Tyr Met Ile Gly Ala Thr Gly Val Tyr Pro Thr Ala
705                 710                 715                 720

Val Leu Tyr Met Ala Leu Lys Leu Val Thr Gly Lys Gly Ile Tyr Phe
                725                 730                 735

Arg Leu Thr Ser Lys Gln Thr Asp Ala Cys Ser Asn Asp Lys Phe Ala
            740                 745                 750

Asp Leu Tyr Thr Val Arg Trp Val Pro Leu Leu Phe Pro Thr Val Ala
            755                 760                 765

Val Leu Ile Val Asn Val Ala Ala Val Gly Ala Ala Ile Gly Lys Ala
770                 775                 780

Ala Ala Trp Gly Phe Phe Thr Asp Gln Ala Arg His Val Leu Leu Gly
785                 790                 795                 800

Met Val Phe Asn Val Trp Ile Leu Val Leu Tyr Pro Phe Ala Leu
                805                 810                 815

Gly Ile Met Gly Lys Trp Gly Lys Arg Pro Ile Ile Leu Phe Val Met
            820                 825                 830

Leu Ile Met Ala Ile Gly Ala Val Gly Leu Val Tyr Val Ala Phe His
            835                 840                 845

Asp Pro Tyr Pro Thr Asp Phe Ser Glu Val Ala Ala Ser Leu Gly Glu
850                 855                 860

Ala Ser Leu Thr Gly Pro Ser Gly

<210> SEQ ID NO 9
<211> LENGTH: 2637
<212> TYPE: DNA
<213> ORGANISM: Hordeum vulgare

<400> SEQUENCE: 9

| | | | | | |
|---|---|---|---|---|---|
| atgttgtcgc | cccggacaga | cgccggcgcc | ggcgccgcca | ccgacctcag | ccagccactt | 60 |
| ctctggaacc | gcaatggcgt | tcacgcagga | gcattggtcg | tcatgccagt | cgtggccaat | 120 |
| ggtcacggcg | gcggcgacaa | gcttaagggc | gccccgaaag | ccaaggacaa | gtactggaaa | 180 |
| gacgtcgacc | agccggacga | catggcggca | gcgccagacc | tggacaacgg | cggcggccgg | 240 |
| ccgctgctgt | tctcgaactt | gagagtccag | aatatcatcc | tgtacccegg | cgaggtattg | 300 |
| atcctgatac | gagtaatcgc | cgtaatctta | tttgttggat | ggcgcatcaa | gcataacaat | 360 |
| tcagatgtca | tgtggttttg | gatgatgtcc | gtcgtcgcag | acgtgtggtt | tagcttatca | 420 |
| tggctaagct | accaactgcc | aaagtataat | cccgttaaaa | ggatacccga | ccttgctaca | 480 |
| ctcaggaaac | aatatgacac | accagggagg | agctcccagc | tgccaagcat | tgacgtcatc | 540 |
| gtcaccactg | ccagtgctac | cgatgagccc | atattgtaca | ccatgaactg | tgttctctct | 600 |
| atacttgcag | ctgactatca | tattggcagg | tgcaactgct | acctatcaga | tgatagcggc | 660 |
| tcattggtcc | tttatgaggc | attggttgag | actgcaaagt | ttgctgcttt | atgggttcct | 720 |
| ttctgtagaa | agcatcagat | tgagccaaga | gcaccggaaa | gctattttga | actaaagggc | 780 |
| ccgttgtatg | gagggacgcc | acataaggag | ttctttcagg | attataagca | tgtacgtaca | 840 |
| caatatgaag | agttcaagaa | gaatttagat | atgcttccta | acaccatcca | tcaaaggtcg | 900 |
| ggaacttaca | gtaaaacagg | aacggaggat | gaagatgcaa | aagtgacttg | gatggctgac | 960 |
| ggaacacaat | ggccaggcac | atggcttgac | ccagcagaaa | acatagggc | cgggcatcat | 1020 |
| gcaggaattg | ttaagattgt | gcagagccat | ccagaacatg | tggttcaacc | aggcgtacaa | 1080 |
| gagagccttg | acaacccact | cagctttgac | gatgttgatg | tgcgcctgcc | catgttggta | 1140 |
| tatgtggctc | gtgaaaagag | tccaggtatc | gagcataaca | aaaaggcagg | cgctttgaat | 1200 |
| gcagagctac | gtatctcagc | tctactctct | aatgcacctt | tcttcattaa | ctttgactgc | 1260 |
| gaccactaca | tcaacaattc | agaagcccta | cgtgcagctg | tttgcttcat | gctagaccca | 1320 |
| cgtgaagggg | ataatactgg | atttgttcag | ttcccgcaaa | gatttgataa | tgtcgaccca | 1380 |
| actgaccggt | atggaaacca | taatcgagtc | tttttttgatg | gtgccatgta | tggcctcaat | 1440 |
| ggtcaacaag | ggcctactta | ccttggcaca | ggttgcatgt | tccgtcccct | tgcactctat | 1500 |
| ggaattgatc | caccttgctg | gagagccgag | gacatcatag | tcgacagtaa | caggtttggc | 1560 |
| aactcattac | ccttcctcaa | ctcagtacta | gcagccataa | agcaagagga | aggtgtcaca | 1620 |
| ctaccaccac | cactgatga | ttcatttctt | gaagagatga | caaaagttgt | gtcatgttcc | 1680 |
| tatgatgatt | ccactgattg | gggtagggggc | attggctaca | tatacaatat | ggcaacagaa | 1740 |
| gacatagtaa | caggatttcg | tatccatggg | caagggtggt | gctccatgta | tgttaccatg | 1800 |
| gaacgtgaag | cgttccgtgg | cactgcaccg | atcaatctaa | cagagcgcct | ccgccaaata | 1860 |
| gtgcgatggt | ctggtggttc | cctagagatg | ttcttctcgc | acatcagccc | actattcgct | 1920 |
| ggtcgtcgac | tcagtttggt | gcagcgactc | tcgtacatca | atttcactat | atacccattg | 1980 |
| acatcactct | ttatcctaat | gtatgccttc | tgtccagtga | tgtggcttct | tccaacagaa | 2040 |
| atacttatac | aaaggccata | taccaggtac | attgtgtacc | ttatcattgt | cgtcgcgatg | 2100 |

```
atccatgtga ttggcatgtt tgagataatg tgggcaggaa tcacatggtt ggattggtgg    2160
cgcaacgagc aattttttcat gatcggctcg gtaactgcat atccaacggc ggtgttgcac    2220
atggtggtga atatccttac aaaaaagggt atacacttca gagtaaccac aaagcaacca    2280
gtggctgata cagatgacaa gtatgctgag atgtatgaag tgcattgggt acccatgatg    2340
gtccccgcgg ttgtggtatt gttttccaac atcttggcta ttggtgtagc aattggtaaa    2400
tcagtcttat acatggggac atggtctgta gcacagaaaa ggcatggtgc actagggcta    2460
ttgttcaacc tgtggattat ggtgctcctt tacccatttg cattggcgat tattggaaga    2520
tgggccaaga gaaccggaat cctattcatc ttactaccca ttgctttctt ggccaccgca    2580
ttgatgtaca ttggcatcca tacattcctt ttacatttct ttccatccat gttggta       2637

<210> SEQ ID NO 10
<211> LENGTH: 879
<212> TYPE: PRT
<213> ORGANISM: Hordeum vulgare

<400> SEQUENCE: 10

Met Leu Ser Pro Arg Thr Asp Ala Gly Ala Gly Ala Ala Thr Asp Leu
1               5                   10                  15

Ser Gln Pro Leu Leu Trp Asn Arg Asn Gly Val His Ala Gly Ala Leu
            20                  25                  30

Val Val Met Pro Val Ala Asn Gly His Gly Gly Asp Lys Leu
        35                  40                  45

Lys Gly Ala Pro Lys Ala Lys Asp Lys Tyr Trp Lys Asp Val Asp Gln
    50                  55                  60

Pro Asp Asp Met Ala Ala Ala Pro Asp Leu Asp Asn Gly Gly Gly Arg
65                  70                  75                  80

Pro Leu Leu Phe Ser Asn Leu Arg Val Gln Asn Ile Ile Leu Tyr Pro
                85                  90                  95

Gly Glu Val Leu Ile Leu Ile Arg Val Ile Ala Val Ile Leu Phe Val
            100                 105                 110

Gly Trp Arg Ile Lys His Asn Asn Ser Asp Val Met Trp Phe Trp Met
        115                 120                 125

Met Ser Val Val Ala Asp Val Trp Phe Ser Leu Ser Trp Leu Ser Tyr
    130                 135                 140

Gln Leu Pro Lys Tyr Asn Pro Val Lys Arg Ile Pro Asp Leu Ala Thr
145                 150                 155                 160

Leu Arg Lys Gln Tyr Asp Thr Pro Gly Arg Ser Ser Gln Leu Pro Ser
                165                 170                 175

Ile Asp Val Ile Val Thr Thr Ala Ser Ala Thr Asp Glu Pro Ile Leu
            180                 185                 190

Tyr Thr Met Asn Cys Val Leu Ser Ile Leu Ala Ala Asp Tyr His Ile
        195                 200                 205

Gly Arg Cys Asn Cys Tyr Leu Ser Asp Asp Ser Gly Ser Leu Val Leu
    210                 215                 220

Tyr Glu Ala Leu Val Glu Thr Ala Lys Phe Ala Ala Leu Trp Val Pro
225                 230                 235                 240

Phe Cys Arg Lys His Gln Ile Glu Pro Arg Ala Pro Glu Ser Tyr Phe
                245                 250                 255

Glu Leu Lys Gly Pro Leu Tyr Gly Gly Thr Pro His Lys Glu Phe Phe
            260                 265                 270

Gln Asp Tyr Lys His Val Arg Thr Gln Tyr Glu Glu Phe Lys Lys Asn
```

-continued

```
            275                 280                 285
Leu Asp Met Leu Pro Asn Thr Ile His Gln Arg Ser Gly Thr Tyr Ser
290                 295                 300
Lys Thr Gly Thr Glu Asp Glu Asp Ala Lys Val Thr Trp Met Ala Asp
305                 310                 315                 320
Gly Thr Gln Trp Pro Gly Thr Trp Leu Asp Pro Ala Glu Lys His Arg
                325                 330                 335
Ala Gly His His Ala Gly Ile Val Lys Ile Val Gln Ser His Pro Glu
                340                 345                 350
His Val Val Gln Pro Gly Val Gln Glu Ser Leu Asp Asn Pro Leu Ser
                355                 360                 365
Phe Asp Asp Val Asp Val Arg Leu Pro Met Leu Val Tyr Val Ala Arg
370                 375                 380
Glu Lys Ser Pro Gly Ile Glu His Asn Lys Lys Ala Gly Ala Leu Asn
385                 390                 395                 400
Ala Glu Leu Arg Ile Ser Ala Leu Leu Ser Asn Ala Pro Phe Phe Ile
                405                 410                 415
Asn Phe Asp Cys Asp His Tyr Ile Asn Asn Ser Glu Ala Leu Arg Ala
                420                 425                 430
Ala Val Cys Phe Met Leu Asp Pro Arg Glu Gly Asp Asn Thr Gly Phe
                435                 440                 445
Val Gln Phe Pro Gln Arg Phe Asp Asn Val Asp Pro Thr Asp Arg Tyr
450                 455                 460
Gly Asn His Asn Arg Val Phe Phe Asp Gly Ala Met Tyr Gly Leu Asn
465                 470                 475                 480
Gly Gln Gln Gly Pro Thr Tyr Leu Gly Thr Gly Cys Met Phe Arg Pro
                485                 490                 495
Leu Ala Leu Tyr Gly Ile Asp Pro Pro Cys Trp Arg Ala Glu Asp Ile
                500                 505                 510
Ile Val Asp Ser Asn Arg Phe Gly Asn Ser Leu Pro Phe Leu Asn Ser
                515                 520                 525
Val Leu Ala Ala Ile Lys Gln Glu Glu Gly Val Thr Leu Pro Pro Pro
                530                 535                 540
Leu Asp Asp Ser Phe Leu Glu Glu Met Thr Lys Val Val Ser Cys Ser
545                 550                 555                 560
Tyr Asp Asp Ser Thr Asp Trp Gly Arg Gly Ile Gly Tyr Ile Tyr Asn
                565                 570                 575
Met Ala Thr Glu Asp Ile Val Thr Gly Phe Arg Ile His Gly Gln Gly
                580                 585                 590
Trp Cys Ser Met Tyr Val Thr Met Glu Arg Glu Ala Phe Arg Gly Thr
                595                 600                 605
Ala Pro Ile Asn Leu Thr Glu Arg Leu Arg Gln Ile Val Arg Trp Ser
                610                 615                 620
Gly Gly Ser Leu Glu Met Phe Phe Ser His Ile Ser Pro Leu Phe Ala
625                 630                 635                 640
Gly Arg Arg Leu Ser Leu Val Gln Arg Leu Ser Tyr Ile Asn Phe Thr
                645                 650                 655
Ile Tyr Pro Leu Thr Ser Leu Phe Ile Leu Met Tyr Ala Phe Cys Pro
                660                 665                 670
Val Met Trp Leu Leu Pro Thr Glu Ile Leu Ile Gln Arg Pro Tyr Thr
                675                 680                 685
Arg Tyr Ile Val Tyr Leu Ile Ile Val Val Ala Met Ile His Val Ile
690                 695                 700
```

```
Gly Met Phe Glu Ile Met Trp Ala Gly Ile Thr Trp Leu Asp Trp Trp
705                 710                 715                 720

Arg Asn Glu Gln Phe Phe Met Ile Gly Ser Val Thr Ala Tyr Pro Thr
                725                 730                 735

Ala Val Leu His Met Val Val Asn Ile Leu Thr Lys Lys Gly Ile His
            740                 745                 750

Phe Arg Val Thr Thr Lys Gln Pro Val Ala Asp Thr Asp Asp Lys Tyr
        755                 760                 765

Ala Glu Met Tyr Glu Val His Trp Val Pro Met Met Val Pro Ala Val
    770                 775                 780

Val Val Leu Phe Ser Asn Ile Leu Ala Ile Gly Val Ala Ile Gly Lys
785                 790                 795                 800

Ser Val Leu Tyr Met Gly Thr Trp Ser Val Ala Gln Lys Arg His Gly
                805                 810                 815

Ala Leu Gly Leu Leu Phe Asn Leu Trp Ile Met Val Leu Leu Tyr Pro
            820                 825                 830

Phe Ala Leu Ala Ile Ile Gly Arg Trp Ala Lys Arg Thr Gly Ile Leu
        835                 840                 845

Phe Ile Leu Leu Pro Ile Ala Phe Leu Ala Thr Ala Leu Met Tyr Ile
    850                 855                 860

Gly Ile His Thr Phe Leu Leu His Phe Phe Pro Ser Met Leu Val
865                 870                 875

<210> SEQ ID NO 11
<211> LENGTH: 2691
<212> TYPE: DNA
<213> ORGANISM: Hordeum vulgare

<400> SEQUENCE: 11
atgggttctt tggcggcagc caacggggcc ggtcatgcga gcaatggcgc cggcgtcgcg       60
gaccaggcgc tggcactgga aacggcacc ggcaatgggc acaaggccag cgacgccaac       120
cgagcgacgc cggtacagca ggcaaacggc agcagcaagg ccgcggggaa ggttagcccg       180
aaggacaagt actgggtggc cgtcgatgag ggagagatgg cggccgccat agcggacggc       240
ggcgaggacg ccggcgaccc gctgctgtac cggacgttca aggtcaaggg catcctcctg       300
catccctaca ggttgctgag cttgatcaga ttggttgcta cgtcctattt tttcgtatgg       360
cgtgtcaggc acccatacgc tgatggcatg tggctctggt ggatatcgat ggttggggat       420
ctttggtttg cgtcacttg gttgctaaac caagttgcaa agctcaaccc tgtcaagcgt       480
gtccccaacc ttgcgctttt gcaacagcag tttgatctcc ctgacggcaa ctccaacctt       540
ccttgtcttg atgtcttcat caacaccgtt gatcccatta atgaacctat gatatacact       600
atgaactcca tcatatccat ccttgctgca gactatccgg ttgacaagca tgcttgctac       660 cttttcagatg atggtgggtc aataatccat tatgatggtt tgcttgagac tgcaaaattt       720
gctgcattat gggttccctt tgcagaaaaa cattccattg agccaagagc ccctgagagc       780 tattttttctt tgaatacacg cccatacact ggaaatgcac acaagactt tgtcaatgac       840 cgcagacaca tgtgtagaga gtatgatgag ttcaaggagc gcttagatgc acttttttacc       900 ctcattccca acggtcaga tgtgtacaat catgctgctg gcaaagaagg tgcaaaggca       960
acttggatgg cagatgggac acagtggcca ggcacatgga ttgacccagc tgaaaaccat      1020
aagaaaggac aacatgctgg gatcgttaag gttttgttga acatccaag ttatgaacca      1080 gaacttggtc taggagcaag caccaacagt cctctagact tcagtgcagt tgatgtgcgc      1140
```

```
ctcccaatgc tcgtttacat ctcccgtgag aagagtccaa gctgtgatca tcaaagaag    1200 gcaggtgcca tgaacgtaca gttgcgagtc tctgccctcc tgaccaatgc gcccttatc    1260 atcaactttg atggtgacca ctacgtcaac aactcgaaag ccttccgtgc tggcatatgt   1320
ttcatgctcg atcgccgtga aggtgacaat actgcctttg tccagtttcc ccaacgcttc   1380
gatgatgttg atcccacaga taggtactgc aatcacaatc gtgtcttctt tgacgccacc   1440
ttgctcggct ccaatggcat ccaagggccg tcttatgttg gcactggttg catgttccgc   1500
cgtgtcgcac tttacggtgt tgacccacct cgctggagac ctgatgacgt gaagatcgtg   1560
gacagctcca gcaagtttgg cagttcagag tcattcatca gctcaatact gccagcagca   1620
gaccaagaac gctccatcat gtcgccaccg gcacttgaag agtctgtcat ggctgactta   1680
gctcatgtca tgacttgtgc atatgaggac gggactgaat ggggcagaga agttggttgg   1740
gtgtacaaca ttgcaactga ggatgtggtg accggcttcc ggctgcaccg gaatgggtgg   1800
cgatccatgt actgccgcat ggaaccagat gcattcgccg gcaccgcgcc aatcaacctc   1860
actgagcggc tctaccagat cctgcgctgg tcgggggggct cccttgagat gttcttctcg   1920
cacaactgcc cactcctggc tggccgccgc ctccacccaa tgcaaagaat tgcctatgcc   1980
aacatgacag cctacccagt ttcatctgtc tttcttgtgt tctatctcct cttcccggtg   2040
atatggatct tccgtgggca attctacata cagaagccat tccccacgta tgtgttgtac   2100
ctcgtcatcg tcatagccct gaccgagtta atcggtatgg ttgagatcaa gtgggctggg   2160
ctcacgctgc tggactggat ccgcaacgag cagttctaca ttattggtgc aacagccgtg   2220
taccctacag cagtatttca catagtgctg aagctgtttg gcctgaaggg tgtttcattc   2280
aagctgacgg caaaacaggt agcaagcagt accagcgata agtttgctga actgtatgcc   2340
gtgcagtggg ctccgatgct gatccctacc atggtggtta tagcggtgaa tgtttgtgcc   2400
attggcgcgt cgataggcaa ggcggtagtg ggaggatggt cactgatgca gatggccgat   2460
gcaggacttg ggctggtgtt caacgcgtgg attctggtgc tgatctaccc gttttgcactg  2520 ggcatgattg gacggtggag caagaggccc tacatcctgt tcattctgtt tgtcattgcg   2580
tttattttga tcgcattggt ggatatcgcc atccaggcca tgcggtctgg gattgttcgg   2640
ttccacttta aaagctcagg tggcgccact tttcccacaa gctggggttt g             2691
```

<210> SEQ ID NO 12
<211> LENGTH: 897
<212> TYPE: PRT
<213> ORGANISM: Hordeum vulgare

<400> SEQUENCE: 12

```
Met Gly Ser Leu Ala Ala Ala Asn Gly Ala Gly His Ala Ser Asn Gly
1               5                   10                  15

Ala Gly Val Ala Asp Gln Ala Leu Ala Leu Glu Asn Gly Thr Gly Asn
            20                  25                  30

Gly His Lys Ala Ser Asp Ala Asn Arg Ala Thr Pro Val Gln Gln Ala
        35                  40                  45

Asn Gly Ser Ser Lys Ala Ala Gly Lys Val Ser Pro Lys Asp Lys Tyr
    50                  55                  60

Trp Val Ala Val Asp Glu Gly Glu Met Ala Ala Ala Ile Ala Asp Gly
65                  70                  75                  80

Gly Glu Asp Gly Arg Arg Pro Leu Leu Tyr Arg Thr Phe Lys Val Lys
                85                  90                  95
```

-continued

```
Gly Ile Leu Leu His Pro Tyr Arg Leu Leu Ser Leu Ile Arg Leu Val
            100                 105                 110

Ala Ile Val Leu Phe Phe Val Trp Arg Val Arg His Pro Tyr Ala Asp
        115                 120                 125

Gly Met Trp Leu Trp Trp Ile Ser Met Val Gly Asp Leu Trp Phe Gly
    130                 135                 140

Val Thr Trp Leu Leu Asn Gln Val Ala Lys Leu Asn Pro Val Lys Arg
145                 150                 155                 160

Val Pro Asn Leu Ala Leu Leu Gln Gln Gln Phe Asp Leu Pro Asp Gly
                165                 170                 175

Asn Ser Asn Leu Pro Cys Leu Asp Val Phe Ile Asn Thr Val Asp Pro
            180                 185                 190

Ile Asn Glu Pro Met Ile Tyr Thr Met Asn Ser Ile Ile Ser Ile Leu
        195                 200                 205

Ala Ala Asp Tyr Pro Val Asp Lys His Ala Cys Tyr Leu Ser Asp Asp
    210                 215                 220

Gly Gly Ser Ile Ile His Tyr Asp Gly Leu Leu Glu Thr Ala Lys Phe
225                 230                 235                 240

Ala Ala Leu Trp Val Pro Phe Cys Arg Lys His Ser Ile Glu Pro Arg
                245                 250                 255

Ala Pro Glu Ser Tyr Phe Ser Leu Asn Thr Arg Pro Tyr Thr Gly Asn
            260                 265                 270

Ala Pro Gln Asp Phe Val Asn Asp Arg Arg His Met Cys Arg Glu Tyr
        275                 280                 285

Asp Glu Phe Lys Glu Arg Leu Asp Ala Leu Phe Thr Leu Ile Pro Lys
    290                 295                 300

Arg Ser Asp Val Tyr Asn His Ala Ala Gly Lys Glu Gly Ala Lys Ala
305                 310                 315                 320

Thr Trp Met Ala Asp Gly Thr Gln Trp Pro Gly Thr Trp Ile Asp Pro
                325                 330                 335

Ala Glu Asn His Lys Lys Gly Gln His Ala Gly Ile Val Lys Val Leu
            340                 345                 350

Leu Lys His Pro Ser Tyr Glu Pro Glu Leu Gly Leu Gly Ala Ser Thr
        355                 360                 365

Asn Ser Pro Leu Asp Phe Ser Ala Val Asp Val Arg Leu Pro Met Leu
    370                 375                 380

Val Tyr Ile Ser Arg Glu Lys Ser Pro Ser Cys Asp His Gln Lys Lys
385                 390                 395                 400

Ala Gly Ala Met Asn Val Gln Leu Arg Val Ser Ala Leu Leu Thr Asn
                405                 410                 415

Ala Pro Phe Ile Ile Asn Phe Asp Gly Asp His Tyr Val Asn Asn Ser
            420                 425                 430

Lys Ala Phe Arg Ala Gly Ile Cys Phe Met Leu Asp Arg Arg Glu Gly
        435                 440                 445

Asp Asn Thr Ala Phe Val Gln Phe Pro Gln Arg Phe Asp Asp Val Asp
    450                 455                 460

Pro Thr Asp Arg Tyr Cys Asn His Asn Arg Val Phe Phe Asp Ala Thr
465                 470                 475                 480

Leu Leu Gly Ser Asn Gly Ile Gln Gly Pro Ser Tyr Val Gly Thr Gly
                485                 490                 495

Cys Met Phe Arg Arg Val Ala Leu Tyr Gly Val Asp Pro Pro Arg Trp
            500                 505                 510

Arg Pro Asp Asp Val Lys Ile Val Asp Ser Ser Ser Lys Phe Gly Ser
```

-continued

```
            515                 520                 525
Ser Glu Ser Phe Ile Ser Ser Ile Leu Pro Ala Ala Asp Gln Glu Arg
530                 535                 540

Ser Ile Met Ser Pro Pro Ala Leu Glu Glu Ser Val Met Ala Asp Leu
545                 550                 555                 560

Ala His Val Met Thr Cys Ala Tyr Glu Asp Gly Thr Glu Trp Gly Arg
                565                 570                 575

Glu Val Gly Trp Val Tyr Asn Ile Ala Thr Glu Asp Val Val Thr Gly
            580                 585                 590

Phe Arg Leu His Arg Asn Gly Trp Arg Ser Met Tyr Cys Arg Met Glu
        595                 600                 605

Pro Asp Ala Phe Ala Gly Thr Ala Pro Ile Asn Leu Thr Glu Arg Leu
610                 615                 620

Tyr Gln Ile Leu Arg Trp Ser Gly Gly Ser Leu Glu Met Phe Phe Ser
625                 630                 635                 640

His Asn Cys Pro Leu Leu Ala Gly Arg Arg Leu His Pro Met Gln Arg
                645                 650                 655

Ile Ala Tyr Ala Asn Met Thr Ala Tyr Pro Val Ser Ser Val Phe Leu
            660                 665                 670

Val Phe Tyr Leu Leu Phe Pro Val Ile Trp Ile Phe Arg Gly Gln Phe
        675                 680                 685

Tyr Ile Gln Lys Pro Phe Pro Thr Tyr Val Leu Tyr Leu Val Ile Val
690                 695                 700

Ile Ala Leu Thr Glu Leu Ile Gly Met Val Glu Ile Lys Trp Ala Gly
705                 710                 715                 720

Leu Thr Leu Leu Asp Trp Ile Arg Asn Glu Gln Phe Tyr Ile Ile Gly
                725                 730                 735

Ala Thr Ala Val Tyr Pro Thr Ala Val Phe His Ile Val Leu Lys Leu
            740                 745                 750

Phe Gly Leu Lys Gly Val Ser Phe Lys Leu Thr Ala Lys Gln Val Ala
        755                 760                 765

Ser Ser Thr Ser Asp Lys Phe Ala Glu Leu Tyr Ala Val Gln Trp Ala
770                 775                 780

Pro Met Leu Ile Pro Thr Met Val Val Ile Ala Val Asn Val Cys Ala
785                 790                 795                 800

Ile Gly Ala Ser Ile Gly Lys Ala Val Val Gly Gly Trp Ser Leu Met
                805                 810                 815

Gln Met Ala Asp Ala Gly Leu Gly Leu Val Phe Asn Ala Trp Ile Leu
            820                 825                 830

Val Leu Ile Tyr Pro Phe Ala Leu Gly Met Ile Gly Arg Trp Ser Lys
        835                 840                 845

Arg Pro Tyr Ile Leu Phe Leu Phe Val Ile Ala Phe Ile Leu Ile
850                 855                 860

Ala Leu Val Asp Ile Ala Ile Gln Ala Met Arg Ser Gly Ile Val Arg
865                 870                 875                 880

Phe His Phe Lys Ser Ser Gly Gly Ala Thr Phe Pro Thr Ser Trp Gly
                885                 890                 895

Leu
```

<210> SEQ ID NO 13
<211> LENGTH: 3489
<212> TYPE: DNA
<213> ORGANISM: Hordeum vulgare

<400> SEQUENCE: 13

```
tgcatcccag cccataaatc ccccacgtac tttactcgtc atttctcgca cctcctcctc      60
cccctccccc tcgcctacat tcattcattg cttccttttc tctctccctg cccatgttaa     120
agcctgcctc ggccattgcc tgagcctgcc attgttggac cttggacctg ttctccttgt     180
cgtaaaggca aaggagagcg cgtgcattga ggacgacggc catggcgcca gcggtggccg     240
gagggggccg cgtgcggagc aatgagccgg ttgctgctgc tgccgccgcg ccggcggcca     300
gcggcaagcc ctgcgtgtgc ggcttccagg tttgcgcctg cacggggtcg gccgcggtgg     360
cctccgccgc ctcgtcgctg acatggacat cgtggccat ggggcagatc ggcgccgtca      420
acgacgagag ctgggtgggc gtggagctcg gcgaagatgg cgagaccgac gaaagcggtg     480
ccgccgttga cgaccgcccc gtattccgca ccgagaagat caagggtgtc tcctccacc      540
cctaccgggt gctgattttc gttcgtctga tcgccttcac gctgttcgtg atctggcgta     600
tctcccacaa gaacccagac gcgatgtggc tgtgggtgac atccatctgc ggcgagttct     660
ggttcggttt ctcgtggctg ctagatcagc tgcccaagct gaaccccatc aaccgcgtgc     720
cggacctggc ggtgctgcgg cagcgcttcg accgcccga cggcacctcc acgctcccgg      780
ggctggacat cttcgtcacc acggccgacc ccatcaagga gcccatcctc tccaccgcca     840
actcggtgct ctccatcctg gccgccgact accccgtgga ccgcaacaca tgctacgtct     900
ccgacgacag tggcatgctg ctcacctacg aggccctggc agagtcctcc aagttcgcca     960
cgctctgggt gcccttctgc cgcaagcacg ggatcgagcc caggggtccg gagagctact    1020
tcgagctcaa gtcacaccct tacatgggga gagcccagga cgagttcgtc aacgaccgcc    1080
gccgcgttcg caaggagtac gacgagttca aggccaggat caacagcctg gagcatgaca    1140
tcaagcagcg caacgacggg tacaacgccg ccattgccca cagccaaggc gtgccccggc    1200
ccacctggat ggcggacggc acccagtggg agggcacatg ggtcgacgcc tccgagaacc    1260
accgcagggg cgaccacgcc ggcatcgtac tggtgctgct gaaccacccg agccaccgcc    1320
ggcagacggg cccgccggcg agcgctgaca acccactgga cttgagcggc gtggatgtgc    1380
gtctccccat gctggtgtac gtgtcccgtg agaagcgccc cggcacgac caccagaaga    1440
aggccggtgc catgaacgcg cttacccgcg cctcggcgct gctctccaac tccccctca   1500
tcctcaacct cgactgcgat cattacatca acaactccca ggcccttcgc gccggcatct    1560
gcttcatggt gggacgggac agcgacacgg ttgccttcgt ccagttcccg cagcgcttcg    1620
agggcgtcga ccccaccgac ctctacgcca accacaaccg catcttcttc gacgcaccc     1680
tccgtgccct ggacggcatg cagggcccca tctacgtcgg cactgggtgt ctcttccgcc    1740
gcatcaccgt ctacggcttc gaccgcccga ggatcaacgt cggcggtccc tgcttccca    1800
ggctcgccgg gctcttcgcc aagaccaagt acgagaagcc cgggctcgag atgaccacgg    1860
ccaaggccaa ggccgcgccc gtgcccgcca agggtaagca cggcttcttg ccactgccca    1920
agaagacgta cggcaagtcg gacgccttcg tggacaccat cccgcgcgcg tcgcacccgt    1980
cgccctacgc cgcggcggct gaggggatcg tggccgacga ggcgaccatc gtcgaggcgg    2040
tgaacgtgac ggccgccgcg ttcgagaaga gaccggctg gggcaaagag atcggctggg    2100
tgtacgacac cgtcacggag gacgtggtca ccggctaccg gatgcatatc aagggtggc     2160
ggtcacgcta ctgctccatc tacccacacg ccttcatcgg caccgccccc atcaacctca    2220
cggagaggct cttccaggtg ctccgctggt ccacggatc cctcgagatc ttcttctcca    2280
agaacaaccc gctcttcggc agcacatacc tccacccgct gcagcgcgtc gcctacatca    2340
```

```
acatcaccac ttaccccttc accgccatct tcctcatctt ctacaccacc gtgccggcgc    2400
tatccttcgt caccggccac ttcatcgtgc agcgcccgac caccatgttc tacgtctacc    2460
tgggcatcgt gctatccacg ctgctcgtca tcgccgtgct ggaggtcaag tgggccgggg    2520
tcacagtctt cgagtggttc aggaacggcc agttctggat gacagcaagt tgctccgcct    2580
acctcgccgc cgtctgccag gtgctgacca aggtgatatt ccggcgggac atctccttca    2640
agctcacatc caagctaccc tcgggagacg agaagaagga cccctacgcc gacctctacg    2700
tggtgcgctg gacgccgctc atgattacac ccatcatcat catcttcgtc aacatcatcg    2760
gatccgccgc ggccttcgcc aaggttctcg acggcgagtg gacgcactgg ctcaaggtcg    2820
ccggcggcgt cttcttcaac ttctgggtgc tcttccacct ctaccccttc gccaagggca    2880
tcctggggaa gcacggaaag acgccagtcg tggtgctcgt ctggtgggca ttcaccttcg    2940
tcatcaccgc cgtgctctac atcaacatcc cccacatgca tacctcggga ggcaagcaca    3000
caacggtgca tggtcaccat ggcaagaagt tggtcgacac agggctctat ggctggctcc    3060
attgatgact ttgcccggac aagacgacct gagacaagaa acaactcatc cactcaacag    3120
tcagtgcatg catccatctc atcgagaagc agagcccgcc aaagtttgaa ttttttaatt    3180
ttttttcttc acttttttgc ccgtttcttt ttagttttgt ccagaaaaaa gatggtgttg    3240
atttgattta gttataatt acctgtggta attaattatg tacttaatta tacattccgc    3300
gaacaacaag ggagacagac gacttacggg gtactggctc gggtggtaag agcttgcact    3360
gtactgtaca tgctcgacga tgtatagaga tgcacagagg agaggatggg agtgctggga    3420
ccgtggggtg gacggcggta ttcttttagt attatatatg gaaacaataa atttaatttc    3480
attaaaaaa                                                             3489
```

<210> SEQ ID NO 14
<211> LENGTH: 2799
<212> TYPE: DNA
<213> ORGANISM: Hordeum vulgare

<400> SEQUENCE: 14

```
gtgcaccacc ggcgccgctg gctcacatcc tagcttctcc tcccttcctg ctccggtcgg      60
gaaacctggg agtgggagac atggcgtcgg cggccggtgc tgctgggtca aatgccagcc     120
tcgccgcccc gctgctggcg agccgcgagg gaggagccaa gaagccggtc ggtgccaagg     180
gcaagcactg ggaggccgcc gacaaggacg agcggcgggc cgccaaggag agcggcggcg     240
aggacggcag gccgctgctg ttccggacgt acaaggtcaa aggcaccctc ctgcacccat     300
acagggcgct aatcttcatt cgcttaattg cggtccttct attcttcgta tggcgcatca     360
agcacaacaa atccgacatc atgtggtttt ggacaatatc agtcgtcggg gacgtatggt     420
tcgggttctc gtggctgctc aaccaactcc caaagttcaa ccctatcaaa accataccctg    480 atatggtcgc ccttaggcga caatacgatc tttcagatgg gacatctaca ctcccgggca     540
tagatgtctt tgtcaccacc gctgacccaa tcgatgagcc gatactatac accatgaatt     600
gtgtcctttc tatccttgct tctgactatc ctgtcgatag gtgtgcctgc tatctcccag     660
atgatagtgg agcattgatt caatacgagg ccttagttga gaccgcaaag tttgctactt     720
tgtgggtccc attttgtcgg aagcattgca ttgagccaag agcccagaa agctactttg      780 aaatagaggc accgttgtac actggaactg caccagagga gttcaagaat gattatagta     840
gtgtacataa agagtatgat gagttcaaag agcgcttgga ctcactatcc gatgctattt     900
```

```
ccaagcgttc tgatgcttac aacagcatga agactgagga aggagatgca aaggccacgt      960
ggatggcaaa tgggacacaa tggccaggat catggattga cacaacgaaa atccatagaa     1020
aaggacatca tgccggaatt gttaaggttg tgttggacca ttcgatccgt gggcataatc     1080
ttggttcaca agaaagcacc cacaacctca gtttcgccaa caccgatgag cgcctcccga     1140
tgcttgtgta tatctctcgt ggaaagaacc caagctatga ccacaacaag aaagctggtg     1200
ccttgaatgc gcaattgcgt gcctctgcac tactctccaa cgcacaattc atcatcaact     1260
ttgactgcga ccactacatc aacaactctc aagccctacg tgcagctatg tgcttcatgc     1320
ttgatcaaag gcaaggtgat aacactgcct tgttcaatt ccctcaacgc ttcgacaatg      1380
ttgatccatc agaccgatat ggaaaccaca accgtgtctt ctttgacggc acaatgctcg     1440
ccctcaatgg cctccaaggg ccatcttacc ttggcactgg ttgcatgttc cgccgcatag     1500
cactttatgg cattgaccca cctgactgga gacatgacaa catcatagtt gatgataaaa     1560
agtttggtag ctccataccc ttcctagatt ccgtatcaaa agccataaac caagaaaggt     1620
ctaccatacc tccacccatt agtgaaacat tggtggctga gatggaaagg gttgtgtcgg     1680
cttcacacga taaagccact ggttggggca agggtgttgg gtacatatat gacatagcca     1740
cagaggatat cgtgactggt ttccgcatcc atgggcaagg ttggcgttcc atgtattgta     1800
caatggagcg tgacgccttc tgtggcattg caccaatcaa cctaaccgag cgcctccacc     1860 aaaattgtgcg ctggtccggt ggatctttag agatgttctt ctcactaaat aacccactca     1920
taggtggtcg ccggatccac gcccttcagc gtgtctccta cctcaacatg acagtctacc     1980
cagtcacatc actctttatc ctactctatg ctctcagccc agtgatgtgg cttatccctg     2040
atgaagtata catccagagg ccattcacca aatatgtcgt gttccttctc gtgatcattc     2100
tgatgatcca tataattggg tggctcgaga taaaatgggc gggggtcaca tggttggatt     2160
actggaggaa tgaacagttc tttatgatcg ggtcgacgag tgcataccca gcagccgtgc     2220
tgcacatggt ggtgaatctc cttacaaaga agggtataca cttcagagtt acttcgaagc     2280
aaacaacggc agacaccaat gacaagtttg ctgacttgta tgacatgcga tgggtgccaa     2340
tgttaatccc tacaacagtg gtgctgattg ccaatgttgg tgcaatcggt gtagccatgg     2400
gtaaaacgat agtatacatg ggagcatgga caattgcaca gaagacacat gccgcattgg     2460
gtctgctctt caacgtgtgg atcatggtcc tgctctatcc gtttgcattg gcgatcatgg     2520
gacggtgggc aaagaggcca gtcatcctgg tggtcttgtt gccggttgcc tttacaatag     2580
tttgccttgt atatgtttct gttcatatat tacttcttag ttttcttcca ttttagccaa     2640
ttgatatagt acaaaaccat tgtattgttt aggttctgta gtaagctggg agccaaatat     2700
gctatgtgta tccaataaac cattgtagta cttgtacttt gtaccaatta atagcggatg     2760
gttataattt aggccttgat ggctaatgtt acaacttac                            2799

<210> SEQ ID NO 15
<211> LENGTH: 2785
<212> TYPE: DNA
<213> ORGANISM: Hordeum vulgare

<400> SEQUENCE: 15
tcagttcact gcttggctgc ttgctcccct acatcactct ctcactctca ctcactcagg       60
gtgcaagaac aggctctgct acttggtagg cggaccaaag gtggcatggc ttctccggcg      120
gccgtcggcg ggggtcgtct agccgaccca ctgctggccg ccgacgtcgt cgtcgtcggc      180
gccaaagaca agtactgggt gcccgccgac gagagagaga tcctggcgtc gcagagcagc      240
```

```
ggcggcggtg aacaggacgg ccgggcaccg ctgctatacc gcacgttcag ggtcaagggc      300
ttcttcatca acctttacag gttattgact ctggtcagag ttatcgtggt tattctattc      360
ttcacgtggc gcatgaggca ccgggactcg gacgcgatgt ggctgtggtg gatctcggtc      420
gtgggcgacc tctggttcgg agtcacctgg ctgctcaacc agatcaccaa gctcaagccc      480
aggaaatgcg tccccagcat ctccgtcctg agagagcagc tcgaccagcc cgacggcggc      540
tccgacctgc cccttctcga cgtgttcatc aacaccgtcg acccggtgga cgagccgatg      600
ctctacacca tgaactccat cctctccatc ctggccaccg actacccgt ccagaagtac       660 gccacctatt tctccgatga cggcgggtcg ctggtgcact acgaggggct gctgctgacg      720
gcggagttcg ccgcgtcgtg ggtcccgttc tgccggaagc attgcgtcga gcctcgcgcc      780
ccggagagct acttctgggc caagatgcgc ggggagtacg ccggcagcgc ggccaaggag      840
ttccttgacg accatcggag gatgcgcgcg gcgtatgagg agttcaaggc gaggctggac      900
gggctttctg ccgtcatcga gcagcggtcc gaggcgtgca accgcgctgc aaacgagaaa      960
gaagggtgtg ggaacgcgac ttggatggcc gatgggtcga cgcaatggca ggggacgtgg     1020
atcaagccgg ccaagggcca ccggaaagga caccatcctg caattcttca ggttatgctg     1080
gatcaaccta gcaaggatcc tgagctggga atggcggcga gctccgacca ccctctggat     1140
ttcagcgccg tggacgtgcg cctcccgatg ctggtctaca ttgcccggga gaagcggcct     1200
gggtatgacc accagaagaa ggcgggcgcc atgaacgtgc agctgcgcgt gtccgcgctg     1260
ctctccaacg cgcccttcat catcaacttc gacggcgacc actacatcaa caactcgcag     1320
gccttccgcg ccgccatgtg cttcatgctc gacccgcgcg acggcgccga caccgccttc     1380
gtccagttcc cgcagcgctt cgacgacgtc gaccccaccg accgctactg caaccacaac     1440
cgcatgttct tcgacgccac cctcctcggc ctcaacggca tccagggccc ctccttcgtc     1500
ggcaccggat gcatgttccg ccgcgtcgct ctctacagcg ccgaccctcc acggtggcgg     1560
tccgacgacg ccaaggaggc caaggcctcg cacaggccca acatgtttgg caagtctacg     1620
tccttcatca actcaatgcc ggcggccgcc aaccaagaac ggtccgtccc gtcaccggcg     1680
acagtcggcg aggcggagct cgcagacgcg atgacttgcg cgtacgagga cggcaccgag     1740
tggggcaacg acgttgggtg ggtgtacaac atcgcgacgg aggacgtggt gaccggcttc     1800
cggctgcacc ggacggggtg cgcgctccacg tactgcgcca tggagcccga cgcgttccgc     1860
ggcacggcgc ccatcaacct caccgagcgc ctgtaccaga tcctgcgttg gtcgggggga     1920
tccctcgaga tgttcttctc ccgcttctgc ccgctcctgg ccggccgccg cctccacccc     1980
atgcagcgcg tcgcctacat caacatgacc acctacccgg tctccacctt cttcatcctc     2040
atgtattact tctacccggt catgtggctc ttccagggg agttctacat ccagaggccg     2100
ttccagacgt tcgcgctctt cgtcgtcgtc gtcatcgcca cggtggagct catcggcatg     2160
gtggagatca ggtgggcagg cctcacgctg ctcgactggg tccgcaacga gcagttctac     2220
atcatcggca ccaccggcgt gtacccgatg gccatgctgc acatcctcct caggtccctc     2280
ggcataaagg gggtgtcctt caagctgacg gccaagaagc tcacgggggg cgccagggag     2340
aggctcgcga gctgtacga cgtgcagtgg gtgccgttgc tggtgcccac cgtggtggtc     2400
atggccgtga acgtggccgc catcggcgcg gcggcgggca aggcgatcgt tgggcggtgg     2460
tcggcagcgc aggtcgcggg ggcggcgagc gggcttgttt tcaacgtgtg gatgctgctg     2520
ctgctctacc cgttcgcgct cgggataatg gggcactgga gcaagaggcc ctacatcctg     2580
```

```
ttccttgtgc tggtgaccgc ggtcgctgcc accgcgtccg tgtacgtcgc actcgcgggg    2640
tccttgctgt acttgcattc ggggataaaa ctagtttaat ttttgtcaag taatgctgca    2700
waacctgtaa aagctgtgaa acaaaacagc tttaattgca gcatataata aagtttacct    2760
tgaaaaaaaa aaaaaaaaaa aaaaa                                          2785
```

<210> SEQ ID NO 16
<211> LENGTH: 2864
<212> TYPE: DNA
<213> ORGANISM: Hordeum vulgare

<400> SEQUENCE: 16

```
ggcagggaaa tcagctgtct agctagtcgc acgtaggcac ttacactatg gccccggcag     60
tcactcgccg agccaacgct ctccgcgtcg aggccccgga cggcaatgcc gagagcgggc    120
gcgccagcct agcagcagac tccccgcggg ccaagcgggc catcgatgcc aaggacgaag    180
accgggtggc cgcggctgag ggagacgcgt ctggagccag cgccggcaac ggcgaccggc    240
cgccgctgtt ccggaccatg aaggtcaagg gaagcatcct ccatccttac aggttcatga    300
tcctcgtgcg cttggtcgcc gtcgtcgcgt tcttcgcgtg gcgcctgaag cacaagaacc    360
acgacggcat gtggctctgg gccacgtcca tggtcgccga cgtctggttc ggcttctcat    420
ggctcctcaa ccagctgccc aagctcaacc ccatcaagcg cgtccccgac ctggccgccc    480
tcgccgacca gtgcggctcc tccggcgacg ccaacctgcc aggcatcgac atctttgtca    540
ccaccgtgga ccccgtggac gaacccatct tgtacaccgt gaacaccata ctctccatcc    600
tcgccaccga ctaccctgtc gataagtacg cctgctacct ctcagacgac ggcggcacgt    660
tggtgcacta cgaggccatg atcgaagtgg ccaatttcgc ggtgatgtgg gtcccttttt    720
gccggaagca ctgtgtcgag ccaaggtccc ccgagaacta cttttgggatg aaaacgcagc    780 cgtacgtcgg gagtatggct ggagaattca tgagggagca taggcgtgtg cgcagagagt    840
atgatgagtt caaggtgagg atagactccc tgtccaccac catccgccaa agatctgatg    900
cgtacaactc gagcatctca ggagatggtg tgcgtgcaac ctggatggct gatggggcac    960
aatggcctgg tacgtggatt gagcagtttg agaaccaccg gagaggacaa catgctggaa   1020 tgttcaggt catactaagc catcctagtt gcaaaccgca actggggtct ccggcgagca   1080
ctgacaatcc acttgacttc agcaacgttg acacgaggct gcccatgctc gtctacatgt   1140
cccgggagaa gcgccccggt tataaccacc aaaagaaggc aggcgccatg aacgtgatgc   1200
tccgtgtctc ggcgttgctc tccaacgcgc cattcgtcgt caatttttgac tgcgaccact   1260 acatcaacaa cacgcaagct ctccgcgccc ctatgtgctt catgctcgac cctcgcgacg   1320
gtcagaacac ggccttcgtc cagtttccgc agcgcttcga cgacgtcgac ccgacggacc   1380
gctacgccaa ccacaaccgt gtcttcttcg acggtaccat gctctccctc aacggccttc   1440
aagggccttc ctacctcggc actggcacca tgttccgtcg tgtcacgctc tatggcatgg   1500
agccaccacg ttacagagcg gagaacatca agcttgtagg taagacctat gagttcggta   1560
gctcgacgtc tttcatcaat tccatgccgg acggcgcaat ccaagagcgg tctatcacgc   1620
cggtgttggt cgacgaggca ctcagcaatg acctggctac cctgatgacg tgtgcttacg   1680
aggacgggac ctcatggggg agagacgttg ggtgggtgta acatcgcg acggaggacg   1740 tggtgaccgg attccgcatg caccggcagg ggtggcgctc catgtattgc tccatggagc   1800
cggccgcctt ccgcgaaaca gcgccgatca acctcaccga gcgcctttac caggtgctcc   1860
ggtggtcggg cggctctctc gagatgttct tctcccacag caacgctctc atggccggcc   1920
```

| | |
|---|---:|
| gccgtatcca cccctctgcag cgtgtcgcgt acctcaacat gtcgacctac ccgatcgtca | 1980 |
| cggtgttcat cctggcctac aacctcttcc ccgtcatgtg gctcttctcc gagcagttct | 2040 |
| acatccagag gccgttcggc acgtacatca tgtacctcgt cggcgtcata gcgatgattc | 2100 |
| acgtgatcgg catgttcgag gtgaaatggg cggggatcac gctgctcgac tggtgccgca | 2160 |
| acgagcagtt ctacatgatc ggggcgacgg gcgtgtaccc gacggcggtg ctttacatgg | 2220 |
| cgctcaagct tgtcacgggg aaggggatat acttcaggct cacatccaag cagacggacg | 2280 |
| cttgctccaa cgacaagttc gccgacctgt acacggtgcg gtgggtgccg ctgctgttcc | 2340 |
| cgacggtcgc agtgctcatc gtgaacgtcg cggctgtcgg ggcagcgata ggcaaggcag | 2400 |
| cagcgtgggg cttcttcacg gaccaggcgc ggcacgtgct gctcgggatg gtgttcaacg | 2460 |
| tgtggatcct cgtgctcctc tacccgtttg cgctcgggat catggggaaa tgggggaaga | 2520 |
| gacccatcat cctgttcgtc atgttgatca tggtcattgg cgccgtcggg ctcgtgtatg | 2580 |
| tcgccttcca tgatccctac ccactgattt tcagagttgc agctcttggt gaagcatcgc | 2640 |
| tgaccgggcc atctgggtag acacgtacgg ctcttttttt tacaagtaca gccagagtca | 2700 |
| ctgcaataat ttgagtgtgt gtattcatgt ctacttatat agcatgagaa ctggtcattg | 2760 |
| tgtgccactc ctctactcta gtagagtata aatgtaccta tcttttcttt ggaaaaaaac | 2820 |
| tgaagtgcgg cttgtgctct tttggtgaga actaaaaaaa aaaa | 2864 |

<210> SEQ ID NO 17
<211> LENGTH: 2910
<212> TYPE: DNA
<213> ORGANISM: Hordeum vulgare

<400> SEQUENCE: 17

| | |
|---|---:|
| tacaactaag cggactctag tatcgtggtt gatgattgca atccggcaat gttgtcgccc | 60 |
| cggacagacg ccggcgccgg cgccgccacc gacctcagcc agccacttct ctggaaccgc | 120 |
| aatggcgttc acgcaggagc attggtcgtc atgccagtcg tggccaatgg tcacggcggc | 180 |
| ggcgacaagc ttaagggcgc cccgaaagcc aaggacaagt actggaagaa cgtcgaccag | 240 |
| ccggacgaca tggcggcagc gccagacctg gacaacggcg gcggccggcc gctgctgttc | 300 |
| tcgaacttga gagtccagaa tatcatcctg taccccggcg aggtattgat cctgatacga | 360 |
| gtaatcgccg taatcttatt tgttggatgg cgcatcaagc ataacaattc agatgtcatg | 420 |
| tggttttgga tgatgtccgt cgtcgcagac gtgtggttta gcttatcatg gctaagctac | 480 |
| caactgccaa agtataatcc cgttaaaagg atacccgacc ttgctacact caggaaacaa | 540 |
| tatgacacac cagggaggag ctcccagctg ccaagcattg acgtcatcgt caccactgcc | 600 |
| agtgctaccg atgagcccat attgtacacc atgaactgtg ttctctctat acttgcagct | 660 |
| gactatcata ttggcaggtg caactgctac ctatcagatg atagcggctc attggtcctt | 720 |
| tatgaggcat tggttgagac tgcaaagttt gctgctttat gggttccttt ctgtagaaag | 780 |
| catcagattg agccaagagc accggaaagc tattttgaac taagggcccc gttgtatgga | 840 |
| gggacgccac ataaggagtt cttttcagga t tataagcatt taggcacaca atatgaagag | 900 |
| ttcaagaaga atttagatat gcttcctaac accatccatc aaaggtcggg aacttacagt | 960 |
| aaaacaggaa cggaggatga agatgcaaaa gtgacttgga tggctgacgg aacacaatgg | 1020 |
| ccaggcacat ggcttgaccc agcagaaaaa catagggccg gcatcatgc aggaattgtt | 1080 |
| aagattgtgc agagccatcc agaacatgtg gttcaaccag gcgtacaaga gagccttgac | 1140 |

```
aacccactca gctttgacga tgttgatgtg cgcctgccca tgttggtata tgtggctcgt      1200
gaaaagagtc caggtatcga gcataacaaa aaggcaggcg cttttgaatgc agagctacgt     1260 atctcagctc tactctctaa tgcacctttc ttcattaact ttgactgcga ccactacatc      1320
aacaattcag aagccctacg tgcagctgtt tgcttcatgc tagacccacg tgaaggggat      1380
aatactggat ttgttcagtt cccgcaaaga tttgataatg tcgacccaac tgaccggtat      1440
ggaaaccata atcgagtctt ttttgatggt gccatgtatg gcctcaatgg tcaacaaggg      1500
cctacttacc ttggcacagg ttgcatgttc cgtccccttg cactctatgg aattgatcca      1560
ccttgctgga gagccgagga catcatagtc gacagtaaca ggtttggcaa ctcattaccc      1620
ttcctcaact cagtactagc agccataaag caagaggaag gtgtcacact accaccacca      1680
ctagatgatt catttcttga agagatgaca aaagttgtgt catgttccta tgatgattcc      1740
actgattggg gtaggggcat tggctacata tacaatatgg caacagaaga catagtaaca      1800
ggatttcgta tccatgggca agggtggtgc tccatgtatg ttaccatgga acgtgaagcg      1860
ttccgtggca ctgcaccgat caatctaaca gagcgcctcc gccaaatagt gcgatggtct      1920
ggtggttccc tagagatgtt cttctcgcac atcagcccac tattcgctgg tcgtcgactc      1980
agtttggtgc agcgactctc gtacatcaat ttcactatat acccattgac atcactcttt      2040
atcctaatgt atgccttctg tccagtgatg tggcttcttc caacagaaat acttatacaa      2100
aggccatata ccaggtacat tgtgtacctt atcattgtcg tcgcgatgat ccatgtgatt      2160
ggcatgtttg agataatgtg ggcaggaatc acatggttgg attggtggcg caacgagcaa      2220
tttttcatga tcggctcggt aactgcatat ccaacggcgg tgttgcacat ggtggtgaat      2280
atccttacaa aaagggtat acacttcaga gtaaccacaa agcaaccagt ggctgataca      2340
gatgacaagt atgctgagat gtatgaagtg cattgggtac ccatgatggt ccccgcggtt      2400
gtggtattgt tttccaacat cttggctatt ggtgtagcaa ttggtaaatc agtcttatac      2460
atggggacat ggtctgtagc acagaaaagg catggtgcac tagggctatt gttcaacctg      2520
tggattatgg tgctcctttta cccatttgca ttggcgatta ttggaagatg gccaagaga       2580 accggaatcc tattcatctt actacccatt gctttcttgg ccaccgcatt gatgtacatt      2640
ggcatccata cattccttttt acatttctttt ccatccatgt tggtatagaa aatacctagc     2700 acactttttct atggatcagt atgacaaatg aagatatctc cttcaggaag ggacttatgt      2760
agttgaacgt gtactttgtg atatagtaat atactagaag ccaacgtgtg cttcgccaca      2820
ccgttcttaa aaaaaaaaaa gaaacacggg gcgttacgga ttccaggaat agatgagtgg      2880
agccgatctc gaaaggaaaa gtaatgggcc                                       2910
```

<210> SEQ ID NO 18
<211> LENGTH: 2943
<212> TYPE: DNA
<213> ORGANISM: Hordeum vulgare

<400> SEQUENCE: 18

```
aatcgtggga catgggttct ttggcggcag ccaacggggc cggtcatgcg agcaatggcg        60
ccggcgtcgc ggaccaggcg ctggcactgg agaacggcac cggcaatggg cacaaggcca       120
gcgacgccaa ccgagcgacg ccggtacagc aggcaaacgg cagcagcaag gccgcgggga       180
aggttagccc gaaggacaag tactgggtgg ccgtcgatga gggagagatg gcggccgcca       240
tagcggacgg cggcgaggac ggccggcgac cgctgctgta ccggacgttc aaggtcaagg       300
gcatcctcct gcatccctac aggttgctga gcttgatcag attggttgct atcgtcctat       360
```

```
tttcgtatg gcgtgtcagg cacccatacg ctgatggcat gtggctctgg tggatatcga    420
tggttgggga tctttggttt ggcgtcactt ggttgctaaa ccaagttgca aagctcaacc    480
ctgtcaagcg tgtccccaac cttgcgcttt tgcaacagca gtttgatctc cctgacggca    540
actccaacct tccttgtctt gatgtcttca tcaacaccgt tgatcccatt aatgaaccta    600
tgatatacac tatgaactcc atcatatcca tccttgctgc agactatccg gttgacaagc    660
atgcttgcta cctttcagat gatggtgggt caataatcca ttatgatggt ttgcttgaga    720
ctgcaaaatt tgctgcatta tgggttccct tttgcagaaa acattccatt gagccaagag    780
cccctgagag ctattttttct ttgaatacac gcccatacac tggaaatgca ccacaagact    840
tgtcaatga ccgcagacac atgtgtagag agtatgatga gttcaaggag cgcttagatg    900
cacttttttac cctcattccc aaacggtcag atgtgtacaa tcatgctgct ggcaaagaag    960
gtgcaaaggc aacttggatg cagatggga cacagtggcc aggcacatgg attgacccag   1020
ctgaaaacca taagaaagga caacatgctg ggatcgttaa ggttttgttg aaacatccaa   1080
gttatgaacc agaacttggt ctaggagcaa gcaccaacag tcctctagac ttcagtgcag   1140
ttgatgtgcg cctcccaatg ctcgtttaca tctcccgtga aagagtcca agctgtgatc   1200
atcaaaagaa ggcaggtgcc atgaacgtac agttgcgagt ctctgccctc ctgaccaatg   1260
cgcccttat catcaacttt gatggtgacc actacgtcaa caactcgaaa gccttccgtg   1320
ctggcatatg tttcatgctc gatcgccgtg aaggtgacaa tactgccttt gtccagtttc   1380
cccaacgctt cgatgatgtt gatcccacag ataggtactg caatcacaat cgtgtcttct   1440
ttgacgccac cttgctcggc tccaatggca tccaagggcc gtcttatgtt ggcactggtt   1500
gcatgttccg ccgtgtcgca ctttacggtg ttgacccacc tcgctggaga cctgatgacg   1560
tgaagatcgt ggacagctcc agcaagtttg gcagttcaga gtcattcatc agctcaatac   1620
tgccagcagc agaccaagaa cgctccatca tgtcgccacc ggcacttgaa gagtctgtca   1680
tggctgactt agctcatgtc atgacttgtg catatgagga cgggactgaa tggggcagag   1740
aagttggttg ggtgtacaac attgcaactg aggatgtggt gaccggcttc cggctgcacc   1800
ggaatgggtg gcgatccatg tactgccgca tggaaccaga tgcattcgcc ggcaccgcgc   1860
caatcaacct cactgagcgg ctctaccaga tcctgcgctg gtcgggggc tcccttgaga   1920
tgttcttctc gcacaactgc ccactcctgg ctggccgccg cctccaccca atgcaaagaa   1980
ttgcctatgc caacatgaca gcctacccag tttcatctgt ctttcttgtg ttctatctcc   2040
tcttcccggt gatatggatc ttccgtgggc aattctacat acagaagcca ttccccacgt   2100
atgtgttgta cctcgtcatc gtcatagccc tgaccgagtt aatcggtatg gttgagatca   2160
agtgggctgg gctcacgctg ctggactgga tccgcaacga gcagttctac attattggtg   2220
caacagccgt gtaccctaca gcagtatttc acatagtgct gaagctgttt ggcctgaagg   2280
gtgtttcatt caagctgacg gcaaaacagg tagcaagcag taccagcgat aagtttgctg   2340
aactgtatgc cgtgcagtgg gctccgatgc tgatccctac catggtggtt atagcggtga   2400
atgtttgtgc cattggcgcg tcgataggca aggcggtagt gggaggatgg tcactgatgc   2460
agatggccga tgcaggactt gggctggtgt tcaacgcgtg gattctggtg ctgatctacc   2520
cgttttgcact gggcatgatt ggacggtgga gcaagaggcc ctacatcctg ttcattctgt   2580
ttgtcattgc gtttattttg atcgcattgg tggatatcgc catccaggcc atgcggtctg   2640
ggattgttcg gttccacttt aaaagctcag gtggcgccac tttcccacaa agctggggtt   2700
```

| | |
|---|---:|
| tgtaagttcc tcccttttgct gggaagttcc ttttcctttg tggtgtgggt tttttctttt | 2760 |
| ttccttttct tgttattgca tatatagacc atttgtggtg tgaatcatat ataggctgta | 2820 |
| caagtttgtg gaaataatgt aaaattggcc atttgcctgg aagaaaaaga gatgtggcaa | 2880 |
| agcaacagct gtagtatatt ggatataatg ttgaggatgc ctggaagtat atctattcct | 2940 |
| gta | 2943 |

<210> SEQ ID NO 19
<211> LENGTH: 2583
<212> TYPE: DNA
<213> ORGANISM: Oryza sativa

<400> SEQUENCE: 19

| | |
|---|---:|
| atgtccgcgg cggcagcggt gacaagctgg actaacggat gctggtcgcc cgcggctacg | 60 |
| cgggtgaacg acggcggcaa ggacgatgtg tgggtggccg tcgacgaagc ggacgtgtcg | 120 |
| ggggcccgcg gcagcgacgg cggcggccgg ccgccgctgt tccagacgta caaggtcaag | 180 |
| ggcagcatcc ttcatcctta caggttcttg atcctggcgc gactgatcgc catcgtcgcc | 240 |
| ttcttcgcgt ggcgcatacg tcacaagaac cgcgacggcg cgtggctgtg gacaatgtcc | 300 |
| atggtcggcg acgtctggtt cggcttctcg tgggtgctca accagctacc gaagcagagc | 360 |
| cccatcaagc gcgtcccgga catcgccgcc ctcgccgacc ggcactccgg cgacctaccc | 420 |
| ggcgtcgacg tcttcgtcac caccgtcgac cctgtcgacg agccgatact ctacaccgtg | 480 |
| aacaccatcc tctccattct cgccgccgac tacccggtgg acaggtacgc ttgctacctc | 540 |
| tccgacgacg gcgggacgct ggtccactac gaggctatgg tggaggtcgc caagttcgcc | 600 |
| gagctgtggg tgcccttctg ccggaagcac tgcgtcgagc cgaggtcgcc ggagaactac | 660 |
| ttcgcgatga agacgcaggc gtacaaaggc ggcgtcccg gcgagctgat gagcgatcac | 720 |
| cggcgtgtgc ggcgagagta cgaggagttc aaggtcagga tcgactccct ctcgagcacc | 780 |
| attcgccagc gatctgatgt gtacaacgcc aaacatgccg cgaaaatgc gacatggatg | 840 |
| gctgatggca cacattggcc cggcacatgg tttgagccgg ctgacaacca ccagagaggg | 900 |
| aaacatgctg gaattgttca ggttttactg aaccatccaa gctgtaaacc gaggcttgga | 960 |
| ttggcggcga gtgctgagaa tccggttgat ttcagcggtg tcgacgtgcg gctccccatg | 1020 |
| ctggtgtaca tctcgcgcga gaagcggccc ggatacaacc accagaagaa ggccggcgcc | 1080 |
| atgaacgtga tgctccgcgt gtccgcgctg ctgtcgaacg cgccgttcgt catcaacttc | 1140 |
| gacggcgacc actacgtcaa caactcgcag gcgttcaggg cgccgatgtg cttcatgctc | 1200 |
| gacggccgcg gccgcggcgg cgagaacacg gcgttcgtcc agttcccgca gcggttcgac | 1260 |
| gacgttgacc gacggaccg gtacgcgaac cataaccgcg tcttcttcga cggcaccatg | 1320 |
| ctctcccctca acggcctcca ggggccctcc tacctcggca ccggcaccat gttccgccgc | 1380 |
| gtcgcgctct acggcgtgga gccgccgcgc tggggagcgg cggcgagcca gatcaaggct | 1440 |
| atggacatcg ccaacaagtt cggcagctcg acgtcgttcg tcggcacgat gctggacggc | 1500 |
| gccaaccaag aacggtcgat cacgccgctg gcggtgctcg acgagtcggt cgccggcgac | 1560 |
| ctcgccgccc tgacgcgtg cgcgtatgag gacgggacgt catggggag agacgtcggg | 1620 |
| tgggtgtaca acatcgcgac ggaggacgtg gtgaccgggt tccgcatgca ccggcagggg | 1680 |
| tggcgctccg tatacgcctc agtggagccc gccgcgttcc gcggcacggc gccgatcaac | 1740 |
| ctcaccgagc gcctctacca gatcctccgg tggtcgggcg gctcgctgga gatgttcttc | 1800 |
| tcccacagca acgcgctcct cgccggccgc cgcctccacc cgctgcagcg cgtcgcctac | 1860 |

-continued

```
ctcaatatgt ccacctaccc gatcgtgacc gtgttcatct tcttctacaa cctcttcccg    1920
gtgatgtggc tcatctccga gcagtattac atccagcggc cgttcggcga gtacctcctc    1980
tacctcgtcg ccgtcatcgc catgatccac gtgatcggca tgttcgaggt gaagtgggct    2040
ggcatcacgc tgctggactg gtgccgcaac gagcagttct acatgatcgg atccacgggg    2100
gtgtacccga cggcggtgct gtacatggcg ctcaagctcg tcaccgggaa gggcatctac    2160
ttccgcctca cgtcgaagca gacggcagcc agctccggcg acaagttcgc cgacctgtac    2220
accgtgcggt gggtgcctct gctgatcccg accatcgtca tcatggtcgt gaacgtcgcc    2280
gccgtcgggg tggcggtcgg caaggcggcg cgtgggggc cgctcaccga gccggggtgg    2340
ctcgccgtgc tcgggatggt gttcaacgtg tggatcctgg tgctcctcta cccgttcgcg    2400
ctcggggtca tgggtcaatg ggggaagcgg ccggccgtgc tgttcgtggc gatggcgatg    2460
gccgtcgccg ccgtggcggc catgtacgtc gccttcggtg caccgtacca agctgagttg    2520
tcaggtgttg ctgcttctct cggtaaagtg gcggcggcat cgctgactgg gccatctggg    2580
tag                                                                  2583
```

<210> SEQ ID NO 20
<211> LENGTH: 860
<212> TYPE: PRT
<213> ORGANISM: Oryza sativa

<400> SEQUENCE: 20

```
Met Ser Ala Ala Ala Val Thr Ser Trp Thr Asn Gly Cys Trp Ser
1               5                   10                  15

Pro Ala Ala Thr Arg Val Asn Asp Gly Gly Lys Asp Val Trp Val
                20                  25                  30

Ala Val Asp Glu Ala Asp Val Ser Gly Ala Arg Gly Ser Asp Gly Gly
                35                  40                  45

Gly Arg Pro Pro Leu Phe Gln Thr Tyr Lys Val Lys Gly Ser Ile Leu
    50                  55                  60

His Pro Tyr Arg Phe Leu Ile Leu Ala Arg Leu Ile Ala Ile Val Ala
65                  70                  75                  80

Phe Phe Ala Trp Arg Ile Arg His Lys Asn Arg Asp Gly Ala Trp Leu
                85                  90                  95

Trp Thr Met Ser Met Val Gly Asp Val Trp Phe Gly Phe Ser Trp Val
                100                 105                 110

Leu Asn Gln Leu Pro Lys Gln Ser Pro Ile Lys Arg Val Pro Asp Ile
            115                 120                 125

Ala Ala Leu Ala Asp Arg His Ser Gly Asp Leu Pro Gly Val Asp Val
        130                 135                 140

Phe Val Thr Thr Val Asp Pro Val Asp Glu Pro Ile Leu Tyr Thr Val
145                 150                 155                 160

Asn Thr Ile Leu Ser Ile Leu Ala Ala Asp Tyr Pro Val Asp Arg Tyr
                165                 170                 175

Ala Cys Tyr Leu Ser Asp Asp Gly Gly Thr Leu Val His Tyr Glu Ala
                180                 185                 190

Met Val Glu Val Ala Lys Phe Ala Glu Leu Trp Val Pro Phe Cys Arg
            195                 200                 205

Lys His Cys Val Glu Pro Arg Ser Pro Glu Asn Tyr Phe Ala Met Lys
        210                 215                 220

Thr Gln Ala Tyr Lys Gly Gly Val Pro Gly Glu Leu Met Ser Asp His
225                 230                 235                 240
```

-continued

```
Arg Arg Val Arg Arg Glu Tyr Glu Glu Phe Lys Val Arg Ile Asp Ser
            245                 250                 255

Leu Ser Ser Thr Ile Arg Gln Arg Ser Asp Val Tyr Asn Ala Lys His
            260                 265                 270

Ala Gly Glu Asn Ala Thr Trp Met Ala Asp Gly Thr His Trp Pro Gly
            275                 280                 285

Thr Trp Phe Glu Pro Ala Asp Asn His Gln Arg Gly Lys His Ala Gly
            290                 295                 300

Ile Val Gln Val Leu Leu Asn His Pro Ser Cys Lys Pro Arg Leu Gly
305                 310                 315                 320

Leu Ala Ala Ser Ala Glu Asn Pro Val Asp Phe Ser Gly Val Asp Val
            325                 330                 335

Arg Leu Pro Met Leu Val Tyr Ile Ser Arg Glu Lys Arg Pro Gly Tyr
            340                 345                 350

Asn His Gln Lys Lys Ala Gly Ala Met Asn Val Met Leu Arg Val Ser
            355                 360                 365

Ala Leu Leu Ser Asn Ala Pro Phe Val Ile Asn Phe Asp Gly Asp His
370                 375                 380

Tyr Val Asn Asn Ser Gln Ala Phe Arg Ala Pro Met Cys Phe Met Leu
385                 390                 395                 400

Asp Gly Arg Gly Arg Gly Gly Glu Asn Thr Ala Phe Val Gln Phe Pro
            405                 410                 415

Gln Arg Phe Asp Asp Val Asp Pro Thr Asp Arg Tyr Ala Asn His Asn
            420                 425                 430

Arg Val Phe Phe Asp Gly Thr Met Leu Ser Leu Asn Gly Leu Gln Gly
            435                 440                 445

Pro Ser Tyr Leu Gly Thr Gly Thr Met Phe Arg Arg Val Ala Leu Tyr
450                 455                 460

Gly Val Glu Pro Pro Arg Trp Gly Ala Ala Ser Gln Ile Lys Ala
465                 470                 475                 480

Met Asp Ile Ala Asn Lys Phe Gly Ser Ser Thr Ser Phe Val Gly Thr
            485                 490                 495

Met Leu Asp Gly Ala Asn Gln Glu Arg Ser Ile Thr Pro Leu Ala Val
            500                 505                 510

Leu Asp Glu Ser Val Ala Gly Asp Leu Ala Ala Leu Thr Ala Cys Ala
            515                 520                 525

Tyr Glu Asp Gly Thr Ser Trp Gly Arg Asp Val Gly Trp Val Tyr Asn
            530                 535                 540

Ile Ala Thr Glu Asp Val Val Thr Gly Phe Arg Met His Arg Gln Gly
545                 550                 555                 560

Trp Arg Ser Val Tyr Ala Ser Val Glu Pro Ala Ala Phe Arg Gly Thr
            565                 570                 575

Ala Pro Ile Asn Leu Thr Glu Arg Leu Tyr Gln Ile Leu Arg Trp Ser
            580                 585                 590

Gly Gly Ser Leu Glu Met Phe Phe Ser His Ser Asn Ala Leu Leu Ala
            595                 600                 605

Gly Arg Arg Leu His Pro Leu Gln Arg Val Ala Tyr Leu Asn Met Ser
            610                 615                 620

Thr Tyr Pro Ile Val Thr Val Phe Ile Phe Tyr Asn Leu Phe Pro
625                 630                 635                 640

Val Met Trp Leu Ile Ser Glu Gln Tyr Tyr Ile Gln Arg Pro Phe Gly
            645                 650                 655
```

```
Glu Tyr Leu Leu Tyr Leu Val Ala Val Ile Ala Met Ile His Val Ile
             660                 665                 670
Gly Met Phe Glu Val Lys Trp Ala Gly Ile Thr Leu Leu Asp Trp Cys
        675                 680                 685
Arg Asn Glu Gln Phe Tyr Met Ile Gly Ser Thr Gly Val Tyr Pro Thr
    690                 695                 700
Ala Val Leu Tyr Met Ala Leu Lys Leu Val Thr Gly Lys Gly Ile Tyr
705                 710                 715                 720
Phe Arg Leu Thr Ser Lys Gln Thr Ala Ala Ser Ser Gly Asp Lys Phe
                725                 730                 735
Ala Asp Leu Tyr Thr Val Arg Trp Val Pro Leu Leu Ile Pro Thr Ile
            740                 745                 750
Val Ile Met Val Val Asn Val Ala Ala Val Gly Val Ala Val Gly Lys
        755                 760                 765
Ala Ala Ala Trp Gly Pro Leu Thr Glu Pro Gly Trp Leu Ala Val Leu
    770                 775                 780
Gly Met Val Phe Asn Val Trp Ile Leu Val Leu Leu Tyr Pro Phe Ala
785                 790                 795                 800
Leu Gly Val Met Gly Gln Trp Gly Lys Arg Pro Ala Val Leu Phe Val
                805                 810                 815
Ala Met Ala Met Ala Val Ala Ala Val Ala Ala Met Tyr Val Ala Phe
            820                 825                 830
Gly Ala Pro Tyr Gln Ala Glu Leu Ser Gly Val Ala Ala Ser Leu Gly
        835                 840                 845
Lys Val Ala Ala Ala Ser Leu Thr Gly Pro Ser Gly
    850                 855                 860

<210> SEQ ID NO 21
<211> LENGTH: 2670
<212> TYPE: DNA
<213> ORGANISM: Oryza sativa

<400> SEQUENCE: 21
atggcggcca ccgcggcttc cacgatgtcc gcagcggcgg cagtgactcg ccggatcaac    60
gctgccctcc gcgtggacgc caccagcggt gacgtcgcgg ccggcgccga cgggcagaac   120
gggcgccggt cgcccgtggc caagcgggtg aacgacggcg gtggcggcaa ggatgacgtg   180
tgggtggccg tcgacgaaaa ggacgtgtgc ggggcccgcg gcggcgatgg cgccgcccgg   240
ccgccgctgt ccggacgtac aaggtcaagg gcagcatcct tcatcctta caggttcctg    300
atccttcttc gactgatcgc catcgtcgcc ttcttcgcgt ggcgcgtacg tcacaagaac   360
cgcgacggcg tgtggctgtg acaatgtcc atggtcggcg acgtctggtt cggcttctcg    420
tgggtgctca accagctccc gaagctgagc cccatcaagc gcgtcccgga cctcgccgcc    480
ctcgccgacc ggcactccgg cgacctaccc ggcgtcgacg tcttcgtcac caccgtcgac    540
cccgtcgacg agccgatact ctacaccgtg aacaccatcc tctccatcct cgccgccgac   600
tacccggtgg acaggtacgc ctgctacctg tccgacgacg cgggacgct ggtccactac    660
gaggccatgg tggaggtcgc caagttcgcc gagctgtggg tgcccttctg ccggaagcac   720
tgcgtcgagc cgaggtcgcc ggagaactac ttcgcgatga agacgcaggc gtacaaaggc   780
ggcgtccccg cgagctgat gagcgatcac cggcgtgtgc ggcgagagta cgaggagttc   840
aaggtcagga tcgactccct ctcgagcacc attcgccagc gatcagatgt gtacaacgcc   900
aaacatgccg gcgaaaatgc gacatggatg gctgatggca cacattggcc cggcacatgg   960
```

```
tttgagccgg ctgacaacca ccagagaggg aaacatgctg gaattgttca ggttttactg    1020
aaccatccaa gctgtaaacc gaggcttgga ttggcggcga gtgctgagaa tccggttgat    1080
ttcagcggtg tcgacgtgcg gctccccatg ctggtgtaca tctcgcgcga agagggccc     1140 ggatacaacc accagaagaa ggccggcgcc atgaacgtga tgctccgcgt gtccgcgctg    1200
ctgtcgaacg cgccgttcgt catcaacttc gacggcgacc actacgtcaa caactcgcag    1260
gcgttcaggg cgccgatgtg cttcatgctc gacggccgcg gcgcggcgg cgagaacacg     1320 gcgttcgtcc agttcccgca gcggttcgac gacgttgacc cgacggaccg gtacgcgaac    1380
cataaccgcg tcttcttcga cggcaccatg ctctccctca cggcctcca ggggccctcc     1440 tacctcggca ccggcaccat gttccgccgc gtcgcgctct acggcgtgga gccgccgcgc    1500
tggggagcgg cggcgagcca gatcaaggct atggacatcg ccaacaagtt cggcagctcg    1560
acgtcgttcg tcggcacgat gctggacggc gccaaccaag aacggtcgat cacgccgctg    1620
gcggtgctcg acgagtcggt cgccggcgac ctcgccgccc tgacggcgtg cgcgtatgag    1680
gacgggacgt catggggggag agacgtcggg tgggtgtaca acatcgcgac ggaggacgtg   1740
gtgaccgggt tccgcatgca ccggcagggg tggcgctccg tatacgcctc agtggagccc    1800
gccgcgttcc gcggcacggc gccgatcaac ctcaccgagc gcctctacca gatcctccgg    1860
tggtcgggcg gctcgctgga gatgttcttc tcccacagca acgcgctcct cgccggccgc    1920
cgcctccacc cgctgcagcg cgtcgcctac ctcaatatgt ccacctaccc gatcgtgacc    1980
gtgttcatct tcttctacaa cctcttcccg gtgatgtggc tcatctccga gcagtattac    2040
atccagcggc cgttcggcga gtacctcctc tacctcgtcg ccgtcatcgc catgatccac    2100
gtgatcggca tgttcgaggt gaagtgggct ggcatcacgc tgctggactg gtgccgcaac    2160
gagcagttct acatgatcgg atccacgggg gtgtacccga cggcggtgct gtacatggcg    2220
ctcaagctcg tcaccgggaa gggcatctac ttccggctca cgtcgaagca gacgacggcc    2280
agctccggcg acaagttcgc cgacctgtac accgtgcggt gggtgccgct gctgataccg    2340
accatcgtca tcattgtcgt gaacgtcgcc gccgtcgggg tggcggtcgg caaggcggcg    2400
gcgtgggggc cgctcaccga gccggggtgg ctcgccgtgc tcgggatggt gttcaacgtg    2460
tggatcctgg tgctcctcta cccgttcgcg ctcggggtca tgggtcaatg ggggaagcgg    2520
ccggccgtgc tgttcgtggc gatggcgatg ccgtcgccg ccgtggcggc catgtacgtc     2580
gccttcggtg caccgtacca agctgagttg tcaggtggtg ctgcttctct cggaaaagcg    2640
gcggcgtcgc tgaccgggcc atccgggtag                                    2670
```

<210> SEQ ID NO 22
<211> LENGTH: 889
<212> TYPE: PRT
<213> ORGANISM: Oryza sativa

<400> SEQUENCE: 22

```
Met Ala Ala Thr Ala Ala Ser Thr Met Ser Ala Ala Ala Val Thr
1               5                   10                  15

Arg Arg Ile Asn Ala Ala Leu Arg Val Asp Ala Thr Ser Gly Asp Val
            20                  25                  30

Ala Ala Gly Ala Asp Gly Gln Asn Gly Arg Arg Ser Pro Val Ala Lys
        35                  40                  45

Arg Val Asn Asp Gly Gly Gly Gly Lys Asp Asp Val Trp Val Ala Val
    50                  55                  60

Asp Glu Lys Asp Val Cys Gly Ala Arg Gly Gly Asp Gly Ala Ala Arg
```

-continued

```
                65                  70                  75                  80

Pro Pro Leu Phe Arg Thr Tyr Lys Val Lys Gly Ser Ile Leu His Pro
                85                  90                  95

Tyr Arg Phe Leu Ile Leu Leu Arg Leu Ile Ala Ile Val Ala Phe Phe
               100                 105                 110

Ala Trp Arg Val Arg His Lys Asn Arg Asp Gly Val Trp Leu Trp Thr
               115                 120                 125

Met Ser Met Val Gly Asp Val Trp Phe Gly Phe Ser Trp Val Leu Asn
               130                 135                 140

Gln Leu Pro Lys Leu Ser Pro Ile Lys Arg Val Pro Asp Leu Ala Ala
145                 150                 155                 160

Leu Ala Asp Arg His Ser Gly Asp Leu Pro Gly Val Asp Val Phe Val
                   165                 170                 175

Thr Thr Val Asp Pro Val Asp Glu Pro Ile Leu Tyr Thr Val Asn Thr
               180                 185                 190

Ile Leu Ser Ile Leu Ala Ala Asp Tyr Pro Val Asp Arg Tyr Ala Cys
               195                 200                 205

Tyr Leu Ser Asp Asp Gly Gly Thr Leu Val His Tyr Glu Ala Met Val
210                 215                 220

Glu Val Ala Lys Phe Ala Glu Leu Trp Val Pro Phe Cys Arg Lys His
225                 230                 235                 240

Cys Val Glu Pro Arg Ser Pro Glu Asn Tyr Phe Ala Met Lys Thr Gln
                   245                 250                 255

Ala Tyr Lys Gly Gly Val Pro Gly Glu Leu Met Ser Asp His Arg Arg
               260                 265                 270

Val Arg Arg Glu Tyr Glu Glu Phe Lys Val Arg Ile Asp Ser Leu Ser
           275                 280                 285

Ser Thr Ile Arg Gln Arg Ser Asp Val Tyr Asn Ala Lys His Ala Gly
           290                 295                 300

Glu Asn Ala Thr Trp Met Ala Asp Gly Thr His Trp Pro Gly Thr Trp
305                 310                 315                 320

Phe Glu Pro Ala Asp Asn His Gln Arg Gly Lys His Ala Gly Ile Val
                   325                 330                 335

Gln Val Leu Leu Asn His Pro Ser Cys Lys Pro Arg Leu Gly Leu Ala
               340                 345                 350

Ala Ser Ala Glu Asn Pro Val Asp Phe Ser Gly Val Asp Val Arg Leu
               355                 360                 365

Pro Met Leu Val Tyr Ile Ser Arg Glu Lys Arg Pro Gly Tyr Asn His
370                 375                 380

Gln Lys Lys Ala Gly Ala Met Asn Val Met Leu Arg Val Ser Ala Leu
385                 390                 395                 400

Leu Ser Asn Ala Pro Phe Val Ile Asn Phe Asp Gly Asp His Tyr Val
                   405                 410                 415

Asn Asn Ser Gln Ala Phe Arg Ala Pro Met Cys Phe Met Leu Asp Gly
               420                 425                 430

Arg Gly Arg Gly Gly Glu Asn Thr Ala Phe Val Gln Phe Pro Gln Arg
               435                 440                 445

Phe Asp Asp Val Asp Pro Thr Asp Arg Tyr Ala Asn His Asn Arg Val
450                 455                 460

Phe Phe Asp Gly Thr Met Leu Ser Leu Asn Gly Leu Gln Gly Pro Ser
465                 470                 475                 480

Tyr Leu Gly Thr Gly Thr Met Phe Arg Arg Val Ala Leu Tyr Gly Val
                   485                 490                 495
```

Glu Pro Pro Arg Trp Gly Ala Ala Ser Gln Ile Lys Ala Met Asp
                500                 505                 510

Ile Ala Asn Lys Phe Gly Ser Ser Thr Ser Phe Val Gly Thr Met Leu
        515                 520                 525

Asp Gly Ala Asn Gln Glu Arg Ser Ile Thr Pro Leu Ala Val Leu Asp
530                 535                 540

Glu Ser Val Ala Gly Asp Leu Ala Ala Leu Thr Ala Cys Ala Tyr Glu
545                 550                 555                 560

Asp Gly Thr Ser Trp Gly Arg Asp Val Gly Trp Val Tyr Asn Ile Ala
                565                 570                 575

Thr Glu Asp Val Val Thr Gly Phe Arg Met His Arg Gln Gly Trp Arg
                580                 585                 590

Ser Val Tyr Ala Ser Val Glu Pro Ala Ala Phe Arg Gly Thr Ala Pro
                595                 600                 605

Ile Asn Leu Thr Glu Arg Leu Tyr Gln Ile Leu Arg Trp Ser Gly Gly
        610                 615                 620

Ser Leu Glu Met Phe Phe Ser His Ser Asn Ala Leu Leu Ala Gly Arg
625                 630                 635                 640

Arg Leu His Pro Leu Gln Arg Val Ala Tyr Leu Asn Met Ser Thr Tyr
                645                 650                 655

Pro Ile Val Thr Val Phe Ile Phe Phe Tyr Asn Leu Phe Pro Val Met
                660                 665                 670

Trp Leu Ile Ser Glu Gln Tyr Tyr Ile Gln Arg Pro Phe Gly Glu Tyr
        675                 680                 685

Leu Leu Tyr Leu Val Ala Val Ile Ala Met Ile His Val Ile Gly Met
        690                 695                 700

Phe Glu Val Lys Trp Ala Gly Ile Thr Leu Leu Asp Trp Cys Arg Asn
705                 710                 715                 720

Glu Gln Phe Tyr Met Ile Gly Ser Thr Gly Val Tyr Pro Thr Ala Val
                725                 730                 735

Leu Tyr Met Ala Leu Lys Leu Val Thr Gly Lys Gly Ile Tyr Phe Arg
                740                 745                 750

Leu Thr Ser Lys Gln Thr Thr Ala Ser Ser Gly Asp Lys Phe Ala Asp
        755                 760                 765

Leu Tyr Thr Val Arg Trp Val Pro Leu Leu Ile Pro Thr Ile Val Ile
770                 775                 780

Ile Val Val Asn Val Ala Ala Val Gly Val Ala Val Gly Lys Ala Ala
785                 790                 795                 800

Ala Trp Gly Pro Leu Thr Glu Pro Gly Trp Leu Ala Val Leu Gly Met
                805                 810                 815

Val Phe Asn Val Trp Ile Leu Val Leu Leu Tyr Pro Phe Ala Leu Gly
                820                 825                 830

Val Met Gly Gln Trp Gly Lys Arg Pro Ala Val Leu Phe Val Ala Met
        835                 840                 845

Ala Met Ala Val Ala Val Ala Met Tyr Val Ala Phe Gly Ala
        850                 855                 860

Pro Tyr Gln Ala Glu Leu Ser Gly Gly Ala Ala Ser Leu Gly Lys Ala
865                 870                 875                 880

Ala Ala Ser Leu Thr Gly Pro Ser Gly
                885

<210> SEQ ID NO 23
<211> LENGTH: 2607

<212> TYPE: DNA
<213> ORGANISM: Oryza sativa

<400> SEQUENCE: 23

```
atggcttcgc cggcgtcggt cgccggcggt ggtgaggata gcaatggctg cagcagcctc      60
atcgacccgc tgctagtgag ccgcacgagc agcatcggcg gcgcggagag gaaggcggcc     120
ggcggcggcg gcggcggcgc caaggggaag cactgggccg ccgccgataa gggggagcgg     180
cgcgcggcga aggagtgcgg cggcgaggac ggccgccggc cgctgctgtt caggtcgtac     240
agggtcaagg gctccctcct gcacccgtac agggctctga tctttgcacg cttgattgcc     300
gttctcctct tcttcggatg gcggatcagg cacaataatt ctgacataat gtggttctgg     360
acaatgtcag tcgccggtga tgtttggttt ggttttttcat ggctacttaa ccaactccca     420
aagttcaatc cggtcaaaac catacctgac cttactgccc taaggcagta ctgtgatctc     480
gccgacggaa gctacagact tcccggcatc gatgttttcg tcaccaccgc tgatccaatc     540
gacgaaccgg ttctatacac catgaattgt gttctctcta ttcttgcggc tgactaccct     600
gttgataggt cagcctgcta tctctctgat gatagtggag cattgatcct atatgaagca     660
ttggttgaga cagccaaatt tgctactcta tgggttccat tttgccggaa gcattgcatt     720
gagcctagat ccccagagag ctactttgag cttgaggcac catcgtatac tggaagtgca     780
ccagaggagt tcaagaatga ctctaggatt gtgcatcttg agtatgatga gttcaaggtg     840
cgattggaag cacttcctga gactattcgt aaacgatcag atgtttacaa tagtatgaaa     900
actgatcaag gagcaccaaa tgcgacttgg atggctaatg ggacccaatg gccaggcacg     960
tggattgagc aatagaaaaa tcacaggaaa ggacaccatg ctggaattgt taaggttgtg    1020
ttggaccatc ccatccgtgg ccacaatctt agcctgaagg atagcacggg caacaatctt    1080
aattttaatg ccactgatgt gcgcatcccg atgcttgtct atgtgtctcg tggaaagaac    1140
ccaaattatg atcataataa gaaggcgggt gcattaaatg cgcaacttcg tgcctctgct    1200
ctactctcca atgcacaatt catcatcaac tttgattgtg atcactacat caacaattct    1260
caagccttcc gtgcagcaat ttgtttcatg cttgaccaaa gagaaggtga taatactgcc    1320
tttgttcagt tcccacaacg cttttgacaat gttgacccaa aagaccgata tggcaatcat    1380
aatcgtgtat tctttgatgg cacaatgctt gccctaaatg gtctccaagg accttcatac    1440
cttggtactg gttgcatgtt ccgtcgctta gctctctatg gtattgatcc tcctcattgg    1500
agacaagaca acatcacacc tgaagctagc aagtttggta actccatact cttattagag    1560
tcagtgttag aagccctaaa ccaagaccga tttgctacac catcaccggt caatgacata    1620
tttgtcaatg agctggagat ggttgtgtca gcttcattcg acaaagaaac cgattggggc    1680
aagggtgttg gatacatata tgacatagcc acagaagata tagtcacggg ttttcgcatc    1740
catgggcaag gttggcgatc catgtattgc accatggagc atgatgcatt ctgtggcact    1800
gcacctataa atctaacaga acgtcttcac caaattgtac gttggtctgg tggatcccta    1860
gagatgttct tctcccacaa taacccactt attggaggtc gtcggctcca acctctccag    1920
cgtgtctcat acctcaatat gacaatctac ccggtgacat cactctttat tttactctat    1980
gctatcagcc ctgtgatgtg cttatcccc gatgaagtat atattcagag gccattcact    2040
aggtatgtgg tgtaccttct cgtgatcatt tgatgattc atatgatcgg atggctcgag    2100
ataaagtggg cagggatcac atggttagat tattggcgca atgagcagtt cttcatgatc    2160
ggctcaacga gtgcttaccc aacagctgtg cttcatatgg tggtcaatct tctcacaaag    2220
```

-continued

```
aagggtatac attttagagt cacttcaaag caaacaaccg ctgacaccaa cgataaattt    2280
gctgacttat atgagatgag atgggttccc atgttaatcc caacaatggt agttttagtt    2340
gctaatatcg gtgccattgg tgtagctatt ggaaagacgg cagtatatat gggagtatgg    2400
acgatagcac agaagagaca tgctgcaatg ggactcctat tcaacatgtg ggttatgttt    2460
ctcctttacc catttgcact agcaatcatg gggagatggg caaagaggtc aatcattctt    2520
gttgttttgt tgccaattat ctttgtaatt gttgcccttg tatatgttgc tacccatatc    2580
ttactagcaa acattattcc attctag                                        2607
```

<210> SEQ ID NO 24
<211> LENGTH: 868
<212> TYPE: PRT
<213> ORGANISM: Oryza sativa

<400> SEQUENCE: 24

```
Met Ala Ser Pro Ala Ser Val Ala Gly Gly Gly Glu Asp Ser Asn Gly
1               5                   10                  15

Cys Ser Ser Leu Ile Asp Pro Leu Leu Val Ser Arg Thr Ser Ser Ile
            20                  25                  30

Gly Gly Ala Glu Arg Lys Ala Ala Gly Gly Gly Gly Gly Ala Lys
        35                  40                  45

Gly Lys His Trp Ala Ala Ala Asp Lys Gly Glu Arg Arg Ala Ala Lys
    50                  55                  60

Glu Cys Gly Gly Glu Asp Gly Arg Arg Pro Leu Leu Phe Arg Ser Tyr
65                  70                  75                  80

Arg Val Lys Gly Ser Leu Leu His Pro Tyr Arg Ala Leu Ile Phe Ala
                85                  90                  95

Arg Leu Ile Ala Val Leu Leu Phe Phe Gly Trp Arg Ile Arg His Asn
            100                 105                 110

Asn Ser Asp Ile Met Trp Phe Trp Thr Met Ser Val Ala Gly Asp Val
        115                 120                 125

Trp Phe Gly Phe Ser Trp Leu Leu Asn Gln Leu Pro Lys Phe Asn Pro
    130                 135                 140

Val Lys Thr Ile Pro Asp Leu Thr Ala Leu Arg Gln Tyr Cys Asp Leu
145                 150                 155                 160

Ala Asp Gly Ser Tyr Arg Leu Pro Gly Ile Asp Val Phe Val Thr Thr
                165                 170                 175

Ala Asp Pro Ile Asp Glu Pro Val Leu Tyr Thr Met Asn Cys Val Leu
            180                 185                 190

Ser Ile Leu Ala Ala Asp Tyr Pro Val Asp Arg Ser Ala Cys Tyr Leu
        195                 200                 205

Ser Asp Asp Ser Gly Ala Leu Ile Leu Tyr Glu Ala Leu Val Glu Thr
    210                 215                 220

Ala Lys Phe Ala Thr Leu Trp Val Pro Phe Cys Arg Lys His Cys Ile
225                 230                 235                 240

Glu Pro Arg Ser Pro Glu Ser Tyr Phe Glu Leu Glu Ala Pro Ser Tyr
                245                 250                 255

Thr Gly Ser Ala Pro Glu Glu Phe Lys Asn Asp Ser Arg Ile Val His
            260                 265                 270

Leu Glu Tyr Asp Glu Phe Lys Val Arg Leu Glu Ala Leu Pro Glu Thr
        275                 280                 285

Ile Arg Lys Arg Ser Asp Val Tyr Asn Ser Met Lys Thr Asp Gln Gly
    290                 295                 300
```

```
Ala Pro Asn Ala Thr Trp Met Ala Asn Gly Thr Gln Trp Pro Gly Thr
305                 310                 315                 320

Trp Ile Glu Pro Ile Glu Asn His Arg Lys Gly His His Ala Gly Ile
                325                 330                 335

Val Lys Val Val Leu Asp His Pro Ile Arg Gly His Asn Leu Ser Leu
            340                 345                 350

Lys Asp Ser Thr Gly Asn Asn Leu Asn Phe Asn Ala Thr Asp Val Arg
        355                 360                 365

Ile Pro Met Leu Val Tyr Val Ser Arg Gly Lys Asn Pro Asn Tyr Asp
    370                 375                 380

His Asn Lys Lys Ala Gly Ala Leu Asn Ala Gln Leu Arg Ala Ser Ala
385                 390                 395                 400

Leu Leu Ser Asn Ala Gln Phe Ile Ile Asn Phe Asp Cys Asp His Tyr
                405                 410                 415

Ile Asn Asn Ser Gln Ala Phe Arg Ala Ala Ile Cys Phe Met Leu Asp
            420                 425                 430

Gln Arg Glu Gly Asp Asn Thr Ala Phe Val Gln Phe Pro Gln Arg Phe
        435                 440                 445

Asp Asn Val Asp Pro Lys Asp Arg Tyr Gly Asn His Asn Arg Val Phe
    450                 455                 460

Phe Asp Gly Thr Met Leu Ala Leu Asn Gly Leu Gln Gly Pro Ser Tyr
465                 470                 475                 480

Leu Gly Thr Gly Cys Met Phe Arg Arg Leu Ala Leu Tyr Gly Ile Asp
                485                 490                 495

Pro Pro His Trp Arg Gln Asp Asn Ile Thr Pro Glu Ala Ser Lys Phe
            500                 505                 510

Gly Asn Ser Ile Leu Leu Glu Ser Val Leu Glu Ala Leu Asn Gln
        515                 520                 525

Asp Arg Phe Ala Thr Pro Ser Pro Val Asn Asp Ile Phe Val Asn Glu
    530                 535                 540

Leu Glu Met Val Val Ser Ala Ser Phe Asp Lys Glu Thr Asp Trp Gly
545                 550                 555                 560

Lys Gly Val Gly Tyr Ile Tyr Asp Ile Ala Thr Glu Asp Ile Val Thr
                565                 570                 575

Gly Phe Arg Ile His Gly Gln Gly Trp Arg Ser Met Tyr Cys Thr Met
            580                 585                 590

Glu His Asp Ala Phe Cys Gly Thr Ala Pro Ile Asn Leu Thr Glu Arg
        595                 600                 605

Leu His Gln Ile Val Arg Trp Ser Gly Gly Ser Leu Glu Met Phe Phe
    610                 615                 620

Ser His Asn Asn Pro Leu Ile Gly Gly Arg Arg Leu Gln Pro Leu Gln
625                 630                 635                 640

Arg Val Ser Tyr Leu Asn Met Thr Ile Tyr Pro Val Thr Ser Leu Phe
                645                 650                 655

Ile Leu Leu Tyr Ala Ile Ser Pro Val Met Trp Leu Ile Pro Asp Glu
            660                 665                 670

Val Tyr Ile Gln Arg Pro Phe Thr Arg Tyr Val Val Tyr Leu Leu Val
        675                 680                 685

Ile Ile Leu Met Ile His Met Ile Gly Trp Leu Glu Ile Lys Trp Ala
    690                 695                 700

Gly Ile Thr Trp Leu Asp Tyr Trp Arg Asn Glu Gln Phe Phe Met Ile
705                 710                 715                 720

Gly Ser Thr Ser Ala Tyr Pro Thr Ala Val Leu His Met Val Val Asn
```

```
                     725                 730                 735
Leu Leu Thr Lys Lys Gly Ile His Phe Arg Val Thr Ser Lys Gln Thr
            740                 745                 750

Thr Ala Asp Thr Asn Asp Lys Phe Ala Asp Leu Tyr Glu Met Arg Trp
            755                 760                 765

Val Pro Met Leu Ile Pro Thr Met Val Val Leu Val Ala Asn Ile Gly
            770                 775                 780

Ala Ile Gly Val Ala Ile Gly Lys Thr Ala Val Tyr Met Gly Val Trp
785                 790                 795                 800

Thr Ile Ala Gln Lys Arg His Ala Ala Met Gly Leu Leu Phe Asn Met
            805                 810                 815

Trp Val Met Phe Leu Leu Tyr Pro Phe Ala Leu Ala Ile Met Gly Arg
            820                 825                 830

Trp Ala Lys Arg Ser Ile Ile Leu Val Val Leu Leu Pro Ile Ile Phe
            835                 840                 845

Val Ile Val Ala Leu Val Tyr Val Ala Thr His Ile Leu Leu Ala Asn
            850                 855                 860

Ile Ile Pro Phe
865

<210> SEQ ID NO 25
<211> LENGTH: 2670
<212> TYPE: DNA
<213> ORGANISM: Oryza sativa

<400> SEQUENCE: 25
atgtccgcgg cggccgtgac tcgccggatc aacgcgggcg gcctccgcgt cgaggtcacc        60
aacggcaatg gcgcggccgg cgtctacgtg gcggcggcgg cggcaccgtg ctcgccggcg       120
gccaagcggg tgaacgacgg cggcggcaag gatgacgtgt gggtggccgt cgacgaggcg       180
gacgtgtcgg ggcccagcgg cggcgatggc gttcggccga cgctgttccg gacgtacaag       240
gtcaagggca gcatcctgca tccttacagg ttcttgatcc tagttcgact gatcgccatc       300
gtcgccttct tcgcgtggcg cgtacgccac aagaaccgcg acggcgcgtg gctgtggaca       360
atgtccatgg ccgcgacgt ctggttcggc ttctcgtggg cgctcaacca gctcccgaag       420 ctgaaccca tcaagcgcgt cgcggacctc gccgccctcg ccgaccggca gcagcacggc       480
acctccggcg gcggcgagct ccccggcgtc gacgtcttcg tcaccaccgt cgaccccgtc       540
gacgagccga tcctctacac cgtgaactcc atcctctcca tcctcgccgc cgactacccg       600
gtggacaggt acgcctgcta cctgtccgac gacggcggga cgctggtcca ctacgaggcc       660
atggtggagg tcgccaagtt cgctgagctg tgggtgccct tctgccggaa gcactgcgtc       720
gagccgaggc gccggagag ctacttcgcg atgaagacgc aggcgtacag gggcggcgtc       780
gccggcgagc tgatgagcga tcgccgccgc gtgcggcgag agtacgagga gttcaaggtc       840
aggatcgact cgctgttcag caccattcgc aagcgatctg acgcgtacaa cagagcgaag       900
gatggcaaag atgacggtga aaacgcgaca tggatggctg atgggacgca ttggcccggc       960
acatggtttg agccggcgga gaatcaccgg aaagggcaac acgctgggat tgttcaggtt      1020
ttactgaacc atcccaccag taagccacgg tttggagtgg cggcgagtgt tgacaacccg      1080
ttggacttca gcggcgtgga cgtgcggctc cccatgctgg tgtacatctc gcgcgagaag      1140
cgccccgggt acaaccacca gaagaaggcc ggcgccatga cgcgctgct ccgcgtgtcc      1200 gcgctgctgt cgaacgcgcc cttcatcatc aacttcgact gcgaccacta cgtcaacaac      1260
```

```
tcgcaggcgt tccgtgcgcc gatgtgcttc atgctcgacc ggcgcggcgg cggcgacgac    1320
gtggcgttcg tccagttccc gcagcggttc gacgacgtcg acccgacgga ccggtacgcg    1380
aaccacaacc gcgtcttctt cgacggcacc acgctctccc tcaacggcct ccagggcccc    1440
tcctacctcg gcaccggcac catgttccgc cgcgccgcgc tctacggcct ggagccgccg    1500
cggtgggggg cggcggggag ccagatcaag gccatggaca atgccaacaa gttcggcgcc    1560
tcgtcgacgc tagtcagctc gatgctggac ggcgccaacc aagaacggtc gatcacgccg    1620
cccgtggcga tcgacgggtc ggtcgcccgt gacctcgccg ccgtgacggc gtgcggctac    1680
gacctcggga cgtcgtgggg gagagacgcc gggtgggtgt acgacatcgc gacggaggac    1740
gtggcgaccg ggttccgcat gcaccagcag ggatggcgct ccgtgtacac ctccatggag    1800
cccgccgcgt tccgcggcac ggcgccgatc aacctcaccg agcgcctcta ccagatccta    1860
aggtggtcgg gcggctcgct cgagatgttc ttctcccaca gcaacgcgct cctcgccggc    1920
cgccgcctcc acccgctgca gcgcatcgcc tacctcaaca tgtcgaccta cccgatcgtc    1980
accgtgttca tcttcttcta caacctcttc ccggtgatgt ggctcatctc cgagcagtac    2040
tacatccagc agccattcgg cgagtacctc ctctacctcg tcgccatcat cgccatgatc    2100
cacgtgatcg gcatgttcga ggtgaagtgg tcgggcatca cggtgctgga ctggtgccgc    2160
aacgagcagt tctacatgat cggctccacg ggggtgtacc cgacggcggt gctgtacatg    2220
gcgctcaagc tcttcaccgg gaagggcatc cacttcaggc tcacgtcgaa gcagacgacg    2280
gccagctccg gcgacaagtt cgccgacctg tacaccgtgc ggtgggtgcc tctgctgatc    2340
ccgaccatcg tcgtcctggc cgtgaacgtc ggcgccgtcg gggtggcggt cggcaaggca    2400
gcggcgtggg ggttgctcac cgagcagggg cggttcgcgg tgctcgggat ggtgttcaac    2460
gtgtggatcc tggcgctcct ctaccgcttc gcgctgggga tcatgggca gcgggggaag    2520
cggccggcgg tgctgttcgt ggcgacggtg atggccgtcg ccgccgtggc gatcatgtac    2580
gccgccttcg gtgcgccgta ccaagctggg ttgtcaggtg tcgcggcttc tctcggtaaa    2640
gcggcgtcgc tgaccgggcc atctgggtag                                     2670

<210> SEQ ID NO 26
<211> LENGTH: 889
<212> TYPE: PRT
<213> ORGANISM: Oryza sativa

<400> SEQUENCE: 26

Met Ser Ala Ala Ala Val Thr Arg Arg Ile Asn Ala Gly Gly Leu Arg
1               5                  10                  15

Val Glu Val Thr Asn Gly Asn Gly Ala Ala Gly Val Tyr Val Ala Ala
                20                  25                  30

Ala Ala Ala Pro Cys Ser Pro Ala Ala Lys Arg Val Asn Asp Gly Gly
            35                  40                  45

Gly Lys Asp Asp Val Trp Val Ala Val Asp Glu Ala Asp Val Ser Gly
        50                  55                  60

Pro Ser Gly Gly Asp Gly Val Arg Pro Thr Leu Phe Arg Thr Tyr Lys
65                  70                  75                  80

Val Lys Gly Ser Ile Leu His Pro Tyr Arg Phe Leu Ile Leu Val Arg
                85                  90                  95

Leu Ile Ala Ile Val Ala Phe Phe Ala Trp Arg Val Arg His Lys Asn
            100                 105                 110

Arg Asp Gly Ala Trp Leu Trp Thr Met Ser Met Ala Gly Asp Val Trp
        115                 120                 125
```

```
Phe Gly Phe Ser Trp Ala Leu Asn Gln Leu Pro Lys Leu Asn Pro Ile
    130                 135                 140

Lys Arg Val Ala Asp Leu Ala Ala Leu Ala Asp Arg Gln Gln His Gly
145                 150                 155                 160

Thr Ser Gly Gly Gly Glu Leu Pro Gly Val Asp Val Phe Val Thr Thr
                165                 170                 175

Val Asp Pro Val Asp Glu Pro Ile Leu Tyr Thr Val Asn Ser Ile Leu
            180                 185                 190

Ser Ile Leu Ala Ala Asp Tyr Pro Val Asp Arg Tyr Ala Cys Tyr Leu
        195                 200                 205

Ser Asp Asp Gly Gly Thr Leu Val His Tyr Glu Ala Met Val Glu Val
210                 215                 220

Ala Lys Phe Ala Glu Leu Trp Val Pro Phe Cys Arg Lys His Cys Val
225                 230                 235                 240

Glu Pro Arg Ala Pro Glu Ser Tyr Phe Ala Met Lys Thr Gln Ala Tyr
                245                 250                 255

Arg Gly Gly Val Ala Gly Glu Leu Met Ser Asp Arg Arg Val Arg
            260                 265                 270

Arg Glu Tyr Glu Glu Phe Lys Val Arg Ile Asp Ser Leu Phe Ser Thr
        275                 280                 285

Ile Arg Lys Arg Ser Asp Ala Tyr Asn Arg Ala Lys Asp Gly Lys Asp
    290                 295                 300

Asp Gly Glu Asn Ala Thr Trp Met Ala Asp Gly Thr His Trp Pro Gly
305                 310                 315                 320

Thr Trp Phe Glu Pro Ala Glu Asn His Arg Lys Gly Gln His Ala Gly
                325                 330                 335

Ile Val Gln Val Leu Leu Asn His Pro Thr Ser Lys Pro Arg Phe Gly
            340                 345                 350

Val Ala Ala Ser Val Asp Asn Pro Leu Asp Phe Ser Gly Val Asp Val
        355                 360                 365

Arg Leu Pro Met Leu Val Tyr Ile Ser Arg Glu Lys Arg Pro Gly Tyr
370                 375                 380

Asn His Gln Lys Lys Ala Gly Ala Met Asn Ala Leu Leu Arg Val Ser
385                 390                 395                 400

Ala Leu Leu Ser Asn Ala Pro Phe Ile Ile Asn Phe Asp Cys Asp His
                405                 410                 415

Tyr Val Asn Asn Ser Gln Ala Phe Arg Ala Pro Met Cys Phe Met Leu
            420                 425                 430

Asp Arg Arg Gly Gly Asp Val Ala Phe Val Gln Phe Pro Gln
        435                 440                 445

Arg Phe Asp Asp Val Asp Pro Thr Asp Arg Tyr Ala Asn His Asn Arg
450                 455                 460

Val Phe Phe Asp Gly Thr Thr Leu Ser Leu Asn Gly Leu Gln Gly Pro
465                 470                 475                 480

Ser Tyr Leu Gly Thr Gly Thr Met Phe Arg Arg Ala Ala Leu Tyr Gly
                485                 490                 495

Leu Glu Pro Pro Arg Trp Gly Ala Ala Gly Ser Gln Ile Lys Ala Met
            500                 505                 510

Asp Asn Ala Asn Lys Phe Gly Ala Ser Ser Thr Leu Val Ser Ser Met
        515                 520                 525

Leu Asp Gly Ala Asn Gln Glu Arg Ser Ile Thr Pro Pro Val Ala Ile
530                 535                 540
```

```
Asp Gly Ser Val Ala Arg Asp Leu Ala Ala Val Thr Ala Cys Gly Tyr
545                 550                 555                 560

Asp Leu Gly Thr Ser Trp Gly Arg Asp Ala Gly Trp Val Tyr Asp Ile
            565                 570                 575

Ala Thr Glu Asp Val Ala Thr Gly Phe Arg Met His Gln Gln Gly Trp
        580                 585                 590

Arg Ser Val Tyr Thr Ser Met Glu Pro Ala Ala Phe Arg Gly Thr Ala
    595                 600                 605

Pro Ile Asn Leu Thr Glu Arg Leu Tyr Gln Ile Leu Arg Trp Ser Gly
610                 615                 620

Gly Ser Leu Glu Met Phe Phe Ser His Ser Asn Ala Leu Leu Ala Gly
625                 630                 635                 640

Arg Arg Leu His Pro Leu Gln Arg Ile Ala Tyr Leu Asn Met Ser Thr
            645                 650                 655

Tyr Pro Ile Val Thr Val Phe Ile Phe Phe Tyr Asn Leu Phe Pro Val
        660                 665                 670

Met Trp Leu Ile Ser Glu Gln Tyr Tyr Ile Gln Gln Pro Phe Gly Glu
    675                 680                 685

Tyr Leu Leu Tyr Leu Val Ala Ile Ile Ala Met Ile His Val Ile Gly
690                 695                 700

Met Phe Glu Val Lys Trp Ser Gly Ile Thr Val Leu Asp Trp Cys Arg
705                 710                 715                 720

Asn Glu Gln Phe Tyr Met Ile Gly Ser Thr Gly Val Tyr Pro Thr Ala
            725                 730                 735

Val Leu Tyr Met Ala Leu Lys Leu Phe Thr Gly Lys Gly Ile His Phe
        740                 745                 750

Arg Leu Thr Ser Lys Gln Thr Thr Ala Ser Ser Gly Asp Lys Phe Ala
    755                 760                 765

Asp Leu Tyr Thr Val Arg Trp Val Pro Leu Leu Ile Pro Thr Ile Val
770                 775                 780

Val Leu Ala Val Asn Val Gly Ala Val Gly Val Ala Val Gly Lys Ala
785                 790                 795                 800

Ala Ala Trp Gly Leu Leu Thr Glu Gln Gly Arg Phe Ala Val Leu Gly
            805                 810                 815

Met Val Phe Asn Val Trp Ile Leu Ala Leu Leu Tyr Pro Phe Ala Leu
        820                 825                 830

Gly Ile Met Gly Gln Arg Gly Lys Arg Pro Ala Val Leu Phe Val Ala
    835                 840                 845

Thr Val Met Ala Val Ala Val Ala Ile Met Tyr Ala Ala Phe Gly
850                 855                 860

Ala Pro Tyr Gln Ala Gly Leu Ser Gly Val Ala Ala Ser Leu Gly Lys
865                 870                 875                 880

Ala Ala Ser Leu Thr Gly Pro Ser Gly
            885

<210> SEQ ID NO 27
<211> LENGTH: 2859
<212> TYPE: DNA
<213> ORGANISM: Oryza sativa

<400> SEQUENCE: 27
atggcgccag cggtggccgg cggcggaggg aggaggaaca atgaggggt gaacgggaac      60 gcggcggcgc cggcgtgcgt gtgcgggttc ccggtgtgcg cgtgcgcggg ggcggcggcg     120
gtggcgtcgg cggcgtcgtc ggcggacatg gacatcgtgg cggcggggca gatcggcgcc     180
```

```
gtcaacgacg agagctgggt cgccgtcgac ctcagcgaca gcgacgacgc ccccgccgcc    240
ggcgacgtcc agggcgccct cgacgaccgc cccgtcttcc gtaccgagaa gatcaagggc    300
gtcctcctcc acccctaccg ggtgctgatc tttgtgaggc tgatcgcgtt cacactgttc    360
gtgatatggc gtatcgagca caagaacccg gacgcgatgt ggctgtgggt gacgtcgatc    420
gccggcgagt tctggttcgg gttctcgtgg ctgctcgacc agctccccaa gctgaacccg    480
atcaaccgcg tccccgacct cgccgtcctc cgccgccgct tcgaccacgc cgacgggacc    540
tcctccctcc cggggctgga catcttcgtc accaccgccg acccgatcaa ggagcccatc    600
ctgtcgacgc cgaactccat cctctccatc ctcgccgccg actaccccgt cgaccgcaac    660
acctgctacc tctccgacga ctctgggatg ctcctcacct acgaggccat ggcggaggcg    720
gccaagttcg cgacgctgtg ggtgcccttc tgccggaagc acgccatcga gccgcgcggg    780
cctgagagct acttcgagct caagtcccac ccctacatgg ggagggcgca ggaggagttc    840
gtcaacgacc gccgccgcgt ccgcaaggag tacgacgact tcaaggccag gatcaacggc    900
ctcgagcacg acatcaagca gaggtccgac tcctacaacg ccgccgccgg cgtcaaggac    960
ggcgagcccc gcgccacctg gatggccgac gggtcgcagt gggagggcac ctggatcgag    1020
cagtcggaga accaccgcaa gggcgaccac gccggcatcg tcctggtgtt gctgaaccac    1080
ccgagccacg cacggcagct ggggccgccg gcgagcgccg acaacccgct ggacttcagc    1140
ggcgtggacg tgcggctgcc gatgctggtg tacgtcgcac gtgagaagcg ccccgggtgc    1200
aaccaccaga agaaggccgg cgccatgaac gcgctgaccc gcgcctccgc cgtgctctcc    1260 aactcccсcct tcatcctcaa cctcgactgc gaccactaca tcaacaactc ccaggcgctc    1320
cgcgccggca tctgcttcat gctcggccgc gacagcgaca ccgtcgcgtt cgtccagttc    1380
ccgcagcgct tcgagggcgt cgaccccacc gacctctatg ctaaccacaa ccgtatcttc    1440
ttcgacggca cgctccgtgc cctcgacggg ctgcaggggc ctatctacgt cggcaccggg    1500
tgtctcttcc gccgcatcac gctgtacggg ttcgagccgc cgaggatcaa cgtcggcgga    1560
ccgtgcttcc cgaggctcgg tgggatgttc gccaagaaca ggtaccagaa gcctgggttc    1620
gagatgacca agcctggtgc caagccggtg gcgccgccgc cggcggcgac ggtggcgaag    1680
gggaagcacg ggttcctgcc gatgcccaag aaggcgtacg gcaagtcgga cgcgttcgcc    1740
gacaccatcc cgcgcgcgtc gcacccgtcg ccgtacgcgg cggaggcggc ggtggcggcc    1800
gacgaggcgg cgatcgcgga ggccgtgatg gtgacggcgg cggcgtacga gaagaagacc    1860
gggtggggga gcgacatcgg gtgggtgtac ggcacggtga cggaggacgt ggtgaccggc    1920
taccggatgc acatcaaggg gtggaggtcg cgctactgct ccatctaccc gcacgcgttc    1980
atcgggacgc cgccgatcaa cctgacggag aggctgttcc aggtgctccg gtggtcgacg    2040
ggttcgctgg agatcttctt ctcgaggaac aacccgctgt cgggagcac gttcctgcac    2100 ccgctgcagc gcgtggcgta catcaacatc accacctacc cgttcacggc gctgttcctc    2160
atcttctaca ccaccgtgcc ggcgctgtcg ttcgtgacgg ggcacttcat cgtgcagagg    2220
ccgaccacca tgttctacgt ctacctcgcc atcgtgctcg ggacgctgct catcctcgcc    2280
gtgctggagg tgaagtgggc gggggtcacc gtgttcgagt ggttcaggaa cgggcagttc    2340
tggatgacgg ccagctgctc cgcctacctc gccgccgtgc tgcaggtggt caccaaggtg    2400
gtgttccggc gggacatctc gttcaagctc acctccaagc tccccgccgg cgacgagaag    2460
aaggacccct acgccgacct gtacgtggtg cggtggacgt ggctcatgat caccccccatc    2520
```

-continued

| | |
|---|---|
| atcatcatcc tcgtcaacat catcggctcc gccgtcgcct tcgccaaggt gctcgacggc | 2580 |
| gagtggacgc actggctcaa ggtcgccggc ggcgtgttct tcaacttctg ggtcctcttc | 2640 |
| cacctctacc ccttcgccaa gggcatcctc gggaagcacg gcaagacgcc ggtggtggtg | 2700 |
| ctcgtctggt gggccttcac cttcgtcatc accgccgtgc tctacatcaa catccccac | 2760 |
| atccatggcc ccggccgcca cggcgccgcc tcaccatccc acggccacca cagcgcccat | 2820 |
| ggcaccaaga agtacgactt cacctacgcc tggccatga | 2859 |

```
<210> SEQ ID NO 28
<211> LENGTH: 952
<212> TYPE: PRT
<213> ORGANISM: Oryza sativa

<400> SEQUENCE: 28
```

Met Ala Pro Ala Val Ala Gly Gly Gly Arg Arg Asn Asn Glu Gly
1               5                   10                  15

Val Asn Gly Asn Ala Ala Ala Pro Ala Cys Val Cys Gly Phe Pro Val
            20                  25                  30

Cys Ala Cys Ala Gly Ala Ala Ala Val Ala Ser Ala Ala Ser Ser Ala
        35                  40                  45

Asp Met Asp Ile Val Ala Ala Gly Gln Ile Gly Ala Val Asn Asp Glu
    50                  55                  60

Ser Trp Val Ala Val Asp Leu Ser Asp Ser Asp Ala Pro Ala Ala
65                  70                  75                  80

Gly Asp Val Gln Gly Ala Leu Asp Asp Arg Pro Val Phe Arg Thr Glu
                85                  90                  95

Lys Ile Lys Gly Val Leu Leu His Pro Tyr Arg Val Leu Ile Phe Val
            100                 105                 110

Arg Leu Ile Ala Phe Thr Leu Phe Val Ile Trp Arg Ile Glu His Lys
        115                 120                 125

Asn Pro Asp Ala Met Trp Leu Trp Val Thr Ser Ile Ala Gly Glu Phe
    130                 135                 140

Trp Phe Gly Phe Ser Trp Leu Leu Asp Gln Leu Pro Lys Leu Asn Pro
145                 150                 155                 160

Ile Asn Arg Val Pro Asp Leu Ala Val Leu Arg Arg Phe Asp His
                165                 170                 175

Ala Asp Gly Thr Ser Ser Leu Pro Gly Leu Asp Ile Phe Val Thr Thr
            180                 185                 190

Ala Asp Pro Ile Lys Glu Pro Ile Leu Ser Thr Ala Asn Ser Ile Leu
        195                 200                 205

Ser Ile Leu Ala Ala Asp Tyr Pro Val Asp Arg Asn Thr Cys Tyr Leu
    210                 215                 220

Ser Asp Asp Ser Gly Met Leu Leu Thr Tyr Glu Ala Met Ala Glu Ala
225                 230                 235                 240

Ala Lys Phe Ala Thr Leu Trp Val Pro Phe Cys Arg Lys His Ala Ile
                245                 250                 255

Glu Pro Arg Gly Pro Glu Ser Tyr Phe Glu Leu Lys Ser His Pro Tyr
            260                 265                 270

Met Gly Arg Ala Gln Glu Glu Phe Val Asn Asp Arg Arg Arg Val Arg
        275                 280                 285

Lys Glu Tyr Asp Asp Phe Lys Ala Arg Ile Asn Gly Leu Glu His Asp
    290                 295                 300

Ile Lys Gln Arg Ser Asp Ser Tyr Asn Ala Ala Ala Gly Val Lys Asp
305                 310                 315                 320

```
Gly Glu Pro Arg Ala Thr Trp Met Ala Asp Gly Ser Gln Trp Glu Gly
            325                 330                 335

Thr Trp Ile Glu Gln Ser Glu Asn His Arg Lys Gly Asp His Ala Gly
        340                 345                 350

Ile Val Leu Val Leu Leu Asn His Pro Ser His Ala Arg Gln Leu Gly
            355                 360                 365

Pro Pro Ala Ser Ala Asp Asn Pro Leu Asp Phe Ser Gly Val Asp Val
370                 375                 380

Arg Leu Pro Met Leu Val Tyr Val Ala Arg Glu Lys Arg Pro Gly Cys
385                 390                 395                 400

Asn His Gln Lys Lys Ala Gly Ala Met Asn Ala Leu Thr Arg Ala Ser
            405                 410                 415

Ala Val Leu Ser Asn Ser Pro Phe Ile Leu Asn Leu Asp Cys Asp His
            420                 425                 430

Tyr Ile Asn Asn Ser Gln Ala Leu Arg Ala Gly Ile Cys Phe Met Leu
        435                 440                 445

Gly Arg Asp Ser Asp Thr Val Ala Phe Val Gln Phe Pro Gln Arg Phe
    450                 455                 460

Glu Gly Val Asp Pro Thr Asp Leu Tyr Ala Asn His Asn Arg Ile Phe
465                 470                 475                 480

Phe Asp Gly Thr Leu Arg Ala Leu Asp Gly Leu Gln Gly Pro Ile Tyr
                485                 490                 495

Val Gly Thr Gly Cys Leu Phe Arg Arg Ile Thr Leu Tyr Gly Phe Glu
            500                 505                 510

Pro Pro Arg Ile Asn Val Gly Gly Pro Cys Phe Pro Arg Leu Gly Gly
        515                 520                 525

Met Phe Ala Lys Asn Arg Tyr Gln Lys Pro Gly Phe Glu Met Thr Lys
    530                 535                 540

Pro Gly Ala Lys Pro Val Ala Pro Pro Ala Ala Thr Val Ala Lys
545                 550                 555                 560

Gly Lys His Gly Phe Leu Pro Met Pro Lys Lys Ala Tyr Gly Lys Ser
                565                 570                 575

Asp Ala Phe Ala Asp Thr Ile Pro Arg Ala Ser His Pro Ser Pro Tyr
            580                 585                 590

Ala Ala Glu Ala Ala Val Ala Ala Asp Glu Ala Ala Ile Ala Glu Ala
        595                 600                 605

Val Met Val Thr Ala Ala Ala Tyr Glu Lys Lys Thr Gly Trp Gly Ser
    610                 615                 620

Asp Ile Gly Trp Val Tyr Gly Thr Val Thr Glu Asp Val Val Thr Gly
625                 630                 635                 640

Tyr Arg Met His Ile Lys Gly Trp Arg Ser Arg Tyr Cys Ser Ile Tyr
                645                 650                 655

Pro His Ala Phe Ile Gly Thr Ala Pro Ile Asn Leu Thr Glu Arg Leu
            660                 665                 670

Phe Gln Val Leu Arg Trp Ser Thr Gly Ser Leu Glu Ile Phe Phe Ser
        675                 680                 685

Arg Asn Asn Pro Leu Phe Gly Ser Thr Phe Leu His Pro Leu Gln Arg
    690                 695                 700

Val Ala Tyr Ile Asn Ile Thr Thr Tyr Pro Phe Thr Ala Leu Phe Leu
705                 710                 715                 720

Ile Phe Tyr Thr Thr Val Pro Ala Leu Ser Phe Val Thr Gly His Phe
                725                 730                 735
```

```
Ile Val Gln Arg Pro Thr Thr Met Phe Tyr Val Tyr Leu Ala Ile Val
            740                 745                 750

Leu Gly Thr Leu Leu Ile Leu Ala Val Leu Glu Val Lys Trp Ala Gly
        755                 760                 765

Val Thr Val Phe Glu Trp Phe Arg Asn Gly Gln Phe Trp Met Thr Ala
    770                 775                 780

Ser Cys Ser Ala Tyr Leu Ala Ala Val Leu Gln Val Val Thr Lys Val
785                 790                 795                 800

Val Phe Arg Arg Asp Ile Ser Phe Lys Leu Thr Ser Lys Leu Pro Ala
                805                 810                 815

Gly Asp Glu Lys Lys Asp Pro Tyr Ala Asp Leu Tyr Val Arg Trp
            820                 825                 830

Thr Trp Leu Met Ile Thr Pro Ile Ile Ile Leu Val Asn Ile Ile
            835                 840                 845

Gly Ser Ala Val Ala Phe Ala Lys Val Leu Asp Gly Glu Trp Thr His
850                 855                 860

Trp Leu Lys Val Ala Gly Val Phe Asn Phe Trp Val Leu Phe
865                 870                 875                 880

His Leu Tyr Pro Phe Ala Lys Gly Ile Leu Gly Lys His Gly Lys Thr
                885                 890                 895

Pro Val Val Leu Val Trp Trp Ala Phe Thr Phe Val Ile Thr Ala
            900                 905                 910

Val Leu Tyr Ile Asn Ile Pro His Ile His Gly Pro Gly Arg His Gly
            915                 920                 925

Ala Ala Ser Pro Ser His Gly His His Ser Ala His Gly Thr Lys Lys
        930                 935                 940

Tyr Asp Phe Thr Tyr Ala Trp Pro
945                 950
```

<210> SEQ ID NO 29
<211> LENGTH: 2493
<212> TYPE: DNA
<213> ORGANISM: Oryza sativa

<400> SEQUENCE: 29

```
atgccgccgt cagcaggctt ggccactgag agcttgccgg cggcgacatg cccggccaag      60
aaggatgcct atgccgcggc ggcgtcgccg gagtccgaga cgaagctggc cgccggcgac     120
gagagggcgc cgctcgtccg gacgactcgc atctcgacaa ctaccatcaa gttatacagg     180
ctcaccatct ttgttcgcat cgccatcttc gtgctcttct tcaagtggag aatcacctac     240
gctgctcgcg ccatcagctc caccgacgcc ggcggcatcg gcatgagcaa gcggcgacaa     300
ttttggacgg cgtccatcgc cggcgagctc tggttcgcgt tcatgtgggt gctcgaccag     360
ctgcccaaga cgatgcccgt ccggcgcgcc gtcgacgtca cggcgctgaa cgacgacacg     420
ctgctcccgg cgatggacgt gttcgtcacc accgccgacc ccgacaagga gccgccgctc     480
gccacggcga acaccgtgct gtccatcctc gccgcgggct accccgccgg caaggtgacg     540
tgctacgtct ccgacgacgc cggcgcggag gtgacacgcg gggcggtcgt ggaggcggcc     600
cggttcgcgg cactgtgggt gcccttctgc cggaagcacg cgtcgagcc gaggaacccg      660 gaggcgtact tcaacggcgg cgagggtggc ggtggtggcg gcaaggcgag ggtggtggcg     720
agggggagct acaaggggag gcgtggccg gagctggtgc gcgacaggag cgggtgcgc       780 cgcgagtacg aggagatgcg gctgcggatc acgcgctgc aggccgccga cgcgcgccgc      840
cggcgctgcg gcgcggccga tgaccacgcc ggagttgtgc aggtactgat cgattctgct     900
```

```
gggagcgcgc cacagctcgg cgtcgcggac gggagcaagc tcatcgacct cgcctccgtc      960
gacgtgcgcc tcccggcgct tgtgtacgtg tgccgcgaga agcgccgcgg ccgcgcacac     1020
caccggaagg ccggcgccat gaacgcgctg ctgcgcgcat ccgccgtgct ctcgaacgcg     1080
cccttcatcc tcaacctcga ctgcgaccac tatgtcaaca actcgcaggc cctccgcgcc     1140
ggcatttgct tcatgatcga acgccgcggc ggcggcgccg aagacgccgg cgatgtcgcg     1200
ttcgtccagt tcccgcagcg gttcgacggc gtcgatcccg cgaccgcta cgccaaccac     1260
aaccgcgtct tcttcgactg taccgagctt ggcctcgacg gcctccaggg ccccatctac     1320
gtcggcaccg gctgcttgtt ccgccgcgtc gcgctctacg gcgtcgaccc accgcgctgg     1380
agatcgcccg cggcggtgt cgccgcggac cctgccaagt tcggcgagtc ggcgccgttc     1440
ctagcctccg ttcgggcgga gcagagtcac agtcgcgacg acggcgacgc cattgccgag     1500
gcgagtgcgc tcgtgtcgtg cgcgtacgag gacgggacgg cgtggggcag ggacgtcggc     1560
tgggtgtacg gcaccgtgac ggaggacgtg gccacgggct tctgcatgca ccggcgaggg     1620
tggcgctccg cctactacgc cgccgcgccc gacgcgttcc gcggcacggc gccgatcaac     1680
ctcgccgacc gcctccacca ggtgctccgc tgggcggcgg gctccctcga gatcttcttc     1740
tcccgcaaca acgcactcct cgccggcggc cgccgccgcc tccacccgct gcagcgcgcc     1800
gcctacctca acacgacggt gtacccgttc acgtcgctct tcctcatggc ctactgcctc     1860
ttcccggcga tcccgctcat cgccggcggc ggcggctgga acgccgcgcc gacaccgacg     1920
tacgtcgcgt tcctggcggc gctgatggtg acgctcgcgg cggtggccgt gctggagacg     1980
aggtggtcgg ggatcgcgct gggtgagtgg tggcggaacg agcagttctg gatggtgtcc     2040
gcgacgagcg cgtacctcgc cgcggtggcg caggtggcgc tcaaggtcgc gacggggaag     2100
gaaatatcgt tcaagctgac ctcgaagcat ctcgcgtcgt cggcgacgcc ggtcgccggt     2160
aaggataggc agtacgcgga gctgtacgcc gtgaggtgga cggcgctgat ggcgccgacg     2220
gcggcggctc tggcagtgaa cgtggcgtcg atggcggcgg cgggtggtgg tggccggtgg     2280
tggtggtggg acgctccgtc ggcggcggcg gcggcggcgg cggcactccc ggtggcgttc     2340
aacgtgtggg tggtggtgca tctctacccg ttcgcgctcg ggctgatggg tcgccggagc     2400
aaggcggtgc gccccattct gttcctgttc gccgtcgtcg cctacctcgc cgtccgcttc     2460
ctttgtctct tgttacaatt ccatacggct taa                                 2493
```

<210> SEQ ID NO 30
<211> LENGTH: 830
<212> TYPE: PRT
<213> ORGANISM: Oryza sativa

<400> SEQUENCE: 30

```
Met Pro Pro Ser Ala Gly Leu Ala Thr Glu Ser Leu Pro Ala Ala Thr
1               5                   10                  15

Cys Pro Ala Lys Lys Asp Ala Tyr Ala Ala Ala Ser Pro Glu Ser
            20                  25                  30

Glu Thr Lys Leu Ala Ala Gly Asp Glu Arg Ala Pro Leu Val Arg Thr
        35                  40                  45

Thr Arg Ile Ser Thr Thr Thr Ile Lys Leu Tyr Arg Leu Thr Ile Phe
    50                  55                  60

Val Arg Ile Ala Ile Phe Val Leu Phe Phe Lys Trp Arg Ile Thr Tyr
65                  70                  75                  80

Ala Ala Arg Ala Ile Ser Ser Thr Asp Ala Gly Gly Ile Gly Met Ser
```

```
                        85                  90                  95
Lys Ala Ala Thr Phe Trp Thr Ala Ser Ile Ala Gly Glu Leu Trp Phe
                100                 105                 110

Ala Phe Met Trp Val Leu Asp Gln Leu Pro Lys Thr Met Pro Val Arg
        115                 120                 125

Arg Ala Val Asp Val Thr Ala Leu Asn Asp Asp Thr Leu Leu Pro Ala
    130                 135                 140

Met Asp Val Phe Val Thr Thr Ala Asp Pro Asp Lys Glu Pro Pro Leu
145                 150                 155                 160

Ala Thr Ala Asn Thr Val Leu Ser Ile Leu Ala Ala Gly Tyr Pro Ala
                165                 170                 175

Gly Lys Val Thr Cys Tyr Val Ser Asp Asp Ala Gly Ala Glu Val Thr
                180                 185                 190

Arg Gly Ala Val Val Glu Ala Ala Arg Phe Ala Ala Leu Trp Val Pro
            195                 200                 205

Phe Cys Arg Lys His Gly Val Glu Pro Arg Asn Pro Glu Ala Tyr Phe
        210                 215                 220

Asn Gly Gly Glu Gly Gly Gly Gly Gly Lys Ala Arg Val Val Ala
225                 230                 235                 240

Arg Gly Ser Tyr Lys Gly Arg Ala Trp Pro Glu Leu Val Arg Asp Arg
                245                 250                 255

Arg Arg Val Arg Arg Glu Tyr Glu Glu Met Arg Leu Arg Ile Asp Ala
                260                 265                 270

Leu Gln Ala Ala Asp Ala Arg Arg Arg Cys Gly Ala Ala Asp Asp
            275                 280                 285

His Ala Gly Val Val Gln Val Leu Ile Asp Ser Ala Gly Ser Ala Pro
            290                 295                 300

Gln Leu Gly Val Ala Asp Gly Ser Lys Leu Ile Asp Leu Ala Ser Val
305                 310                 315                 320

Asp Val Arg Leu Pro Ala Leu Val Tyr Val Cys Arg Glu Lys Arg Arg
                325                 330                 335

Gly Arg Ala His His Arg Lys Ala Gly Ala Met Asn Ala Leu Leu Arg
            340                 345                 350

Ala Ser Ala Val Leu Ser Asn Ala Pro Phe Ile Leu Asn Leu Asp Cys
        355                 360                 365

Asp His Tyr Val Asn Asn Ser Gln Ala Leu Arg Ala Gly Ile Cys Phe
        370                 375                 380

Met Ile Glu Arg Arg Gly Gly Ala Glu Asp Ala Gly Asp Val Ala
385                 390                 395                 400

Phe Val Gln Phe Pro Gln Arg Phe Asp Gly Val Asp Pro Gly Asp Arg
                405                 410                 415

Tyr Ala Asn His Asn Arg Val Phe Phe Asp Cys Thr Glu Leu Gly Leu
            420                 425                 430

Asp Gly Leu Gln Gly Pro Ile Tyr Val Gly Thr Gly Cys Leu Phe Arg
            435                 440                 445

Arg Val Ala Leu Tyr Gly Val Asp Pro Pro Arg Trp Arg Ser Pro Gly
    450                 455                 460

Gly Gly Val Ala Ala Asp Pro Ala Lys Phe Gly Glu Ser Ala Pro Phe
465                 470                 475                 480

Leu Ala Ser Val Arg Ala Glu Gln Ser His Ser Arg Asp Asp Gly Asp
                485                 490                 495

Ala Ile Ala Glu Ala Ser Ala Leu Val Ser Cys Ala Tyr Glu Asp Gly
                500                 505                 510
```

```
       Thr Ala Trp Gly Arg Asp Val Gly Trp Val Tyr Gly Thr Val Thr Glu
               515                 520                 525

Asp Val Ala Thr Gly Phe Cys Met His Arg Arg Gly Trp Arg Ser Ala
               530                 535                 540

Tyr Tyr Ala Ala Ala Pro Asp Ala Phe Arg Gly Thr Ala Pro Ile Asn
   545                 550                 555                 560

Leu Ala Asp Arg Leu His Gln Val Leu Arg Trp Ala Ala Gly Ser Leu
               565                 570                 575

Glu Ile Phe Phe Ser Arg Asn Asn Ala Leu Leu Ala Gly Gly Arg Arg
               580                 585                 590

Arg Leu His Pro Leu Gln Arg Ala Ala Tyr Leu Asn Thr Thr Val Tyr
               595                 600                 605

Pro Phe Thr Ser Leu Phe Leu Met Ala Tyr Cys Leu Phe Pro Ala Ile
               610                 615                 620

Pro Leu Ile Ala Gly Gly Gly Trp Asn Ala Ala Pro Thr Pro Thr
   625                 630                 635                 640

Tyr Val Ala Phe Leu Ala Ala Leu Met Val Thr Leu Ala Ala Val Ala
               645                 650                 655

Val Leu Glu Thr Arg Trp Ser Gly Ile Ala Leu Gly Glu Trp Trp Arg
               660                 665                 670

Asn Glu Gln Phe Trp Met Val Ser Ala Thr Ser Ala Tyr Leu Ala Ala
               675                 680                 685

Val Ala Gln Val Ala Leu Lys Val Ala Thr Gly Lys Glu Ile Ser Phe
               690                 695                 700

Lys Leu Thr Ser Lys His Leu Ala Ser Ser Ala Thr Pro Val Ala Gly
   705                 710                 715                 720

Lys Asp Arg Gln Tyr Ala Glu Leu Tyr Ala Val Arg Trp Thr Ala Leu
               725                 730                 735

Met Ala Pro Thr Ala Ala Leu Ala Val Asn Val Ala Ser Met Ala
               740                 745                 750

Ala Ala Gly Gly Gly Gly Arg Trp Trp Trp Asp Ala Pro Ser Ala
               755                 760                 765

Ala Ala Ala Ala Ala Ala Leu Pro Val Ala Phe Asn Val Trp Val
               770                 775                 780

Val Val His Leu Tyr Pro Phe Ala Leu Gly Leu Met Gly Arg Arg Ser
   785                 790                 795                 800

Lys Ala Val Arg Pro Ile Leu Phe Leu Phe Ala Val Val Ala Tyr Leu
                               805                 810                 815

Ala Val Arg Phe Leu Cys Leu Leu Leu Gln Phe His Thr Ala
               820                 825                 830

<210> SEQ ID NO 31
<211> LENGTH: 2655
<212> TYPE: DNA
<213> ORGANISM: Oryza sativa

<400> SEQUENCE: 31
atggcgcttt cgccggcggc ggctggccgt accggccgaa acaacaataa cgacgccggc        60
ctcgcggacc tctgctgcc ggctggcggc ggcggcggcg gcgtaagga caagtactgg       120 gtgcccgccg acgaggagga agagatttgc cgcggcgagg acgcggccg cccgccggcg       180 ccgccgctgc tgtaccggac gttcaaggtc agcggcgtcc tcctccatcc ctacaggtta       240
ctgaccttag tcaggctgat cgccgtcgtc ctcttcctcg catggcgcct gaagcaccgg       300
```

```
gactccgacg ccatgtggct ctggtggatc tcgatcgccg gcgacttctg gttcggcgtc    360
acctggctgc tcaaccaggc ctccaagctc aacccccgtca agcgcgtccc cgacctctcc   420
ctcctcaggc ggcgcttcga cgacggcggc ctccccggca tcgacgtgtt catcaacacc    480
gtcgaccccg tcgacgagcc gatgctctac accatgaact ccatcctgtc catcctcgcc    540
accgactacc ccgccgaccg gcacgccgcc tacctctccg acgacggcgc gtcgctggcc    600
cactacgagg ggctgatcga gacggcgagg ttcgccgcgc tgtgggtccc gttctgccgg    660
aagcaccgcg tcgagccgag ggcgcccgag agctacttcg cggcgaaggc ggcgccgtac    720
gccgggccgg cgctgccgga ggagttcttc ggcgaccgca ggctcgtgcg ccgggagtac    780
gaggagttca aggcgcggct cgatgcgctg ttcactgaca ttccgcaacg atcggaagcg    840
agtgttggca atgcaaacac caaaggcgcg aaggccactc tgatggcaga tgggacccct    900
tggccaggga catggaccga ccagcagag aatcacaaaa aaggacagca cgccggaatc     960
gttaaggtaa tgttgagcca tccgggtgaa gagcctcagc tcggcatgcc ggcgagctcc    1020
ggccacccct tggacttcag cgccgtcgac gtgcgcctcc cgatactggt ctacatcgcc    1080
cgggagaagc ggccgggata cgaccaccag aagaaggccg cgccatgaa cgcgcagctg     1140
cgcgtatccg cgctgctgtc gaacgcgccc ttcatcttca acttcgacgg cgaccactac    1200
atcaacaact cccaggcgtt ccgcgccgcc ctgtgcttca tgctcgactg ccgccacggc    1260
gacgacaccg cattcgtcca gttcccgcag cgcttcgacg acgtcgaccc gaccgaccgg    1320
tactgcaacc acaaccgcgt cttcttcgac gccacgctgc tcggcctcaa cggcgtccag    1380
ggcccgtcct acgtcggcac cggctgcatg ttccgccgcg tcgcgctcta cggcgccgac    1440
ccgccgcgt ggaggccgga ggacgacgac gccaaggcgc tgggctgccc cggcaggtat     1500
ggaaactcga tgccgttcat caacacgata ccggcggcgg cgagccaaga acggtccatc    1560
gcgtcgccgg cggcggcgtc gctcgacgag acggcggcca tggcggaggt ggaggaggtg    1620
atgacgtgcg cgtacgagga cgggacggaa tggggcgacg cgtcgggtg ggtgtacgac     1680
atcgcgacgg aggacgtggt gaccggcttc cggctgcacc ggaaggggtg gcggtccatg    1740
tactgcgcca tggagcccga cgcgttccgg ggcacggcgc cgatcaacct cacggagcgc    1800
ctctaccaga tcctgcggtg gtcgggcggc tcgctcgaga tgttcttctc ccgcaactgc    1860
ccgctcctcg ccggctgccg gctgcgcccc atgcagcgcg tcgcgtacgc caacatgacg    1920
gcgtacccgg tctcggcgct gttcatggtc gtctacgacc tcctcccggt gatctggctc    1980
tcccaccacg gcgagttcca catccagaag ccgttctcga cgtacgtcgc ctacctcgtc    2040
gccgtcatcg ccatgatcga ggtgatcggc ctggtcgaga tcaagtgggc ggggctcacc    2100
ctgctcgact ggtggcgcaa cgagcagttc tacatgatcg gcgccacggg ggtgtacctg    2160
gcggcggtgc tgcacatcgt gctcaagagg ctcctcggac tgaagggcgt gcggttcaag    2220
ctgacggcga agcagctggc cggcggcgcg agggagaggt tcgcggagct gtacgacgtg    2280
cactggtcgc cgctgctggc gccgacgtg gtggtgatgg cggtgaacgt gactgccatc     2340
ggcgcggcgg cggggaaggc ggtcgtcggg gggtggacgc cggcgcaggt cgccggcgcg    2400
tcggcggggc tggtgttcaa cgtgtgggtc ctggtgctgc tctacccgtt cgcgctcggg    2460
atcatgggga ggtggagcaa gaggccgtgc gcgctcttcg cgctgctcgt ggccgcgtgc    2520
gcggcggtcg cggcggggtt cgtgccgtc catgccgtgc tcgccgccgg ctccgccgcg    2580
ccgtcctggt tgggatggtc tcgtggcgcc actgccattt tgccgtcaag ctggcgactt    2640
aagcggggtt tctga                                                    2655
```

<210> SEQ ID NO 32
<211> LENGTH: 884
<212> TYPE: PRT
<213> ORGANISM: Oryza sativa

<400> SEQUENCE: 32

| | | | | | | | | | | | | | | |
|---|---|---|---|---|---|---|---|---|---|---|---|---|---|---|
| Met | Ala | Leu | Ser | Pro | Ala | Ala | Gly | Arg | Thr | Gly | Arg | Asn | Asn | Asn |
| 1 | | | | 5 | | | | | 10 | | | | | 15 |
| Asn | Asp | Ala | Gly | Leu | Ala | Asp | Pro | Leu | Leu | Pro | Ala | Gly | Gly | Gly |
| | | | 20 | | | | | 25 | | | | | 30 | |
| Gly | Gly | Gly | Lys | Asp | Lys | Tyr | Trp | Val | Pro | Ala | Asp | Glu | Glu | Glu |
| | | 35 | | | | | 40 | | | | | 45 | | |
| Ile | Cys | Arg | Gly | Glu | Asp | Gly | Arg | Pro | Pro | Ala | Pro | Pro | Leu | Leu |
| | 50 | | | | | 55 | | | | | 60 | | | |
| Tyr | Arg | Thr | Phe | Lys | Val | Ser | Gly | Val | Leu | Leu | His | Pro | Tyr | Arg | Leu |
| 65 | | | | | 70 | | | | | 75 | | | | | 80 |
| Leu | Thr | Leu | Val | Arg | Leu | Ile | Ala | Val | Val | Leu | Phe | Leu | Ala | Trp | Arg |
| | | | | 85 | | | | | 90 | | | | | 95 | |
| Leu | Lys | His | Arg | Asp | Ser | Asp | Ala | Met | Trp | Leu | Trp | Trp | Ile | Ser | Ile |
| | | | 100 | | | | | 105 | | | | | 110 | | |
| Ala | Gly | Asp | Phe | Trp | Phe | Gly | Val | Thr | Trp | Leu | Leu | Asn | Gln | Ala | Ser |
| | | 115 | | | | | 120 | | | | | 125 | | | |
| Lys | Leu | Asn | Pro | Val | Lys | Arg | Val | Pro | Asp | Leu | Ser | Leu | Leu | Arg | Arg |
| | 130 | | | | | 135 | | | | | 140 | | | | |
| Arg | Phe | Asp | Asp | Gly | Gly | Leu | Pro | Gly | Ile | Asp | Val | Phe | Ile | Asn | Thr |
| 145 | | | | | 150 | | | | | 155 | | | | | 160 |
| Val | Asp | Pro | Val | Asp | Glu | Pro | Met | Leu | Tyr | Thr | Met | Asn | Ser | Ile | Leu |
| | | | | 165 | | | | | 170 | | | | | 175 | |
| Ser | Ile | Leu | Ala | Thr | Asp | Tyr | Pro | Ala | Asp | Arg | His | Ala | Ala | Tyr | Leu |
| | | | 180 | | | | | 185 | | | | | 190 | | |
| Ser | Asp | Asp | Gly | Ala | Ser | Leu | Ala | His | Tyr | Glu | Gly | Leu | Ile | Glu | Thr |
| | | 195 | | | | | 200 | | | | | 205 | | | |
| Ala | Arg | Phe | Ala | Ala | Leu | Trp | Val | Pro | Phe | Cys | Arg | Lys | His | Arg | Val |
| | 210 | | | | | 215 | | | | | 220 | | | | |
| Glu | Pro | Arg | Ala | Pro | Glu | Ser | Tyr | Phe | Ala | Ala | Lys | Ala | Ala | Pro | Tyr |
| 225 | | | | | 230 | | | | | 235 | | | | | 240 |
| Ala | Gly | Pro | Ala | Leu | Pro | Glu | Glu | Phe | Phe | Gly | Asp | Arg | Arg | Leu | Val |
| | | | | 245 | | | | | 250 | | | | | 255 | |
| Arg | Arg | Glu | Tyr | Glu | Glu | Phe | Lys | Ala | Arg | Leu | Asp | Ala | Leu | Phe | Thr |
| | | | 260 | | | | | 265 | | | | | 270 | | |
| Asp | Ile | Pro | Gln | Arg | Ser | Glu | Ala | Ser | Val | Gly | Asn | Ala | Asn | Thr | Lys |
| | | 275 | | | | | 280 | | | | | 285 | | | |
| Gly | Ala | Lys | Ala | Thr | Leu | Met | Ala | Asp | Gly | Thr | Pro | Trp | Pro | Gly | Thr |
| | 290 | | | | | 295 | | | | | 300 | | | | |
| Trp | Thr | Glu | Pro | Ala | Glu | Asn | His | Lys | Lys | Gly | Gln | His | Ala | Gly | Ile |
| 305 | | | | | 310 | | | | | 315 | | | | | 320 |
| Val | Lys | Val | Met | Leu | Ser | His | Pro | Gly | Glu | Glu | Pro | Gln | Leu | Gly | Met |
| | | | | 325 | | | | | 330 | | | | | 335 | |
| Pro | Ala | Ser | Ser | Gly | His | Pro | Leu | Asp | Phe | Ser | Ala | Val | Asp | Val | Arg |
| | | | 340 | | | | | 345 | | | | | 350 | | |
| Leu | Pro | Ile | Leu | Val | Tyr | Ile | Ala | Arg | Glu | Lys | Arg | Pro | Gly | Tyr | Asp |
| | | 355 | | | | | 360 | | | | | 365 | | | |
| His | Gln | Lys | Lys | Ala | Gly | Ala | Met | Asn | Ala | Gln | Leu | Arg | Val | Ser | Ala |

```
              370             375             380
Leu Leu Ser Asn Ala Pro Phe Ile Phe Asn Phe Asp Gly Asp His Tyr
385             390             395             400

Ile Asn Asn Ser Gln Ala Phe Arg Ala Ala Leu Cys Phe Met Leu Asp
                405             410             415

Cys Arg His Gly Asp Asp Thr Ala Phe Val Gln Phe Pro Gln Arg Phe
                420             425             430

Asp Asp Val Asp Pro Thr Asp Arg Tyr Cys Asn His Asn Arg Val Phe
                435             440             445

Phe Asp Ala Thr Leu Leu Gly Leu Asn Gly Val Gln Gly Pro Ser Tyr
        450             455             460

Val Gly Thr Gly Cys Met Phe Arg Arg Val Ala Leu Tyr Gly Ala Asp
465             470             475             480

Pro Pro Arg Trp Arg Pro Glu Asp Asp Ala Lys Ala Leu Gly Cys
                485             490             495

Pro Gly Arg Tyr Gly Asn Ser Met Pro Phe Ile Asn Thr Ile Pro Ala
                500             505             510

Ala Ala Ser Gln Glu Arg Ser Ile Ala Ser Pro Ala Ala Ala Ser Leu
                515             520             525

Asp Glu Thr Ala Ala Met Ala Glu Val Glu Val Met Thr Cys Ala
        530             535             540

Tyr Glu Asp Gly Thr Glu Trp Gly Asp Gly Val Gly Trp Val Tyr Asp
545             550             555             560

Ile Ala Thr Glu Asp Val Val Thr Gly Phe Arg Leu His Arg Lys Gly
                565             570             575

Trp Arg Ser Met Tyr Cys Ala Met Glu Pro Asp Ala Phe Arg Gly Thr
                580             585             590

Ala Pro Ile Asn Leu Thr Glu Arg Leu Tyr Gln Ile Leu Arg Trp Ser
                595             600             605

Gly Gly Ser Leu Glu Met Phe Phe Ser Arg Asn Cys Pro Leu Leu Ala
        610             615             620

Gly Cys Arg Leu Arg Pro Met Gln Arg Val Ala Tyr Ala Asn Met Thr
625             630             635             640

Ala Tyr Pro Val Ser Ala Leu Phe Met Val Val Tyr Asp Leu Leu Pro
                645             650             655

Val Ile Trp Leu Ser His His Gly Glu Phe His Ile Gln Lys Pro Phe
                660             665             670

Ser Thr Tyr Val Ala Tyr Leu Val Ala Val Ile Ala Met Ile Glu Val
                675             680             685

Ile Gly Leu Val Glu Ile Lys Trp Ala Gly Leu Thr Leu Leu Asp Trp
        690             695             700

Trp Arg Asn Glu Gln Phe Tyr Met Ile Gly Thr Gly Val Tyr Leu
705             710             715             720

Ala Ala Val Leu His Ile Val Leu Lys Arg Leu Leu Gly Leu Lys Gly
                725             730             735

Val Arg Phe Lys Leu Thr Ala Lys Gln Leu Ala Gly Gly Ala Arg Glu
                740             745             750

Arg Phe Ala Glu Leu Tyr Asp Val His Trp Ser Pro Leu Leu Ala Pro
        755             760             765

Thr Val Val Met Ala Val Asn Val Thr Ala Ile Gly Ala Ala Ala
        770             775             780

Gly Lys Ala Val Val Gly Gly Trp Thr Pro Ala Gln Val Ala Gly Ala
785             790             795             800
```

Ser Ala Gly Leu Val Phe Asn Val Trp Val Leu Val Leu Leu Tyr Pro
            805                 810                 815

Phe Ala Leu Gly Ile Met Gly Arg Trp Ser Lys Arg Pro Cys Ala Leu
        820                 825                 830

Phe Ala Leu Leu Val Ala Ala Cys Ala Ala Val Ala Ala Gly Phe Val
        835                 840                 845

Ala Val His Ala Val Leu Ala Ala Gly Ser Ala Ala Pro Ser Trp Leu
    850                 855                 860

Gly Trp Ser Arg Gly Ala Thr Ala Ile Leu Pro Ser Ser Trp Arg Leu
865                 870                 875                 880

Lys Arg Gly Phe

<210> SEQ ID NO 33
<211> LENGTH: 2661
<212> TYPE: DNA
<213> ORGANISM: Oryza sativa

<400> SEQUENCE: 33

| | |
|---|---|
| atggcggcca acggcggcgg cggcggcgcc ggtggctgca gcaatggtgg cgtggcggc | 60 |
| gccgtgaacg gcgcggcggc gaatggcggc ggcggcggag gaggcggcag taagggcgcg | 120 |
| acgacgagga gggcgaaggt cagcccgatg acaggtact gggtgcccac cgacgagaag | 180 |
| gagatggcgc cggcggtcgc cgacggcggc gaggacggcc ggcggccgct gctgttccgg | 240 |
| acgttcacgg tcagggggcat cctcctccac ccctacaggt tattgacatt ggtcagattg | 300 |
| gttgctatcg tcctattttt catatggcgt atcaggcacc cgtacgccga tggcatgttt | 360 |
| ttctggtgga tatctgtgat tggagatttt tggtttggtg ttagttggct gctaaaccaa | 420 |
| gtggcaaagc tgaaaccgat caggcgtgtt cccgatctta acctcttaca acaacagttt | 480 |
| gatcttcctg atggaaactc caacctccct ggccttgatg tattcatcaa caccgtcgat | 540 |
| cccataaatg agcctatgat atacactatg aacgccattt atccattct gcagcagac | 600 |
| tacccagttg acaagcatgc ttgctatctt tcggatgatg gtggatcgat catccattat | 660 |
| gatggtttac ttgagactgc aaagtttgct gcgttatggg ttcccttttg ccgaaaacat | 720 |
| tccattgagc ctagggcccc tgagagctat tttgcagtga agtcacgtcc atacgctgga | 780 |
| agtgcaccag aggattttct cagtgaccac agatacatgc gtaggagta tgatgagttc | 840 |
| aaggtacgct tagatgcgct tttttactgtc attcccaaac ggtcagatgc atacaaccag | 900 |
| gcacatgccg aagaaggtgt gaaggcaacc tggatggcag atgggacaga gtggcctggt | 960 |
| acatggattg atccatctga gaaccataag aaaggaaatc acgctggaat tgttcaggtt | 1020 |
| atgttgaacc atccgagcaa tcaacctcaa cttggtctac cagcaagcac tgacagccct | 1080 |
| gtggacttca gcaatgttga tgtgcgcctt cctatgcttg tatacatagc ccgcgagaag | 1140 |
| cgcccaggct atgaccacca aaagaaggca ggtgccatga acgtgcagct gcgagtatct | 1200 |
| gccctcctca ccaatgcacc attcatcatc aactttgatg gtgaccacta gtcaacaac | 1260 |
| tcgaaggcct tccgtgctgg tatatgtttc atgctcgatc gacgtgaagg tgacaacact | 1320 |
| gccttgtcc aattccccca acgttttgat gacgttgacc caactgatag gtattgcaat | 1380 |
| cacaaccgag tcttctttga tgctactttg ctcggcctca atggtatcca gggcccctct | 1440 |
| tatgttggca ccggttgcat gttccgccga gtcgcactgt atggtgttga cccacctcgt | 1500 |
| tggagacccg atgatggcaa tattgtggat agctccaaaa agttcggcaa cttggactcc | 1560 |
| ttcatcagct caataccta t agcagcaaac caagaacgct caatcatatc accacctgcc | 1620 |

```
cttgaagagt ctatcctgca ggagttgagt gatgccatgg catgtgcata tgaggatggg    1680
actgactggg gcaaggatgt tggttgggtt tacaatattg caaccgagga tgtggtgact    1740
ggtttccgat tgcatcggac agggtggcgc tcaatgtact gccgcatgga gcctgatgca    1800
ttccgcggca ctgcaccaat caacctcact gagcgcctct accagattct gcgctggtca    1860
ggtggctccc ttgagatgtt cttctcacat aactgcccac tccttgctgg ccgccgactc    1920
aactttatgc aacgaattgc ttacattaac atgacaggct acccagttac atcagtcttc    1980
cttttgttct atctcctctt ccctgtcata tggatctttc gcggcatatt ctacatacag    2040
aagccatttc ctacatatgt attgtacctt gtgatcgtca tatttatgtc agaaatgatc    2100
ggtatggttg agatcaagtg ggcggggcta acactactgg actggatccg caatgaacag    2160
ttctacatta ttggagcaac agctgtttac ccgcttgcag tcctgcacat agtgctgaag    2220
tgttttggtt tgaagggtgt ctcattcaag ctgacagcaa acaagtagc aagcagcacc     2280 agcgagaagt ttgcagaact gtatgatgtt caatgggcac cattgttgtt cccgacgata    2340
gtggtgatag cagtgaatat ctgtgccatt ggcgcggcaa taggcaaggc tctctttgga    2400
ggatggtcac tgatgcagat gggagatgcg tcgctcgggc tggtattcaa cgtgtggatc    2460
ctgctgctga tatatccatt tgcactgggt atcatgggaa gatggagcaa gagaccctat    2520
atcctgttcg tcttgattgt gatttcattt gttataatcg cattggccga tattgccatc    2580
caggcaatgc gttctggatc cgttcggctc cactttagac ggtcaggtgg agccaacttc    2640
cctacaagct gggggtttta g                                              2661
```

<210> SEQ ID NO 34
<211> LENGTH: 886
<212> TYPE: PRT
<213> ORGANISM: Oryza sativa

<400> SEQUENCE: 34

Met Ala Ala Asn Gly Gly Gly Gly Ala Gly Gly Cys Ser Asn Gly
1               5                   10                  15

Gly Gly Gly Ala Val Asn Gly Ala Ala Ala Asn Gly Gly Gly Gly
            20                  25                  30

Gly Gly Gly Gly Ser Lys Gly Ala Thr Thr Arg Arg Ala Lys Val Ser
        35                  40                  45

Pro Met Asp Arg Tyr Trp Val Pro Thr Asp Glu Lys Glu Met Ala Ala
    50                  55                  60

Ala Val Ala Asp Gly Gly Glu Asp Gly Arg Arg Pro Leu Leu Phe Arg
65                  70                  75                  80

Thr Phe Thr Val Arg Gly Ile Leu Leu His Pro Tyr Arg Leu Leu Thr
                85                  90                  95

Leu Val Arg Leu Val Ala Ile Val Leu Phe Phe Ile Trp Arg Ile Arg
            100                 105                 110

His Pro Tyr Ala Asp Gly Met Phe Phe Trp Trp Ile Ser Val Ile Gly
        115                 120                 125

Asp Phe Trp Phe Gly Val Ser Trp Leu Leu Asn Gln Val Ala Lys Leu
    130                 135                 140

Lys Pro Ile Arg Arg Val Pro Asp Leu Asn Leu Gln Gln Gln Phe
145                 150                 155                 160

Asp Leu Pro Asp Gly Asn Ser Asn Leu Pro Gly Leu Asp Val Phe Ile
                165                 170                 175

Asn Thr Val Asp Pro Ile Asn Glu Pro Met Ile Tyr Thr Met Asn Ala

```
                180             185             190
Ile Leu Ser Ile Leu Ala Ala Asp Tyr Pro Val Asp Lys His Ala Cys
            195             200             205
Tyr Leu Ser Asp Asp Gly Gly Ser Ile Ile His Tyr Asp Gly Leu Leu
            210             215             220
Glu Thr Ala Lys Phe Ala Ala Leu Trp Val Pro Phe Cys Arg Lys His
225             230             235             240
Ser Ile Glu Pro Arg Ala Pro Glu Ser Tyr Phe Ala Val Lys Ser Arg
            245             250             255
Pro Tyr Ala Gly Ser Ala Pro Glu Asp Phe Leu Ser Asp His Arg Tyr
            260             265             270
Met Arg Arg Glu Tyr Asp Glu Phe Lys Val Arg Leu Asp Ala Leu Phe
            275             280             285
Thr Val Ile Pro Lys Arg Ser Asp Ala Tyr Asn Gln Ala His Ala Glu
            290             295             300
Glu Gly Val Lys Ala Thr Trp Met Ala Asp Gly Thr Glu Trp Pro Gly
305             310             315             320
Thr Trp Ile Asp Pro Ser Glu Asn His Lys Lys Gly Asn His Ala Gly
            325             330             335
Ile Val Gln Val Met Leu Asn His Pro Ser Asn Gln Pro Gln Leu Gly
            340             345             350
Leu Pro Ala Ser Thr Asp Ser Pro Val Asp Phe Ser Asn Val Asp Val
            355             360             365
Arg Leu Pro Met Leu Val Tyr Ile Ala Arg Glu Lys Arg Pro Gly Tyr
            370             375             380
Asp His Gln Lys Lys Ala Gly Ala Met Asn Val Gln Leu Arg Val Ser
385             390             395             400
Ala Leu Leu Thr Asn Ala Pro Phe Ile Ile Asn Phe Asp Gly Asp His
            405             410             415
Tyr Val Asn Asn Ser Lys Ala Phe Arg Ala Gly Ile Cys Phe Met Leu
            420             425             430
Asp Arg Arg Glu Gly Asp Asn Thr Ala Phe Val Gln Phe Pro Gln Arg
            435             440             445
Phe Asp Asp Val Asp Pro Thr Asp Arg Tyr Cys Asn His Asn Arg Val
            450             455             460
Phe Phe Asp Ala Thr Leu Leu Gly Leu Asn Gly Ile Gln Gly Pro Ser
465             470             475             480
Tyr Val Gly Thr Gly Cys Met Phe Arg Arg Val Ala Leu Tyr Gly Val
            485             490             495
Asp Pro Pro Arg Trp Arg Pro Asp Asp Gly Asn Ile Val Asp Ser Ser
            500             505             510
Lys Lys Phe Gly Asn Leu Asp Ser Phe Ile Ser Ile Pro Ile Ala
            515             520             525
Ala Asn Gln Glu Arg Ser Ile Ile Ser Pro Pro Ala Leu Glu Glu Ser
            530             535             540
Ile Leu Gln Glu Leu Ser Asp Ala Met Ala Cys Ala Tyr Glu Asp Gly
545             550             555             560
Thr Asp Trp Gly Lys Asp Val Gly Trp Val Tyr Asn Ile Ala Thr Glu
            565             570             575
Asp Val Val Thr Gly Phe Arg Leu His Arg Thr Gly Trp Arg Ser Met
            580             585             590
Tyr Cys Arg Met Glu Pro Asp Ala Phe Arg Gly Thr Ala Pro Ile Asn
            595             600             605
```

```
Leu Thr Glu Arg Leu Tyr Gln Ile Leu Arg Trp Ser Gly Gly Ser Leu
    610                 615                 620
Glu Met Phe Phe Ser His Asn Cys Pro Leu Leu Ala Gly Arg Arg Leu
625                 630                 635                 640
Asn Phe Met Gln Arg Ile Ala Tyr Ile Asn Met Thr Gly Tyr Pro Val
                645                 650                 655
Thr Ser Val Phe Leu Leu Phe Tyr Leu Leu Phe Pro Val Ile Trp Ile
            660                 665                 670
Phe Arg Gly Ile Phe Tyr Ile Gln Lys Pro Phe Pro Thr Tyr Val Leu
        675                 680                 685
Tyr Leu Val Ile Val Ile Phe Met Ser Glu Met Ile Gly Met Val Glu
    690                 695                 700
Ile Lys Trp Ala Gly Leu Thr Leu Leu Asp Trp Ile Arg Asn Glu Gln
705                 710                 715                 720
Phe Tyr Ile Ile Gly Ala Thr Ala Val Tyr Pro Leu Ala Val Leu His
                725                 730                 735
Ile Val Leu Lys Cys Phe Gly Leu Lys Gly Val Ser Phe Lys Leu Thr
            740                 745                 750
Ala Lys Gln Val Ala Ser Ser Thr Ser Glu Lys Phe Ala Glu Leu Tyr
        755                 760                 765
Asp Val Gln Trp Ala Pro Leu Leu Phe Pro Thr Ile Val Val Ile Ala
    770                 775                 780
Val Asn Ile Cys Ala Ile Gly Ala Ala Ile Gly Lys Ala Leu Phe Gly
785                 790                 795                 800
Gly Trp Ser Leu Met Gln Met Gly Asp Ala Ser Leu Gly Leu Val Phe
                805                 810                 815
Asn Val Trp Ile Leu Leu Leu Ile Tyr Pro Phe Ala Leu Gly Ile Met
            820                 825                 830
Gly Arg Trp Ser Lys Arg Pro Tyr Ile Leu Phe Val Leu Ile Val Ile
        835                 840                 845
Ser Phe Val Ile Ile Ala Leu Ala Asp Ile Ala Ile Gln Ala Met Arg
    850                 855                 860
Ser Gly Ser Val Arg Leu His Phe Arg Arg Ser Gly Gly Ala Asn Phe
865                 870                 875                 880
Pro Thr Ser Trp Gly Phe
                885

<210> SEQ ID NO 35
<211> LENGTH: 32
<212> TYPE: DNA
<213> ORGANISM: Artificial
<220> FEATURE:
<223> OTHER INFORMATION: synthetic Oligonucleotide Primer

<400> SEQUENCE: 35
agtcagatct gttccgtgca tggcggccac cg                                32

<210> SEQ ID NO 36
<211> LENGTH: 32
<212> TYPE: DNA
<213> ORGANISM: Artificial
<220> FEATURE:
<223> OTHER INFORMATION: synthetic Oligonucleotide Primer

<400> SEQUENCE: 36
cagtacgcgt cgcgatcgaa ctgtccctac cc                                32
```

<210> SEQ ID NO 37
<211> LENGTH: 29
<212> TYPE: DNA
<213> ORGANISM: Artificial
<220> FEATURE:
<223> OTHER INFORMATION: synthetic Oligonucleotide Primer

<400> SEQUENCE: 37
agtcagatct atagagtgct cgtcatggc                               29

<210> SEQ ID NO 38
<211> LENGTH: 32
<212> TYPE: DNA
<213> ORGANISM: Artificial
<220> FEATURE:
<223> OTHER INFORMATION: synthetic Oligonucleotide Primer

<400> SEQUENCE: 38
cagtacgcgt tttatctatg cacctagaat gg                           32

<210> SEQ ID NO 39
<211> LENGTH: 32
<212> TYPE: DNA
<213> ORGANISM: Artificial
<220> FEATURE:
<223> OTHER INFORMATION: synthetic Oligonucleotide Primer

<400> SEQUENCE: 39
agtcaagctt gctacggcct ccacgatgtc cg                           32

<210> SEQ ID NO 40
<211> LENGTH: 32
<212> TYPE: DNA
<213> ORGANISM: Artificial
<220> FEATURE:
<223> OTHER INFORMATION: synthetic Oligonucleotide Primer

<400> SEQUENCE: 40
cagtactagt catgtcgtcc ctacccagat gg                           32

<210> SEQ ID NO 41
<211> LENGTH: 32
<212> TYPE: DNA
<213> ORGANISM: Artificial
<220> FEATURE:
<223> OTHER INFORMATION: synthetic Oligonucleotide Primer

<400> SEQUENCE: 41
agtcaagctt gcgacgatcg atggcgcttt cg                           32

<210> SEQ ID NO 42
<211> LENGTH: 31
<212> TYPE: DNA
<213> ORGANISM: Artificial
<220> FEATURE:
<223> OTHER INFORMATION: synthetic Oligonucleotide Primer

<400> SEQUENCE: 42
cagtactact tgcatcaatc agaaaccccg c                            31

<210> SEQ ID NO 43
<211> LENGTH: 25
<212> TYPE: DNA
<213> ORGANISM: Artificial
<220> FEATURE:
<223> OTHER INFORMATION: synthetic Oligonucleotide Primer

```
<400> SEQUENCE: 43
tggttgatct cgttgtgcag gtctc                                         25

<210> SEQ ID NO 44
<211> LENGTH: 24
<212> TYPE: DNA
<213> ORGANISM: Artificial
<220> FEATURE:
<223> OTHER INFORMATION: synthetic Oligonucleotide Primer

<400> SEQUENCE: 44
gtcagccaag tcaacaactc tctg                                          24

<210> SEQ ID NO 45
<211> LENGTH: 20
<212> TYPE: DNA
<213> ORGANISM: Artificial
<220> FEATURE:
<223> OTHER INFORMATION: synthetic Oligonucleotide Primer

<400> SEQUENCE: 45
atgtgggtga gggtatggaa                                               20

<210> SEQ ID NO 46
<211> LENGTH: 25
<212> TYPE: DNA
<213> ORGANISM: Artificial
<220> FEATURE:
<223> OTHER INFORMATION: synthetic Oligonucleotide Primer
<220> FEATURE:
<221> NAME/KEY: misc_feature
<222> LOCATION: (18)..(18)
<223> OTHER INFORMATION: n is a, c, g, or t

<400> SEQUENCE: 46
ccgacaacct tcttagtnct cctct                                         25

<210> SEQ ID NO 47
<211> LENGTH: 23
<212> TYPE: DNA
<213> ORGANISM: Artificial
<220> FEATURE:
<223> OTHER INFORMATION: synthetic Oligonucleotide Primer

<400> SEQUENCE: 47
gagttcttca cgcgatacct cca                                           23

<210> SEQ ID NO 48
<211> LENGTH: 27
<212> TYPE: DNA
<213> ORGANISM: Artificial
<220> FEATURE:
<223> OTHER INFORMATION: synthetic Oligonucleotide Primer

<400> SEQUENCE: 48
gaccaccttt attaccccca tttacca                                       27

<210> SEQ ID NO 49
<211> LENGTH: 23
<212> TYPE: DNA
<213> ORGANISM: Artificial
<220> FEATURE:
<223> OTHER INFORMATION: synthetic Oligonucleotide Primer

<400> SEQUENCE: 49
```

-continued

```
tggcgaacgc tggtcctaat aca                                              23

<210> SEQ ID NO 50
<211> LENGTH: 24
<212> TYPE: DNA
<213> ORGANISM: Artificial
<220> FEATURE:
<223> OTHER INFORMATION: synthetic Oligonucleotide Primer

<400> SEQUENCE: 50
caaaaactcc tctgcccaa tcaa                                              24

<210> SEQ ID NO 51
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 51
gtgcgcatac gaggatggga cg                                               22

<210> SEQ ID NO 52
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 52
agaacatctc cagcgagccg cc                                               22

<210> SEQ ID NO 53
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 53
ccgattgggg caagggtgtt gg                                               22

<210> SEQ ID NO 54
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 54
gacacgctgg agaggttgga gc                                               22

<210> SEQ ID NO 55
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 55
ctccgtgtac acctccatgg ag                                               22

<210> SEQ ID NO 56
<211> LENGTH: 22
<212> TYPE: DNA
<213> ORGANISM: Artificial
```

```
<220> FEATURE:
<223> OTHER INFORMATION: synthetic Oligonucleotide Primer

<400> SEQUENCE: 56
ctcggagatg agccacatca cc                                              22

<210> SEQ ID NO 57
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 57
tacgacatcg cgacggagga cg                                              22

<210> SEQ ID NO 58
<211> LENGTH: 22
<212> TYPE: DNA
<213> ORGANISM: Artificial
<220> FEATURE:
<223> OTHER INFORMATION: synthetic Oligonucleotide Primer

<400> SEQUENCE: 58
gtcatgttgg cgtacgcgac gc                                              22

<210> SEQ ID NO 59
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 59
ggagagcgcg tgcattgagg acg                                             23

<210> SEQ ID NO 60
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 60
tgtccgggca aagtcatcaa                                                 20

<210> SEQ ID NO 61
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 61
cggtcgggaa acctgggagt gg                                              22

<210> SEQ ID NO 62
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 62
gctcccagct tactacagaa cc                                              22
```

```
<210> SEQ ID NO 63
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 63
gtagctggct actgtgcata gc                                              22

<210> SEQ ID NO 64
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 64
gaacttacaa accccagctt gtgg                                            24

<210> SEQ ID NO 65
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 65
gtcgatcgac agatccggtc                                                 20

<210> SEQ ID NO 66
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 66
gggagtttag cgagagcctg                                                 20

<210> SEQ ID NO 67
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 67
tgggcattca ccttcgtcat                                                 20

<210> SEQ ID NO 68
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 68
tgtccgggca aactcatcaa                                                 20

<210> SEQ ID NO 69
<211> LENGTH: 20
<212> TYPE: DNA
<213> ORGANISM: Artificial
<220> FEATURE:
<223> OTHER INFORMATION: synthetic oligonucleotide primer
```

```
<400> SEQUENCE: 69
ccgtcgggct cgtgtatgtc                                                    20

<210> SEQ ID NO 70
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 70
ttgcagtgac tctggctgta cttg                                               24

<210> SEQ ID NO 71
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 71
gggattgttc ggttccactt t                                                  21

<210> SEQ ID NO 72
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 72
gctgttgctt tgccacatct c                                                  21

<210> SEQ ID NO 73
<211> LENGTH: 19
<212> TYPE: DNA
<213> ORGANISM: Artificial
<220> FEATURE:
<223> OTHER INFORMATION: synthetic UAS comprising GAL4 DNA binding
      domain

<400> SEQUENCE: 73
cggagtactg tcctccgag                                                     19
```